(12) United States Patent
Pendharkar et al.

(10) Patent No.: US 12,428,395 B2
(45) Date of Patent: Sep. 30, 2025

(54) HETEROCYCLIC COMPOUNDS AS KINASE INHIBITOR AND USES THEREOF

(71) Applicant: SPEROGENIX THERAPEUTICS LIMITED, Hong Kong (CN)

(72) Inventors: Dhananjay Pendharkar, Greater Noida (IN); Sreekanth A. Ramachandran, Greater Noida (IN); Pradeep S. Jadhavar, Greater Noida (IN); Dayanand Panpatil, Noida (IN); Uzma Saeed, New Delhi (IN); Vivek Kumar, Delhi (IN); Dipshe Bist, Noida (IN)

(73) Assignee: SPEROGENIX THERAPEUTICS LIMITED, Hong Kong (CN)

(*) Notice: Subject to any disclaimer, the term of this patent is extended or adjusted under 35 U.S.C. 154(b) by 877 days.

(21) Appl. No.: 17/631,765

(22) PCT Filed: Jul. 31, 2020

(86) PCT No.: PCT/IB2020/057281
§ 371 (c)(1),
(2) Date: Jan. 31, 2022

(87) PCT Pub. No.: WO2021/019514
PCT Pub. Date: Feb. 4, 2021

(65) Prior Publication Data
US 2022/0281842 A1  Sep. 8, 2022

(30) Foreign Application Priority Data
Aug. 1, 2019 (IN) .............................. 201911004152

(51) Int. Cl.
| | | |
|---|---|---|
| *C07D 401/14* | (2006.01) | |
| *C07D 403/12* | (2006.01) | |
| *C07D 403/14* | (2006.01) | |
| *C07D 405/14* | (2006.01) | |
| *C07D 413/14* | (2006.01) | |
| *C07D 417/14* | (2006.01) | |

(52) U.S. Cl.
CPC ......... *C07D 401/14* (2013.01); *C07D 403/12* (2013.01); *C07D 403/14* (2013.01); *C07D 405/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| | | |
|---|---|---|
| 2013/0345191 A1 | 12/2013 | Jia et al. |
| 2019/0152948 A1* | 5/2019 | Liu .......................... A61P 29/00 |

FOREIGN PATENT DOCUMENTS

| | | | | |
|---|---|---|---|---|
| CN | 104470363 A | 3/2015 | | |
| CN | 104884454 A | 9/2015 | | |
| WO | WO-02/059112 A2 | 8/2002 | | |
| WO | 2014074661 A1 | 5/2014 | | |
| WO | WO-2015123453 A1 * | 8/2015 | ........... | C07D 237/24 |
| WO | WO-2019/103952 A1 | 5/2019 | | |

OTHER PUBLICATIONS

International Search Report and Written Opinion for PCT/IB2020/057281 dated Nov. 12, 2020, 10 pages.

* cited by examiner

*Primary Examiner* — Jeffrey S Lundgren
*Assistant Examiner* — Anthony Joseph Seitz
(74) *Attorney, Agent, or Firm* — Clark & Elbing LLP

(57) ABSTRACT

The present disclosure relates generally to compounds useful in treatment of conditions associated with Checkpoint kinase (CHK), particularly CHK-1 enzymes. Specifically, the present invention discloses compound of formula (IA), which exhibits inhibitory activity against CHK-1 enzymes. Methods of treating conditions associated with excessive activity of CHK-1 enzymes with such compounds is disclosed. Uses thereof, pharmaceutical compositions, kits and method of synthesis also disclosed.

Formula (IA)

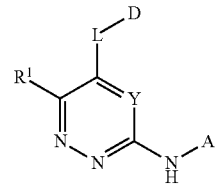

18 Claims, No Drawings

HETEROCYCLIC COMPOUNDS AS KINASE INHIBITOR AND USES THEREOF

CROSS REFERENCE TO RELATED APPLICATION

This application claims the priority benefit of INDIAN Provisional Patent Application No. 201911004152, filed on Aug. 1, 2019, disclosures of which is incorporated herein by reference in its entireties.

FIELD OF THE INVENTION

The present invention generally relates to compounds having Checkpoint kinase-1 (CHK-1) inhibitory activity. The invention also discloses method of treating conditions associated with excessive activity of CHK-1 enzymes using such compounds, pharmaceutical compositions, methods of treating using said pharmaceutical compositions and kits. Method of synthesis of said compounds is also disclosed.

BACKGROUND OF THE INVENTION

A wide range of cancer chemotherapeutic agents act through DNA damaging pathway to induce DNA damage causing tumor growth inhibition. However, these chemotherapeutic agents lead to cell cycle arrest by induction of checkpoints at either S-phase or G2/M boundary. The G2 arrest allows the cell time to repair the damaged DNA before entering mitosis. Checkpoint kinase-1 (CHK-1) and an unrelated serine/threonine kinase, Checkpoint kinase-2 (CHK-2), play a central role in arresting the cell cycle at the G2-M boundary (O'Connell et al EMBO J (1997) vol. 16 p. 545-554). CHK-1 and/or CHK-2 induce this checkpoint by phosphorylating serine 216 of the CDC25 phosphatase, inhibiting the removal of two inactivating phosphates on cyclin dependent kinases (CDKs) (Zheng et al Nature (1998) vol. 395 p. 507-510). Another overlapping pathway mediated by p53 also elicits cycle arrest in response to DNA-damage. However, p53 is mutationally inactivated in many cancers, resulting in a partial deficiency in their ability to initiate a DNA-repair response. If CHK-1 activity is also inhibited in p53-negative cancers, all ability to arrest and repair DNA in response to DNA-damage is removed resulting in mitotic catastrophe and enhancing the effect of the DNA damaging agents (Konarias et al. Oncogene (2001) vol. 20 p 7453-7463, Bunch and Eastman Clin. Can. Res. (1996) vol. 2 p 791-797, Tenzer and Pruschy Curr. Med Chem (2003) vol 3 p 35-46).

CHK-1 inhibition, therefore, represents a novel therapeutic strategy to increase the lethality of DNA-damaging chemotherapeutic drugs in p53 pathway defective cancers. Abrogation of the remaining intact checkpoint should result in increased tumor cell death. CHK-1 inhibitors have demonstrated potentiation of a range of cytotoxic chemotherapy drugs both in vitro and in a range of pre-clinical models of human cancer including gemcitabine, irinotecan, cytarabine, and cisplatin. This "synthetic lethality" approach should increase the therapeutic activity of the chemotherapeutic drug without increasing the systemic toxicity as normal cells should remain protected by their functional p53 pathway. CHK-1 inhibitors have, therefore, the potential to be combined with a wide range of cytotoxic chemotherapeutic agents for the treatment of a diverse selection of human cancers.

Various attempts have been made to develop CHK-1 kinase inhibitors. For example, U.S. Ser. No. 10/000,481B2 (Vernalis) disclose 1H-pyrrolo[2,3-B] pyridine derivatives compounds as CHK-1 kinase inhibitors. U.S. Ser. No. 10/010,547B2 (Cascadian Therapeutics) discloses pyrazol amino pyrazine derivatives as kinase inhibitors. WO/2018/086546A1 (Zhejiang university) disclose 2-polysubstituted aromatic ring-pyrimidine derivatives as CHK-1 inhibitors. Few small molecule inhibitors of CHK-1 (Prexasertib/LY2606368, LY2603618 and SRA737) are currently in Phase I/II clinical evaluation in combination with gemcitabine, pemetrexed, fludarabine, cytarabine, and cisplatin.

Thus, there remains a continuing need for developing new CHK-1 inhibitors with pharmacokinetic and pharmacodynamic properties making them suitable for use as pharmaceutical agents. The object of the present invention is to provide such pharmaceutical agents and treatments.

SUMMARY OF THE INVENTION

In one aspect, the present invention provides a compound of formula (IA):

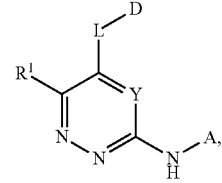

Formula (IA)

or a salt thereof, wherein A, D, L, Y and $R^1$ are as detailed herein.

In one aspect, the compound of formula (IA) or a salt thereof, is a compound of formula (I) or a salt thereof, as detailed herein.

In one aspect, the compound of formula (IA) or a salt thereof, is a compound of formula (II) or a salt thereof, as detailed herein.

In one aspect, the compound of formula (IA) or a salt thereof, is a compound of formula (III) or a salt thereof, as detailed herein.

In one aspect, the compound of formula (IA) or a salt thereof, is a compound of formula (IV) or a salt thereof, as detailed herein.

In some aspects, the compound of formula (II) or a salt thereof, is any of the compounds of formula (IIa-1) to (IIa-10) or a salt thereof, as detailed herein.

In some aspects, the compound of formula (II) or a salt thereof, is any of the compounds of formula (IIb-1) to (IIb-20) or a salt thereof, as detailed herein.

In some aspects, the compound of formula (III) or a salt thereof, is any of the compounds of formula (IIIa-1) to (IIIa-10) or a salt thereof, as detailed herein.

In some aspects, the compound of formula (III) or a salt thereof, is any of the compounds of formula (IIIb-1) to (IIIb-20) or a salt thereof, as detailed herein.

In some aspects, the compound of formula (IV) or a salt thereof, is any of the compounds of formula (IVa-1) to (IVa-15) or a salt thereof, as detailed herein.

In some another aspects, the present invention provides method of treating a disease or disorder associated with this CHK kinase enzymes, more specifically CHK-1 kinase enzymes in an individual in need thereof, wherein the method comprises administering to the individual an effective amount of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)), or a salt thereof.

In some another aspects, the present invention provides method of inhibiting CHK-1 kinase enzyme in an individual in need thereof, wherein the method comprises administering to the individual an effective amount of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)), or a salt thereof.

In some another aspects, the present invention provides method of treating cancer in an individual in need thereof, wherein the method comprises administering to the individual an effective amount of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)), or a salt thereof.

In some another aspects, the present invention provides method of treating a disease or disorder associated with this CHK kinase enzymes, or more specifically CHK-1 kinase enzymes in an individual in need thereof, wherein the method comprises administering to the individual an effective amount of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)), or a salt thereof in combination with another therapeutic agent.

In some another aspects, the present invention provides pharmaceutical compositions, comprising a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)), or a salt thereof, and at least one pharmaceutically acceptable carrier.

In some another aspects, the present invention provides method of treating a disease or disorder associated with this CHK kinase enzymes, or more specifically CHK-1 kinase enzymes in an individual in need thereof, wherein the method comprises administering to the individual an effective amount of a pharmaceutical composition comprising a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)), or a salt thereof.

In some another aspects, the present invention provides method of treating a disease or disorder associated with this CHK kinase enzymes, or more specifically CHK-1 kinase enzymes in an individual in need thereof, wherein the method comprises administering to the individual an effective amount of a pharmaceutical composition comprising a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)), or a salt thereof in combination with another therapeutic agent.

In some another aspects, the present invention provides processes for preparing compounds and intermediates thereof disclosed in the present invention.

DETAILED DESCRIPTION OF THE INVENTION

Definitions

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C═C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Carbonyl" refers to the group C═O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantly, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to imidazolyl, pyrrolyl, pyrazolyl, 1,2,4-triazolyl, thiophenyl, furanyl, thiazolyl, isothiazolyl, thiadiazolyl, oxazolyl, isoxazolyl, oxadiazolyl, pyridyl, pyrimidyl, pyridazinyl or pyrazinyl, and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, aziridinyl, azetidinyl, oxetanyl, morpholinyl, thiomorpholinyl, azepanyl tetrahydropyranyl, dihydropyranyl, piperidinyl, piperazinyl, pyrrolidinyl, thiazolinyl, thiazolidinyl, tetrahydrofuranyl, tetrahydrothiophenyl, and the like.

"Oxo" refers to the moiety =O.

"CHK" refers to Checkpoint kinase, which includes Checkpoint kinase-1 (CHK-1) and Checkpoint kinase-2 (CHK-2). Preferably, CHK refers to CHK-1.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Compounds

The present invention provides a compound of formula (IA):

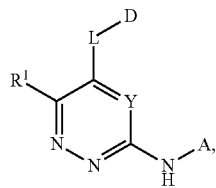

formula (IA)

wherein,
Y is N or $CR^y$;
A is 5- to 6-membered heteroaryl optionally substituted with 0-4 $R^x$;
$R^x$ and $R^y$ are independently hydrogen, $C_1$-$C_6$ alkyl, $C_3$-$C_6$ cycloalkyl, 3- to 6-membered heterocyclyl, —CN, halogen, $C_1$-$C_6$ alkoxy, $C_1$-$C_6$haloalkoxy, $C_1$-$C_6$ haloalkyl, —$OR^7$, —$NR^8R^9$, —$C(O)R^7$, —$NR^7C(O)R^8$, —$C(O)OR^7$, —$C(O)NR^8R^9$, each of which is optionally substituted by oxo, halogen, CN, —$OR^{10}$ or —$NR^{11}R^{12}$;
D is —($C_1$-$C_6$ alkylene)$OR^{10}$, —($C_1$-$C_6$ alkylene)$NR^{11}R^{12}$, 3- to 6-membered heterocyclyl, —($C_1$-$C_6$ alkylene)$C_3$-$C_6$ cycloalkyl or —($C_1$-$C_6$ alkylene)3- to 10-membered heterocyclyl, each of which is optionally substituted by $R^2$;
L is —$CH_2$—, —O—, —NH—, —$N(CH_3)$—, —$SO_2$—, —$C(O)$—, —$C(O)NH$— or —$NHC(O)$—;
$R^1$ is hydrogen, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$ aryl, 5- to 10-membered heteroaryl, —CN, halogen, $C_1$-$C_6$ alkoxy, $C_1$-$C_6$haloalkoxy, $C_1$-$C_6$haloalkyl, —$OR^{13}$, —$SR^{13}$, —$S(O)_2R^{13}$, —$S(O)_2NR^{14}R^{15}$, —$NR^{13}S(O)_2R^{14}$, —$NR^{14}R^{15}$, —$C(O)R^{13}$, —$NR^{13}C(O)R^{14}$, —$NR^{13}C(O)NR^{14}R^{15}$, —$C(O)OR^{13}$, —$C(O)ONR^{14}R^{15}$, —$C(O)NR^{14}R^{15}$, —($C_1$-$C_3$ alkylene)$OR^{13}$, —($C_1$-$C_3$ alkylene)$SR^{13}$, —($C_1$-$C_3$ alkylene)$S(O)_2R^{13}$, —($C_1$-$C_3$ alkylene)$S(O)_2NR^{14}R^{15}$, —($C_1$-$C_3$ alkylene)$NR^{13}S(O)_2R^{14}$, —($C_1$-$C_3$ alkylene)$NR^{14}R^{15}$, —($C_1$-$C_3$ alkylene)$C(O)R^{13}$, —($C_1$-$C_3$ alkylene)$NR^{13}C(O)R^{14}$, —($C_1$-$C_3$ alkylene)$NR^{13}C(O)NR^{14}R^{15}$, —($C_1$-$C_3$ alkylene)$C(O)OR^{13}$, —($C_1$-$C_3$ alkylene)$C(O)ONR^{14}R^{15}$, —($C_1$-$C_3$ alkylene)($C_3$-$C_8$ cycloalkyl) or —($C_1$-$C_3$ alkylene)(3-10-membered heterocyclyl); wherein $R^1$ is optionally substituted by $R^3$;
$R^2$ is oxo, $C_2$-$C_6$ alkenyl, $C_2$-$C_6$ alkynyl, —CN, halogen, $C_1$-$C_6$ alkoxy, $C_1$-$C_6$haloalkoxy, —$OR^{16}$, —$SR^{16}$, —$S(O)_2R^{16}$, —$S(O)_2NR^{17}R^{18}$, —$NR^{16}S(O)_2R^{17}$, —$NR^{17}R^{18}$, —$C(O)R^{16}$, —$NR^{16}C(O)R^{17}$, —$C(O)OR^{16}$, or $C_1$-$C_6$ alkyl optionally substituted by oxo, —OH, halogen or —$NH_2$;
$R^3$ is oxo, $C_2$-$C_6$ alkenyl, $C_2$-$C_6$ alkynyl, —CN, halogen, $C_1$-$C_6$alkoxy, $C_1$-$C_6$haloalkoxy, —$OR^{16}$, —$SR^{16}$, —$S(O)_2R^{16}$, —$S(O)_2NR^{17}R^{18}$, —$NR^{16}S(O)_2R^{17}$, —$NR^{17}R^{18}$, —$C(O)R^{16}$, —$NR^{16}C(O)R^{17}$, —$C(O)OR^{16}$, $C_3$-$C_6$ cycloalkyl, $C_6$ aryl, 5- to 6-membered heteroaryl, 3- to 6-membered heterocyclyl, or $C_1$-$C_6$ alkyl optionally substituted by oxo, —OH, halogen or —$NH_2$;
each $R^7$, $R^8$ and $R^9$ is independently hydrogen or $C_1$-$C_6$ alkyl optionally substituted by oxo, —OH, halogen or —$NH_2$;
$R^{10}$ is hydrogen, $C_1$-$C_6$ alkyl, $C_3$-$C_8$ cycloalkyl or 3- to 10-membered heterocyclyl, wherein each of which is optionally substituted by $R^2$;
each $R^{11}$ and $R^{12}$ is independently hydrogen, $C_1$-$C_6$ alkyl, $C_3$-$C_8$ cycloalkyl or 3- to 10-membered heterocyclyl, wherein each of which is optionally substituted by $R^2$;
or $R^{11}$ and $R^{12}$ are taken together with the atom to which they attached to form a 3- to 6-membered heterocyclyl optionally substituted by $R^2$;
each $R^{13}$, $R^{14}$ and $R^{15}$ is independently hydrogen, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, 3- to 6-membered heterocyclyl, $C_6$ aryl, 5- to 6-membered heteroaryl, —($C_1$-$C_3$ alkylene) $C_3$-$C_6$ cycloalkyl, —($C_1$-$C_3$ alkylene)3- to 6-membered heterocyclyl, or —($C_1$-$C_3$ alkylene)5- to 6-membered heteroaryl, wherein each of $R^{13}$, $R^{14}$ and $R^{15}$ is independently optionally substituted by oxo, $C_2$-$C_6$ alkenyl, $C_2$-$C_6$ alkynyl, —CN, halogen, $C_1$-$C_6$ alkoxy, $C_1$-$C_6$ haloalkoxy, —$OR^{16}$, —$SR^{16}$, —$S(O)_2R^{16}$, —$S(O)_2NR^{17}R^{18}$, $NR^{17}R^{18}$, $NR^{16}S(O)_2R^{17}$, $NR^{17}R^{18}$, $C(O)R^{16}$, —$NR^{16}C(O)R^{17}$, $C(O)OR^{16}$ or $C_1$-$C_6$ alkyl optionally substituted by oxo, —OH, halogen or —$NH_2$;
or $R^{14}$ and $R^{15}$ are taken together with the atom to which they attached to form a 3- to 6-membered heterocyclyl optionally substituted by oxo, OH or halogen, or $C_1$-$C_6$ alkyl optionally substituted by oxo, —OH, halogen or —$NH_2$;

each $R^{16}$, $R^{17}$ and $R^{18}$ is independently hydrogen, $C_2$-$C_6$ alkenyl, $C_2$-$C_6$ alkynyl, $C_6$ aryl, 5- to 6-membered heteroaryl, 3- to 6-membered heterocyclyl, $C_3$-$C_6$ cycloalkyl or $C_1$-$C_6$ alkyl optionally substituted by oxo, —OH, halogen or —NH$_2$; and or $R^{17}$ and $R^{18}$ are taken together with the atom to which they attached to form a 3- to 6-membered heterocyclyl optionally substituted by oxo, —OH, halogen or —NH$_2$, or $C_1$-$C_6$ alkyl optionally substituted by oxo, —OH, halogen or —NH$_2$ or a salt thereof.

In some embodiments, a compound of formula (IA) is a compound of formula

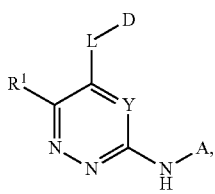

formula (I)

wherein,

Y is N or CR$^y$;

A is 5- to 6-membered heteroaryl optionally substituted with 0-4 R$^x$;

R$^x$ and R$^y$ are independently hydrogen, $C_1$-$C_6$ alkyl, $C_3$-$C_6$ cycloalkyl, 3- to 6-membered heterocyclyl, —CN, halogen, $C_1$-$C_6$ alkoxy, $C_1$-$C_6$ haloalkoxy, $C_1$-$C_6$ haloalkyl, —OR$^7$, —NR$^8$R$^9$, —C(O)R$^7$, —NR$^7$C(O)R$^8$, —C(O)OR$^7$, —C(O)NR$^8$R$^9$, each of which is optionally substituted by oxo, halogen, CN, —OR$^{10}$ or —NR$^{11}$R$^{12}$;

D is —($C_1$-$C_6$ alkylene)OR$^{10}$, —($C_1$-$C_6$ alkylene)NR$^{11}$R$^{12}$, —($C_1$-$C_6$ alkylene)$C_3$-$C_6$ cycloalkyl or —($C_1$-$C_6$ alkylene)3- to 10-membered heterocyclyl, each of which is optionally substituted by R$^2$;

L is —CH$_2$—, —O—, —NH—, —N(CH$_3$)—, —SO$_2$—, —C(O)—, —C(O)NH— or —NHC(O)—;

R$^1$ is $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$ aryl, 5- to 6-membered heteroaryl, —CN, halogen, $C_1$-$C_6$ alkoxy, $C_1$-$C_6$haloalkoxy, $C_1$-$C_6$haloalkyl, —OR$^{13}$, —SR$^{13}$, —S(O)$_2$R$^{13}$, —S(O)$_2$NR$^{14}$R$^{15}$, —NR$^{13}$S(O)$_2$R$^{14}$, —NR$^{14}$R$^{15}$, —C(O)R$^{13}$, —NR$^{13}$C(O)R$^{14}$, —NR$^{13}$C(O)NR$^{14}$R$^{15}$, —C(O)OR$^{13}$, —C(O)ONR$^{14}$R$^{15}$, —C(O)NR$^{14}$R$^{15}$, —($C_1$-$C_3$ alkylene)OR$^{13}$, —($C_1$-$C_3$ alkylene)SR$^{13}$, —($C_1$-$C_3$ alkylene)S(O)$_2$R$^{13}$, —($C_1$-$C_3$ alkylene)S(O)$_2$NR$^{14}$R$^{15}$, —($C_1$-$C_3$ alkylene)NR$^{13}$S(O)$_2$R$^{14}$, —($C_1$-$C_3$ alkylene)NR$^{14}$R$^{15}$, —($C_1$-$C_3$ alkylene)C(O)R$^{13}$, —($C_1$-$C_3$ alkylene)NR$^{13}$C(O)R$^{14}$, —($C_1$-$C_3$ alkylene)NR$^{13}$C(O)NR$^{14}$R$^{15}$, —($C_1$-$C_3$ alkylene)C(O)OR$^{13}$, —($C_1$-$C_3$ alkylene)C(O)ONR$^{14}$R$^{15}$, —($C_1$-$C_3$ alkylene)($C_3$-$C_8$ cycloalkyl) or —($C_1$-$C_3$ alkylene)(3-10-membered heterocyclyl); wherein R$^1$ is optionally substituted by R$^3$;

each R$^2$ and R$^3$ is independently oxo, $C_2$-$C_6$ alkenyl, $C_2$-$C_6$ alkynyl, —CN, halogen, $C_1$-$C_6$ alkoxy, $C_1$-$C_6$ haloalkoxy, —OR$^{16}$, —SR$^{16}$, —S(O)$_2$R$^{16}$, —S(O)$_2$NR$^{17}$R$^{18}$, —NR$^{16}$S(O)$_2$R$^{17}$, —NR$^{17}$R$^{18}$, —C(O)R$^{16}$, —NR$^{16}$C(O)R$^{17}$, —C(O)OR$^{16}$ or $C_1$-$C_6$ alkyl optionally substituted by oxo, —OH, halogen or —NH$_2$;

each R$^7$, R$^8$ and R$^9$ is independently hydrogen or $C_1$-$C_6$ alkyl optionally substituted by oxo, —OH, halogen or —NH$_2$;

R$^{10}$ is hydrogen, $C_1$-$C_6$ alkyl, $C_3$-$C_8$ cycloalkyl or 3- to 10-membered heterocyclyl, wherein each of which is optionally substituted by R$^2$;

each R$^{11}$ and R$^{12}$ is independently hydrogen, $C_1$-$C_6$ alkyl, $C_3$-$C_8$ cycloalkyl or 3- to 10-membered heterocyclyl, wherein each of which is optionally substituted by R$^2$;

or R$^{11}$ and R$^{12}$ are taken together with the atom to which they attached to form a 3- to 6-membered heterocyclyl optionally substituted by R$^2$;

each R$^{13}$, R$^{14}$ and R$^{15}$ is independently hydrogen, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$ aryl or 5- to 6-membered heteroaryl, wherein each of R$^{13}$, R$^{14}$ and R$^{15}$ is independently optionally substituted by oxo, $C_2$-$C_6$ alkenyl, $C_2$-$C_6$ alkynyl, —CN, halogen, $C_1$-$C_6$ alkoxy, $C_1$-$C_6$ haloalkoxy, —OR$^{16}$, —SR$^{16}$, —S(O)$_2$R$^{16}$, —S(O)$_2$NR$^{17}$R$^{18}$, —NR$^{16}$S(O)$_2$R$^{17}$, —NR$^{17}$R$^{18}$, —C(O)R$^{16}$, —NR$^{16}$C(O)R$^{17}$, —C(O)OR$^{16}$ or $C_1$-$C_6$ alkyl optionally substituted by oxo, —OH, halogen or —NH$_2$;

or R$^{14}$ and R$^{15}$ are taken together with the atom to which they attached to form a 3- to 6-membered heterocyclyl optionally substituted by oxo, OH or halogen, or $C_1$-$C_6$ alkyl optionally substituted by oxo, —OH, halogen or —NH$_2$;

each R$^{16}$, R$^{17}$ and R$^{18}$ is independently hydrogen, $C_2$-$C_6$ alkenyl, $C_2$-$C_6$ alkynyl, or $C_1$-$C_6$ alkyl optionally substituted by oxo, —OH, halogen or —NH$_2$; and or R$^{17}$ and R$^{18}$ are taken together with the atom to which they attached to form a 3- to 6-membered heterocyclyl optionally substituted by oxo, —OH, halogen or —NH$_2$, or $C_1$-$C_6$ alkyl optionally substituted by oxo, —OH, halogen or —NH$_2$, or a salt thereof.

In some embodiments of a compound of formula (IA), Y is N. In some embodiments of a compound of formula (IA), Y is CR$^y$. In some embodiments of a compound of formula (IA), when R$^y$ is hydrogen, Y is CH.

In some embodiments of a compound of formula (IA), R$^y$ is selected from hydrogen, $C_1$-$C_6$ alkyl, $C_3$-$C_6$ cycloalkyl, 3- to 6-membered heterocyclyl, —CN, halogen, $C_1$-$C_6$ alkoxy, $C_1$-$C_6$haloalkoxy, $C_1$-$C_6$haloalkyl, —OR$^7$, —NR$^8$R$^9$, —C(O)R$^7$, —NR$^7$C(O)R$^8$, —C(O)OR$^7$, —C(O)NR$^8$R$^9$, each of which is optionally substituted by oxo, halogen, CN, —OR$^{10}$ or —NR$^{11}$R$^{12}$. In some embodiments of a compound of formula (IA), R$^y$ is hydrogen. In some embodiments of a compound of formula (IA), R$^y$ is $C_1$-$C_6$ alkyl optionally substituted by oxo, halogen, CN, —OR$^{10}$ or —NR$^{11}$R$^{12}$. In some embodiments of a compound of formula (IA), R$^y$ is $C_3$-$C_6$ cycloalkyl optionally substituted by oxo, halogen, CN, —OR$^{10}$ or —NR$^{11}$R$^{12}$. In some embodiments of a compound of formula (IA), R$^y$ is 3- to 6-membered heterocyclyl optionally substituted by oxo, halogen, CN, —OR$^{10}$ or —NR$^{11}$R$^{12}$. In some embodiments of a compound of formula (IA), R$^y$ is —CN. In some embodiments of a compound of formula (IA), R$^y$ is halogen. In some embodiments of a compound of formula (IA), R$^y$ is $C_1$-$C_6$ alkoxy. In some embodiments of a compound of formula (IA), R$^y$ is $C_1$-$C_6$haloalkoxy. In some embodiments of a compound of formula (IA), R$^y$ is $C_1$-$C_6$haloalkyl. In some embodiments of a compound of formula (IA), R$^y$ is —OR$^7$. In some embodiments of a compound of formula (IA), R$^y$ is —NR$^8$R$^9$. In some embodiments of a compound of formula (IA), R$^y$ is —C(O)R$^7$. In some embodiments of a compound of formula (IA), R$^y$ is —NR$^7$C(O)R$^8$. In some embodiments of a compound of formula (IA), R$^y$ is —C(O)OR$^7$. In some embodiments of a compound of formula (IA), $R^y$ is —C(O)NR$^8$R$^9$. In some embodiments of a compound of formula (IA), $R^y$ is selected from hydrogen, $C_1$-$C_6$ alkyl, —CN, halogen, —OR$^7$ or —NR$^8$R$^9$. In some embodiments of a compound of formula (IA), $R^y$ is hydrogen, methyl, $C_1$ or F. In some embodiments of a compound of formula (IA), $R^y$ is hydrogen. In some embodiments of a compound of formula (IA), $R^y$ is methyl. In some embodiments of a compound of formula (IA), $R^y$ is $C_1$. In some embodiments of a compound of formula (IA), $R^y$ is F.

In some embodiments of a compound of formula (IA), $CR^y$ is CH.

In some embodiments of a compound of formula (IA), A is 5- to 6-membered heteroaryl optionally substituted with 0-4 $R^x$. In some embodiments of a compound of formula (IA), A is 5-membered heteroaryl optionally substituted with 0-4 $R^x$.

In some embodiments of a compound of formula (IA), A is 5-membered heteroaryl selected from imidazolyl, pyrrolyl, pyrazolyl, triazolyl, thiophenyl, furanyl, thiazolyl, isothiazolyl, thiadiazolyl, oxazolyl, isoxazolyl or oxadiazolyl, wherein each of which is optionally substituted with 0-4 $R^x$. In some embodiments of a compound of formula (IA), A is imidazolyl optionally substituted with 0-4 $R^x$. In some embodiments of a compound of formula (IA), A is pyrazolyl optionally substituted with 0-4 $R^x$. In some embodiments of a compound of formula (IA), A is thiazolyl optionally substituted with 0-4 $R^x$. In some embodiments of a compound of formula (IA), A is isothiazolyl optionally substituted with 0-4 $R^x$. In some embodiments of a compound of formula (IA), A is oxazolyl optionally substituted with 0-4 $R^x$. In some embodiments of a compound of formula (IA), A is isooxazolyl optionally substituted with 0-4 $R^x$.

In some embodiments of a compound of formula (IA), A is 6-membered heteroaryl selected from pyridyl, pyrimidyl, pyridazinyl or pyrazinyl, wherein each of which is optionally substituted with 0-4 $R^x$. In some embodiments of a compound of formula (IA), A is pyridyl optionally substituted with 0-4 $R^x$. In some embodiments of a compound of formula (IA), A is pyrimidyl optionally substituted with 0-4 $R^x$. In some embodiments of a compound of formula (IA), A is pyridazinyl optionally substituted with 0-4 $R^x$. In some embodiments of a compound of formula (IA), A is pyrazinyl optionally substituted with 0-4 $R^x$.

In some embodiments of a compound of formula (IA), $R^x$ is $C_1$-$C_6$ alkyl, $C_3$-$C_6$ cycloalkyl, 3- to 6-membered heterocyclyl, —CN, halogen, $C_1$-$C_6$alkoxy, $C_1$-$C_6$haloalkoxy, $C_1$-$C_6$haloalkyl, —OR$^7$, —NR$^8$R$^9$, —C(O)R$^7$, —NR$^7$C(O)R$^8$, —C(O)OR$^7$, —C(O)NR$^8$R$^9$, each of which is optionally substituted by oxo, halogen, CN, —OR$^{10}$ or —NR$^{11}$R$^{12}$. In some embodiments of a compound of formula (IA), $R^x$ is $C_1$-$C_6$ alkyl, —CN, halogen, —OR$^7$, —NR$^8$R$^9$, —NR$^7$C(O)R$^8$ or —C(O)NR$^8$R$^9$. In some embodiments of a compound of formula (IA), $R^x$ is $C_1$-$C_6$ alkyl. In some embodiments of a compound of formula (IA), $R^x$ is —CN. In some embodiments of a compound of formula (IA), $R^x$ is halogen. In some embodiments of a compound of formula (IA), $R^x$ is —OR$^7$. In some embodiments of a compound of formula (IA), $R^x$ is —NR$^8$R$^9$. In some embodiments of a compound of formula (IA), $R^x$ is —NR$^7$C(O)R$^8$. In some embodiments of a compound of formula (IA), $R^x$ is —C(O)NR$^8$R$^9$.

In some embodiments of a compound of formula (IA), A is imidazolyl, pyrrolyl, pyrazolyl, triazolyl, thiophenyl, furanyl, thiazolyl, isothiazolyl, thiadiazolyl, oxazolyl, isoxazolyl or oxadiazolyl optionally substituted with 0-4 $R^x$, wherein $R^x$ is $C_1$-$C_6$ alkyl, $C_3$-$C_6$ cycloalkyl, 3- to 6-membered heterocyclyl, —CN, halogen, $C_1$-$C_6$alkoxy, $C_1$-$C_6$haloalkoxy, $C_1$-$C_6$haloalkyl, —OR$^7$, —NR$^8$R$^9$, —C(O)R$^7$, —NR$^7$C(O)R$^8$, —C(O)OR$^7$, —C(O)NR$^8$R$^9$, each of $R^x$ is optionally substituted by oxo, halogen, CN, —OR$^{10}$ or —NR$^{11}$R$^{12}$. In some embodiments of a compound of formula (IA), A is imidazolyl, pyrrolyl, pyrazolyl, triazolyl, thiophenyl, furanyl, thiazolyl, isothiazolyl, thiadiazolyl, oxazolyl, isoxazolyl or oxadiazolyl optionally substituted by CN—, —C(O)NR$^8$R$^9$, $C_1$-$C_6$haloalkyl, $C_1$-$C_6$ alkyl optionally substituted with halogen or —OR$^{10}$. In some embodiments of a compound of formula (IA), A is imidazolyl, pyrrolyl, pyrazolyl, triazolyl, thiophenyl, furanyl, thiazolyl, isothiazolyl, thiadiazolyl, oxazolyl, isoxazolyl or oxadiazolyl optionally substituted by 0-4 $R^x$, wherein $R^x$ is selected from —CN, —CONH$_2$, —CH$_3$, —CF$_3$, —CH$_2$CF$_3$ or —CH$_2$OH.

In some embodiments of a compound of formula (IA), A is pyridyl, pyrimidyl, pyridazinyl or pyrazinyl optionally substituted with 0-4 $R^x$, wherein $R^x$ is $C_1$-$C_6$ alkyl, $C_3$-$C_6$ cycloalkyl, 3- to 6-membered heterocyclyl, —CN, halogen, $C_1$-$C_6$alkoxy, $C_1$-$C_6$haloalkoxy, $C_1$-$C_6$haloalkyl, —OR$^7$, —NR$^8$R$^9$, —C(O)R$^7$, —NR$^7$C(O)R$^8$, —C(O)OR$^7$, —C(O)NR$^8$R$^9$, each of $R^x$ is optionally substituted by oxo, halogen, —CN, —OR$^{10}$ or —NR$^{11}$R$^{12}$. In some embodiments of a compound of formula (IA), A is pyridyl, pyrimidyl, pyridazinyl or pyrazinyl optionally substituted by —CN, —C(O)NR$^8$R$^9$, $C_1$-$C_6$haloalkyl, $C_1$-$C_6$ alkyl optionally substituted with halogen or —OR$^{10}$. In some embodiments of a compound of formula (IA), A is pyridyl, pyrimidyl, pyridazinyl or pyrazinyl optionally substituted by —CN, —CONH$_2$, —CH$_3$, —CF$_3$, —CH$_2$CF$_3$ or —CH$_2$OH.

In some embodiments of a compound of formula (IA), A is selected from imidazolyl, pyrrolyl, pyrazolyl, triazolyl, thiophenyl, furanyl, thiazolyl, isothiazolyl, thiadiazolyl, oxazolyl, isoxazolyl, oxadiazolyl, pyridyl, pyrimidyl, pyridazinyl or pyrazinyl substituted with —CN, —CONH$_2$, —CH$_3$, —CF$_3$, —CH$_2$CF$_3$ or —CH$_2$OH.

In some embodiments of a compound of formula (IA), $R^x$ is —CN. In some embodiments of a compound of formula (IA), $R^x$ is —CONH$_2$. In some embodiments of a compound of formula (IA), $R^x$ is —CH$_3$. In some embodiments of a compound of formula (IA), $R^x$ is —CF$_3$. In some embodiments of a compound of formula (IA), $R^x$ is —CH$_2$CF$_3$. In some embodiments of a compound of formula (IA), $R^x$ is —CH$_2$OH.

In some embodiments of a compound of formula (IA), A is pyrazolyl substituted is —CH$_3$. In some embodiments of a compound of formula (IA), A is pyrazinyl substituted by —CN.

In some embodiments of a compound of formula (IA), A is selected from

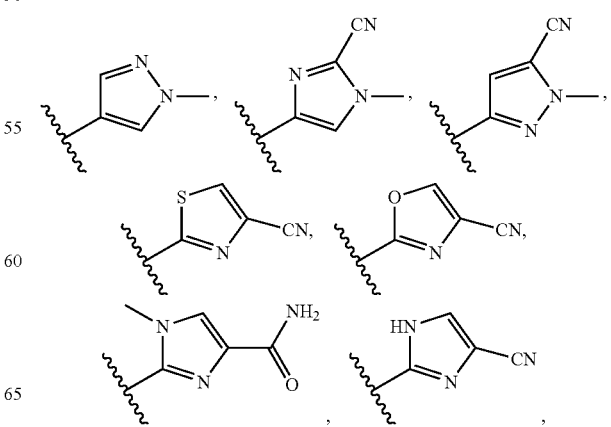

-continued

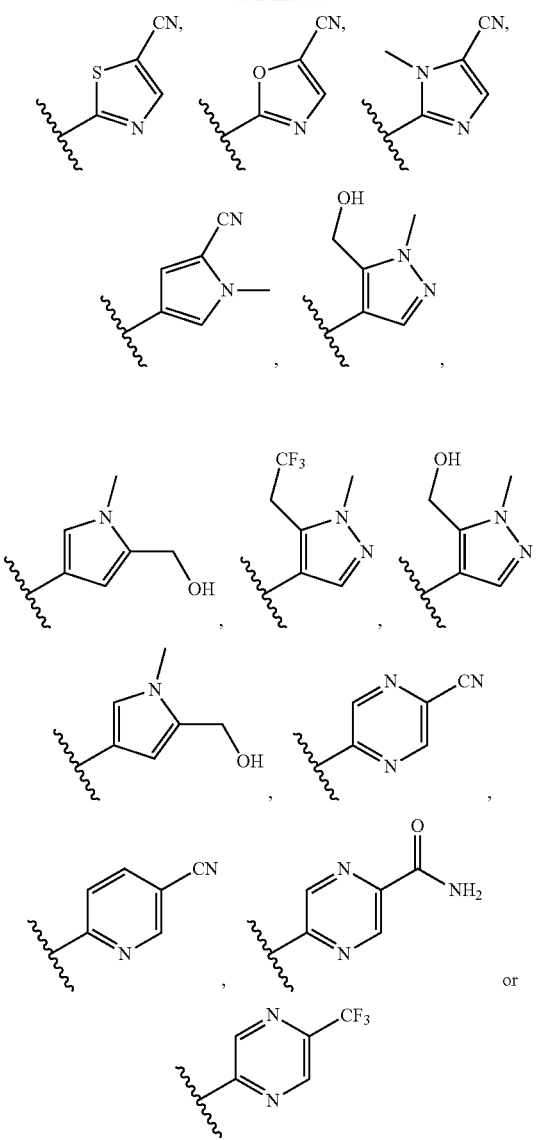

wherein the wavy lines denote attachment points to rest of the molecule.

In some embodiments of a compound of formula (IA), A is selected from

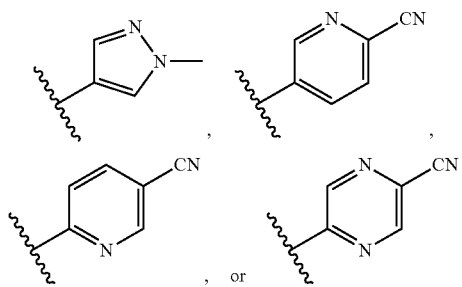

wherein the wavy lines denote attachment points to rest of the molecule.

In some embodiments of a compound of formula (IA), A is

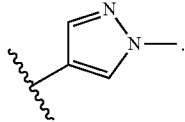 [SMILES: *c1cnn(C)c1]

In some embodiments of a compound of formula (IA), A is

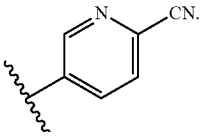

In some embodiments of a compound of formula (IA), A is

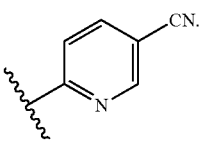

In some embodiments of a compound of formula (IA), A is

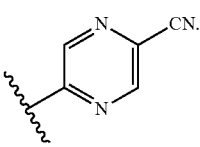 [SMILES: *c1cnc(C#N)cn1]

In some embodiments of a compound of formula (IA), D is —($C_1$-$C_6$ alkylene)$OR^{10}$, —($C_1$-$C_6$ alkylene)$NR^{11}R^{12}$, 3- to 6-membered heterocyclyl, —($C_1$-$C_6$ alkylene)$C_3$-$C_6$ cycloalkyl or —($C_1$-$C_6$ alkylene)3- to 10-membered heterocyclyl, each of which is optionally substituted by $R^2$. In some embodiments of a compound of formula (IA), D is —($C_1$-$C_6$ alkylene)$OR^{10}$ optionally substituted by $R^2$. In some embodiments of a compound of formula (IA), D is —($C_1$-$C_6$ alkylene)$NR^{11}R^{12}$ optionally substituted by $R^2$. In some embodiments of a compound of formula (IA), D is 3- to 6-membered heterocyclyl optionally substituted by $R^2$. In some embodiments of a compound of formula (IA), D is —($C_1$-$C_6$ alkylene)$C_3$-$C_6$ cycloalkyl optionally substituted by $R^2$. In some embodiments of a compound of formula (IA), D is —($C_1$-$C_6$ alkylene)3- to 10-membered heterocyclyl optionally substituted by $R^2$.

In some embodiments of a compound of formula (IA), $C_1$-$C_6$ alkylene of D (wherein D is —($C_1$-$C_6$ alkylene)$OR^{10}$, —($C_1$-$C_6$ alkylene)$NR^{11}R^{12}$, —($C_1$-$C_6$ alkylene)$C_3$-$C_6$ cycloalkyl or —($C_1$-$C_6$ alkylene)3- to 10-membered heterocyclyl as disclosed herein in formula (IA)) is substituted or unsubstituted. In some embodiments of a compound of formula (IA), the $C_1$-$C_6$ alkylene is a linear alkylene such as —$CH_2$—, —$CH_2$—$CH_2$— or —$CH_2$—$CH_2$—$CH_2$. In some embodiments of a compound of formula (IA), the $C_1$-$C_6$ alkylene is a branched alkylene, such as —CH(CH$_3$)—, —C(CH$_3$)$_2$—, —CH(CH$_3$)—CH$_2$— or —CH$_2$—CH(CH$_3$)—. For example, in certain embodiments, the —(C$_1$-C$_6$ alkylene)NR$^{11}$R$^{12}$ is —CH(CH$_3$)CH$_2$—N(CH$_3$)$_2$. For example, in certain embodiments, the —(C$_1$-C$_6$ alkylene)NR$^{11}$R$^{12}$ is —CH$_2$—CH$_2$—N(CH$_3$)$_2$ or —CH$_2$—CH$_2$—CH$_2$—N(CH$_3$)$_2$.

In some embodiments of a compound of formula (IA), D is selected from the group

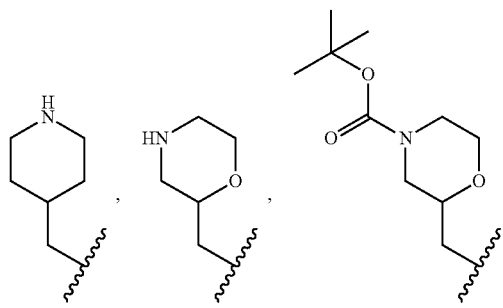

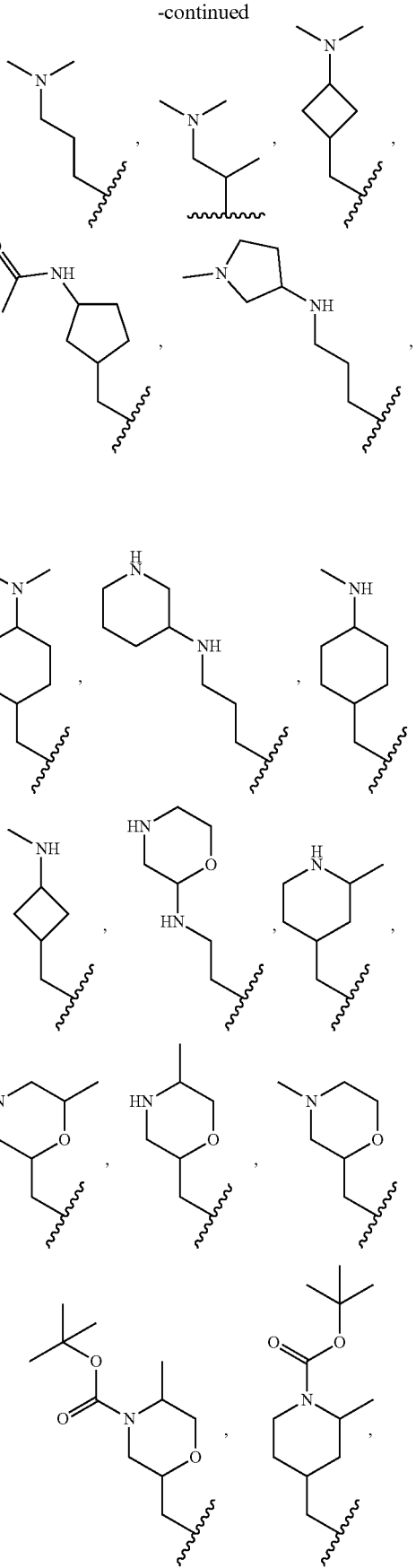

-continued

-continued
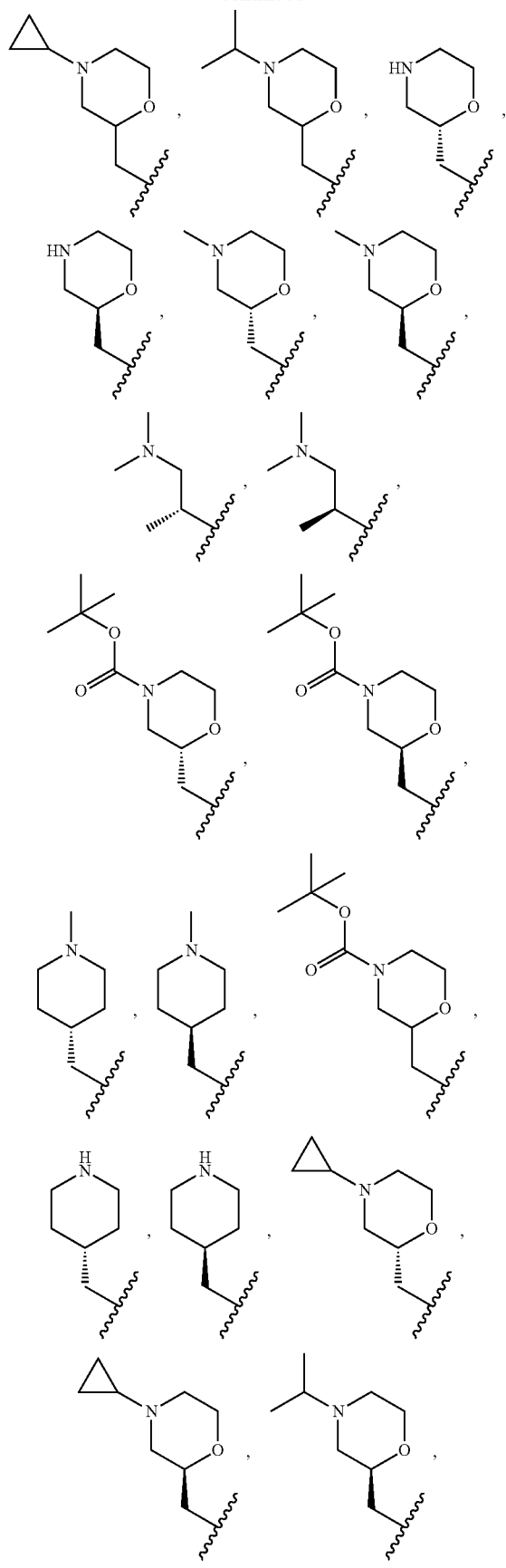
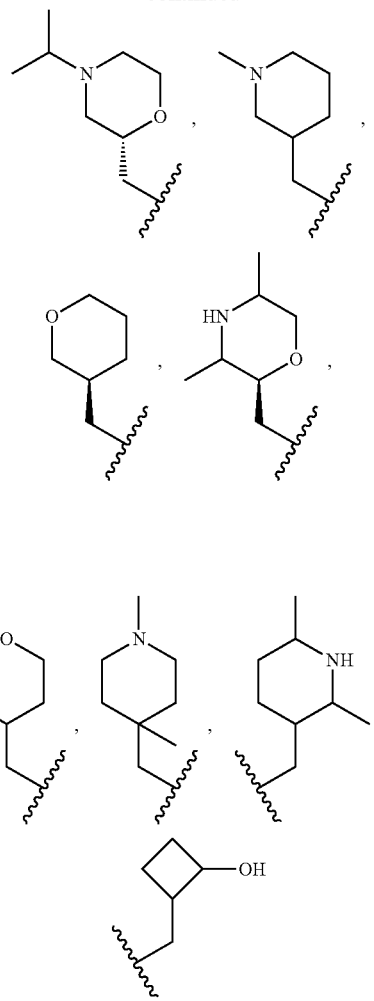
wherein the wavy lines denote attachment points to rest of the molecule.
In some embodiments of a compound of formula (IA), D is selected from
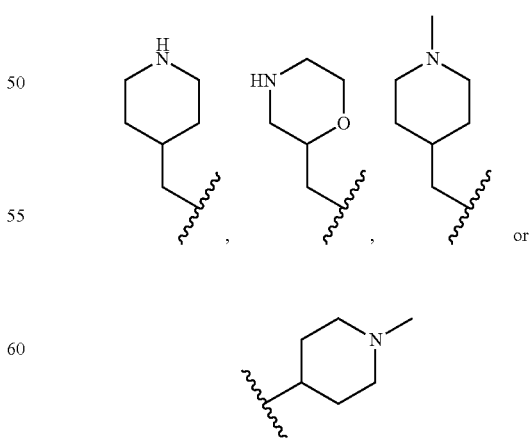
wherein the wavy lines denote attachment points to rest of the molecule.

In some embodiments of a compound of formula (IA), D is

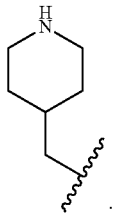

In some embodiments of a compound of formula (IA), D is

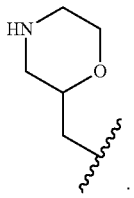

In some embodiments of a compound of formula (IA), D is

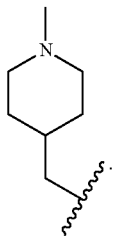 [SMILES: *CC1CCN(C)CC1]

In some embodiments of a compound of formula (IA), D is

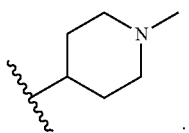 [SMILES: *C1CCN(C)CC1]

In some embodiments of a compound of formula (IA), L is —CH$_2$—, —O—, —NH—, —N(CH$_3$)—, —SO$_2$—, —C(O)—, —C(O)NH— or —NHC(O)—. In some embodiments of a compound of formula (IA), L is —CH$_2$—. In some embodiments of a compound of formula (IA), L is —O—. In some embodiments of a compound of formula (IA), L is —NH—. In some embodiments of a compound of formula (IA), L is —N(CH$_3$)—. In some embodiments of a compound of formula (IA), L is —SO$_2$—. In some embodiments of a compound of formula (IA), L is —C(O)—. In some embodiments of a compound of formula (IA), L is —C(O)NH—. In some embodiments of a compound of formula (IA), L is —NHC(O)—.

In some embodiments of a compound of formula (IA), L is —NH—.

In some embodiments of a compound of formula (IA), L is —O—.

In some embodiments of a compound of formula (IA), R$^1$ is hydrogen, C$_1$-C$_6$ alkyl, C$_2$-C$_6$ alkenyl, C$_2$-C$_6$ alkynyl, C$_3$-C$_6$ cycloalkyl, 3- to 6-membered heterocyclyl, C$_6$ aryl, 5- to 10-membered heteroaryl, —CN, halogen, C$_1$-C$_6$ alkoxy, C$_1$-C$_6$ haloalkoxy, C$_1$-C$_6$ haloalkyl, —OR$^{13}$, —SR$^{13}$, —S(O)$_2$R$^{13}$, —S(O)$_2$NR$^{14}$R$^{15}$, —NR$^{13}$S(O)$_2$R$^{14}$, —NR$^{14}$R$^{15}$, —C(O)R$^{13}$, —NR$^{13}$C(O)R$^{14}$, —NR$^{13}$C(O)NR$^{14}$R$^{15}$, —C(O)OR$^{13}$, —C(O)ONR$^{14}$R$^{15}$, —C(O)NR$^{14}$R$^{15}$, —(C$_1$-C$_3$ alkylene)OR$^{13}$, —(C$_1$-C$_3$ alkylene)SR$^{13}$, —(C$_1$-C$_3$ alkylene)S(O)$_2$R$^{13}$, —(C$_1$-C$_3$ alkylene)S(O)$_2$NR$^{14}$R$^{15}$, —(C$_1$-C$_3$ alkylene)NR$^{13}$S(O)$_2$R$^{14}$, —(C$_1$-C$_3$ alkylene)NR$^{14}$R$^{15}$, —(C$_1$-C$_3$ alkylene)C(O)R$^{13}$, —(C$_1$-C$_3$ alkylene)NR$^{13}$C(O)R$^{14}$, —(C$_1$-C$_3$ alkylene)NR$^{13}$C(O)NR$^{14}$R$^{15}$, —(C$_1$-C$_3$ alkylene)C(O)OR$^{13}$, —(C$_1$-C$_3$ alkylene)C(O)ONR$^{14}$R$^{15}$, —(C$_1$-C$_3$ alkylene)(C$_3$-C$_8$ cycloalkyl) or —(C$_1$-C$_3$ alkylene)(3-10-membered heterocyclyl); wherein each of R$^1$ is optionally substituted by R$^3$. In some embodiments of a compound of formula (IA), R$^1$ is hydrogen. In some embodiments of a compound of formula (IA), R$^1$ is C$_1$-C$_6$ alkyl optionally substituted by R$^3$. In some embodiments of a compound of formula (IA), R$^1$ is methyl, ethyl, isopropyl, ter-butyl optionally substituted by —F, —CN, —OH or —OCH$_3$. In some embodiments of a compound of formula (IA), R$^1$ is C$_2$-C$_6$ alkenyl optionally substituted by R$^3$. In some embodiments of a compound of formula (IA), R$^1$ is isopropylene. In some embodiments of a compound of formula (IA), R$^1$ is C$_2$-C$_6$ alkynyl optionally substituted by R$^3$. In some embodiments of a compound of formula (IA), R$^1$ is ethyne, propyne, butyne optionally substituted by —CH$_3$, —OH or —OCH$_3$. In some embodiments of a compound of formula (IA), R$^1$ is C$_3$-C$_6$ cycloalkyl optionally substituted by R$^3$. In some embodiments of a compound of formula (IA), R$^1$ is cyclopropyl. In some embodiments of a compound of formula (IA), R$^1$ is 3- to 6-membered heterocyclyl optionally substituted by R$^3$. In some embodiments of a compound of formula (IA), R$^1$ is phenyl optionally substituted by R$^3$. In some embodiments of a compound of formula (IA), R$^1$ is 5- to 10-membered heteroaryl optionally substituted by R$^3$. In some embodiments of a compound of formula (IA), R$^1$ is pyrazolyl optionally substituted by methyl, isopropyl or cyclopropyl. In some embodiments of a compound of formula (IA), R$^1$ is —CN. In some embodiments of a compound of formula (IA), R$^1$ is halogen. In some embodiments of a compound of formula (IA), R$^1$ is C$_1$-C$_6$ alkoxy. In some embodiments of a compound of formula (IA), R$^1$ is C$_1$-C$_6$ haloalkoxy. In some embodiments of a compound of formula (IA), R$^1$ is C$_1$-C$_6$ haloalkyl. In some embodiments of a compound of formula (IA), R$^1$ is —CF$_3$. In some embodiments of a compound of formula (IA), R$^1$ is —OR$^{13}$. In some embodiments of a compound of formula (IA), R$^1$ is —OCH$_3$. In some embodiments of a compound of formula (IA), R$^1$ is —SR$^{13}$. In some embodiments of a compound of formula (IA), R$^1$ is —S(O)$_2$R$^{13}$. In some embodiments of a compound of formula (IA), R$^1$ is —S(O)$_2$NR$^{14}$R$^{15}$. In some embodiments of a compound of formula (IA), R$^1$ is —NR$^{13}$S(O)$_2$R$^{14}$. In some embodiments of a compound of formula (IA), R$^1$ is —NR$^{14}$R$^{15}$. In some embodiments of a compound of formula (IA), R$^1$ is —C(O)R$^{13}$. In some embodiments of a compound of formula (IA), R$^1$ is —NR$^{13}$C(O)R$^{14}$. In some embodiments of a compound of formula (IA), R$^1$ is —NR$^{13}$C(O)NR$^{14}$R$^{15}$. In some embodiments of a compound of formula (IA), R$^1$ is —C(O)OR$^{13}$. In some embodiments of a compound of formula (IA), R$^1$ is —C(O)OCH$_3$. In some embodiments of a compound of formula (IA), R$^1$ is —C(O)ONR$^{14}$R$^{15}$. In some embodiments of a compound of formula (IA), $R^1$ is —C(O)NR$^{14}$R$^{15}$. In some embodiments of a compound of formula (IA), $R^1$ is —C(O)NH$_2$.

In some embodiments of a compound of formula (IA), $R^1$ is —C(O)NR$^{14}$R$^{15}$, wherein $R^{14}$ and $R^{15}$ are independently selected from hydrogen, C$_1$-C$_6$ alkyl and C$_3$-C$_6$ cycloalkyl. In some embodiments of a compound of formula (IA), $R^1$ is —C(O)NR$^{14}$R$^{15}$, wherein $R^{14}$ and $R^{15}$ are independently selected from hydrogen and C$_1$-C$_6$ alkyl. In some embodiments of a compound of formula (IA), $R^1$ is —C(O)NR$^{14}$R$^{15}$, wherein $R^{14}$ and $R^{15}$ are independently selected from hydrogen and C$_3$-C$_6$ cycloalkyl. In some embodiments of a compound of formula (IA), $R^1$ is —C(O)NR$^{14}$R$^{15}$, wherein $R^{14}$ and $R^{15}$ are independently selected from hydrogen, methyl and cyclopropyl. In some embodiments of a compound of formula (IA), $R^1$ is —C(O)NR$^{14}$R$^{15}$, wherein $R^{14}$ and $R^{15}$ both are hydrogen. In some embodiments of a compound of formula (IA), $R^1$ is —C(O)NR$^{14}$R$^{15}$, wherein $R^{14}$ is hydrogen and $R^{15}$ is methyl. In some embodiments of a compound of formula (IA), $R^1$ is —C(O)NR$^{14}$R$^{15}$, wherein $R^{14}$ and $R^{15}$ both are methyl. In some embodiments of a compound of formula (IA), $R^1$ is —C(O)NR$^{14}$R$^{15}$, wherein $R^{14}$ is hydrogen and $R^{15}$ is cyclopropyl.

In some embodiments of a compound of formula (IA), $R^1$ is selected from hydrogen, —CH$_3$,

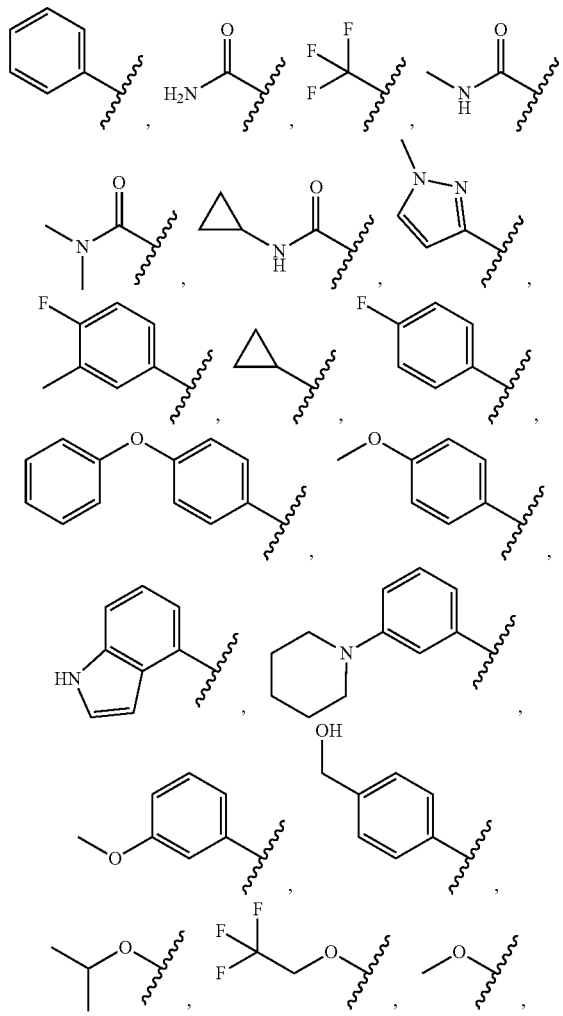

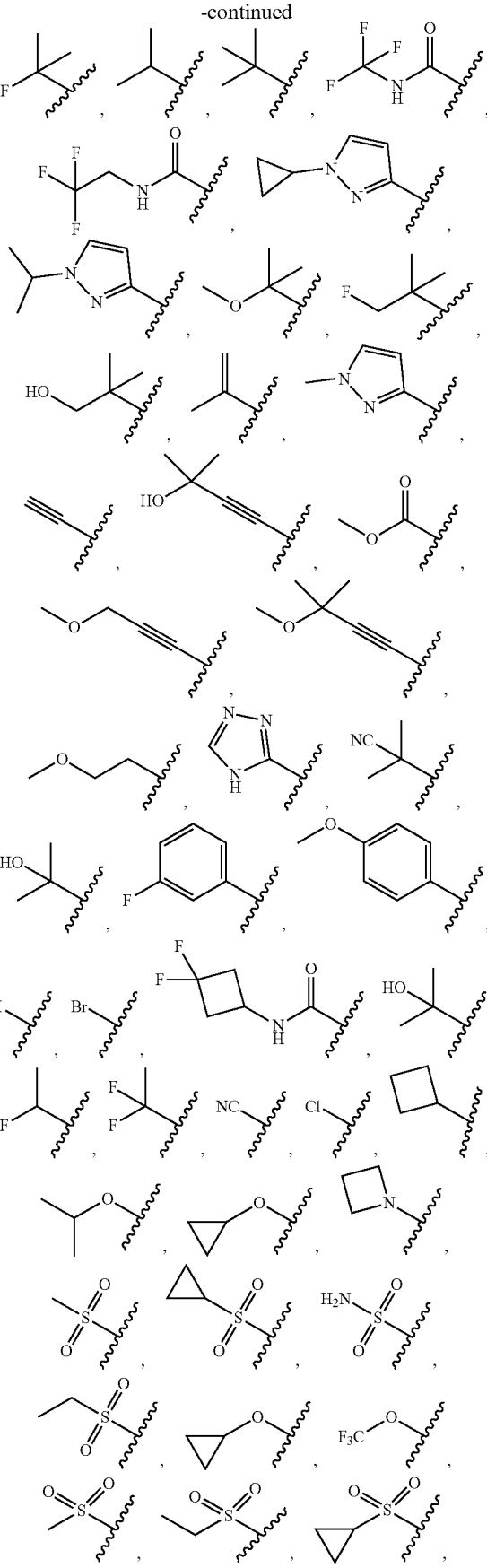

wherein the wavy lines denote attachment points to rest of the molecule.

In some embodiments of a compound of formula (IA), $R^1$ is hydrogen.

In some embodiments of a compound of formula (IA), $R^1$ is —$CH_3$.

In some embodiments of a compound of formula (IA), $R^1$ is

In some embodiments of a compound of formula (IA), $R^1$ is

In some embodiments of a compound of formula (IA), $R^1$ is

In some embodiments of a compound of formula (IA), $R^1$ is

In some embodiments of a compound of formula (IA), $R^1$ is

In some embodiments of a compound of formula (IA), $R^1$ is

In some embodiments of a compound of formula (IA), R¹ is

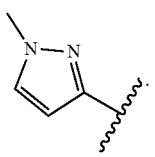 [SMILES: *c1ccn(C)n1]

In some embodiments of a compound of formula (IA), R¹ is

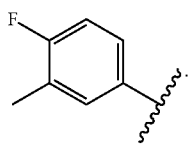

In some embodiments of a compound of formula (IA), R¹ is

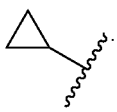

In some embodiments of a compound of formula (IA), R¹ is

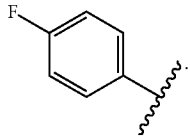

In some embodiments of a compound of formula (IA), R¹ is

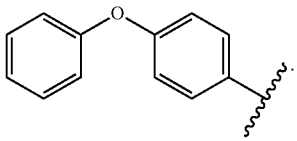 [SMILES: *c1ccc(Oc2ccccc2)cc1]

In some embodiments of a compound of formula (IA), R¹ is

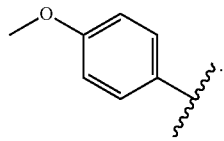 [SMILES: *c1ccc(OC)cc1]

In some embodiments of a compound of formula (IA), R¹ is

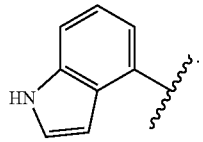

In some embodiments of a compound of formula (IA), R¹ is

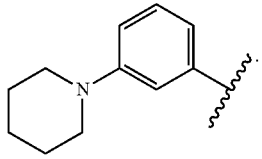 [SMILES: *c1cccc(N2CCCCC2)c1]

In some embodiments of a compound of formula (IA), R¹ is

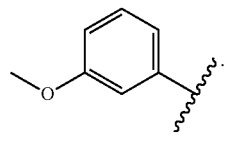 [SMILES: *c1cccc(OC)c1]

In some embodiments of a compound of formula (IA), R¹ is

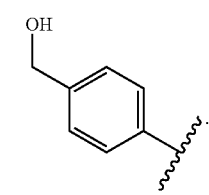 [SMILES: *c1ccc(CO)cc1]

In some embodiments of a compound of formula (IA), R¹ is

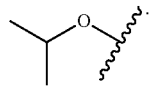

In some embodiments of a compound of formula (IA), R¹ is

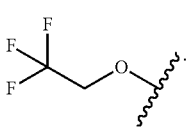

It is understood that each description of A, D, Y, L and R¹ may be independently combined with each description of A, D, Y, L and R¹ the same as if each and every combination were specifically and individually listed.

In some embodiments of a compound of formula (IA), Y is selected from N or CR^y. In some embodiments of a compound of formula (IA), Y is N. In some embodiments of a compound of formula (IA), Y is CR^y, wherein R^y is selected from hydrogen, $C_1$-$C_6$ alkyl, —CN, halogen, —OR^7 or —NR^8R^9. In some embodiments of a compound of formula (IA), Y is CH. In some embodiments of a compound of formula (IA), Y is CH and A is 5- to 6-membered heteroaryl optionally substituted with 0-4 R^x. In some embodiments of a compound of formula (IA), Y is CH and A is selected from pyrazolyl, pyridyl or pyrazinyl substituted with —CH_3 or CN. In some embodiments of a compound of formula (IA), Y is CH and A is selected from

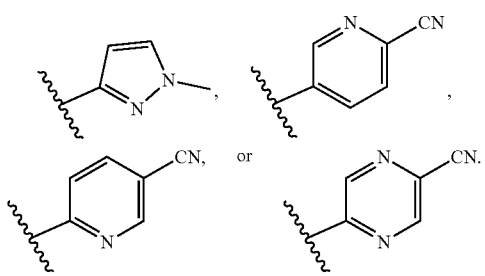

In some embodiments of a compound of formula (IA), Y is CH and A is

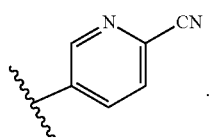 [SMILES: *c1ccc(C#N)nc1]

In some embodiments of a compound of formula (IA), Y is CH and A is

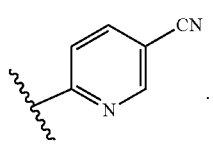

In some embodiments of a compound of formula (IA), Y is CH and A is

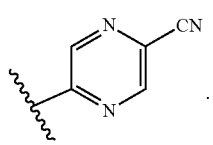 [SMILES: *c1cnc(C#N)cn1]

In some embodiments of a compound of formula (IA), Y is CH, A is

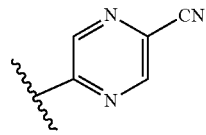 [SMILES: *c1cnc(C#N)cn1]

and L is selected from —NH— or —O—. In some embodiments of a compound of formula (IA), Y is CH, A is

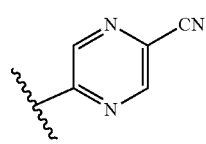 [SMILES: *c1cnc(C#N)cn1]

and L is —NH—. In some embodiments of a compound of formula (IA), Y is CH, A is

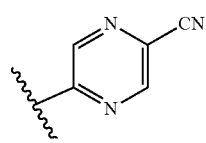 [SMILES: *c1cnc(C#N)cn1]

and L is —O—.

In some embodiments of a compound of formula (IA), Y is CH, A is

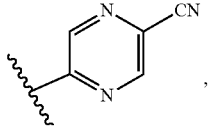 [SMILES: *c1cnc(C#N)cn1]

L is —O— and D is selected from 3- to 6-membered heterocyclyl or —($C_1$-$C_6$ alkylene)3- to 10-membered heterocyclyl, each of which is optionally substituted by R^2. In some embodiments of a compound of formula (IA), Y is CH, A is

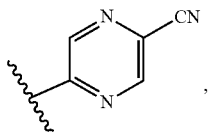 [SMILES: *c1cnc(C#N)cn1]

L is —O— and D is selected from

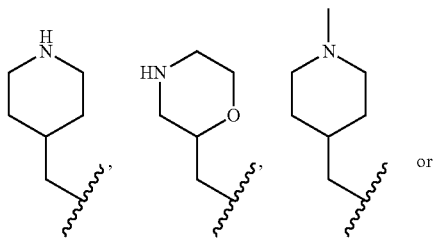

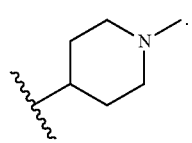

In some embodiments of a compound of formula (IA), Y is CH, A is

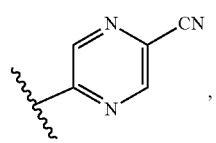 [SMILES: *c1cnc(C#N)cn1]

L is —O— and D is

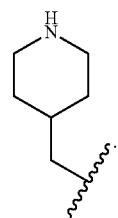

In some embodiments of a compound of formula (IA), Y is CH, A is

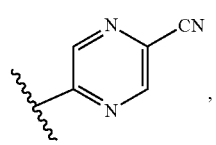 [SMILES: *c1cnc(C#N)cn1]

L is —O— and D is

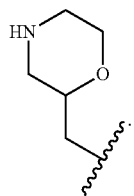

In some embodiments of a compound of formula (IA), Y is CH, A is

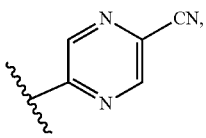 [SMILES: *c1cnc(C#N)cn1]

L is —O— and D is

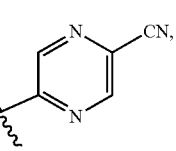

In some embodiments of a compound of formula (IA), Y is CH, A is

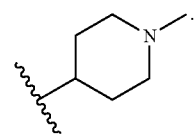

L is —O— and D is

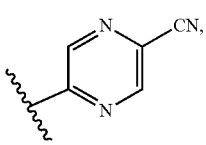

In some embodiments of a compound of formula (IA), Y is CH, A is

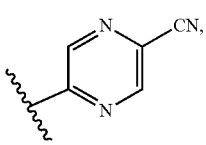

L is —O—, D is

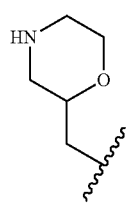

and $R^1$ is selected from hydrogen, $C_1$-$C_6$ alkyl, $C_3$-$C_6$ cycloalkyl, $C_6$ aryl, 5- to 10-membered heteroaryl, $C_1$-$C_6$ alkoxy, $C_1$-$C_6$haloalkoxy, $C_1$-$C_6$haloalkyl, —C(O)NR$^{14}$R$^{15}$, wherein each of $R^1$ is optionally substituted by $R^3$. In some embodiments of a compound of formula (IA), Y is CH, A is

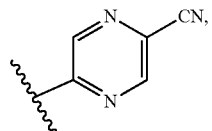 [SMILES: *c1cnc(C#N)cn1]

L is —O—, D is

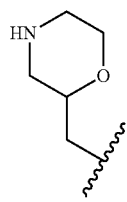

and $R^1$ is selected from hydrogen, —CH$_3$,

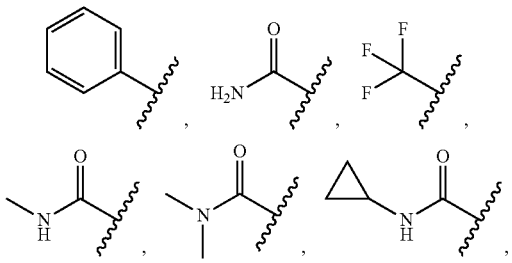

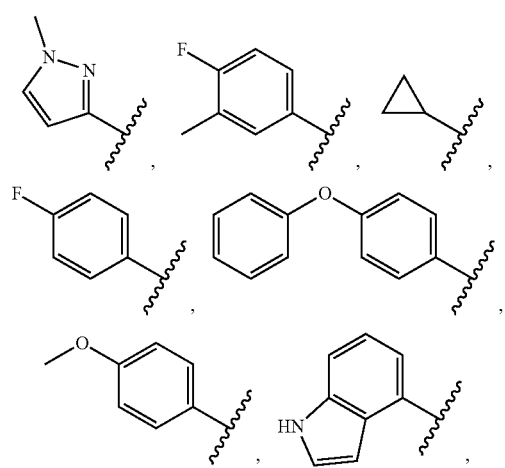

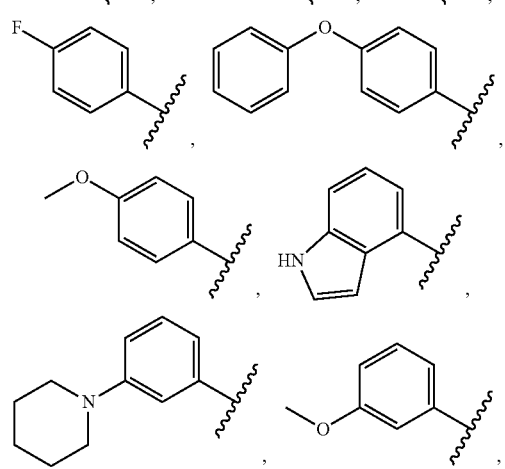

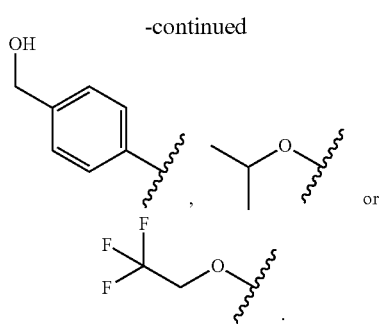

In some embodiments of a compound of formula (IA), Y is CH, A is

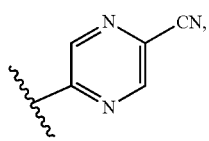

L is —O—, D is

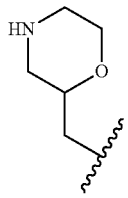

and $R^1$ is hydrogen. In some embodiments of a compound of formula (IA), Y is CH, A is

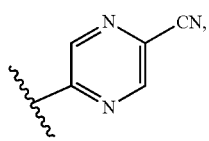

L is —O—, D is

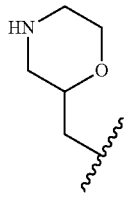

and $R^1$ is

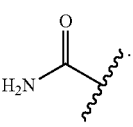

In some embodiments of a compound of formula (IA), Y is CH, A is

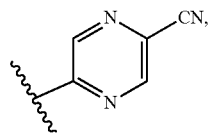 [SMILES: *c1cnc(C#N)cn1]

L is —O—, D is

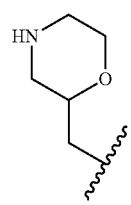

and R[1] is

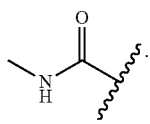

In some embodiments of a compound of formula (IA), Y is CH, A is

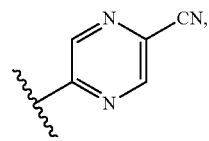 [SMILES: *c1cnc(C#N)cn1]

L is —O—, D is

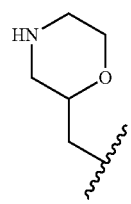

and R[1] is

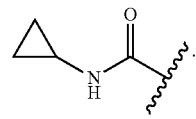

In some embodiments of a compound of formula (IA), Y is CH, A is

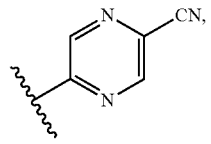 [SMILES: *c1cnc(C#N)cn1]

L is —NH— and D is selected from 3- to 6-membered heterocyclyl or —(C$_1$-C$_6$ alkylene)3- to 10-membered heterocyclyl, each of which is optionally substituted by R$^2$. In some embodiments of a compound of formula (IA), Y is CH, A is

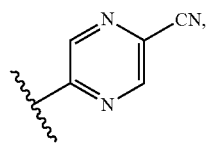 [SMILES: *c1cnc(C#N)cn1]

L is —NH— and D is selected from

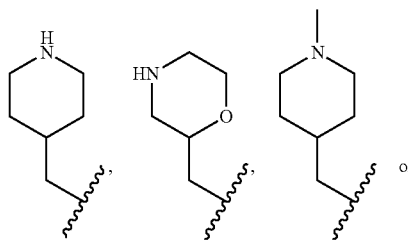

or

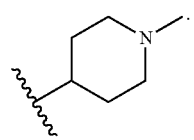

In some embodiments of a compound of formula (IA), Y is CH, A is

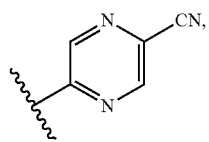

L is —NH— and D is

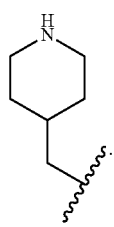

In some embodiments of a compound of formula (IA), Y is CH, A is

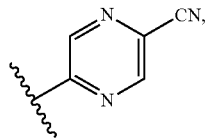 [SMILES: *c1cnc(C#N)cn1]

L is —NH— and D is

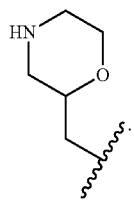

In some embodiments of a compound of formula (IA), Y is CH, A is

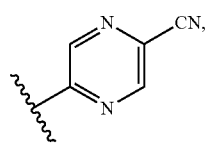 [SMILES: *c1cnc(C#N)cn1]

L is —NH— and D is

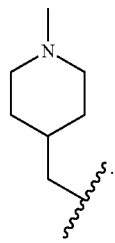

In some embodiments of a compound of formula (IA), Y is CH, A is

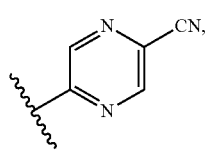 [SMILES: *c1cnc(C#N)cn1]

L is —NH— and D is

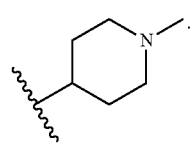 [SMILES: *C1CCN(C)CC1]

In some embodiments of a compound of formula (IA), Y is CH, A is

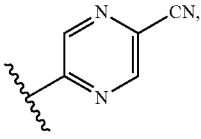 [SMILES: *c1cnc(C#N)cn1]

L is —NH—, D is

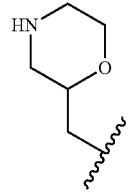

and $R^1$ is selected from hydrogen, $C_1$-$C_6$ alkyl, $C_3$-$C_6$ cycloalkyl, $C_6$ aryl, 5- to 10-membered heteroaryl, $C_1$-$C_6$ alkoxy, $C_1$-$C_6$ haloalkoxy, $C_1$-$C_6$ haloalkyl, —C(O)NR$^{14}$R$^{15}$, wherein each of $R^1$ is optionally substituted by $R^3$. In some embodiments of a compound of formula (IA), Y is CH, A is

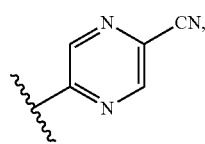 [SMILES: *c1cnc(C#N)cn1]

L is —NH—, D is

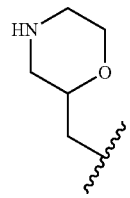

and $R^1$ is selected from hydrogen, —CH$_3$,

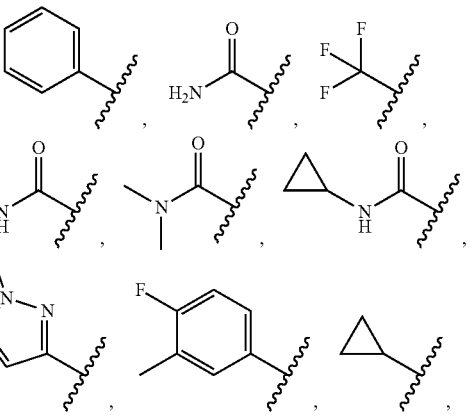

-continued
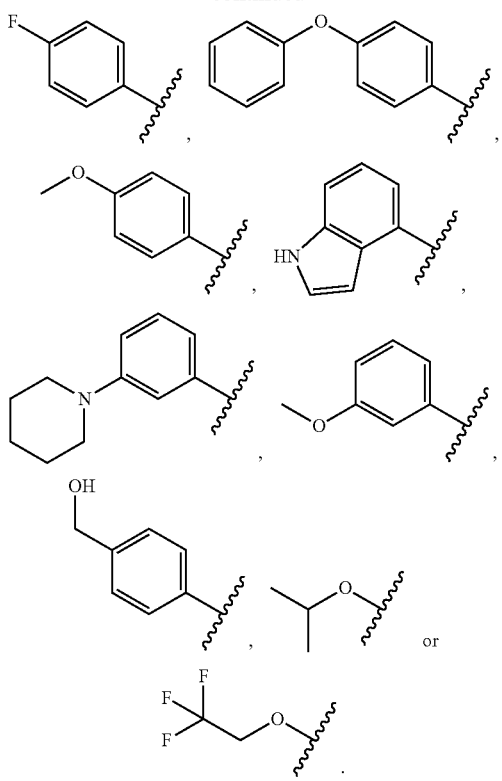
In some embodiments of a compound of formula (IA), Y is CH, A is
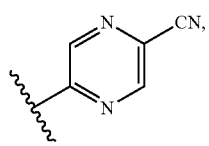 [SMILES: *c1cnc(C#N)cn1]
L is —NH—, D is
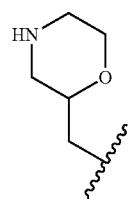 [SMILES: *CC1CNCCO1]
and R¹ is hydrogen. In some embodiments of a compound of formula (IA), Y is CH, A is
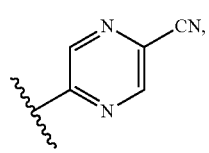 [SMILES: *c1cnc(C#N)cn1]
L is —NH—, D is
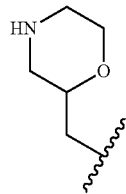
and R¹ is
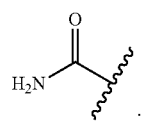
In some embodiments of a compound of formula (IA), Y is CH, A is
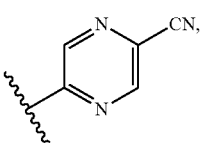 [SMILES: *c1cnc(C#N)cn1]
L is —NH—, D is
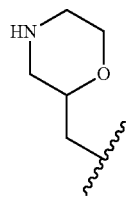 [SMILES: *CC1CNCCO1]
and R¹ is
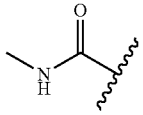
In some embodiments of a compound of formula (IA), Y is CH, A is
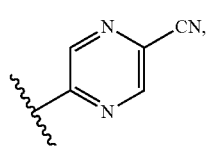 [SMILES: *c1cnc(C#N)cn1]

L is —NH—, D is

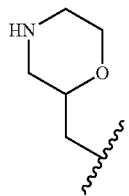 [SMILES: *CC1CNCCO1]

and R¹ is

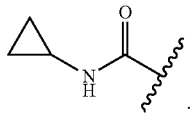 [SMILES: *C(=O)NC1CC1]

In some embodiments, a compound of formula (IA) is a compound of formula

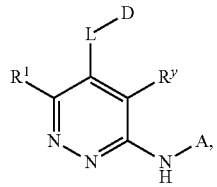

formula (II)

or a salt thereof, wherein A, D, L, R¹ and $R^y$ are as defined for formula (IA).

In some embodiments, a compound of formula (IA) is a compound of any of the compounds of formula (IIa-1) to (IIa-10),

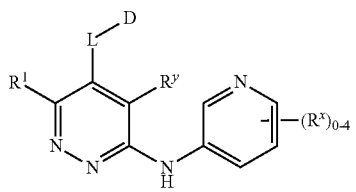

(IIa-1)

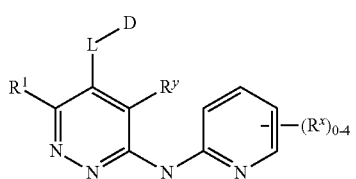

(IIa-2)

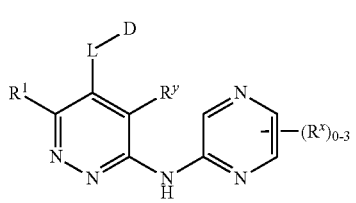

(IIa-3)

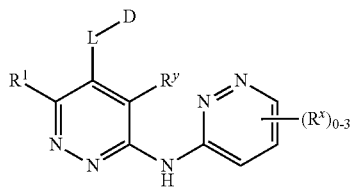

(IIa-4)

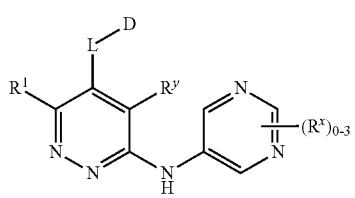

(IIa-5)

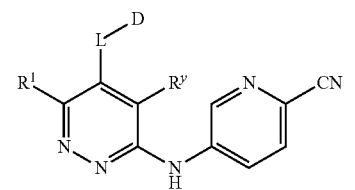

(IIa-6)

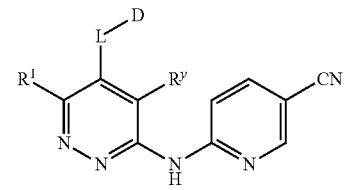

(IIa-7)

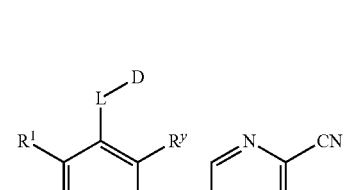

(IIa-8)

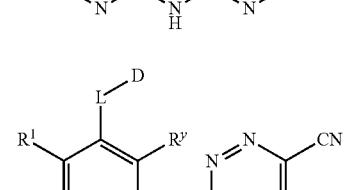

(IIa-9)

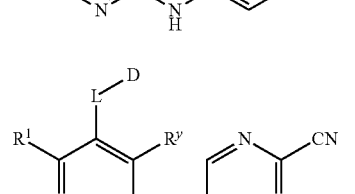

(IIa-10)

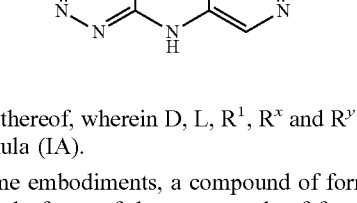

or a salt thereof, wherein D, L, R¹, $R^x$ and $R^y$ are as defined for formula (IA).

In some embodiments, a compound of formula (IA) is a compound of any of the compounds of formula (IIb-1) to (IIb-20), (IIb-1)
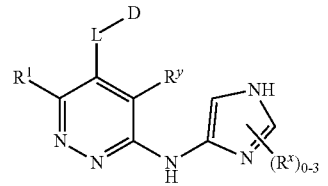
(IIb-2)
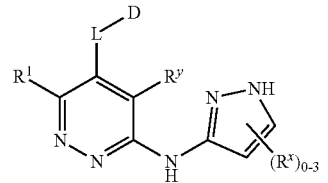
(IIb-3)
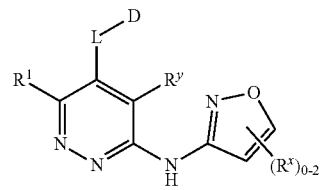
(IIb-4)
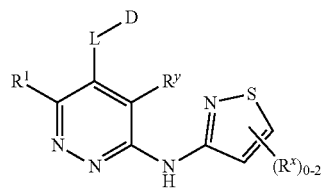
(IIb-5)
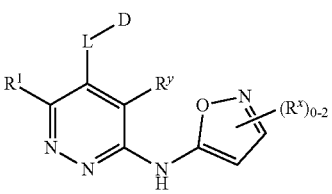
(IIb-6)
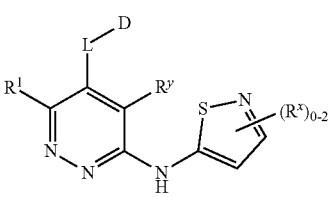
(IIb-7)
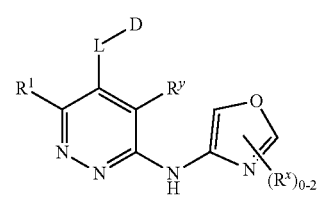
(IIb-8)
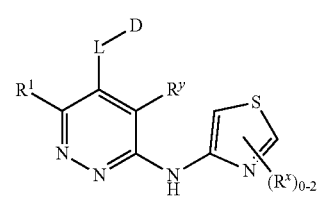
-continued
(IIb-9)
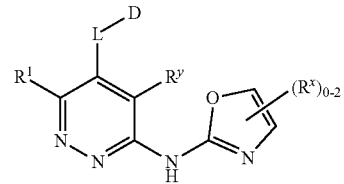
(IIb-10)
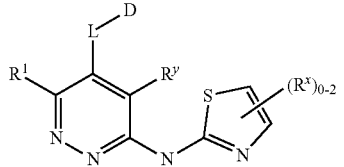
(IIb-11)
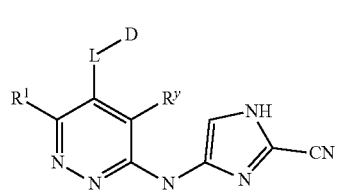
(IIb-12)
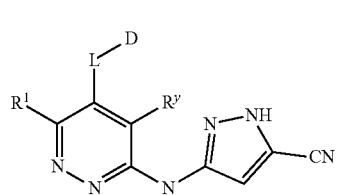
(IIb-13)
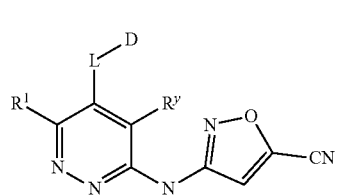
(IIb-14)
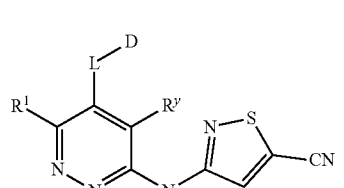
(IIb-15)
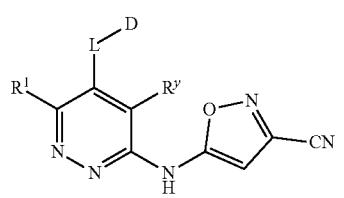
(IIb-16)
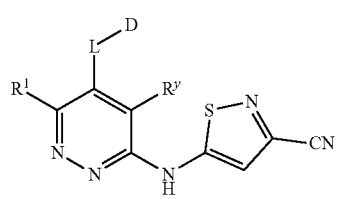

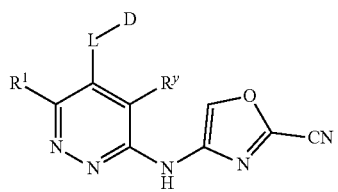 (IIb-17)

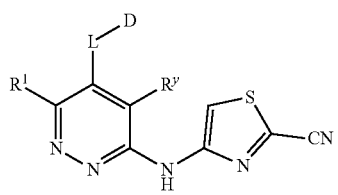 (IIb-18)

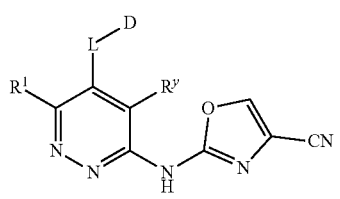 (IIb-19)

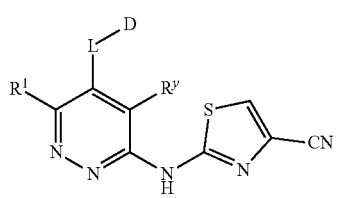 (IIb-20)

or a salt thereof, wherein D, L, $R^1$, $R^x$ and $R^y$ are as defined for formula (IA).

In some embodiments, a compound of formula (IA) is a compound of formula (III),

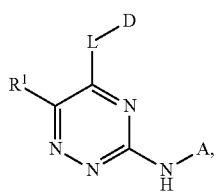 formula (III)

or a salt thereof, wherein A, D, L, and $R^1$ are as defined for formula (IA).

In some embodiments, a compound of formula (IA) is a compound of any of the compounds of formula (IIIa-1) to (IIIa-10),

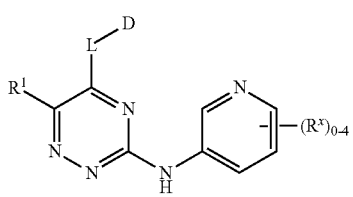 (IIIa-1)

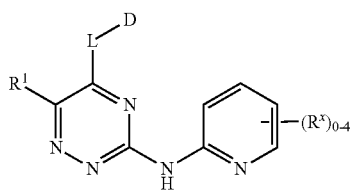 (IIIa-2)

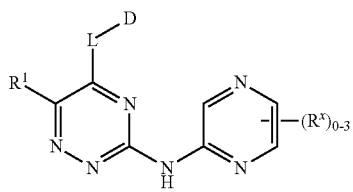 (IIIa-3)

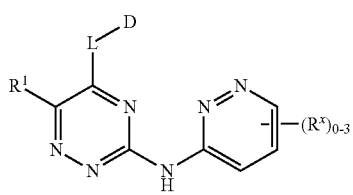 (IIIa-4)

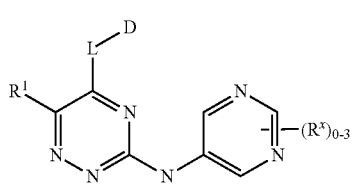 (IIIa-5)

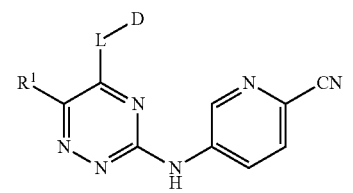 (IIIa-6)

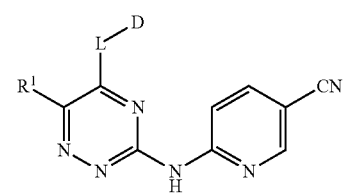 (IIIa-7)

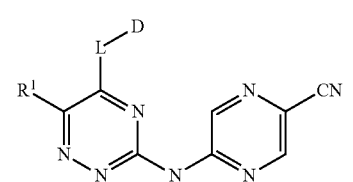 (IIIa-8)

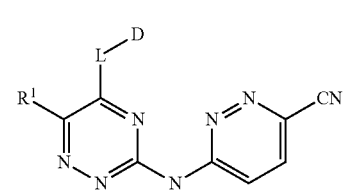 (IIIa-9)

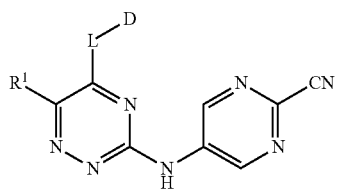
(IIIa-10)
or a salt thereof, wherein D, L, $R^1$ and $R^x$ are as defined for formula (IA).
In some embodiments, a compound of formula (IA) is a compound of any of the compounds of formula (IIIb-1) to (IIIb-20),
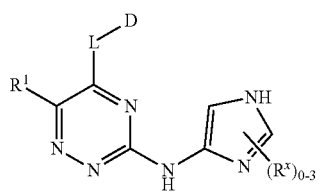
(IIIb-1)
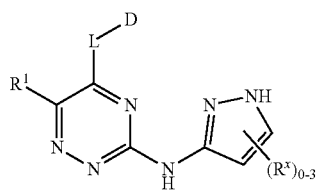
(IIIb-2)
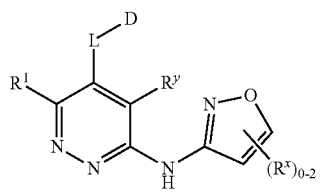
(IIIb-3)
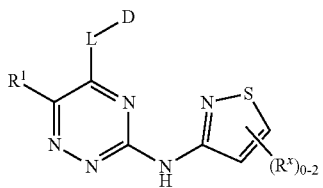
(IIIb-4)
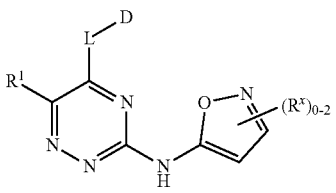
(IIIb-5)
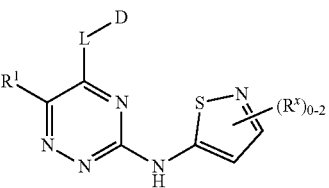
(IIIb-6)
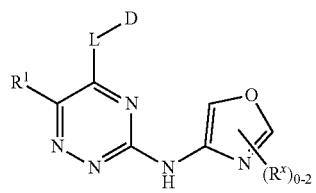
(IIIb-7)
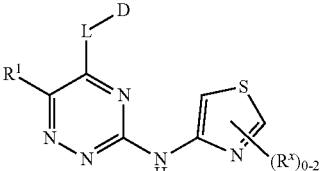
(IIIb-8)
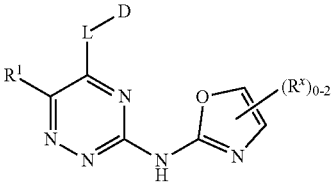
(IIIb-9)
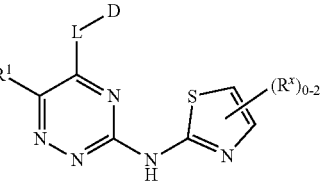
(IIIb-10)
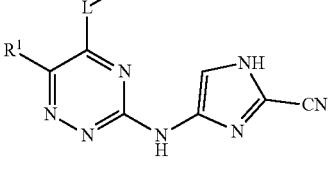
(IIIb-11)
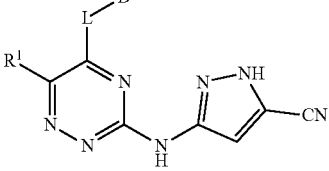
(IIIb-12)
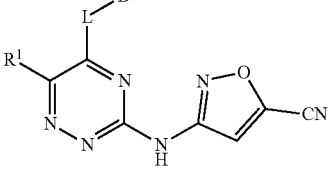
(IIIb-13)
(IIIb-14)

-continued
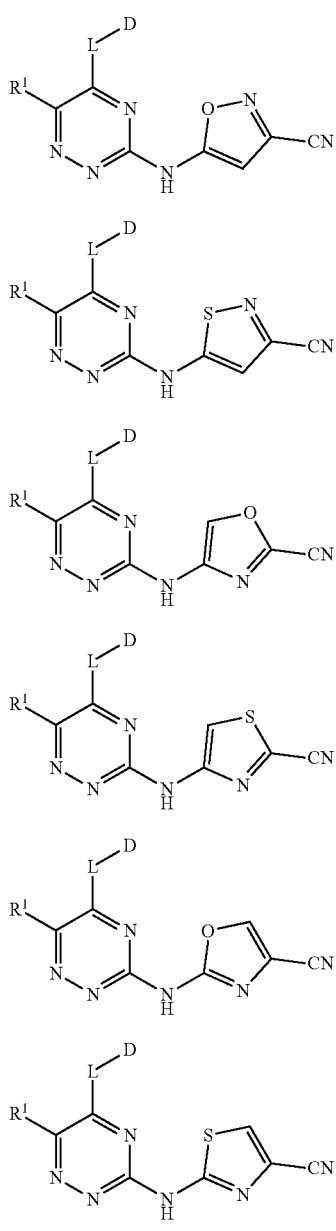
or a salt thereof, wherein D, L, R¹ and Rˣ are as defined for formula (IA).
In some embodiments, a compound of formula (IA) is a compound of formula (IV),
formula (IV)
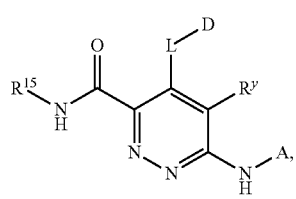
or a salt thereof, wherein A, D, L, R$^y$ and R$^{15}$ are as defined for formula (IA).
In some embodiments, a compound of formula (IA) is a compound of any of the compounds of formula (IVa-1) to (IVa-15),
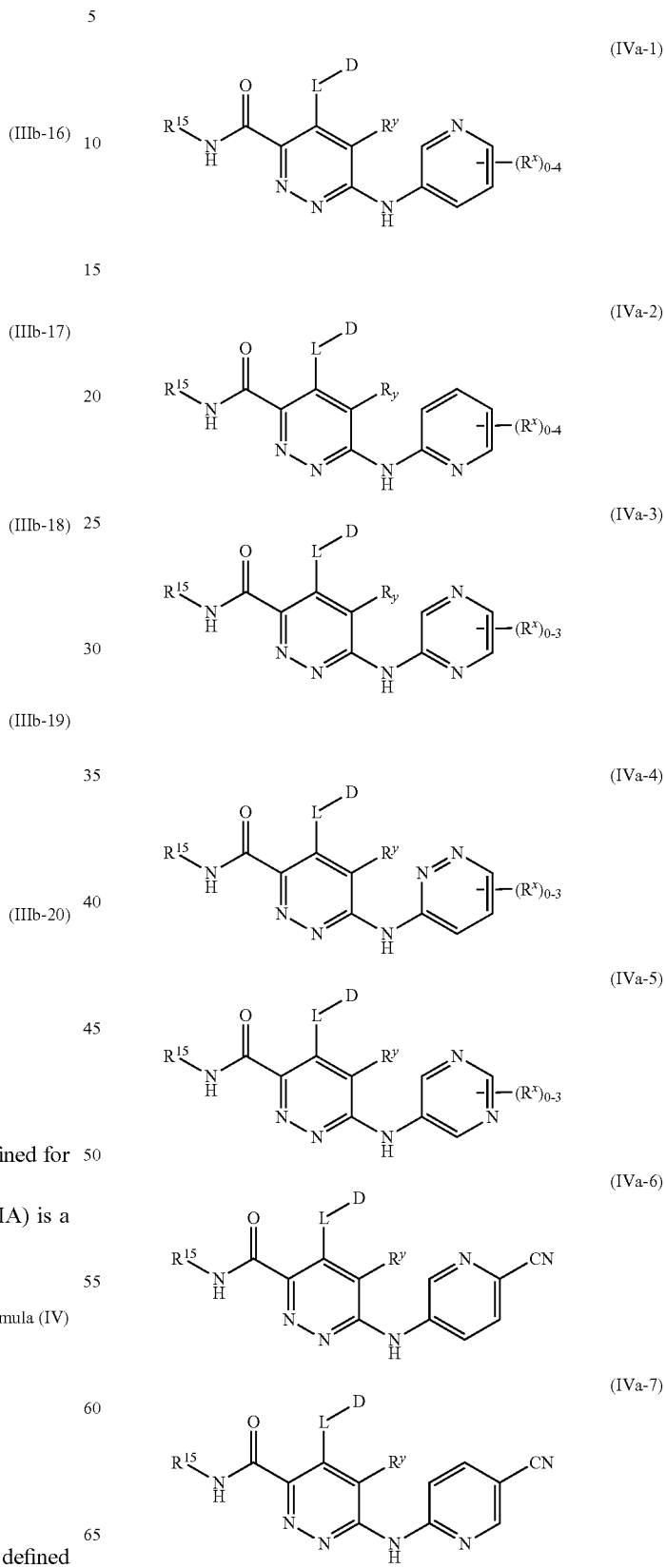

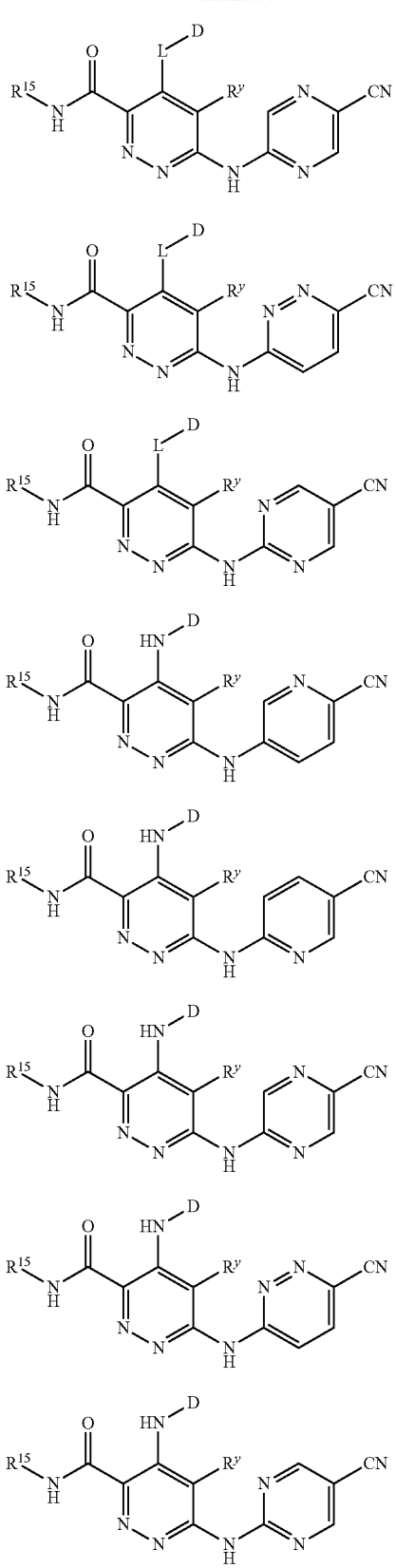

or a salt thereof, wherein D, L, $R^{15}$, $R^x$ and $R^y$ are as defined for formula (IA).

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) are listed in table 1 and table 2. It is understood that individual enantiomers and diastereomers are included in the generic compound structures shown in table 1 and table 2. Specific synthetic methods for preparing compounds of table 1 are provided example herein.

TABLE 1

Compounds

| Cpd No. | Cpd Structure |
|---|---|
| 1.1 | |
| 1.2 | |

TABLE 1-continued

Compounds

| Cpd No. | Cpd Structure |
|---|---|
| 1.3 | (structure) |
| 1.4 | (structure) |
| 1.5 | (structure) |
| 1.6 | (structure) |
| 1.7 | (structure) |
| 1.8 | (structure) |
| 1.9 | (structure) |
| 1.10 | (structure) |

TABLE 1-continued

Compounds

| Cpd No. | Cpd Structure |
|---|---|
| 1.11 | |
| 1.12 | |
| 1.13 | |
| 1.14 | |
| 1.15 | |
| 1.16 | |
| 1.17 | |
| 1.18 | |

TABLE 1-continued
| Cpd No. | Cpd Structure |
|---|---|
| 1.19 | 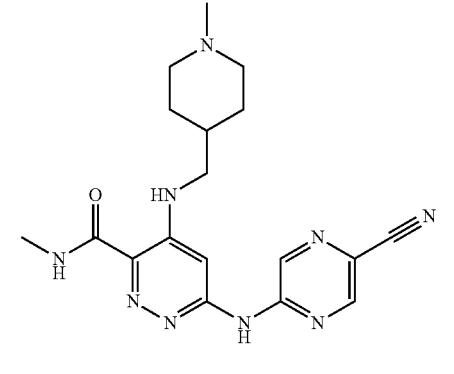 [SMILES: CNC(=O)c1nnc(Nc2cnc(C#N)cn2)cc1NCC1CCN(C)CC1] |
| 1.20 | 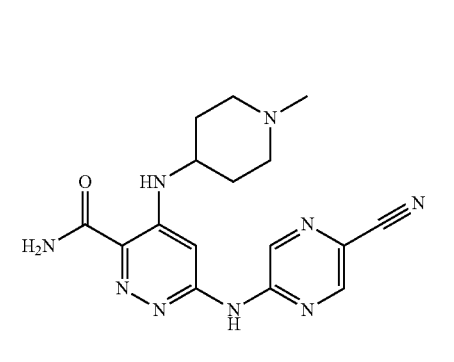 [SMILES: CN1CCC(Nc2cc(Nc3cnc(C#N)cn3)nnc2C(N)=O)CC1] |
| 1.21 | 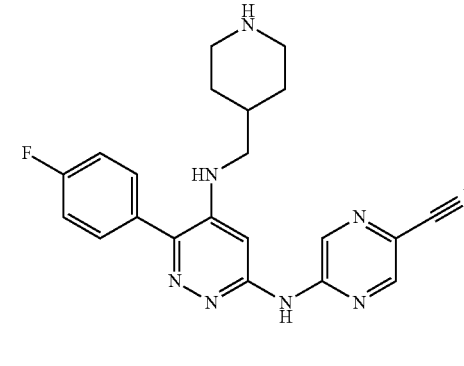 |
| 1.22 | 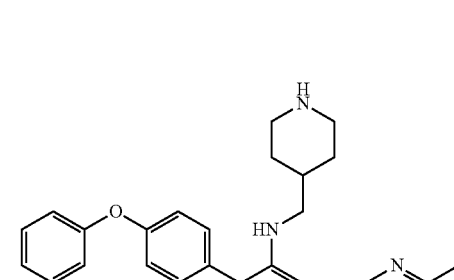 |
| 1.23 | 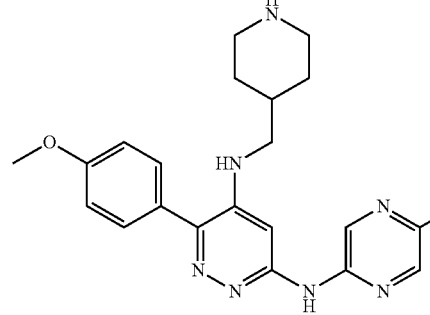 |
| 1.24 | 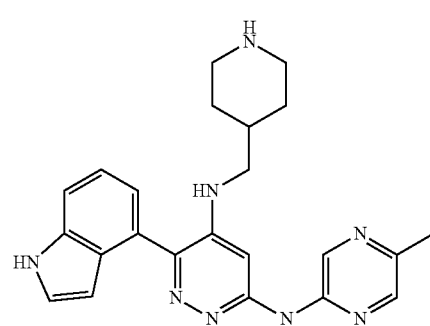 |
| 1.25 | 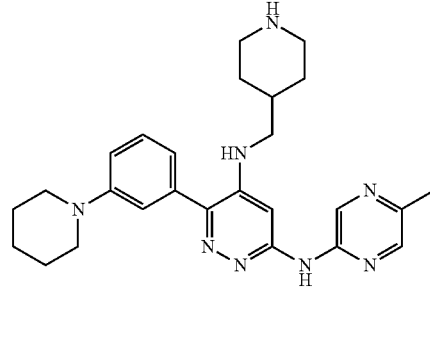 |
| 1.26 | 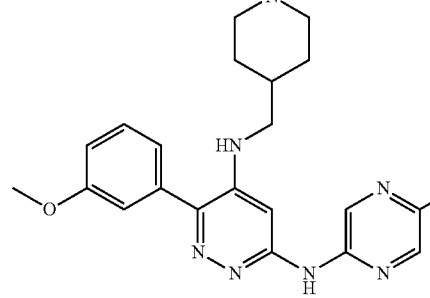 |

TABLE 1-continued

Compounds

| Cpd No. | Cpd Structure |
|---|---|
| 1.27 | |
| 1.28 | |
| 1.29 | |
| 1.30 | |
| 1.31 | |
| 1.32 | |
| 1.33 | |
| 1.34 | |

TABLE 1-continued

Compounds

| Cpd No. | Cpd Structure |
|---|---|
| 1.35 | |
| 1.36 | |

Cpd = Compound

The compounds illustrated in table 2 can be prepared in a manner analogous to the techniques used in connection with the preparation of the compounds given in the table 1 and in accordance, using appropriate, analogous starting materials and by utilizing the general synthetic schemes illustrated below.

TABLE 2

Compounds

| Cpd No. | Cpd Structure |
|---|---|
| 2.1 | |
| 2.2 | |
| 2.3 | |
| 2.4 | |
| 2.5 | |

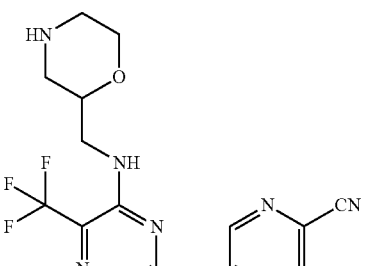

TABLE 2-continued

Compounds

| Cpd No. | Cpd Structure |
|---|---|
| 2.6 | |
| 2.7 | |
| 2.8 | |
| 2.9 | |
| 2.10 | |
| 2.11 | |
| 2.12 | |
| 2.13 | |

TABLE 2-continued
Compounds
| Cpd No. | Cpd Structure |
|---|---|
| 2.14 | 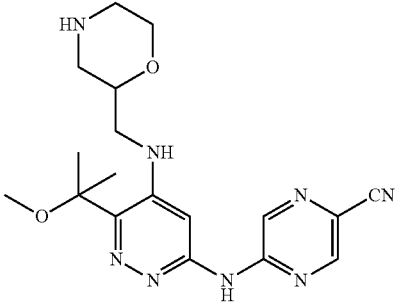 [SMILES: COC(C)(C)c1nnc(Nc2cnc(C#N)cn2)cc1NCC1CNCCO1] |
| 2.15 | 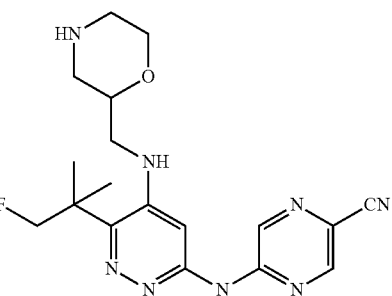 |
| 2.16 | 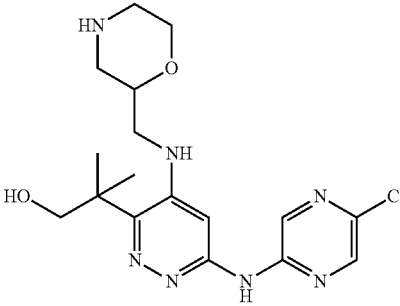 |
| 2.17 | 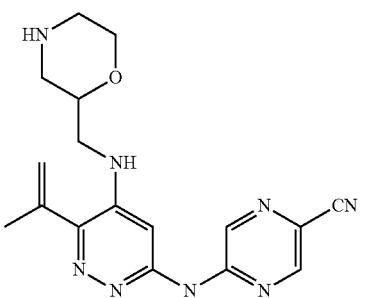 |
| 2.18 | 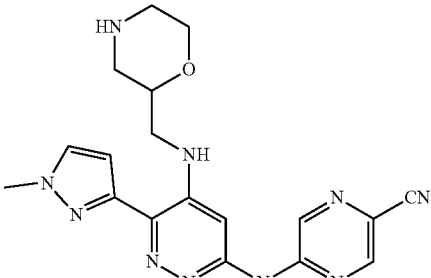 |
| 2.19 | 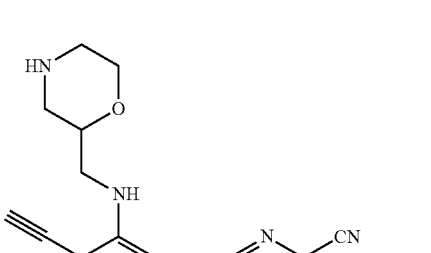 |
| 2.20 | 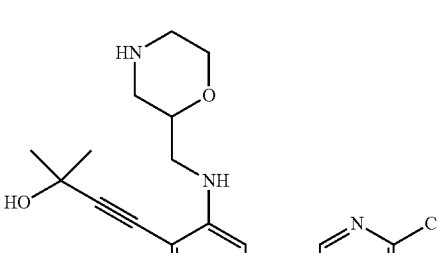 |
| 2.21 | 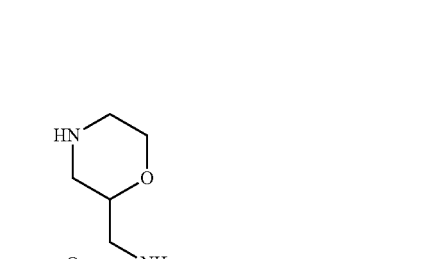 |

TABLE 2-continued

Compounds

| Cpd No. | Cpd Structure |
|---|---|
| 2.22 | |
| 2.23 | |
| 2.24 | |
| 2.25 | |
| 2.26 | |
| 2.27 | |
| 2.28 | |
| 2.29 | |
| 2.30 | |

TABLE 2-continued
Compounds
| Cpd No. | Cpd Structure |
|---|---|
| 2.31 | 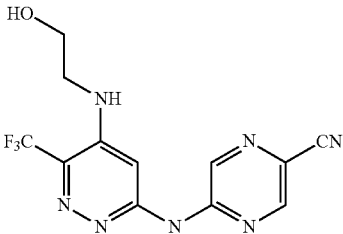 |
| 2.32 | 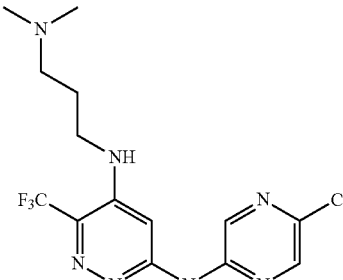 |
| 2.33 | 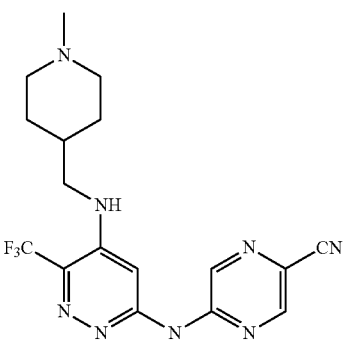 |
| 2.34 | 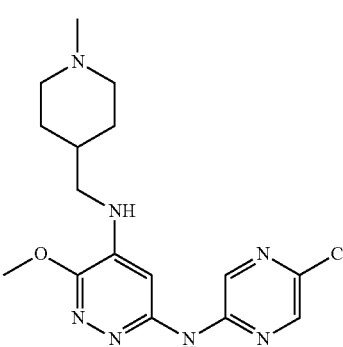 |
| 2.35 | 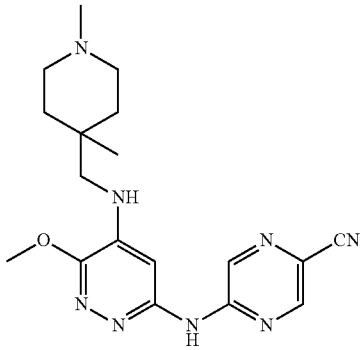 [SMILES: COc1nnc(Nc2cnc(C#N)cn2)cc1NCC1(C)CCN(C)CC1] |
| 2.36 | 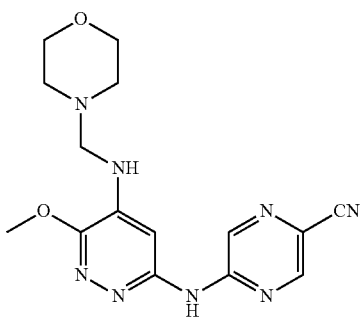 [SMILES: COc1nnc(Nc2cnc(C#N)cn2)cc1NCN1CCOCC1] |
| 2.37 | 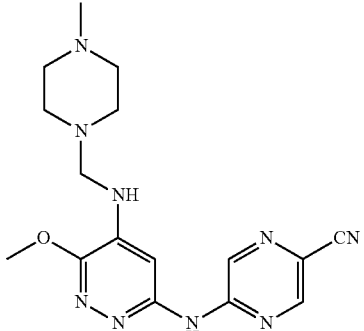 |
| 2.38 | 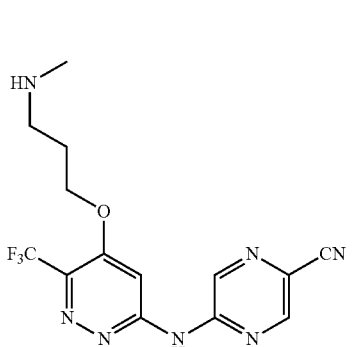 |

TABLE 2-continued

Compounds

| Cpd No. | Cpd Structure |
|---|---|
| 2.39 | |
| 2.40 | |
| 2.41 | |
| 2.42 | |
| 2.43 | |
| 2.44 | |
| 2.45 | |
| 2.46 | |
| 2.47 | |

TABLE 2-continued

Compounds

| Cpd No. | Cpd Structure |
|---|---|
| 2.48 | |
| 2.49 | |
| 2.50 | |
| 2.51 | |
| 2.52 | |
| 2.53 | |
| 2.54 | |
| 2.55 | |

TABLE 2-continued

Compounds

| Cpd No. | Cpd Structure |
|---|---|
| 2.56 | |
| 2.57 | |
| 2.58 | |
| 2.59 | |
| 2.60 | |
| 2.61 | |
| 2.62 | |
| 2.63 | |

TABLE 2-continued
Compounds
| Cpd No. | Cpd Structure |
|---|---|
| 2.64 | 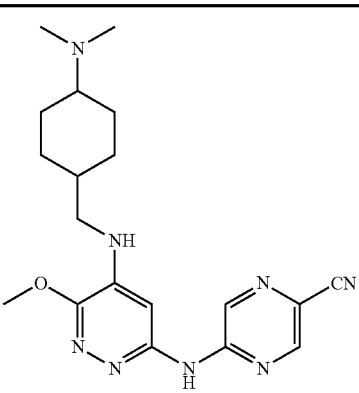 |
| 2.65 | 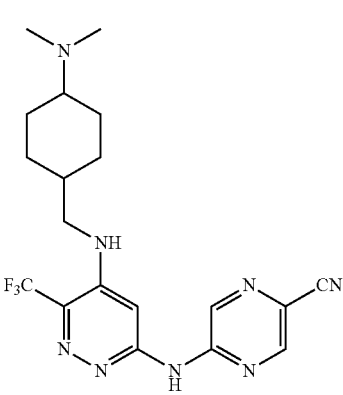 [SMILES: CN(C)C1CCC(CNc2cc(Nc3cnc(C#N)cn3)nnc2C(F)(F)F)CC1] |
| 2.66 | 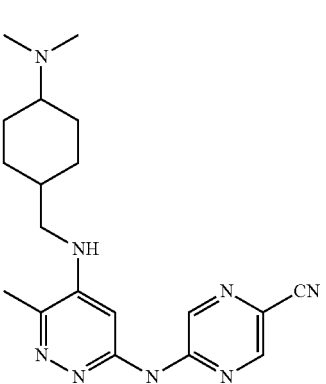 |
| 2.67 | 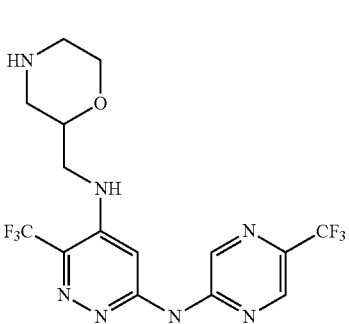 |
| 2.68 | 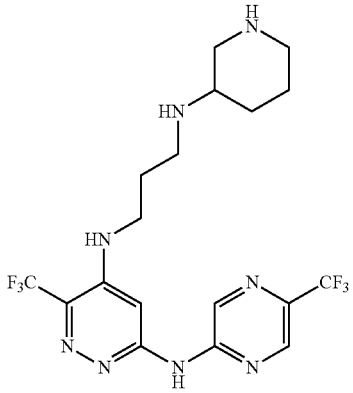 [SMILES: FC(F)(F)c1cnc(Nc2cc(NCCCNC3CCCNC3)c(C(F)(F)F)nn2)cn1] |
| 2.69 | 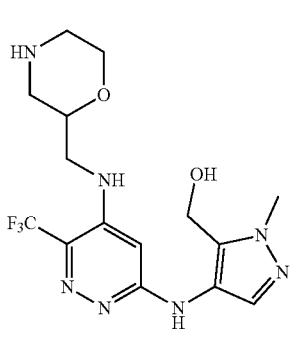 |
| 2.70 | 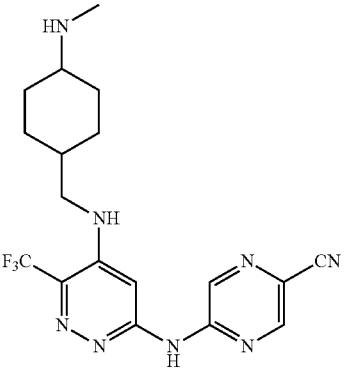 [SMILES: CNC1CCC(CNc2cc(Nc3cnc(C#N)cn3)nnc2C(F)(F)F)CC1] |
| 2.71 | 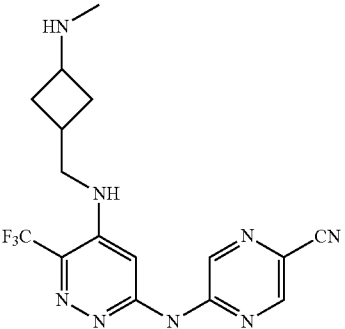 |

TABLE 2-continued

Compounds

| Cpd No. | Cpd Structure |
|---|---|
| 2.72 | |
| 2.73 | |
| 2.74 | |
| 2.75 | |
| 2.76 | |
| 2.77 | |
| 2.78 | |
| 2.79 | |

TABLE 2-continued
Compounds
| Cpd No. | Cpd Structure |
|---|---|
| 2.80 | 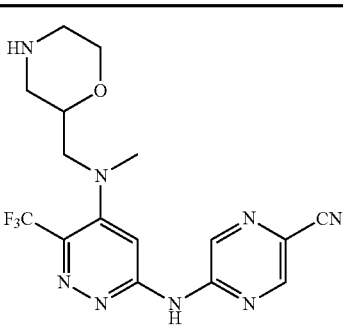 |
| 2.81 | 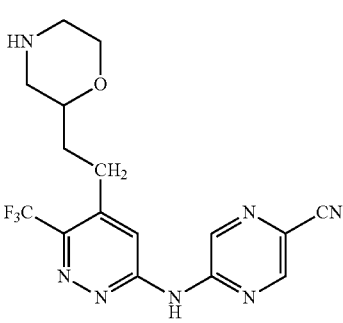 [SMILES: N#Cc1cnc(Nc2cc(CCC3CNCCO3)c(C(F)(F)F)nn2)cn1] |
| 2.82 | 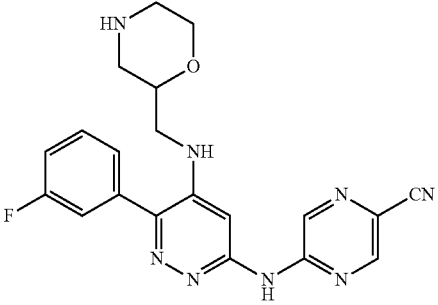 [SMILES: N#Cc1cnc(Nc2cc(NCC3CNCCO3)c(-c3cccc(F)c3)nn2)cn1] |
| 2.83 | 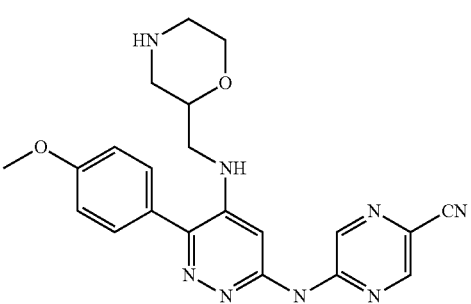 |
| 2.84 | 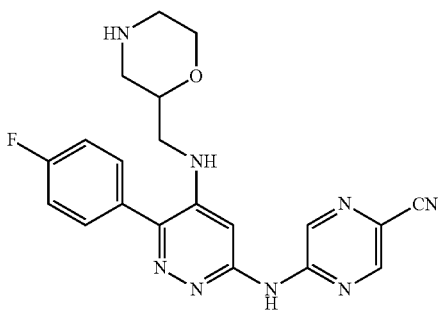 [SMILES: N#Cc1cnc(Nc2cc(NCC3CNCCO3)c(-c3ccc(F)cc3)nn2)cn1] |
| 2.85 | 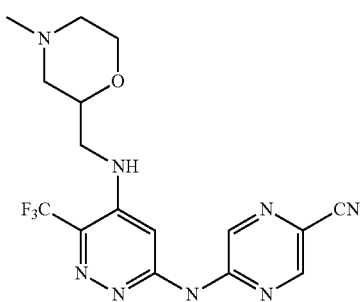 |
| 2.86 | 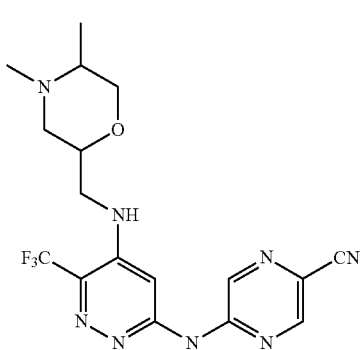 |
| 2.87 | 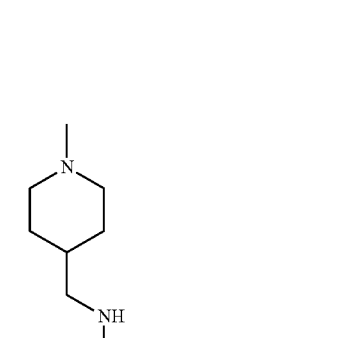 |

TABLE 2-continued

Compounds

| Cpd No. | Cpd Structure |
|---|---|
| 2.88 | (structure) |
| 2.89 | (structure) |
| 2.90 | (structure) |
| 2.91 | (structure) |
| 2.92 | (structure) |
| 2.93 | (structure) |
| 2.94 | (structure) |
| 2.95 | (structure) |

TABLE 2-continued
| Cpd No. | Cpd Structure |
|---|---|
| 2.96 | 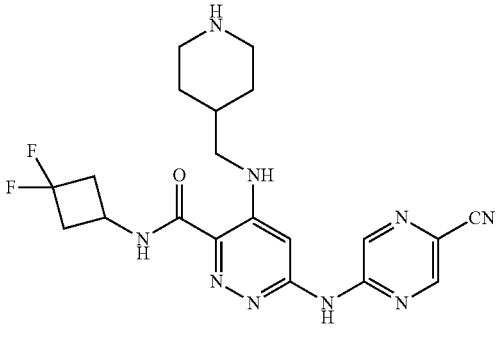 [SMILES: N#Cc1cnc(Nc2cc(NCC3CCNCC3)c(C(=O)NC3CC(F)(F)C3)nn2)cn1] |
| 2.97 | 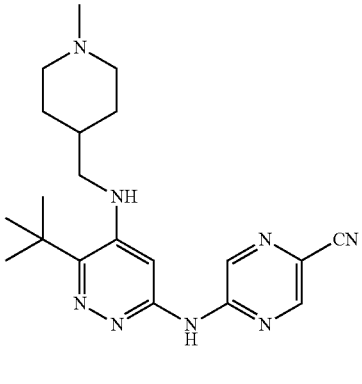 [SMILES: CN1CCC(CNc2cc(Nc3cnc(C#N)cn3)nnc2C(C)(C)C)CC1] |
| 2.98 | 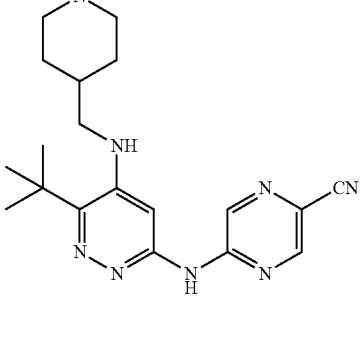 |
| 2.99 | 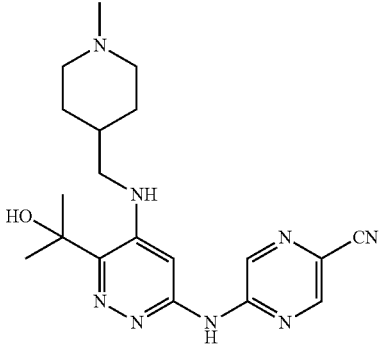 [SMILES: CN1CCC(CNc2cc(Nc3cnc(C#N)cn3)nnc2C(C)(C)O)CC1] |
| 2.100 | 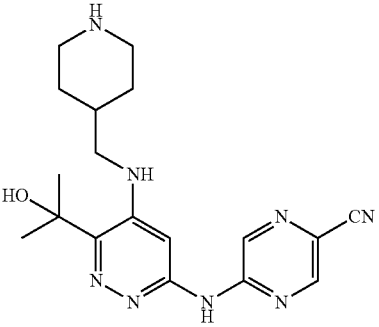 [SMILES: CC(C)(O)c1nnc(Nc2cnc(C#N)cn2)cc1NCC1CCNCC1] |
| 2.101 | 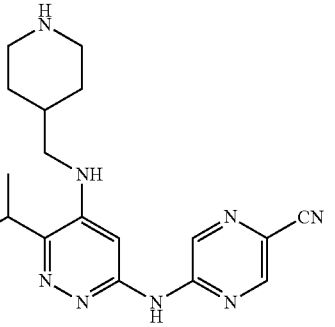 |
| 2.102 | 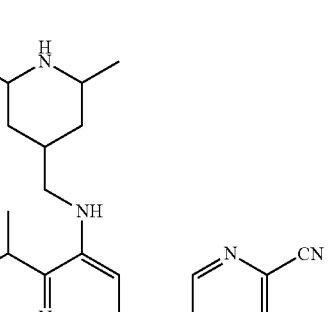 |
| 2.103 | 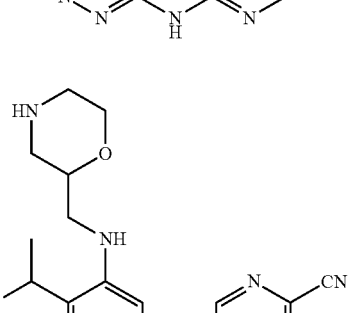 |

TABLE 2-continued

Compounds

| Cpd No. | Cpd Structure |
|---|---|
| 2.104 | |
| 2.105 | |
| 2.106 | |
| 2.107 | |
| 2.108 | |
| 2.109 | |
| 2.110 | |
| 2.111 | |

TABLE 2-continued

Compounds

| Cpd No. | Cpd Structure |
|---|---|
| 2.112 | (piperidin-4-yl)methylamino-cyanopyridazine linked via NH to cyanopyrazine |
| 2.113 | (morpholin-2-yl)methylamino-chloropyridazine linked via NH to cyanopyrazine |
| 2.114 | (piperidin-4-yl)methylamino-chloropyridazine linked via NH to cyanopyrazine |
| 2.115 | (4-methylmorpholin-2-yl)methylamino-chloropyridazine linked via NH to cyanopyrazine |
| 2.116 | (4-cyclopropylmorpholin-2-yl)methylamino-trifluoromethylpyridazine linked via NH to cyanopyrazine |
| 2.117 | (4-isopropylmorpholin-2-yl)methylamino-trifluoromethylpyridazine linked via NH to cyanopyrazine |
| 2.118 | (4-isopropylmorpholin-2-yl)methylamino-iodopyridazine linked via NH to cyanopyrazine |
| 2.119 | (4-isopropylmorpholin-2-yl)methylamino-bromopyridazine linked via NH to cyanopyrazine |

TABLE 2-continued
Compounds
| Cpd No. | Cpd Structure |
|---|---|
| 2.120 | 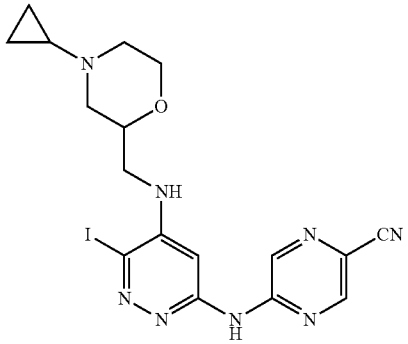 [SMILES: N#Cc1cnc(Nc2cc(NCC3CN(C4CC4)CCO3)c(I)nn2)cn1] |
| 2.121 | 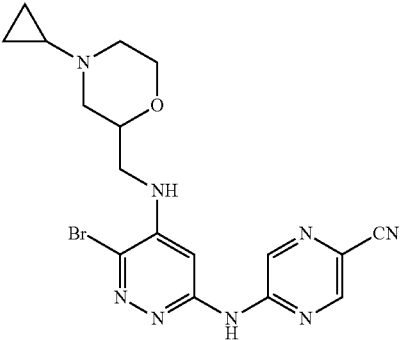 [SMILES: N#Cc1cnc(Nc2cc(NCC3CN(C4CC4)CCO3)c(Br)nn2)cn1] |
| 2.122 | 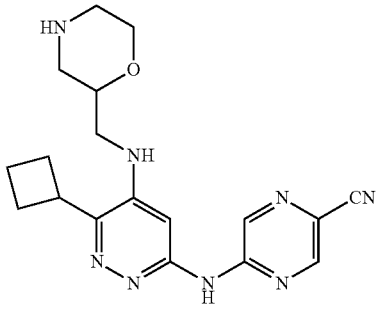 [SMILES: N#Cc1cnc(Nc2cc(NCC3CNCCO3)c(C3CCC3)nn2)cn1] |
| 2.123 | 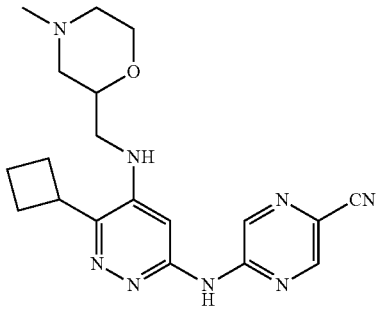 [SMILES: CN1CCOC(CNc2cc(Nc3cnc(C#N)cn3)nnc2C2CCC2)C1] |
| 2.124 | 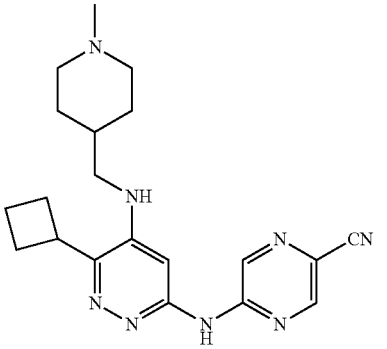 [SMILES: CN1CCC(CNc2cc(Nc3cnc(C#N)cn3)nnc2C2CCC2)CC1] |
| 2.125 | 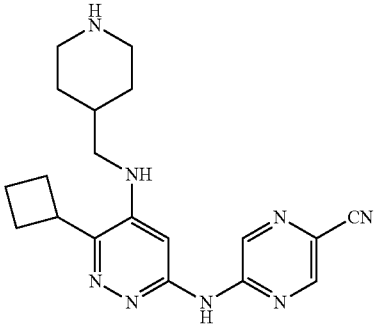 [SMILES: N#Cc1cnc(Nc2cc(NCC3CCNCC3)c(C3CCC3)nn2)cn1] |
| 2.126 | 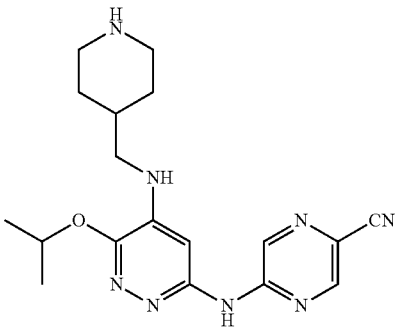 [SMILES: CC(C)Oc1nnc(Nc2cnc(C#N)cn2)cc1NCC1CCNCC1] |
| 2.127 | 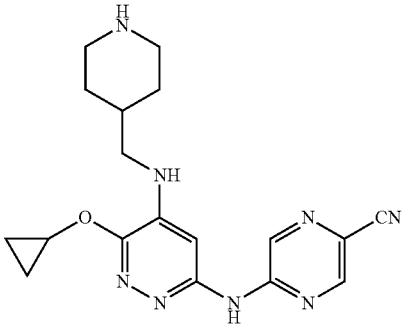 [SMILES: N#Cc1cnc(Nc2cc(NCC3CCNCC3)c(OC3CC3)nn2)cn1] |

TABLE 2-continued

Compounds

| Cpd No. | Cpd Structure |
|---|---|
| 2.128 | (structure) |
| 2.129 | (structure) |
| 2.130 | (structure) |
| 2.131 | (structure) |
| 2.132 | (structure) |
| 2.133 | (structure) |
| 2.134 | (structure) |
| 2.135 | (structure) |

TABLE 2-continued

Compounds

| Cpd No. | Cpd Structure |
|---|---|
| 2.136 | (structure) |
| 2.137 | (structure) |
| 2.138 | (structure) |
| 2.139 | (structure) |
| 2.140 | (structure) |
| 2.141 | (structure) |
| 2.142 | (structure) |
| 2.143 | (structure) |

TABLE 2-continued

Compounds

| Cpd No. | Cpd Structure |
|---|---|
| 2.144 | |
| 2.145 | |
| 2.146 | |
| 2.147 | |
| 2.148 | |
| 2.149 | |
| 2.150 | |
| 2.151 | |

TABLE 2-continued
Compounds
| Cpd No. | Cpd Structure |
|---|---|
| 2.152 | 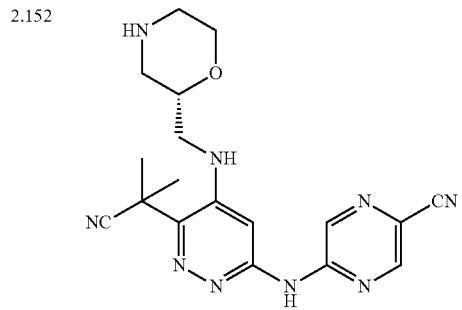 |
| 2.153 | 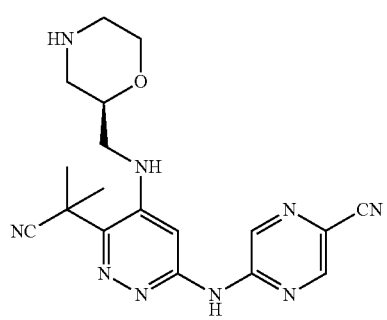 [SMILES: CC(C)(C#N)c1nnc(Nc2cnc(C#N)cn2)cc1NC[C@H]1CNCCO1] |
| 2.154 | 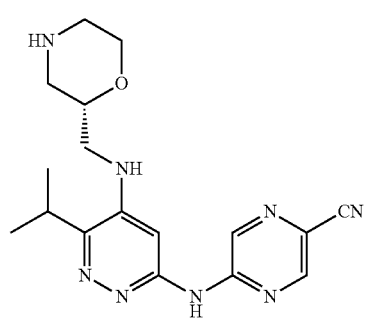 [SMILES: CC(C)c1nnc(Nc2cnc(C#N)cn2)cc1NC[C@@H]1CNCCO1] |
| 2.155 | 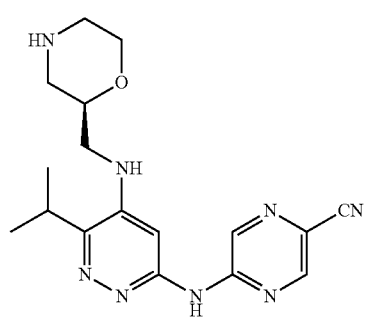 [SMILES: CC(C)c1nnc(Nc2cnc(C#N)cn2)cc1NC[C@H]1CNCCO1] |
| 2.156 | 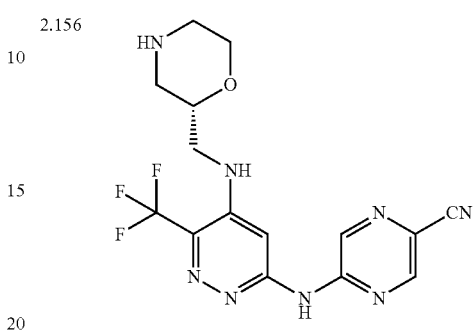 |
| 2.157 | 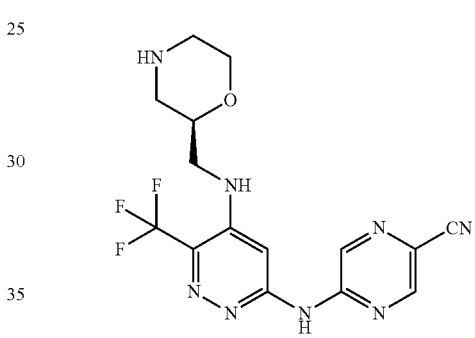 |
| 2.158 | 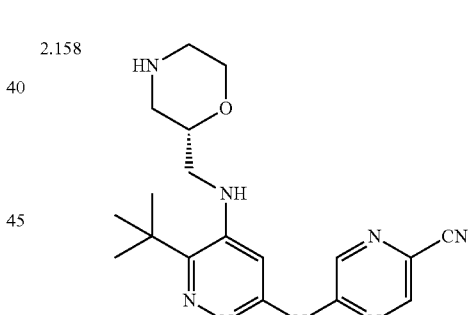 |
| 2.159 | 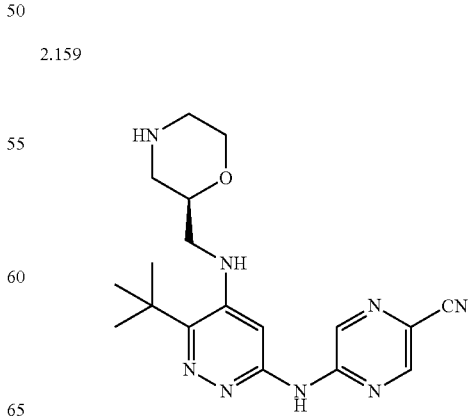 |

TABLE 2-continued
Compounds
| Cpd No. | Cpd Structure |
|---|---|
| 2.160 | 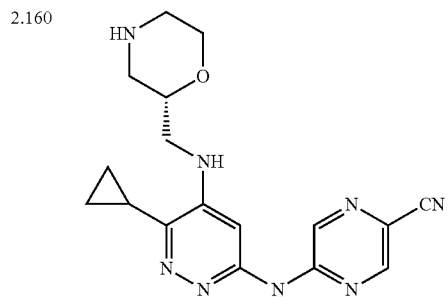 |
| 2.161 | 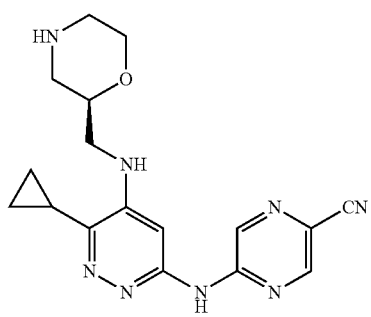 [SMILES: N#Cc1cnc(Nc2cc(NC[C@H]3CNCCO3)c(C3CC3)nn2)cn1] |
| 2.162 | 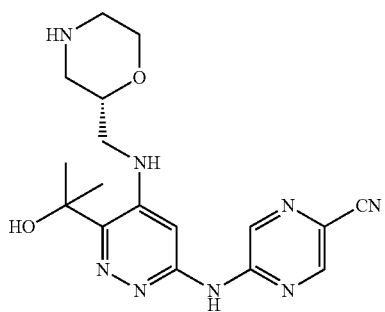 |
| 2.163 | 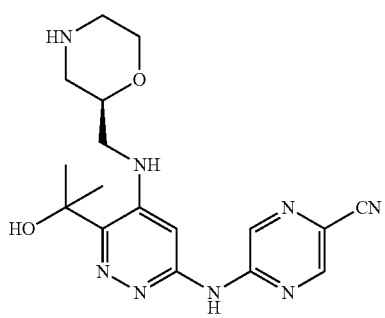 |
TABLE 2-continued
Compounds
| Cpd No. | Cpd Structure |
|---|---|
| 2.164 | 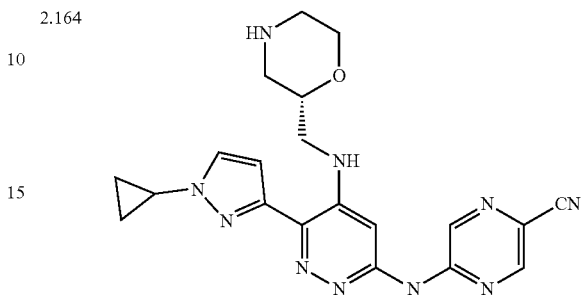 |
| 2.165 | 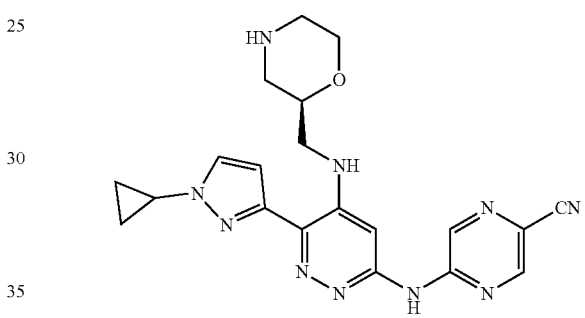 |
| 2.166 | 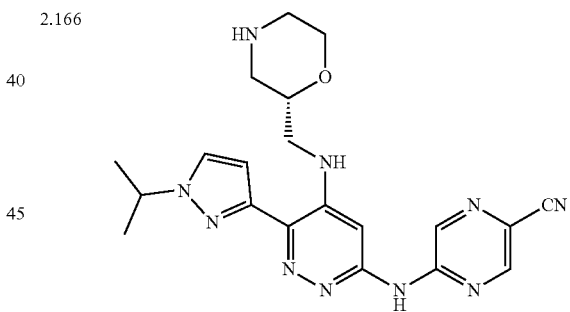 |
| 2.167 | 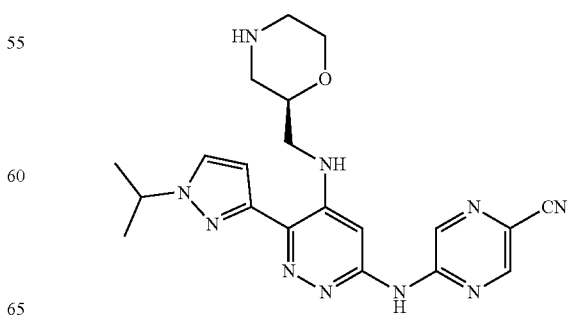 |

TABLE 2-continued

Compounds

| Cpd No. | Cpd Structure |
|---|---|
| 2.168 | |
| 2.169 | |
| 2.170 | |
| 2.171 | |
| 2.172 | |
| 2.173 | |
| 2.174 | |
| 2.175 | |

TABLE 2-continued

Compounds

| Cpd No. | Cpd Structure |
|---|---|
| 2.176 | |
| 2.177 | |
| 2.178 | |
| 2.179 | |
| 2.180 | |
| 2.181 | |
| 2.182 | |
| 2.183 | |

TABLE 2-continued
Compounds
| Cpd No. | Cpd Structure |
|---|---|
| 2.184 | 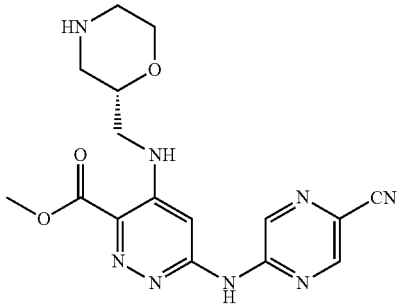 [SMILES: COC(=O)c1nnc(Nc2cnc(C#N)cn2)cc1NC[C@@H]1CNCCO1] |
| 2.185 | 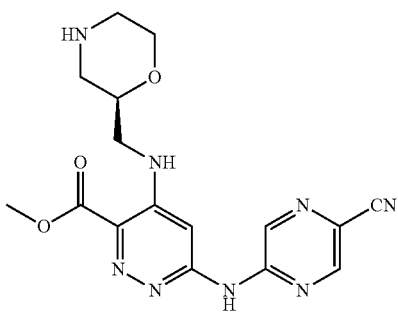 [SMILES: COC(=O)c1nnc(Nc2cnc(C#N)cn2)cc1NC[C@H]1CNCCO1] |
| 2.186 | 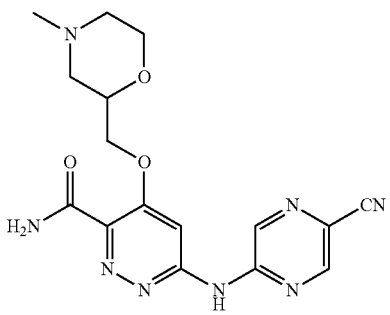 [SMILES: CN1CCOC(COc2cc(Nc3cnc(C#N)cn3)nnc2C(N)=O)C1] |
| 2.187 | 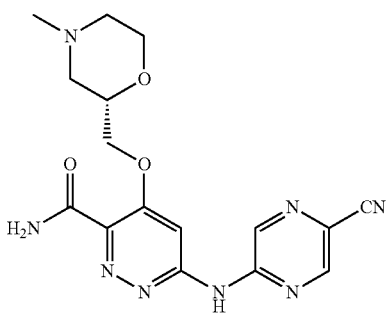 [SMILES: CN1CCO[C@H](COc2cc(Nc3cnc(C#N)cn3)nnc2C(N)=O)C1] |
| 2.188 | 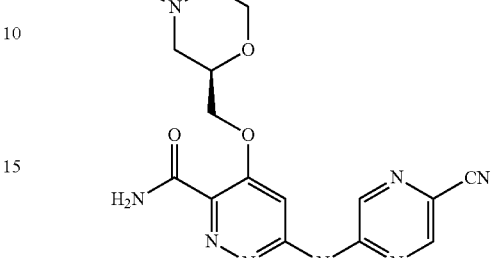 |
| 2.189 | 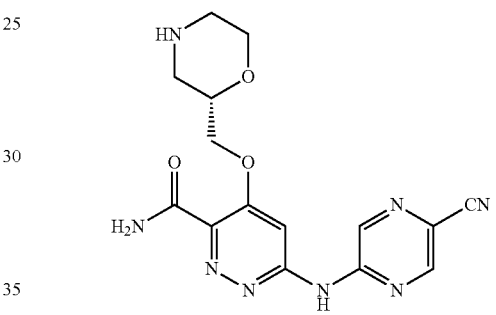 |
| 2.190 | 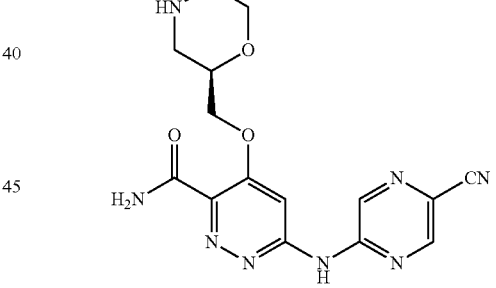 |
| 2.191 | 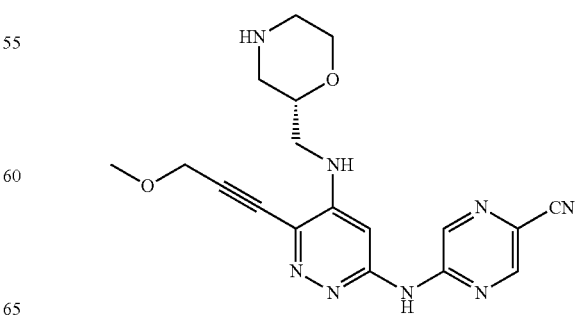 |

TABLE 2-continued

Compounds

| Cpd No. | Cpd Structure |
|---|---|
| 2.192 | |
| 2.193 | |
| 2.194 | |
| 2.195 | |
| 2.196 | |
| 2.197 | |
| 2.198 | |
| 2.199 | |
| 2.200 | |

TABLE 2-continued

Compounds

| Cpd No. | Cpd Structure |
|---|---|
| 2.201 | (structure) |
| 2.202 | (structure) |
| 2.203 | (structure) |
| 2.204 | (structure) |
| 2.205 | (structure) |
| 2.206 | (structure) |
| 2.207 | (structure) |
| 2.208 | (structure) |

TABLE 2-continued
Compounds
| Cpd No. | Cpd Structure |
|---|---|
| 2.209 | 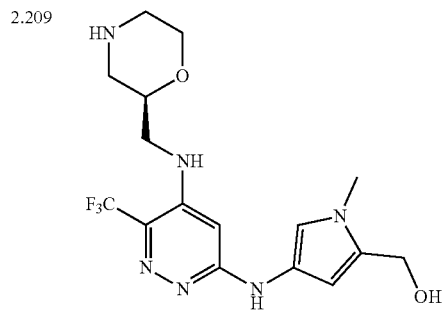 |
| 2.210 | 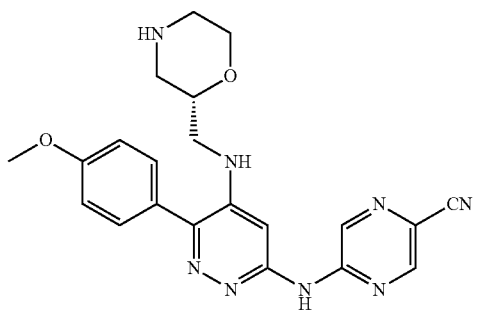 |
| 2.211 | 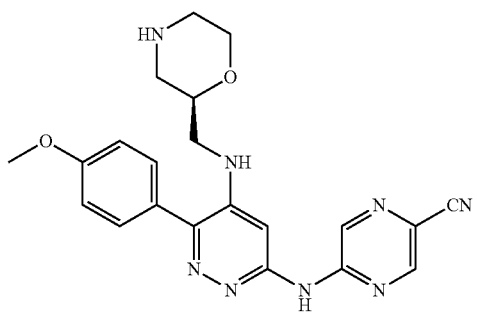 [SMILES: COc1ccc(-c2nnc(Nc3cnc(C#N)cn3)cc2NC[C@H]2CNCCO2)cc1] |
| 2.212 | 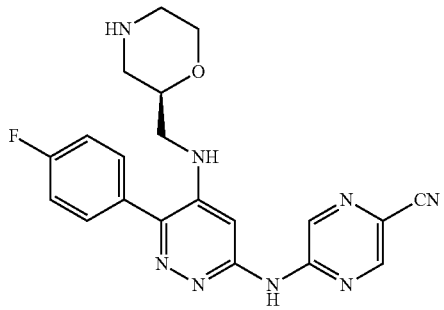 [SMILES: N#Cc1cnc(Nc2cc(NC[C@H]3CNCCO3)c(-c3ccc(F)cc3)nn2)cn1] |
| 2.213 | 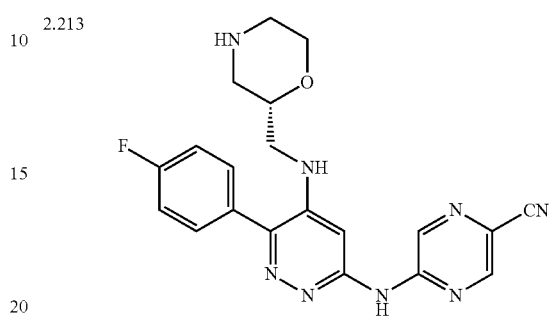 |
| 2.214 | 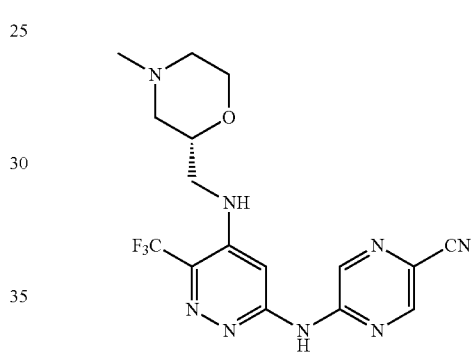 |
| 2.215 | 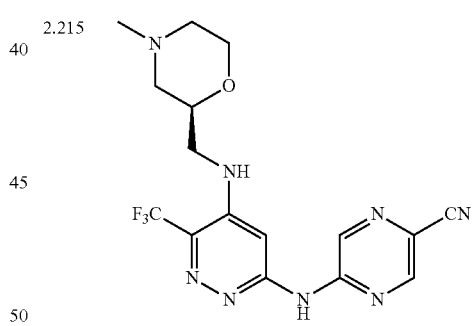 |
| 2.216 | 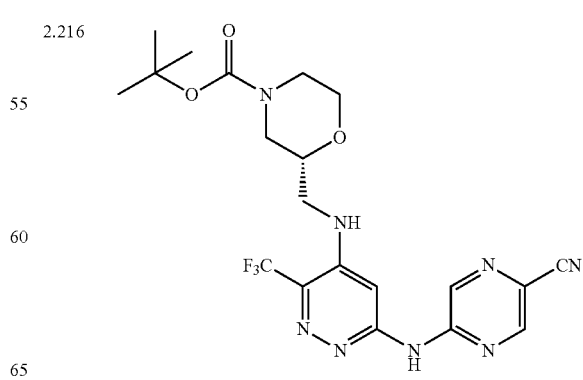 |

TABLE 2-continued

Compounds

| Cpd No. | Cpd Structure |
|---|---|
| 2.217 | |
| 2.218 | |
| 2.219 | |
| 2.220 | |
| 2.221 | |
| 2.222 | |
| 2.223 | |
| 2.224 | |

TABLE 2-continued
Compounds
| Cpd No. | Cpd Structure |
|---|---|
| 2.225 | 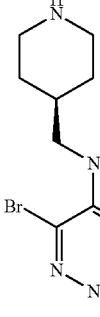 |
| 2.226 | |
| 2.227 | |
| 2.228 | |
| 2.229 | 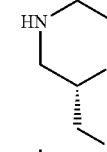 |
| 2.230 | |
| 2.231 | |
| 2.232 | |

TABLE 2-continued

Compounds

| Cpd No. | Cpd Structure |
|---|---|
| 2.233 | (structure) |
| 2.234 | (structure) |
| 2.235 | (structure) |
| 2.236 | (structure) |
| 2.237 | (structure) |
| 2.238 | (structure) |
| 2.239 | (structure) |
| 2.240 | (structure) |

TABLE 2-continued

Compounds

| Cpd No. | Cpd Structure |
|---|---|
| 2.241 | (morpholin-2-ylmethylamino)-chloro-pyridazine linked via NH to pyrazine-CN |
| 2.242 | (4-cyclopropylmorpholin-2-ylmethylamino)-trifluoromethyl-pyridazine linked via NH to pyrazine-CN |
| 2.243 | (4-cyclopropylmorpholin-2-ylmethylamino)-trifluoromethyl-pyridazine linked via NH to pyrazine-CN |
| 2.244 | (4-isopropylmorpholin-2-ylmethylamino)-trifluoromethyl-pyridazine linked via NH to pyrazine-CN |
| 2.245 | (4-isopropylmorpholin-2-ylmethylamino)-trifluoromethyl-pyridazine linked via NH to pyrazine-CN |
| 2.246 | (4-isopropylmorpholin-2-ylmethylamino)-iodo-pyridazine linked via NH to pyrazine-CN |
| 2.247 | (4-isopropylmorpholin-2-ylmethylamino)-bromo-pyridazine linked via NH to pyrazine-CN |
| 2.248 | (4-isopropylmorpholin-2-ylmethylamino)-bromo-pyridazine linked via NH to pyrazine-CN |

TABLE 2-continued

Compounds

| Cpd No. | Cpd Structure |
|---|---|
| 2.249 | (structure) |
| 2.250 | (structure) |
| 2.251 | (structure) |
| 2.252 | (structure) |
| 2.253 | (structure) |
| 2.254 | (structure) |
| 2.255 | (structure) |
| 2.256 | (structure) |

TABLE 2-continued

Compounds

| Cpd No. | Cpd Structure |
|---|---|
| 2.257 | |
| 2.258 | |
| 2.259 | |
| 2.260 | |
| 2.261 | |
| 2.262 | |
| 2.263 | |
| 2.264 | |

TABLE 2-continued
Compounds
| Cpd No. | Cpd Structure |
|---|---|
| 2.265 | |
| 2.266 | |
| 2.267 | |
| 2.268 | |
| 2.269 | |
| 2.270 | |
| 2.271 | |
| 2.272 | |
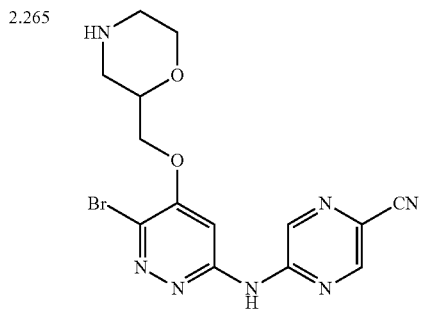
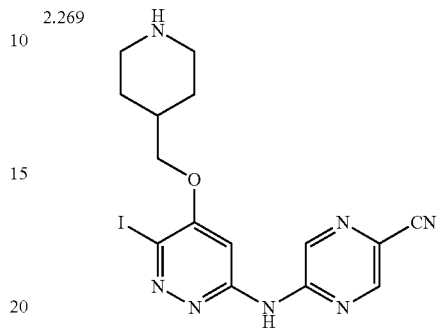
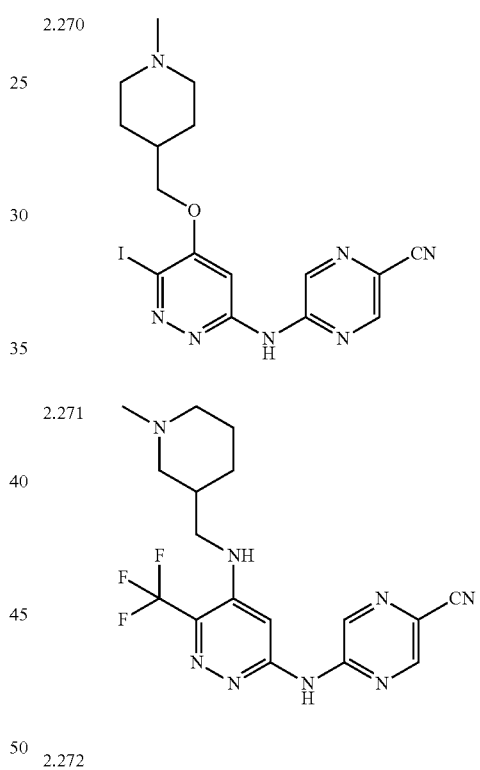

TABLE 2-continued

Compounds

| Cpd No. | Cpd Structure |
|---|---|
| 2.273 | |
| 2.274 | |
| 2.275 | |
| 2.276 | |
| 2.277 | |
| 2.278 | |
| 2.279 | |
| 2.280 | |

TABLE 2-continued

Compounds

| Cpd No. | Cpd Structure |
|---|---|
| 2.281 | |
| 2.282 | |
| 2.283 | |
| 2.284 | |
| 2.285 | |
| 2.286 | |
| 2.287 | |
| 2.288 | |

TABLE 2-continued

Compounds

| Cpd No. | Cpd Structure |
|---|---|
| 2.289 | (structure) |
| 2.290 | (structure) |
| 2.291 | (structure) |
| 2.292 | (structure) |
| 2.293 | (structure) |
| 2.294 | (structure) |
| 2.295 | (structure) |
| 2.296 | (structure) |
| 2.297 | (structure) |
| 2.298 | (structure) |

TABLE 2-continued

Compounds

| Cpd No. | Cpd Structure |
|---|---|
| 2.299 | |
| 2.300 | |
| 2.301 | |
| 2.302 | |
| 2.303 | |
| 2.304 | |
| 2.305 | |
| 2.306 | |

TABLE 2-continued

Compounds

| Cpd No. | Cpd Structure |
|---|---|
| 2.307 | |
| 2.308 | |
| 2.309 | |
| 2.310 | |
| 2.311 | |
| 2.312 | |
| 2.313 | |
| 2.314 | |

TABLE 2-continued

Compounds

| Cpd No. | Cpd Structure |
|---|---|
| 2.315 | |
| 2.316 | |
| 2.317 | |
| 2.318 | |
| 2.319 | |
| 2.320 | |
| 2.321 | |
| 2.322 | |

TABLE 2-continued
Compounds
| Cpd No. | Cpd Structure |
|---|---|
| 2.323 | 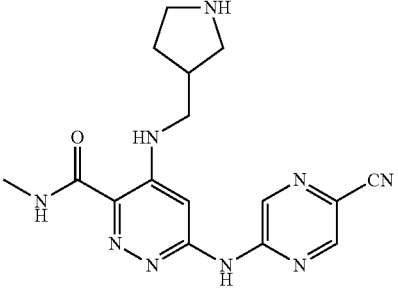 |
| 2.324 | 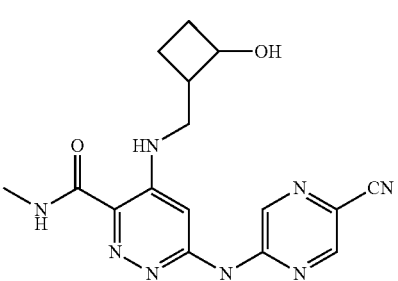 |
| 2.325 | 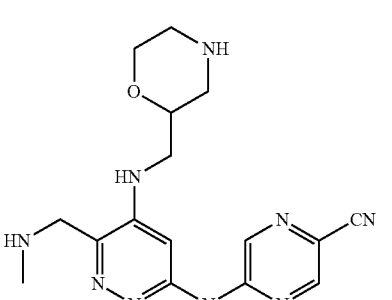 |
| 2.326 | 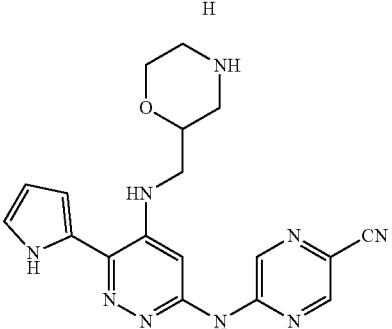 |
| 2.327 | 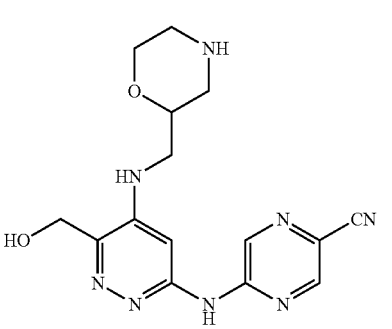 |
| 2.328 | 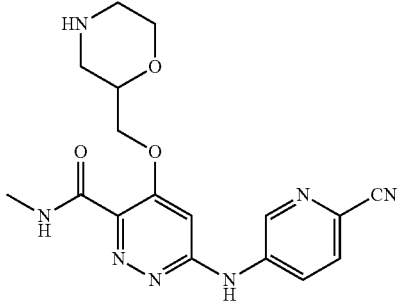 |
| 2.329 | 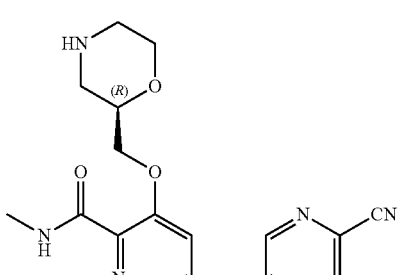 |
| 2.330 | 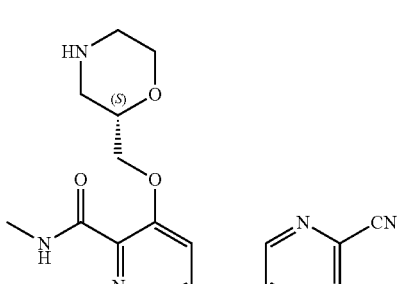 |
| 2.331 | 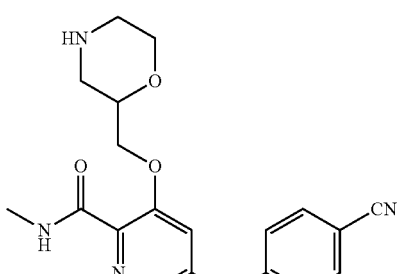 |

TABLE 2-continued

Compounds

| Cpd No. | Cpd Structure |
|---|---|
| 2.332 | 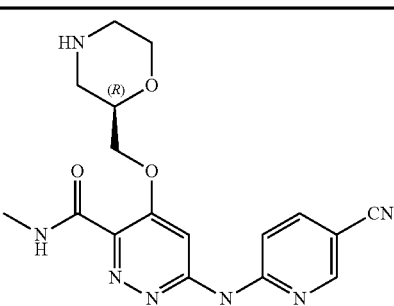 |
| 2.333 | 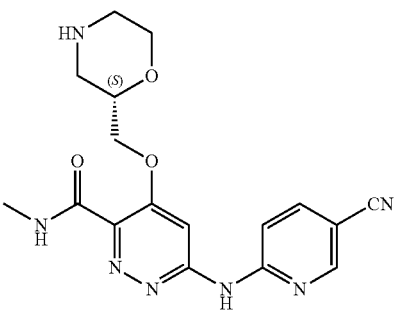 |
| 2.334 | 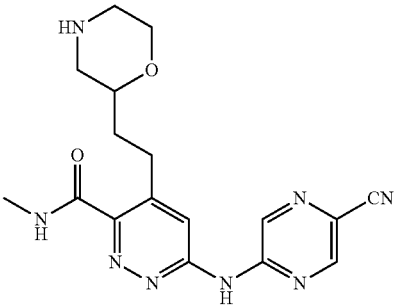 |

Cpd = Compound

In some embodiments, provided herein are compounds described in table 1 and table 2, or a salt thereof, and uses thereof.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (IA) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$ $^{13}N$, $^{15}O$, $^{17}O$, $^{32}P$, $^{35}S$, $^{18}F$, $^{36}Cl$. Certain isotope labeled compounds (e.g. $^3H$ and $^{14}C$) are useful in compound or substrate tissue distribution studies. Incorporation of heavier isotopes such as deuterium ($^2H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Schemes

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

In some embodiments, compounds of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) may be synthesized according to Scheme-1 to Scheme-8.

Scheme-1

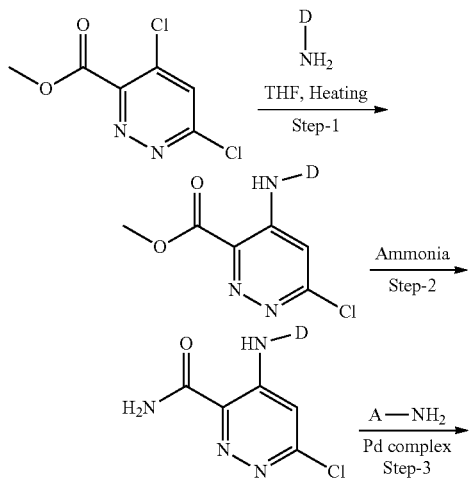

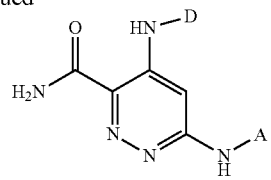

wherein, A and D are defined in formula (IA).

Scheme-2

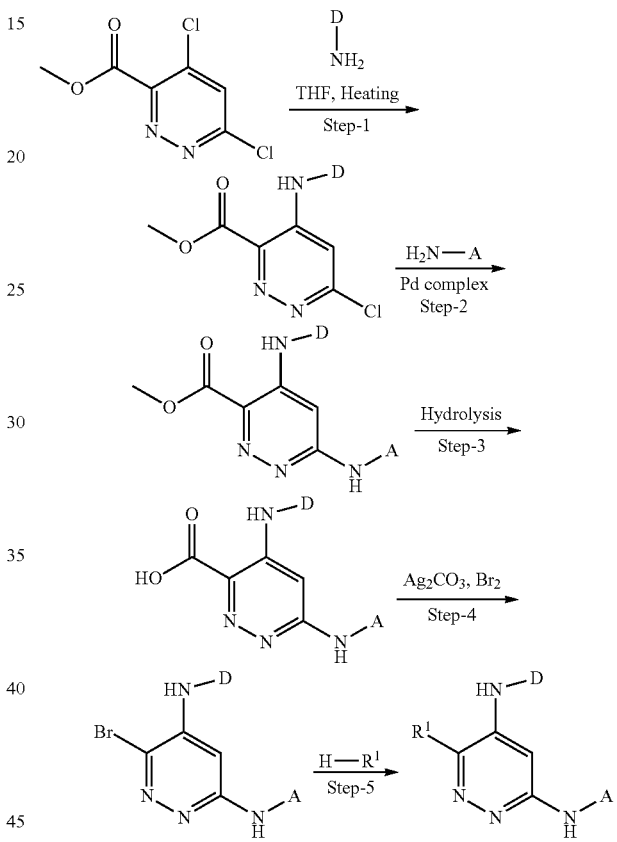

wherein, A, D and R¹ are as defined in formula (IA).

Scheme-3

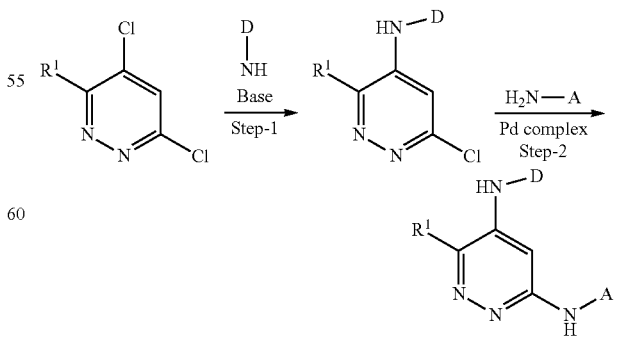

wherein, A, D and R¹ are defined in formula (IA).

Scheme-4
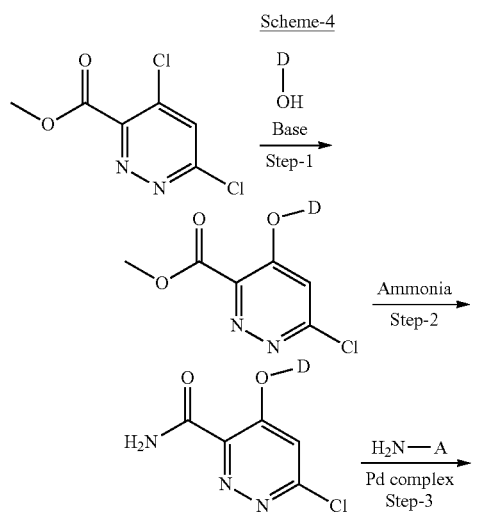
wherein, A and D are as defined in formula (IA).
Scheme-5
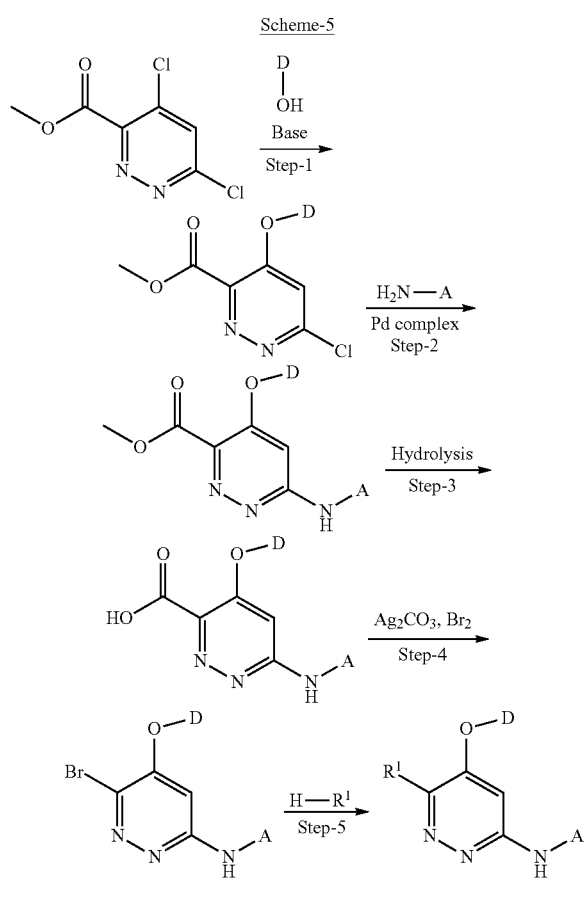
wherein, A, D and R¹ are as defined in formula (IA).
Scheme-6
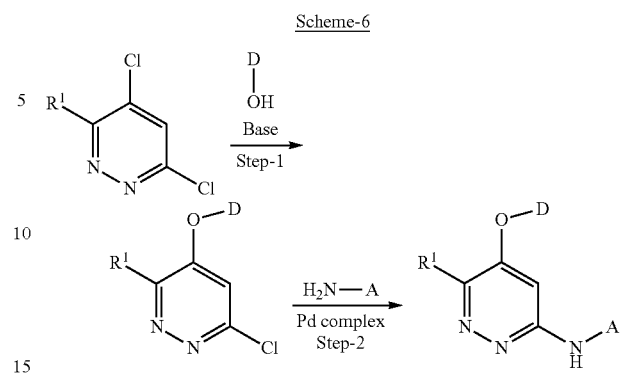
wherein, A, D and R¹ are defined in formula (IA).
Scheme-7
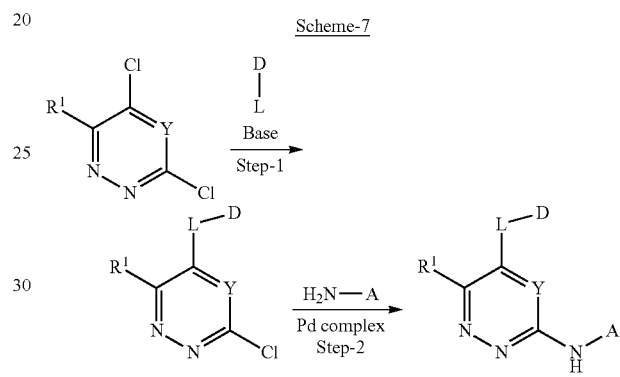
wherein, A, D, L, Y and R¹ are defined in formula (IA).
Scheme-8
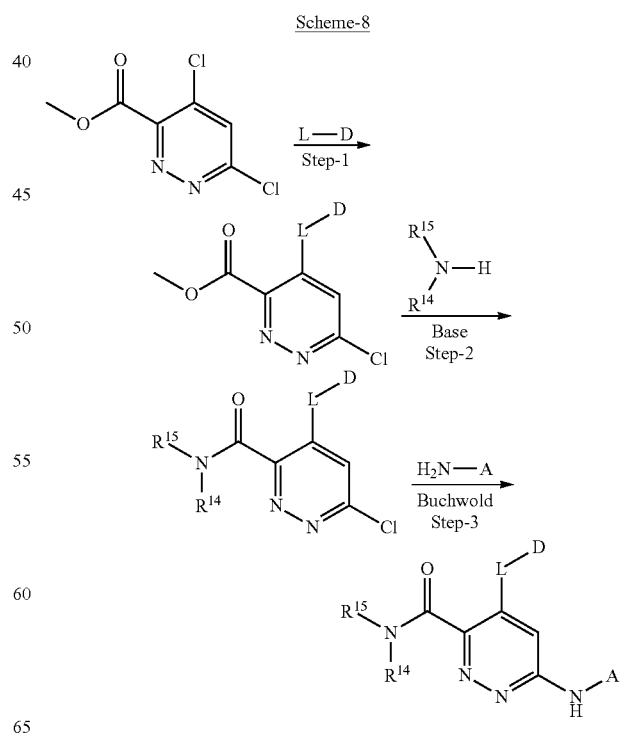
wherein, A, D, L, R¹⁴ and R¹⁵ are defined in formula (IA).

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties.

Pharmaceutical formulations may be prepared by known pharmaceutical methods. Suitable formulations can be found, e.g., in Remington's Pharmaceutical Sciences, Mack Publishing Company, Philadelphia, PA, 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a salt thereof can be incorporated in tablet in an amount ranging from about 1 mg to about 1000 mg.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease in an individual comprising administering an effective amount of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) or any embodiment, variation or aspect thereof or the present compounds or the compounds detailed or described herein) or a pharmaceutically acceptable salt thereof, to the individual. Further provided herein is a method of treating a proliferative disease in an individual, comprising administering an effective amount of the compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) or a pharmaceutically acceptable salt thereof, to the individual. Also provided herein is a method of treating cancer in an individual comprising administering an effective amount of the compound of formula (IA) or a pharmaceutically acceptable salt thereof, to the individual. In some embodiments, the compound is administered to the individual according to a dosage and/or method of administration described herein.

Another aspect of the invention relates to a method of treating a disease or disorder associated with Checkpoint kinase. The method involves administering to a patient in need of a treatment for diseases or disorders associated with Checkpoint kinase an effective amount of the compositions and compounds of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)).

Another aspect of the invention is directed to a method inhibiting Checkpoint kinase. The method involves administering to a patient in need thereof an effective amount of the compositions or compounds of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)).

The use of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) for the manufacture of a medicament for the treatment of a proliferative disease such as cancer.

The use of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) for the manufacture of a medicament for the treatment of cancer, wherein the cancer is selected from carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, hematopoieitic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or habdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; Ewing's sarcoma or Kaposi's sarcoma. The use of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) for the manufacture of a medicament for the treatment of cancer, wherein the cancer is one which is characterized by a defective DNA repair mechanism or defective cell cycle.

The use of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) for the manufacture of a medicament for the treatment of cancer, wherein the cancer is a p53 negative or mutated tumour.

The use of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) for the manufacture of a medicament for the treatment of cancer, wherein the cancer is an MYC oncogene-driven cancer.

The use of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) for the manufacture of a medicament for the treatment of cancer, wherein the MYC oncogene-driven cancer is a B-cell lymphoma, leukemia, neuroblastoma, breast cancer or lung cancer.

The use of a compound of the present invention (collectively, a compound of formula (IA), (I), (II), (IIa-1) to (IIa-10), (IIb-1) to (IIb-20), (III), (IIIa-1) to (IIIa-10), (IIIb-1) to (IIIb-20), (IV) or (IVa-1) to (IVa-15)) for the manufacture of a medicament for the treatment of cancer, wherein the cancer is High grade serious ovarian cancer (HGSOC), Triple negative breast cancer (TNBC) and Small cell lung cancer (SCLC). CCNE1amplification occurs in approximately 20% of the HGSOC tumors. CCNE1$^{amp}$ is known to increase replication stress (RS) and genomic instability, leading to increased reliance on Checkpoint kinase 1 (CHK-1). Hence, CCNE1 amplification correlates to clinical response to CHK-1 inhibitors (Lee et al Lancet Oncol. 2018 19(2), 207). Increased DNA repair and cell cycle checkpoint activation remain as the foremost reasons behind TNBC tumor resistance to chemotherapy and PARP inhibitor resistance. Synergy has been observed with CHK-1 inhibitors and PARP inhibitors in TNBC with elevated RAD51 expression (Mani et al. Breast Cancer Research (2019) 21:104). CHK-1 inhibition may be especially effective in SCLC with MYC amplification or MYC protein overexpression. CHK-1 inhibitors exhibited strong single-agent efficacy, augmented the effects of cisplatin or the PARP inhibitor olaparib, and improved the response of platinum-resistant models. (Cancer Res 2017, 77(14), 3870-3884—Sen et al).

The disclosed compounds of the present invention can be administered in effective amounts to treat or prevent a disorder and/or prevent the development thereof in subjects.

Combination Therapy

The compound of the present invention may be administered either simultaneously with, or before or after, one or more other therapeutic agents. The compound of the present invention may be administered separately, by the same or different route of administration, or together in the same pharmaceutical composition as the other agents.

In some embodiments, the methods described herein comprise the additional step of co-administering to a subject in need thereof a second therapy e.g., an additional cancer therapeutic agent or an additional cancer treatment. Exemplary additional cancer therapeutic agents include for example, In one embodiment, the other active agent is selected from the group consisting of but not limited to antimetabolites, tubulin targeting agents, DNA binder and topoisomerase II inhibitors, alkylating agents, monoclonal antibodies, hormonal therapy, signal transduction inhibitors, proteasome inhibitors, DNA methyl transferases, cytokines and retinoids, hypoxia triggered DNA damaging agents, immunomodulaters (e.g. CTLA-4, LAG-3, PD-1 antagonists etc.) and monoclonal antibodies.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others), and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, Asparaginase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein In some embodiments, the additional cancer therapeutic agents are tyrosine kinase inhibitors, PI3K/mTOR inhibitors, PARP inhibitors such as Olaparib, Rucaparib, Niraparib, Talazoparib, Wee1 inhibitors, CDK4/6 inhibitors such as Palbociclib, Ribociclib, Abemaciclib, DNA-PK inhibitors, ATM inhibitors and ATR inhibitors etc. Any compound of the present invention can be combined with these targeted inhibitors.

The compounds of the invention and combinations with chemotherapeutic agents or radiation therapies as described above may be administered over a prolonged term to maintain beneficial therapeutic effects or may be administered for a short period only. Alternatively they may be administered in a pulsatile or continuous manner.

Other possible additional therapeutic modalities include gene therapy, peptide and dendritic cell vaccines, synthetic chlorotoxins, and radiolabeled drugs and antibodies.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The present disclosure further provides kits for carrying out the methods of the invention, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Example-1: Synthesis of 5-(6-phenyl-5-((piperidin-4-ylmethyl)amino)pyridazin-3-yl)amino)pyrazine-2-carbonitrile (Compound No. 1.1)

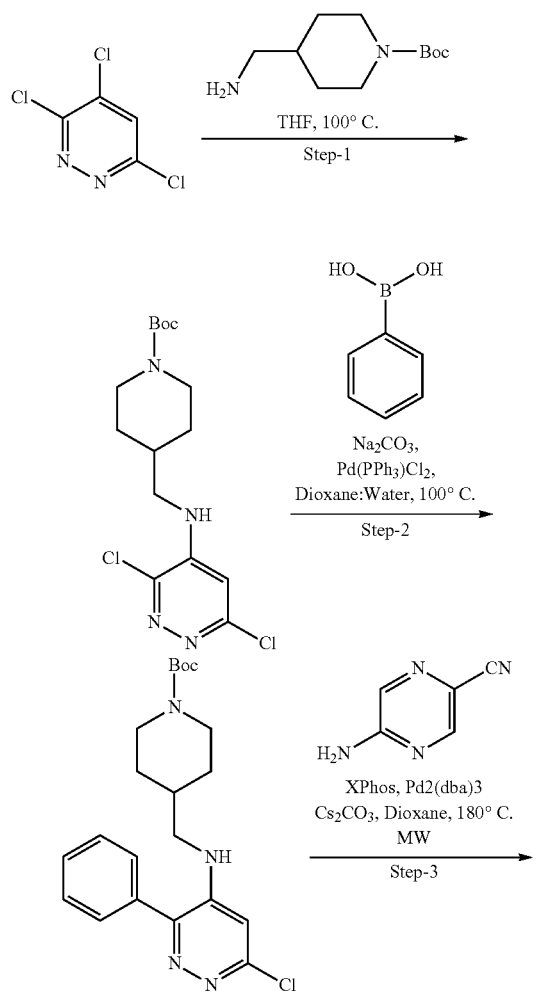

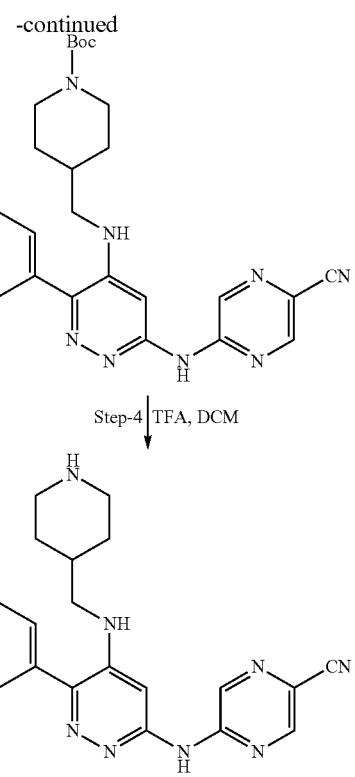

Step-1: Synthesis of tert-butyl 4-(((3,6-dichloropyridazin-4-yl)amino)methyl)piperidine-1-carboxylate: 3,4,6-trichloropyridazine (0.500 g, 2.74 mmols, 1.0 equiv) and tert-butyl 4-(aminomethyl)piperidine-1-carboxylate (0.645 g, 3.02 mmols, 1.10 equiv) were dissolved in THF and heated at 100° C. for overnight. Product formation was confirmed by the LCMS. The reaction mixture was diluted with water and extracted with ethyl acetate (50 mL×2). Combined organic layer was dried over anhydrous $Na_2SO_4$ and concentrated under reduced pressure. The crude product was purified by flash chromatography (0-30% ethyl acetate in hexane as an eluent) to obtain tert-butyl 4-(((3,6-dichloropyridazin-4-yl)amino)methyl)piperidine-1-carboxylate (0.250 g, 26% Yield) as an yellow solid. LCMS: 361.2 $[M+H]^+$; $^1H$ NMR (400 MHz, DMSO-$d_6$) δ 7.30 (t, J=5.5 Hz, 1H), 7.05 (s, 1H), 3.92 (d, J=11.4 Hz, 2H), 3.14 (t, J=6.6 Hz, 2H), 2.67 (br. s., 2H), 1.78 (br. s., 1H), 1.63 (d, J=12.3 Hz, 2H), 1.38 (s, 6H), 1.33 (br. s., 1H), 1.30-1.11 (m, 4H), 1.02 (dt, J=8.1, 11.9 Hz, 2H).

Step-2: Synthesis of tert-butyl 4-(((6-chloro-3-phenylpyridazin-4-yl)amino)methyl)piperidine-1-carboxylate: To a solution of obtain tert-butyl 4-(((3,6-dichloropyridazin-4-yl)amino)methyl)piperidine-1-carboxylate (0.500, 1.38 mmols, 1.0 equiv) in Dioxan:water (10:4 mL) was added phenylboronic acid (0.186 g, 1.52 mmols, 1.1 equiv), $Na_2CO_3$ (0.294 g, 2.77 mmols, 2.0 equiv) followed by the addition of $Pd(PPh_3)Cl_2$ (0.050 g, 0.069 mmols, 0.05 equiv). The resulting reaction mixture was heated at 100° C. for overnight. Product formation was confirmed by LCMS. The reaction mixture was diluted with water and extracted with ethyl acetate (50 mL×2). Combined organic layer was dried over anhydrous $Na_2SO_4$ and concentrated under reduced pressure. The crude product was purified by flash chromatography (0-30% ethyl acetate in hexane as an eluent) to obtain the desired product (0.200 g, 35% Yield) as a yellow solid. LCMS: 403.3 $[M+H]^+$ Step-3: Synthesis of tert-butyl 4-(6-(5-cyanopyrazin-2-yl)amino)-3-phenylpyridazin-4-yl)amino)methyl)piperidine-1-carboxylate-4-carboxylate: To a solution of tert-butyl 4-((6-chloro-3-phenylpyridazin-4-yl)amino)methyl)piperidine-1-carboxylate (0.100 g, 0.248 mmols, 1.0 eq.) was added 5-aminopyrazine-2-carbonitrile (0.036 g, 0.298 mmols, 1.2 eq.), Cs$_2$CO$_3$ (0.122 g, 0.373 mmols, 1.5 eq.), xanthphos (0.015 g, 0.0248 mmols, 0.1 eq.) followed by the addition of Pd$_2$(dba)$_3$ (0.012 g, 0.0124 mmols, 0.05 eq.) under nitrogen atmosphere. The resulting reaction mixture was heated at 180° C. in microwave reactor for 1.5 h. Product formation was confirmed by LCMS. The reaction mixture was diluted with water and extracted with ethyl acetate (50 mL×2). Combined organic layer was dried over anhydrous Na$_2$SO$_4$ and concentrated under reduced pressure. The crude product was purified by flash chromatography (0-3% MeOH in DCM as an eluent) to obtain the desired product (0.035 g, 29% Yield) as an off-white solid. LCMS: 487.3 [M+H]$^+$; $^1$H NMR (400 MHz, DMSO-d$_6$) δ 10.83 (br. s., 1H), 9.04 (br. s., 1H), 8.78 (s, 1H), 7.64-7.43 (m, 4H), 7.28 (s, 2H), 6.32 (br. s., 1H), 3.94 (br. s., 2H), 3.01 (d, J=6.1 Hz, 2H), 2.67 (br. s., 2H), 1.84 (br. s., 1H), 1.67 (d, J=12.3 Hz, 2H), 1.39 (s, 9H), 1.13-0.93 (m, 2H).

Step-4: Synthesis of 5-((6-phenyl-5-((piperidin-4-ylmethyl)amino)pyridazin-3-yl)amino)pyrazine-2-carbonitrile: To a solution of tert-butyl4-(((6-((5-cyanopyrazin-2-yl)amino)-3-phenylpyridazin-4-yl)amino)methyl) piperidine-1-carboxylate-4-carboxylate (0.035 g, 0.072 mmols) in DCM (5 mL) was added TFA (0.3 mL) at RT and the resulting reaction mixture was allowed to stir at RT for overnight. Product formation was confirmed by LCMS. The reaction mixture was concentrated under reduced pressure. The obtained residue was washed with n-pentane and then treated with diethyl ether to obtain the desired product as a TFA salt (0.30 g, 3% Yield) as an off-white solid. LCMS: 387.3 [M+H]$^+$; $^1$H NMR (400 MHz, DMSO-d$_6$) δ 8.94-8.72 (m, 2H), 8.52 (br. s., 1H), 8.22 (br. s., 1H), 7.68-7.46 (m, 3H), 7.31 (s, 1H), 7.06 (br. s., 1H), 3.31 (d, J=12.3 Hz, 2H), 3.22-3.03 (m, 2H), 2.92-2.76 (m, 2H), 1.96 (br. s., 1H), 1.85 (d, J=13.2 Hz, 2H), 1.46-1.22 (m, 2H).

Example-2: Synthesis of 6-((5-cyanopyrazin-2-yl)amino)-4-((morpholin-2-ylmethyl)amino)pyridazine-3-carboxamide (Compound No. 1.2)

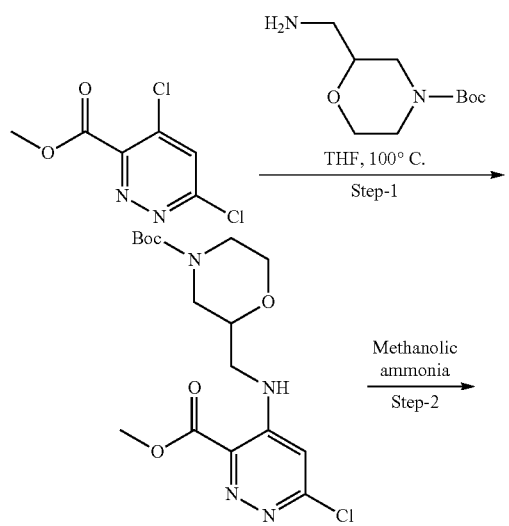

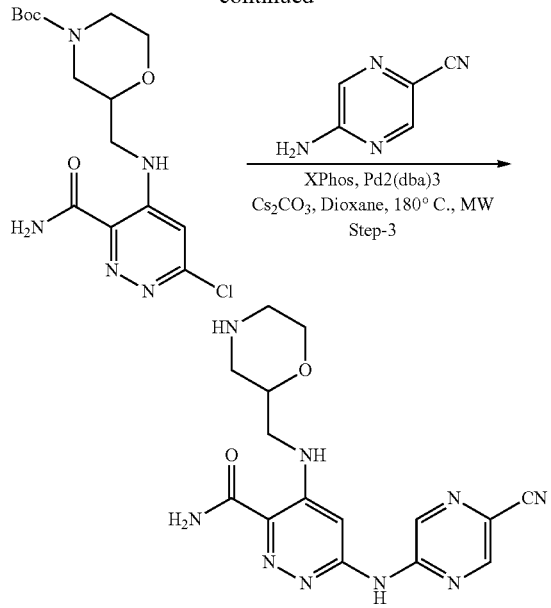

Step-1: Synthesis of tert-butyl 2-(6-chloro-3-(methoxycarbonyl)pyridazin-4-yl)amino)methyl)morpholine-4-carboxylate: To a stirred solution of methyl 4,6-dichloropyridazine-3-carboxylate (1.0 g, 5.0 mmol, 1.0 eq) in THF was added tert-butyl 2-(aminomethyl)morpholine-4-carboxylate (1.07 g, 5.0 mmol, 1.0 eq.) and TEA and the reaction mixture was heated under microwave irradiation at 100° C. for 2 h. After work-up the reaction mixture was purified by column chromatography to get the desired product (0.6 g, 32%). LCMS: 386 [M+1]$^+$ Step-2: Synthesis of tert-butyl 2-(((3-carbamoyl-6-chloropyridazin-4-yl)amino)methyl)morpholine-4-carboxylate: The solution of tert-butyl 2-(((6-chloro-3-(methoxycarbonyl)pyridazin-4-yl)amino)methyl)morpholine-4-carboxylate (0.900 g, 2.32 mmol, 1.0 eq.) in methanolic ammonia (10 mL) was stirred at RT for 15 h. Progress of the reaction was monitored by TLC and LCMS. After completion, the reaction mixture was evaporated under reduced pressure and triturated with DCM:Hexane to get the desired product. (850 mg, 98%) LCMS: 372 [M+1]$^+$ Step-3: Synthesis of 6-((5-cyanopyrazin-2-yl)amino)-4-((morpholin-2-ylmethyl)amino)pyridazine-3-carboxamide: To the stirred solution of tert-butyl 2-(((3-carbamoyl-6-chloropyridazin-4-yl)amino)methyl)morpholine-4-carboxylate (70 mg, 0.188 mmol, 1 eq) and 5-aminopyrazine-2-carbonitrile (27 mg, 0.226 mmol, 1.2 eq) in dioxane (4 mL) added cesium carbonate (184 mg, 0.565 mmol, 3 eq.) to it, purged for 10 minutes then added tris(dibenzylideneacetone) dipalladium(0) (8.62 mg, 0.0094 mmol, 0.05 eq) and Xanthphos (10.91 mg, 0.0188 mmol, 0.1 eq) and further purged for another 15 min, then the reaction mixture was heated using microwave irradiation at 180° C. for 45 minutes. Reaction mixture was extracted using Ethyl acetate (50 mL×3). Combined organic layers were washed with water (20 mL×2), dried over anhydrous sodium sulphate, filtered and concentrated under reduced pressure to afford crude, further dissolved in dioxane (5 mL) added hydrochloric acid in dioxane (0.5 mL) dropwise and allowed the reaction mixture to stir at room temperature until it precipitated out, filtered, washed with diethyl ether (15 mL) and n-pentane (15 mL), dried to afford the crude product which was purified by reverse phase column chromatography to get the desired product (5 mg, 7%). LCMS: 356 [M+1]$^+$. $^1$H NMR (400 MHz, DMSO-d6) δ 11.08 (br. s., 2H), 8.92-9.03 (m, 2H), 8.82 (d, J=1.32 Hz, 1H), 8.38 (br. s., 1H), 7.64 (br. s., 1H), 7.46 (s, 1H), 4.09 (d, J=4.82 Hz, 1H), 3.95 (d, J=8.77 Hz, 1H), 3.83 (br. s., 1H), 3.60-3.71 (m, 1H), 3.12-3.21 (m, 2H), 3.05 (d, J=11.84 Hz, 2H), 2.83-2.96 (m, 1H), 2.70-2.80 (m, 2H), Example-3: Synthesis of 6-((5-cyanopyrazin-2-yl)amino)-4-((piperidin-4-ylmethyl)amino)pyridazine-3-carboxamide (Compound No. 1.3)

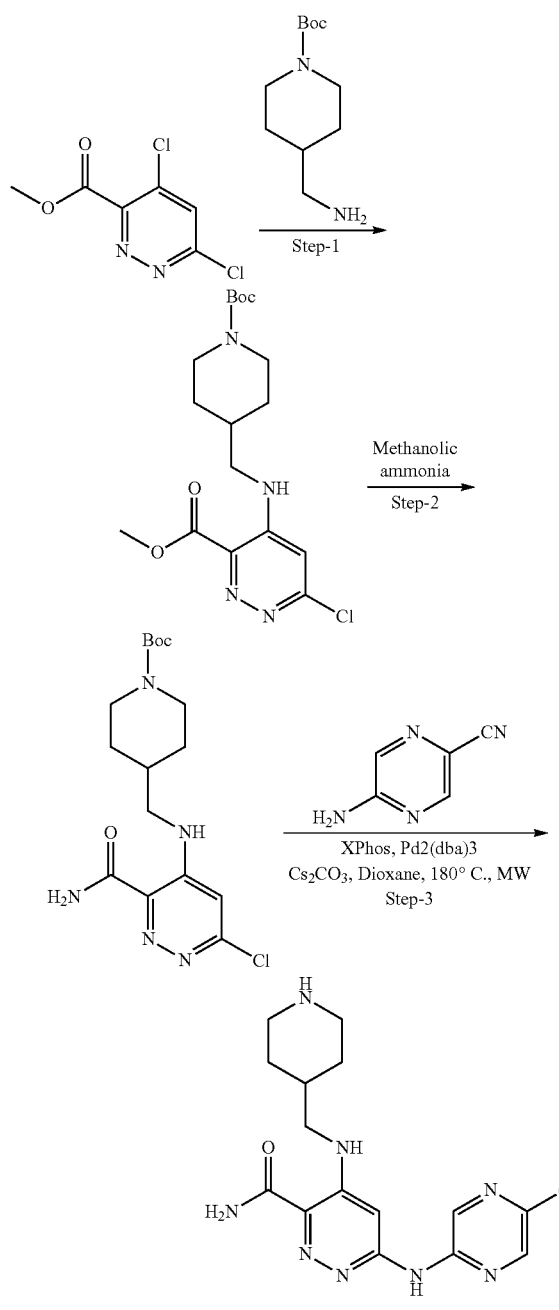

Step-1: Synthesis of methyl 4-(((1-(tert-butoxycarbonyl)piperidin-4-yl)methyl)amino)-6-chloropyridazine-3-carboxylate: To a stirred solution of methyl 4,6-dichloropyridazine-3-carboxylate (1.0 g, 5.0 mmol, 1.0 eq) in THF was added tert-butyl 4-(aminomethyl)piperidine-1-carboxylate (1.06 g, 5.0 mmol, 1.0 eq.) and TEA and the reaction mixture was heated under microwave irradiation at 100° C. for 2 h. After work-up the reaction mixture was purified by column chromatography to get the desired product (0.650 g, 35%). LCMS: 384 [M+1]$^+$ Step-2: synthesis of tert-butyl 4-(((3-carbamoyl-6-chloropyridazin-4-yl)amino)methyl)piperidine-1-carboxylate: The solution of tert-butyl 2-(((6-chloro-3-(methoxycarbonyl)pyridazin-4-yl)amino)methyl)morpholine-4-carboxylate (0.200 g, 2.32 mmol, 1.0 eq.) in methanolic ammonia (5 mL) was stirred at RT for 15 h. Progress of the reaction was monitored by TLC and LCMS. After completion, the reaction mixture was evaporated under reduced pressure and triturated with DCM:Hexane to get the desired product. (180 mg, 94%) LCMS: 370 [M+1]$^+$ Step-3: Synthesis of 6-((5-cyanopyrazin-2-yl)amino)-4-((piperidin-4-ylmethyl)amino)pyridazine-3-carboxamide: To the stirred solution of tert-butyl 4-(((3-carbamoyl-6-chloropyridazin-4-yl)amino)methyl)piperidine-1-carboxylate (100 mg, 0.271 mmol, 1 eq) and 5-aminopyrazine-2-carbonitrile (39.02 mg, 0.3252 mmol, 1.2 eq) in dioxane (6 mL) added cesium carbonate (264087 mg, 0.813 mmol, 3 eq) to it, purged for 10 minutes then added Tris(dibenzylideneacetone) dipalladium(0) (12.39 mg, 0.027 mmol, 0.05 eq) and Xanthphos (10.26 mg, 0.0271 mmol, 0.1 eq) and further purged for another 15 minutes, then the reaction mixture was heated using microwave irradiation at 180° C. for 45 minutes. Combined organic layers were washed with water (20 mL×2), dried over anhydrous sodium sulphate, filtered and concentrated under reduced pressure to afford crude, further dissolved in dioxane (5 mL) added hydrochloric acid in dioxane (0.5 mL) dropwise and allowed the reaction mixture to stir at room temperature until it precipitated out, filtered, washed with diethyl ether (15 mL) and n-pentane (15 mL), dried to afford the crude product which was purified by reverse phase column chromatography to get the desired product (9 mg, 10%). LCMS: 354 [M+1]$^+$. $^1$HNMR (400 MHz, DMSO-d$_6$) δ 8.92-9.04 (m, 2H), 8.83 (s, 1H), 8.37 (br. s., 1H), 7.64 (br. s., 1H), 7.44 (s, 1H), 2.97-3.16 (m, 4H), 2.56-2.72 (m, 2H), 2.33 (br. s., 1H), 1.73 (d, J=13.59 Hz, 2H), 1.26 (d, J=10.52 Hz, 2H)

Example-4: Synthesis of N3-(1-methyl-1H-pyrazol-4-yl)-N5-(morpholin-2-ylmethyl)-6-phenylpyridazine-3,5-diamine (Compound No. 1.4)

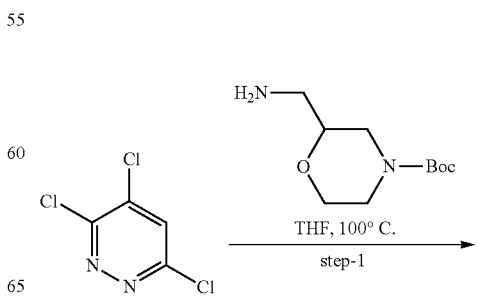

-continued

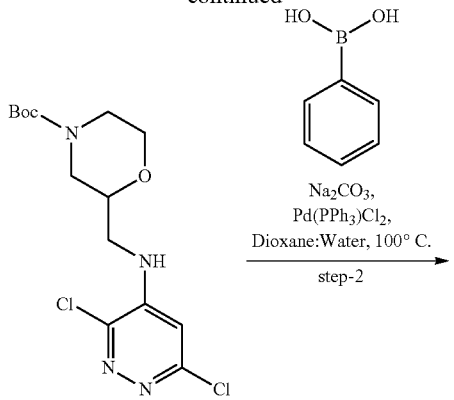

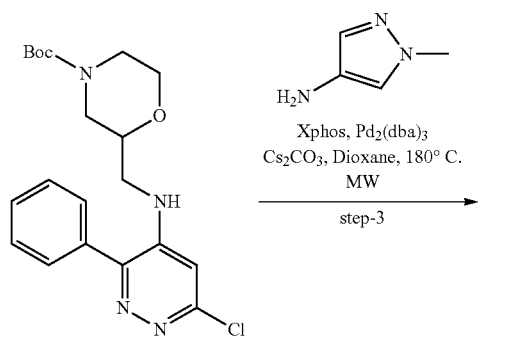

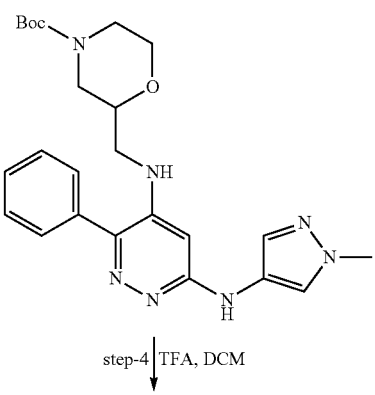

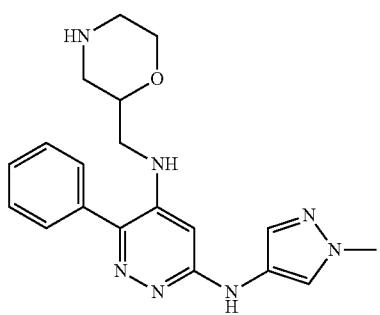

Step-1: Synthesis of tert-butyl 2-(((3,6-dichloropyridazin-4-yl)amino)methyl)morpholine-4-carboxylate: 3,4,6-trichloropyridazine (0.50 g, 2.74 mmol, 1.0 eq.) and tert-butyl 2-(aminomethyl)morpholine-4-carboxylate (0.65 g, 3.02 mmol, 1.10 eq.) were dissolved in THF (10 mL) and heated at 100° C. for overnight. Product formation was confirmed by the LCMS. The reaction mixture was diluted with water and extracted with ethyl acetate (50 mL×2). Combined organic layer was dried over anhydrous Na$_2$SO$_4$ and concentrated under reduced pressure. The crude product was purified by flash chromatography (0-30% ethyl acetate in hexane as an eluent) to obtain desired product (0.25 g, 25%) as an yellow solid. LCMS: 363 [M+H]$^+$ Step-2: tert-butyl 2-(((6-chloro-3-phenylpyridazin-4-yl)amino)methyl)morpholine-4-carboxylate: To a solution of obtain tert-butyl 2-(((3,6-dichloropyridazin-4-yl)amino)methyl)morpholine-4-carboxylate (0.200, 0.552 mmol, 1.0 eq.) in dioxane:water (5:2 mL) was added phenylboronic acid (0.075 g, 0.607 mmol, 1.1 eq.), Na$_2$CO$_3$ (0.118 g, 1.104 mmol, 2.0 eq.) followed by the addition of Pd(PPh$_3$)Cl$_2$ (0.020 g, 0.027 mmol, 0.05 eq.). The resulting reaction mixture was heated at 100° C. for overnight. Product formation was confirmed by LCMS. The reaction mixture was diluted with water and extracted with ethyl acetate (50 mL×2). Combined organic layer was dried over anhydrous Na$_2$SO$_4$ and concentrated under reduced pressure. The crude product was purified by flash chromatography (10-30% ethyl acetate in hexane as an eluent) to obtain the desired product (0.12 g, 54%) as a yellow solid. LCMS: 405 [M+H]$^+$ Step-3: Synthesis of tert-butyl 2-(((6-((1-methyl-1H-pyrazol-4-yl)amino)-3-phenylpyridazin-4-yl)amino)methyl)morpholine-4-carboxylate: To a solution of tert-butyl 2-(((6-chloro-3-phenylpyridazin-4-yl)amino)methyl)morpholine-4-carboxylate (0.100 g, 0.247 mmol, 1.0 eq.) in dioxane (3 mL) was added 1-methyl-1H-pyrazol-4-amine (0.027 g, 0.272 mmol, 1.2 eq.), Cs$_2$CO$_3$ (0.160 g, 0.495 mmol, 2.0 eq.), xanthphos (0.015 g, 0.0248 mmol, 0.1 eq.) followed by the addition of Pd$_2$(dba)$_3$ (0.023 g, 0.024 mmol, 0.10 eq.) under nitrogen atmosphere. The resulting reaction mixture was heated at 140° C. in microwave reactor for 1 h. Product formation was confirmed by LCMS. The reaction mixture was diluted with water and extracted with ethyl acetate (50 mL×2). Combined organic layer was dried over anhydrous Na$_2$SO$_4$ and concentrated under reduced pressure. The crude product was purified by flash chromatography (0-30% Ethyl acetate in Hexane as an eluent) to obtain the desired product. (0.050 g, 40%) as an off-white solid. LCMS: 466 [M+H]$^+$ Step-4: Synthesis of N$^3$-(1-methyl-1H-pyrazol-4-yl)-N$^5$-(morpholin-2-ylmethyl)-6-phenylpyridazine-3,5-diamine: Tert-butyl 2-(((6-((1-methyl-1H-pyrazol-4-yl)amino)-3-phenylpyridazin-4-yl)amino)methyl)morpholine-4-carboxylate (0.050 g, 0.107 mmol) was dissolved in 4 N dioxane (5 mL) and the resulting reaction mixture was allowed to stir at RT for overnight. Product formation was confirmed by LCMS. The reaction mixture was concentrated under reduced pressure. The crude product obtained was purified by reversed phase HPLC to obtain the desired product (0.005 g, 12%) as a brown semi solid. LCMS: 366 [M+H]$^+$; $^1$H NMR: (400 MHz, DMSO-d$_6$) δ 8.65 (br. s., 1H), 7.95 (s, 1H), 7.64-7.35 (m, 5H), 6.03 (s, 1H), 5.51 (br. s., 1H), 3.80 (s, 4H), 3.48-3.33 (m, 4H), 3.06 (dd, J=6.1, 14.0 Hz, 3H), 2.79 (d, J=11.4 Hz, 1H), 2.72-2.57 (m, 2H), 2.39 (d, J=10.1 Hz, 1H).

Example-5: Synthesis of tert-butyl 2-((6-(5-cyano-pyrazin-2-ylamino)-3-(trifluoromethyl)pyridazin-4-ylamino)methyl)morpholine-4-carboxylate (Compound No. 1.5)

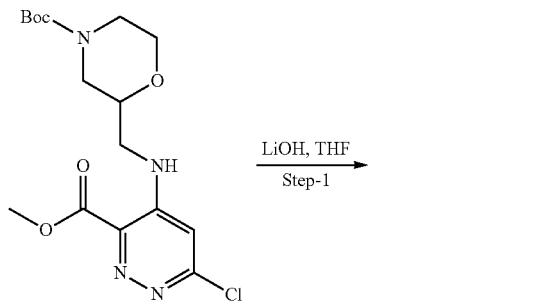

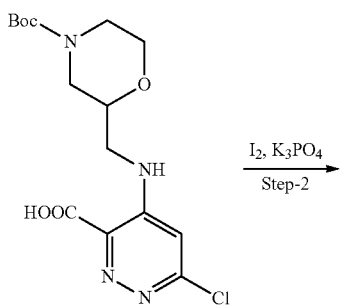

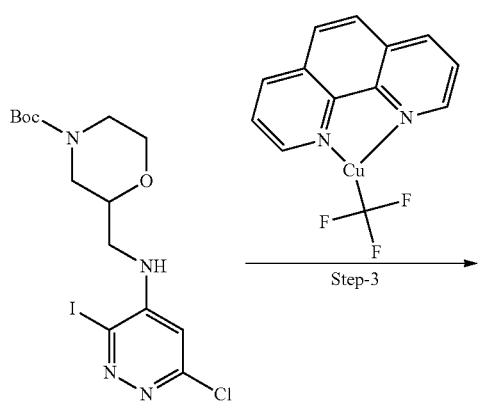

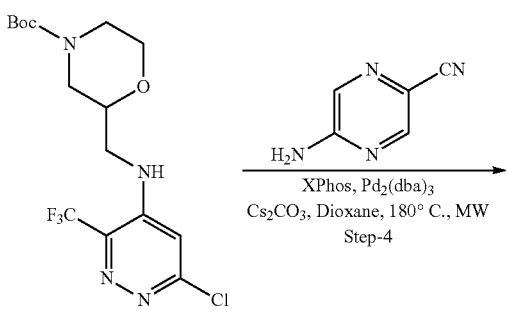

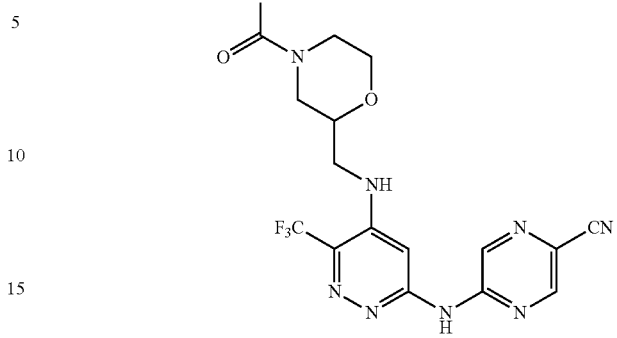

Step-1: Synthesis of 4-((4-(tert-butoxycarbonyl)morpholin-2-yl)methylamino)-6-chloropyridazine-3-carboxylic acid: tert-Butyl 2-((6-chloro-3-(methoxycarbonyl)pyridazin-4-ylamino)methyl)morpholine-4-carboxylate (0.192 g, 0.5 mmol, 1.0 eq) was dissolved in THF (2 mL). To this solution 2 mL aqueous Lithium hydroxide (0.052 g, 1.0 mmol, 2.0 eq) solution was added and the reaction was allowed to stir at RT for 2 h. The reaction mixture was concentrated under vacuum and the reaction mixture was acidified with dilute HCl to get the precipitates which are filtered and dried under vacuum to obtain the title compound (0.090 g, 48%). LCMS: 371 [M+H]+

Step-2: Synthesis of tert-butyl 2-((6-chloro-3-iodopyridazin-4-ylamino)methyl)morpholine-4-carboxylate: A 10 mL microwave vial was charged with I2 (0.101 g, 4.0 eq, 0.4 mmol) followed by addition of anhydrous K3PO4 (0.021 g, 0.1 mmol, 1.0 eq), 4-((4-(tert-butoxycarbonyl)morpholin-2-yl)methylamino)-6-chloropyridazine-3-carboxylic acid (0.037 g, 0.1 mmol, 1.0 eq) and acetonitrile (1.5 mL). The reaction was allowed to heat at 100° C. for 1 h using microwave irradiation; the reaction was allowed to cool to RT and diluted with saturated aqueous sodium thiosulphate (2 mL) solution. The reaction was extracted with ethyl acetate (3×10 mL). The combined organic layer was washed (brine), dried (anhydrous Na2SO4), and concentrated under reduced pressure to get the title compound (0.025 g, 55%)which was used as such for next step without further purification. LCMS: 453 [M+H]+

Step-3: Synthesis of tert-butyl 2-((6-chloro-3-(trifluoromethyl)pyridazin-4-ylamino)methyl)morpholine-4-carboxylate: To a stirred solution of tert-butyl 2-((6-chloro-3-iodopyridazin-4-ylamino)methyl)morpholine-4-carboxylate (0.022 g, 0.05 mmol, 1.0 eq) in DMF (1 mL) was added (1,10-Phenanthroline)(trifluoromethyl)copper(I) (0.019 g, 0.06 mmol, 1.2 eq.). The reaction mixture was purged with N2 and allowed to heat at 80° C. for 18 h. On completion water was added and the reaction mixture was extracted with ethyl acetate (3×10 mL). The combined organic layer was washed (brine), dried (anhydrous Na2SO4), and concentrated under reduced pressure to get the title compound (0.010 g, 52%). LCMS: 397 [M+H]+.

Step-4: Synthesis of tert-butyl 2-((6-(5-cyanopyrazin-2-ylamino)-3-(trifluoromethyl)pyridazin-4-ylamino)methyl)morpholine-4-carboxylate: To a solution of tert-butyl 2-((6-chloro-3-(trifluoromethyl)pyridazin-4-ylamino)methyl)morpholine-4-carboxylate (0.270 g, 0.681 mmol, 1.0 eq.) in dioxane (5 mL) was added 5-aminopyrazine-2-carbonitrile (0.081 g, 0.681 mmol, 1.0 eq.), Cs2CO3 (0.442 g, 1.36 mmol, 2.0 eq.), X-phos (0.031 g, 0.034 mmol, 0.05 eq.)

followed by the addition of $Pd_2(dba)_3$ (0.016 g, 0.034 mmol, 0.0.05 eq.) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×2). Combined organic layer was dried over anhydrous $Na_2SO_4$ and concentrated under reduced pressure. The crude product was purified by flash chromatography followed by RP-HPLC to obtain the title compound product. (0.020 g, 6%). LCMS: 481 $[M+H]^+$ $^1H$ NMR (400 MHz, DMSO-$d_6$) δ 11.20 (br. s., 1H), 8.89 (br. s., 1H), 8.83 (br. s., 1H), 7.68 (s, 1H), 6.94 (br. s., 1H), 3.84 (d, J=11.40 Hz, 2H), 3.69 (d, J=14.47 Hz, 1H), 3.60 (br. s., 1H), 3.38 (br. s., 1H), 2.90 (br. s., 2H).

Example-6: Synthesis of tert-butyl 4-((6-(5-cyano-pyrazin-2-ylamino)-3-(trifluoromethyl)pyridazin-4-ylamino)methyl)piperidine-1-carboxylate (Compound No. 1.6)

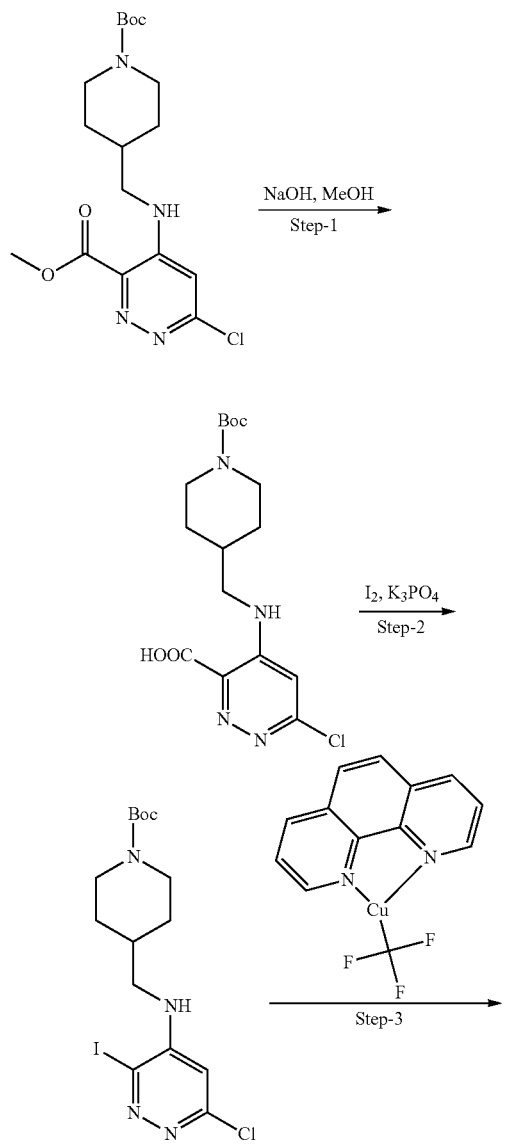

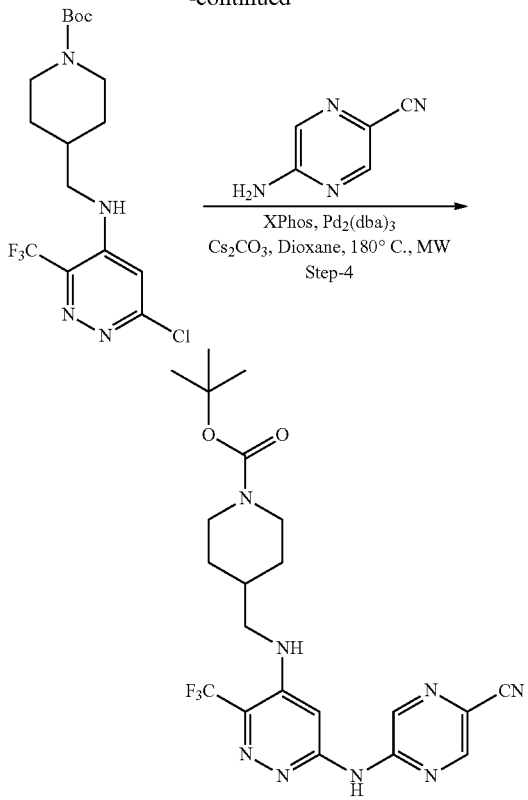

Step-1: Synthesis of 4-((1-(tert-butoxycarbonyl)piperidin-4-yl)methylamino)-6-chloropyridazine-3-carboxylic acid: methyl 4-((1-(tert-butoxycarbonyl)piperidin-4-yl)methylamino)-6-chloropyridazine-3-carboxylate (0.90 g, 2.34 mmol, 1.0 eq) was dissolved in MeOH (5 mL). To this solution aqueous sodium hydroxide (0.28 g, 7.02 mmol, 3.0 eq) solution was added and the reaction was allowed to stir at RT for 2 h. The reaction mixture was concentrated under vacuum and the reaction mixture was acidified with dilute citric acid to get the precipitates which are filtered and dried under vacuum to obtain the title compound (0.6 g, 69%). LCMS: 371.3 $[M+H]^+$ Step-2: Synthesis of tert-butyl 4-((6-chloro-3-iodopyridazin-4-ylamino)methyl)piperidine-1-carboxylate: A 30 mL microwave vial was charged with 12 (1.648 g, 4.0 eq, 6.48 mmol) followed by addition of anhydrous $K_3PO_4$ (0.343 g, 1.62 mmol, 1.0 eq), 4-((1-(tert-butoxycarbonyl)piperidin-4-yl)methylamino)-6-chloropyridazine-3-carboxylic acid (0.6 g, 1.621 mmol, 1.0 eq) and acetonitrile (10 mL). The reaction was allowed to heat at 100° C. for 1 h using microwave irradiation; the reaction was allowed to cool to RT and diluted with saturated aqueous sodium thiosulphate (5 mL) solution. The reaction was extracted with ethyl acetate (3×10 mL). The combined organic layer was washed (brine), dried (anhydrous $Na_2SO_4$), and concentrated under reduced pressure to get the title compound (0.5 g, 68%)which was used as such for next step without further purification. LCMS: 453.2 $[M+H]^+$ Step-3: tert-butyl 4-((6-chloro-3-(trifluoromethyl)pyridazin-4-ylamino)methyl)piperidine-1-carboxylate: To a stirred solution of tert-butyl 4-((6-chloro-3-iodopyridazin-4-ylamino)methyl)piperidine-1-carboxylate (0.5 g, 1.10 mmol, 1.0 eq) in DMF (3 mL) was added (1,10-Phenanthroline)(trifluoromethyl)copper(I) (0.44 g, 1.32 mmol, 1.2 eq).

The reaction mixture was purged with N₂ and allowed to heat at 80° C. for 18 h. On completion water was added and the reaction mixture was extracted with ethyl acetate (3×10 mL). The combined organic layer was washed (brine), dried (anhydrous Na₂SO₄), and concentrated under reduced pressure to get the title compound (0.3 g, 69%). LCMS: 395.3 [M+H]⁺.

Step-4: tert-butyl 4-((6-(5-cyanopyrazin-2-ylamino)-3-(trifluoromethyl)pyridazin-4-ylamino)methyl)piperidine-1-carboxylate: To a solution of tert-butyl 4-((6-chloro-3-(trifluoromethyl)pyridazin-4-ylamino)methyl)piperidine-1-carboxylate (0.3 g, 0.76 mmol, 1.0 eq) in dioxane (5 mL) was added 5-aminopyrazine-2-carbonitrile (0.091 g, 0.76 mmol, 1.0 eq), Cs₂CO₃ (0.494 g, 1.52 mmol, 2.0 eq.), X-phos (0.018 g, 0.038 mmol, 0.05 eq) followed by the addition of Pd₂(dba)₃ (0.034 g, 0.038 mmol, 0.0.05 eq) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×2). Combined organic layer was dried over anhydrous Na₂SO₄ and concentrated under reduced pressure. The crude product was purified by flash chromatography followed by RP-HPLC to obtain the title compound product. (0.020 g, 6%). LCMS: 481 [M+H]⁺ ¹H NMR (400 MHz, DMSO-d₆) δ d 8.56 (br. s., 2H), 7.38 (br. s., 1H), 6.71 (s, 2H), 3.91 (br. s., 2H), 3.08 (d, J=6.14 Hz, 2H), 1.82 (br. s., 1H), 1.54-1.70 (m, 3H), 0.92-1.12 (m, 2H)

Example-7: Synthesis of 2-((6-(5-cyanopyrazin-2-ylamino)-3-(trifluoromethyl)pyridazin-4-ylamino)methyl)morpholin-4-ium 2,2,2-trifluoroacetate (Compound No. 1.7)

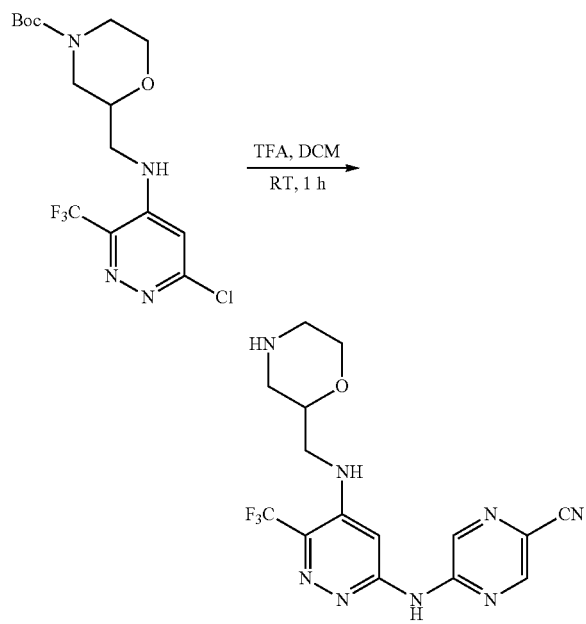

To a solution of tert-butyl 2-((6-chloro-3-(trifluoromethyl)pyridazin-4-ylamino)methyl)morpholine-4-carboxylate (0.010 g, 0.02 mmol) in DCM (3 mL) was added TFA (0.1 mL) at RT and the resulting reaction mixture was allowed to stir at RT for 1 h. Product formation was confirmed by LCMS and TLC. Diethyl ether was added to the reaction mixture to get the precipitates. The solvent was decanted and the solid was dried under vacuum to get the title compound (0.003 g, 39%). LCMS: 381.4 [M+H]⁺; ¹H NMR (400 MHz, DMSO-d₆) δ 11.28 (s, 1H), 8.96 (br. s., 1H), 8.87 (d, J=6.58 Hz, 2H), 7.66-7.75 (m, 1H), 6.96 (d, J=5.70 Hz, 1H), 4.01 (d, J=10.09 Hz, 1H), 3.92 (d, J=8.77 Hz, 1H), 3.64-3.74 (m, 1H), 3.39 (d, J=5.70 Hz, 2H), 3.27 (d, J=12.72 Hz, 1H), 3.19 (d, J=12.28 Hz, 1H), 3.02 (d, J=10.96 Hz, 1H), 2.85 (d, J=10.96 Hz, 1H).

Example-8: Synthesis of 4-((6-(5-cyanopyrazin-2-ylamino)-3-(trifluoromethyl)pyridazin-4-ylamino)methyl)piperidinium 2,2,2-trifluoroacetate (Compound No. 1.8)

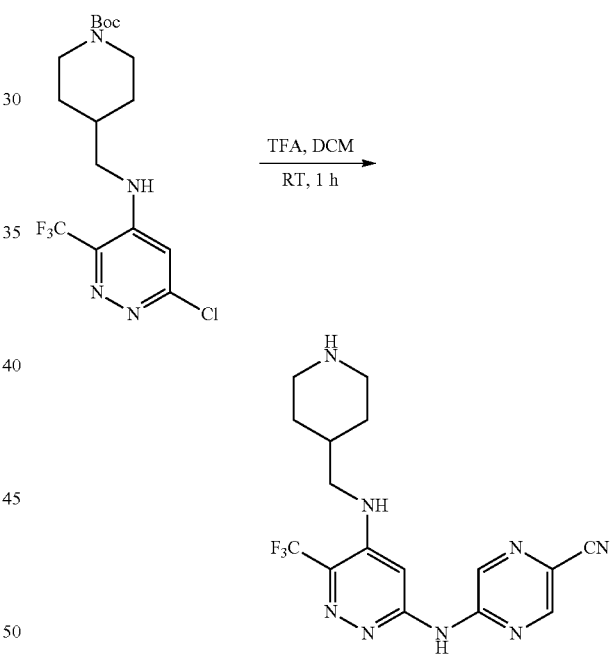

To a solution of tert-butyl 4-((6-chloro-3-(trifluoromethyl)pyridazin-4-ylamino)methyl)piperidine-1-carboxylate (0.015 g, 0.03 mmol) in DCM (3 mL) was added TFA (0.1 mL) at RT and the resulting reaction mixture was allowed to stir at RT for 1 h. Product formation was confirmed by LCMS and TLC. Diethyl ether was added to the reaction mixture to get the precipitates. The solvent was decanted and the solid was dried under vacuum to get the title compound (0.007 g, 61%). LCMS: 379.4 [M+H]⁺; ¹H NMR (400 MHz, DMSO-d₆) δ 11.27 (br. s., 1H), 8.82-8.94 (m, 2H), 8.75 (br. s., 1H), 8.59 (br. s., 1H), 7.68 (s, 1H), 7.11 (br. s., 1H), 3.28 (d, J=12.28 Hz, 2H), 3.16 (br. s., 2H), 2.82 (d, J=8.33 Hz, 2H), 1.95 (br. s., 1H), 1.82 (d, J=12.72 Hz, 2H), 1.32-1.53 (m, 3H), 1.23 (br. s., 1H), 1.06 (d, J=14.03 Hz, 1H).

Example-9: Synthesis of 5-(5-(morpholin-2-yl-methoxy)pyridazin-3-ylamino)pyrazine-2-carbonitrile (Compound No. 1.9)

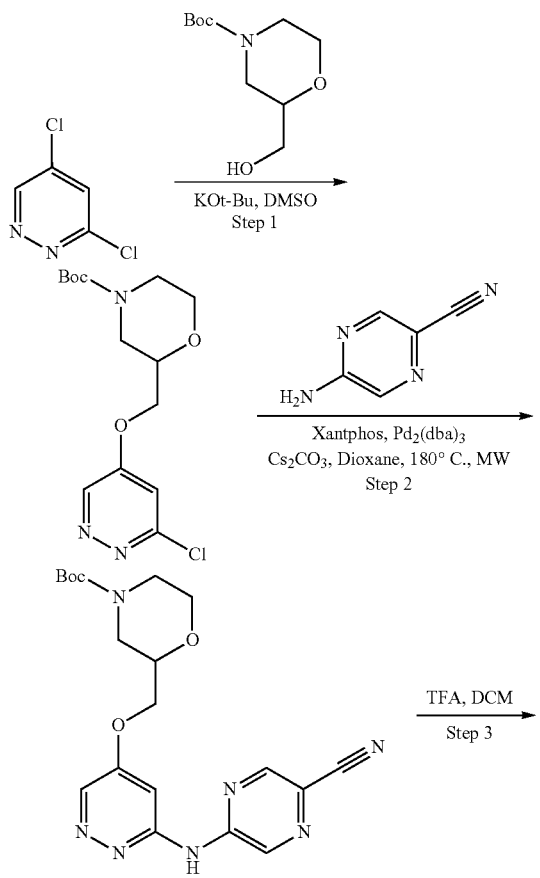

Step-1: Synthesis of tert-butyl 2-((6-chloropyridazin-4-yloxy)methyl)morpholine-4-carboxylate: tert-butyl 2-(hydroxymethyl)morpholine-4-carboxylate (0.733 g, 0.0033 mol, 1.0 eq) was dissolved in DMSO (10 mL). To this solution potassium tert butoxide (0.380 g, 0.0033 mmol, 1.0 eq) solution was added and the reaction mixture was allowed to stir at RT for 20 min. The reaction mixture was cooled to 0° C. and 3,5-dichloropyridazine (0.5 g, 0.0033 mol, 1.0 eq) was added to it and the reaction was stirred at RT for 16 h. The reaction was diluted with water and extracted with ethyl acetate. The combined organic layers were washed (brine), dried (anhydrous $Na_2SO_4$), and concentrated under vacuum and to get the title compound (0.800 g, 74%). LCMS: 330 $[M+H]^+$.

Step-2: Synthesis of tert-butyl 2-((6-(5-cyanopyrazin-2-ylamino)pyridazin-4-yloxy)methyl)morpholine-4-carboxylate: To a solution of tert-butyl 2-((6-chloropyridazin-4-yloxy)methyl)morpholine-4-carboxylate (0.2 g, 0.6 mmol, 1.0 eq) in dioxane (5 mL) was added 5-aminopyrazine-2-carbonitrile (0.072 g, 0.6 mmol, 1.0 eq), $Cs_2CO_3$ (0.395 g, 1.2 mmol, 2.0 eq), Xantphos (0.017 g, 0.038 mmol, 0.05 eq) followed by the addition of $Pd_2(dba)_3$ (0.027 g, 0.038 mmol, 0.05 eq) under nitrogen atmosphere. The resulting reaction mixture was heated at 180° C. in microwave reactor for 2 h. Product formation was confirmed by LCMS. The reaction mixture was diluted with water and extracted with ethyl acetate (50 mL×2). Combined organic layer was dried over anhydrous $Na_2SO_4$ and concentrated under reduced pressure. The crude product was purified by flash chromatography to obtain the title compound. (0.030 g, 12%). LCMS: 414 $[M+H]^+$ Step-3: Synthesis of 5-(5-(morpholin-2-ylmethoxy)pyridazin-3-ylamino)pyrazine-2-carbonitrile: To a solution of tert-butyl 2-((6-(5-cyanopyrazin-2-ylamino)pyridazin-4-yloxy)methyl)morpholine-4-carboxylate (0.030 g, 0.07 mmol) in DCM (5 mL) was added TFA (0.01 mL) at RT and the resulting reaction mixture was allowed to stir at RT for 15 min. Product formation was confirmed by LCMS and TLC. Diethyl ether was added to the reaction mixture to get the precipitates. The solvent was decanted and the solid was dried under vacuum to get the title compound (0.01 g, 45%). LCMS: 314 $[M+H]^+$; $^1H$ NMR (400 MHz, DMSO-d6) δ 11.24 (br. s., 1H), 9.11 (br. s., 2H), 8.95 (br. s., 1H), 8.81 (br. s., 2H), 7.73 (br. s., 1H), 4.28 (br. s., 2H), 4.10 (br. s., 1H), 4.03 (d, J=10.96 Hz, 1H), 3.77 (br. s., 1H), 3.36 (d, J=10.52 Hz, 1H), 3.24 (d, J=9.65 Hz, 1H), 3.03 (br. s., 2H)

Example-10: Synthesis of 5-(5-((1-methylpiperidin-4-yl)methylamino)pyridazin-3-ylamino)pyrazine-2-carbonitrile (Compound No. 1.10)

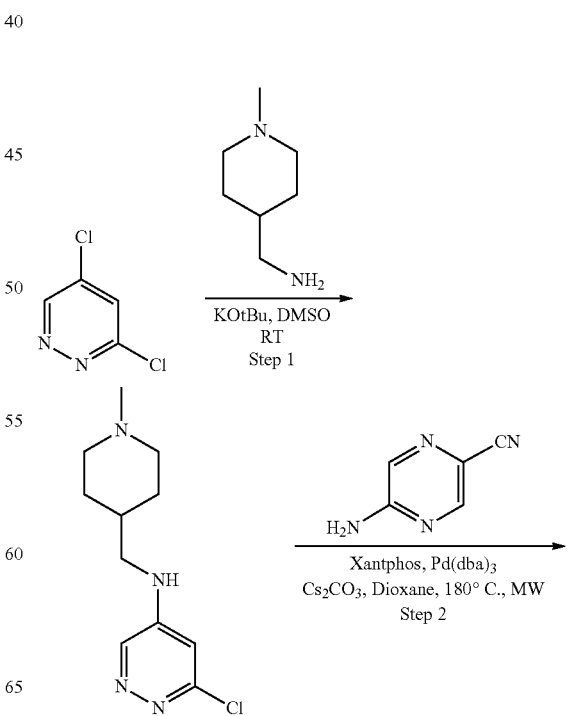

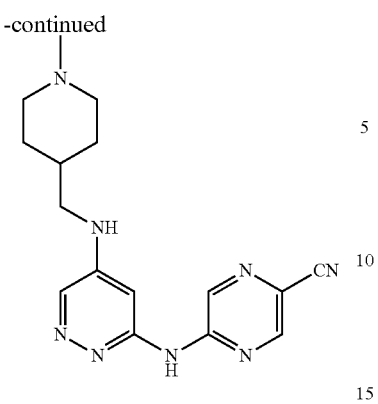

Step-1: Synthesis of 6-chloro-N-((1-methylpiperidin-4-yl)methyl)pyridazin-4-amine: To a solution of 3,5-dichloropyridazine (0.500 g, 0.0033 mol, 1.0 eq) and (1-methylpiperidin-4-yl)methanamine (0.432 g, 0.0033 mol, 1.0 eq) in ACN (10 mL was added DIPEA (1.2 mL, 0.0066 mol, 2.0 eq). The reaction mixture was heated at 80° C. for 3 h. the reaction mixture was allowed to cool to RT and concentrated under vacuum to get the crude which was purified by normal phase silica gel column chromatography to get the title compound (0.500 g, 63%). LCMS: 241[M+H]$^+$.

Step-2: Synthesis of 5-(5-(((1-methylpiperidin-4-yl)methylamino)pyridazin-3-ylamino)pyrazine-2-carbonitrile: To a solution of 6-chloro-N-((1-methylpiperidin-4-yl)methyl) pyridazin-4-amine (0.1 g, 0.41 mmol, 1.0 eq) in DMF (4 mL) was added 5-aminopyrazine-2-carbonitrile (0.055 g, 0.45 mmol, 1.1 eq), Cs$_2$CO$_3$ (0.4 g, 1.23 mmol, 3.0 eq), Xantphos (0.023 g, 0.04 mmol, 0.1 eq.) followed by the addition of Pd$_2$(dba)$_3$ (0.018 g, 0.02 mmol, 005 eq) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×2). Combined organic layer was dried over anhydrous Na$_2$SO$_4$ and concentrated under reduced pressure. The crude product was purified by RP-HPLC to obtain the title compound (0.005 g, 4%). LCMS: 325 [M+H]$^+$ $^1$H NMR (400 MHz, DMSO-d6) δ 8.96 (br. s., 1H), 8.73 (br. s., 1H), 8.34 (br. s., 1H), 7.26 (br. s., 1H), 7.06 (br. s., 1H), 2.98 (br. s., 2H), 2.86 (br. s., 2H), 2.21 (br. s., 2H), 1.90 (br. s., 3H), 1.71 (d, J=10.52 Hz, 2H), 1.23 (br. s., 2H)

Example-11: Synthesis of 6-(5-cyanopyrazin-2-ylamino)-N-methyl-4-(morpholin-2-ylmethylamino) pyridazine-3-carboxamide (Compound No. 1.11)

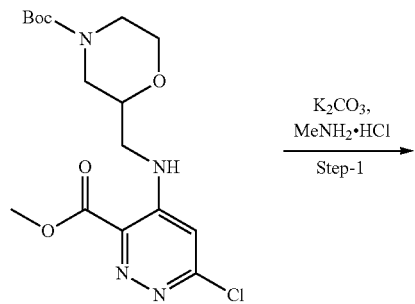

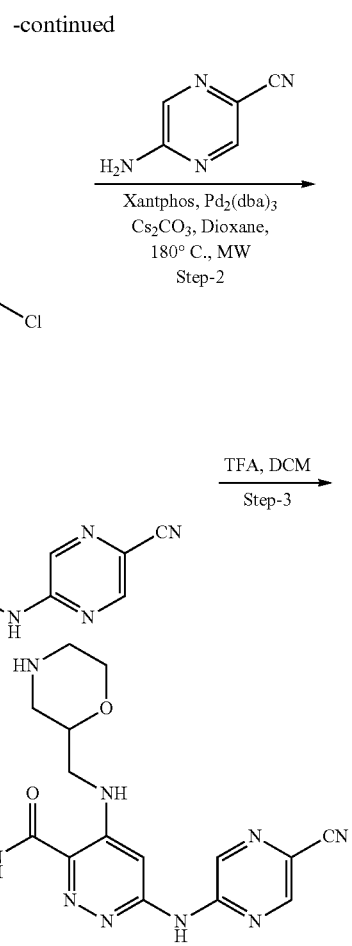

Step-1: Synthesis of tert-butyl 2-((6-chloro-3-(methylcarbamoyl)pyridazin-4-ylamino)methyl)morpholine-4-carboxylate: To a solution of tert-butyl 2-((6-chloro-3-(methoxycarbonyl)pyridazin-4-ylamino)methyl) morpholine-4-carboxylate (0.200 g, 0.51 mmol, 1.0 eq) in methanol was added K$_2$CO$_3$ (0.140 g, 1.05 mmol, 2.0 eq) and methylamine hydrochloride (0.068 g, 1.02 mmol, 2.0 eq). The reaction mixture was allowed to stir at RT for 24 h and poured over ice to get the precipitates which were filtered under vacuum to get the title compound (0.175 g, 63%). LCMS: 386 [M+H]$^+$.

Step-2: Synthesis of tert-butyl 2-((6-(5-cyanopyrazin-2-ylamino)-3-(methylcarbamoyl)pyridazin-4-ylamino) methyl)morpholine-4-carboxylate: To a solution of tert-butyl 2-((6-chloro-3-(methylcarbamoyl)pyridazin-4-ylamino)methyl)morpholine-4-carboxylate (0.17 g, 0.44 mmol, 1.0 eq) in Dioxane (4 mL) was added 5-aminopyrazine-2-carbonitrile (0.058 g, 0.48 mmol, 1.1 eq), Cs$_2$CO$_3$ (0.43 g, 1.32 mmol, 3.0 eq.), Xantphos (0.025 g, 0.044 mmol, 0.1 eq) followed by the addition of Pd$_2$(dba)$_3$ (0.020 g, 0.022 mmol, 0.05 eq) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×3). Combined organic layer was dried over anhydrous Na$_2$SO$_4$ and concentrated under reduced pressure. The crude product was purified by normal phase silica gel column chromatography to obtain the title compound (0.080 g, 39%). LCMS: 470 [M+H]$^+$ Step-3: Synthesis of 6-(5-cyanopyrazin-2-ylamino)-N-methyl-4-(morpholin-2-ylmethylamino)pyridazine-3-carboxamide: To a solution of tert-butyl 2-((6-(5-cyanopyrazin-2-ylamino)-3-(methylcarbamoyl)pyridazin-4-ylamino)methyl)morpholine-4-carboxylate (0.080 g, 0.17 mmol) in DCM (5 mL) was added TFA (0.26 mL) at RT and the resulting reaction mixture was allowed to stir at RT for 15 min. Product formation was confirmed by LCMS and TLC. Diethyl ether was added to the reaction mixture to get the precipitates. The solvent was decanted and the solid was dried under vacuum to get the title compound (0.05 g, 79%). LCMS: 370 [M+H]$^+$; $^1$H NMR (400 MHz, DMSO-d6) δ 11.11 (br. s., 1H), 8.97-9.08 (m, 2H), 8.86-8.95 (m, 2H), 8.81 (s, 1H), 7.50 (s, 1H), 4.05 (d, J=9.65 Hz, 1H), 3.91 (br. s., 1H), 3.68-3.76 (m, 2H), 3.43 (d, J=13.59 Hz, 2H), 3.33 (d, J=11.84 Hz, 2H), 3.22 (d, J=11.84 Hz, 1H), 3.03 (br. s., 1H), 2.89 (d, J=11.40 Hz, 1H), 2.80 (d, J=4.82 Hz, 2H).

Example-12: Synthesis of 6-(5-cyanopyrazin-2-ylamino)-N-cyclopropyl-4-(morpholin-2-ylmethylamino)pyridazine-3-carboxamide (Compound No. 1.12)

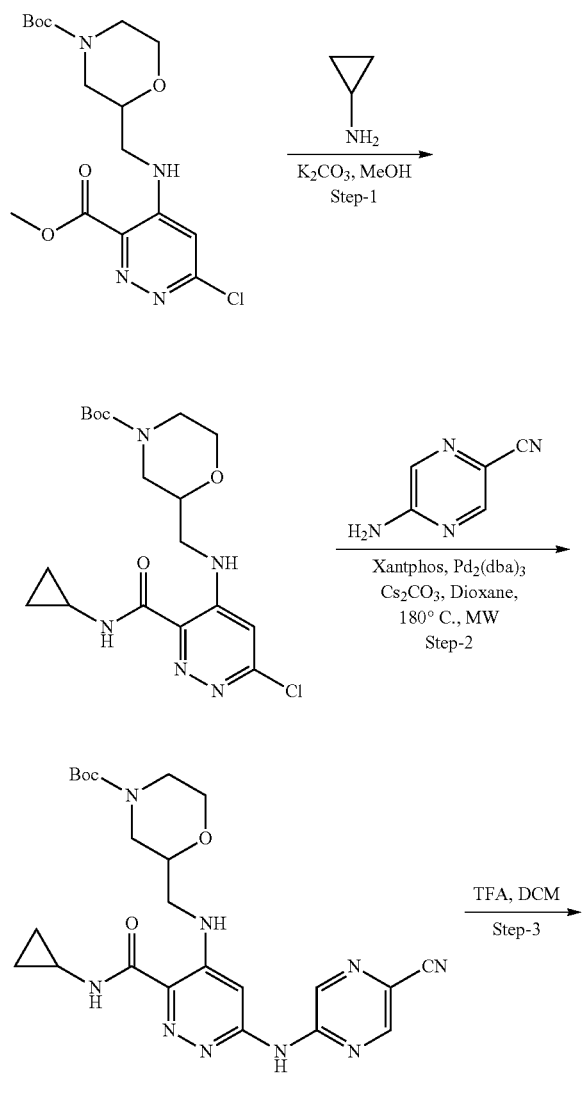

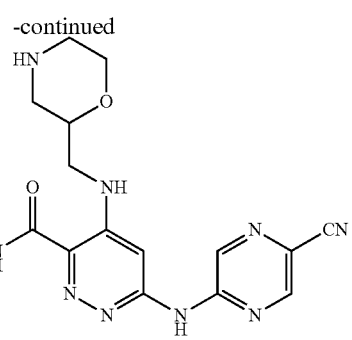

Step-1: Synthesis of tert-butyl 2-((6-chloro-3-(cyclopropylcarbamoyl)pyridazin-4-ylamino)methyl)morpholine-4-carboxylate: To a solution of tert-butyl 2-((6-chloro-3-(methoxycarbonyl)pyridazin-4-ylamino)methyl)morpholine-4-carboxylate (0.205 g, 0.53 mol, 1.0 eq) in methanol was added K$_2$CO$_3$ (0.146 g, 1.06 mmol, 2.0 eq) and cyclopropylamine (0.060 g, 1.06 mmol, 2.0 eq). The reaction mixture was allowed to stir at RT for 24 h and poured over ice to get the precipitates which were filtered under vacuum to get the title compound (0.052 g, 24%). LCMS: 412 [M+H]$^+$.

Step-2: Synthesis of tert-butyl 2-((6-(5-cyanopyrazin-2-ylamino)-3-(cyclopropylcarbamoyl)pyridazin-4-ylamino)methyl)morpholine-4-carboxylate: To a solution of tert-butyl 2-((6-chloro-3-(cyclopropylcarbamoyl)pyridazin-4-ylamino)methyl)morpholine-4-carboxylate (0.05 g, 0.12 mmol, 1.0 eq) in dioxane (3 mL) was added 5-aminopyrazine-2-carbonitrile (0.016 g, 0.13 mmol, 1.1 eq), Cs$_2$CO$_3$ (0.117 g, 0.36 mmol, 3.0 eq.), Xantphos (0.005 g, 0.008 mmol, 0.05 eq) followed by the addition of Pd$_2$(dba)$_3$ (0.003 g, 0.003 mmol, 0.002 eq) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×3). Combined organic layer was dried over anhydrous Na$_2$SO$_4$ and concentrated under reduced pressure. The crude product was purified by normal phase silica gel column chromatography to obtain the title compound (0.032 g, 53%). LCMS: 496 [M+H]$^+$ Step-3: Synthesis of 6-(5-cyanopyrazin-2-ylamino)-N-cyclopropyl-4-(morpholin-2-ylmethylamino)pyridazine-3-carboxamide: To a solution of tert-butyl 2-((6-(5-cyanopyrazin-2-ylamino)-3-(cyclopropylcarbamoyl)pyridazin-4-ylamino)methyl)morpholine-4-carboxylate (0.030 g, 0.006 mmol) in DCM (5 mL) was added TFA (0.5 mL) and the resulting reaction mixture was allowed to stir at RT for 2 h. Progress of the reaction is monitored by LCMS. Diethyl ether (10 mL) was added and the resulting precipitates were filtered and washed with ether to get the title compound as TFA salt (0.023 g, 98% Yield). LCMS: 396 [M+H]$^+$; $^1$H NMR (400 MHz, DMSO-d6) δ 11.09 (s, 1H), 8.97-9.03 (m, 2H), 8.95 (s, 1H), 8.89 (br. s., 1H), 8.82 (s, 1H), 7.47 (s, 1H), 3.72 (br. s., 2H), 3.33 (d, J=12.28 Hz, 3H), 3.22 (d, J=11.84 Hz, 2H), 2.88 (br. s., 2H), 0.66-0.72 (m, 4H)

Example-13: Synthesis of 5-(6-(1-methyl-1H-pyrazol-3-yl)-5-(morpholin-2-ylmethoxy)pyridazin-3-ylamino)pyrazine-2-carbonitrile (Compound No. 1.13)

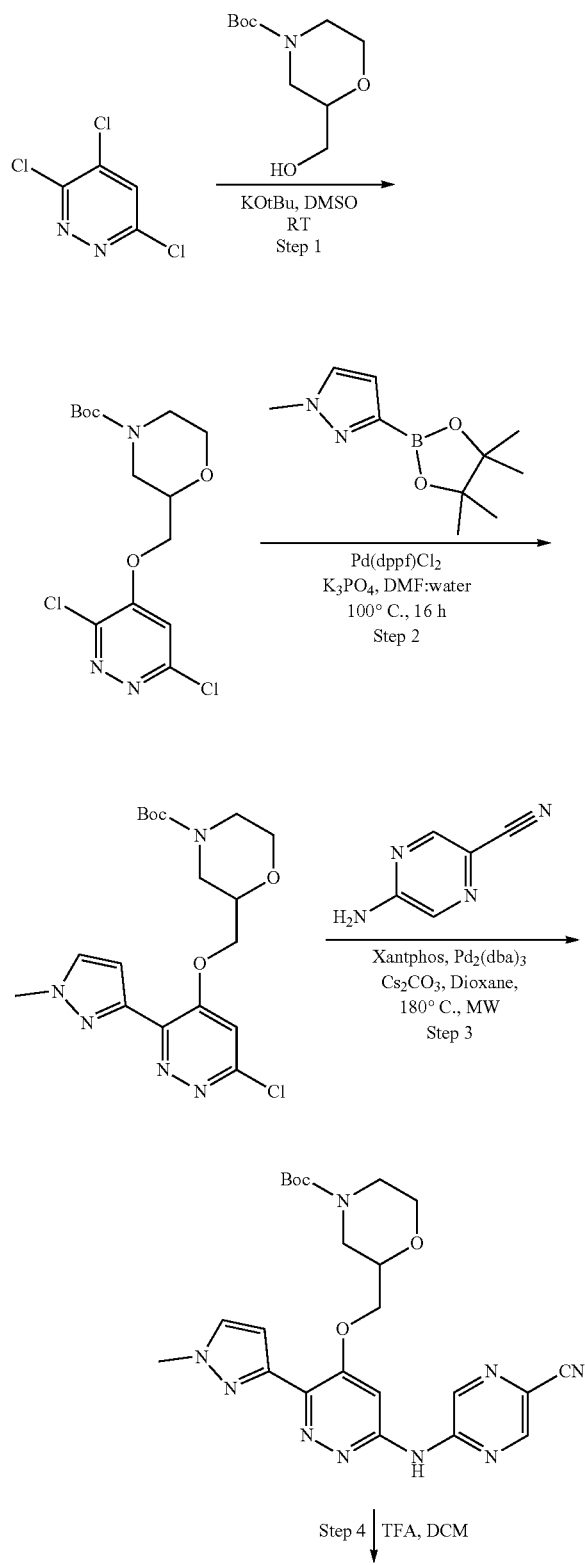

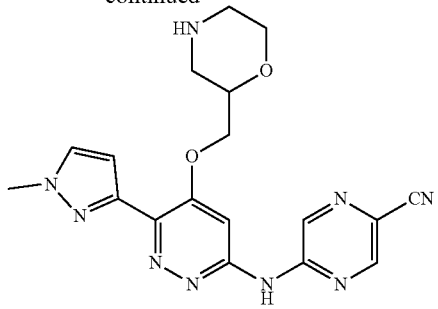

Step-1: Synthesis of tert-butyl 2-((3,6-dichloropyridazin-4-yloxy)methyl)morpholine-4-carboxylate: tert-Butyl 2-(hydroxymethyl)morpholine-4-carboxylate (1.0 g, 0.005 mol, 1.0 eq) was dissolved in DMSO (10 mL). To this solution potassium tert butoxide (0.613 g, 0.005 mmol, 1.0 eq) solution was added and the reaction mixture was allowed to stir at RT for 20 min. The reaction mixture was cooled to 0° C. and 3,4,6-trichloropyridazine (1.0 g, 0.005 mol, 1.0 eq) was added to it and the reaction was stirred at RT for 16 h. The reaction was diluted with water and extracted with ethyl acetate. The combined organic layers were washed (brine), dried (anhydrous $Na_2SO_4$), and concentrated under vacuum to get the title compound (1.0 g, 55%). LCMS: 364 $[M+H]^+$.

Step-2: Synthesis of tert-butyl 2-((6-chloro-3-(1-methyl-1H-pyrazol-3-yl)pyridazin-4-yloxy)methyl)morpholine-4-carboxylate To a stirred solution of tert-butyl 2-((3,6-dichloropyridazin-4-yloxy)methyl)morpholine-4-carboxylate (0.3 g, 0.82 mmol, 1.0 eq) in DMF:water (10 mL; 5 mL) was added 1-methyl-3-(4,4,5,5-tetramethyl-1,3,2-dioxaborolan-2-yl)-1H-pyrazole (0.14 g, 0.66 mmol, 0.8 eq). The reaction mixture was purged with nitrogen for 5 min then charged with $K_3PO_4$ (0.521 g, 2.46 mmol, 3.0 eq) and Pd(dppf)$Cl_2$.DCM complex (27 mg, 5 mol %). The reaction mixture was again purged with nitrogen. The reaction mixture was allowed to heat at 80° C. for 1 h using microwave irradiation. After completion, reaction was diluted with water and extracted with ethyl acetate. Combined organic layer was washed (brine) dried over anhydrous $Na_2SO_4$ and concentrated under reduced pressure. The crude product was purified by flash chromatography to obtain the title compound. (0.1 g, 30%). LCMS: 410 $[M+1]^+$ Step-3: Synthesis of tert-butyl 2-((6-(5-cyanopyrazin-2-ylamino)-3-(1-methyl-1H-pyrazol-3-yl)pyridazin-4-yloxy)methyl)morpholine-4-carboxylate: To a solution of tert-butyl 2-((6-chloro-3-(1-methyl-1H-pyrazol-3-yl)pyridazin-4-yloxy)methyl)morpholine-4-carboxylate (0.2 g, 0.48 mmol, 1.0 eq) in dioxane (5 mL) was added 5-aminopyrazine-2-carbonitrile (0.058 g, 0.48 mmol, 1.0 eq), $Cs_2CO_3$ (0.476 g, 1.46 mmol, 3.0 eq.), Xantphos (0.015 g, 0.002 mmol, 0.05 eq) followed by the addition of $Pd_2(dba)_3$ (0.022 g, 0.002 mmol, 0.05 eq) under nitrogen atmosphere. The resulting reaction mixture was heated at 180° C. in microwave reactor for 1 h. Product formation was confirmed by LCMS. The reaction mixture was diluted with water and extracted with ethyl acetate (75 mL×3). Combined organic layer was dried over anhydrous $Na_2SO_4$ and concentrated under reduced pressure. The crude product was purified by normal phase silica gel column chromatography to obtain the title compound (0.1 g, 42%). LCMS: 494 $[M+H]^+$ Step-4: Synthesis of 5-(6-(1-methyl-1H-pyrazol-3-yl)-5-(morpholin-2-ylmethoxy)pyridazin-3-ylamino)pyrazine-2-carbonitrile: To a solution of tert-butyl 2-((6-(5-cyanopyrazin-2-ylamino)-3-(1-methyl-1H-pyrazol-3-yl)pyridazin-4- yloxy)methyl)morpholine-4-carboxylate (0.1 g, 0.2 mmol, 1.0 eq) in DCM (5 mL) was added TFA (0.5 mL) and the resulting reaction mixture was allowed to stir at RT for 2 h. Progress of the reaction is monitored by LCMS. Diethyl ether (10 mL) was added and the resulting precipitates were filtered and washed with ether to get the title compound as TFA salt (4 mg, 5%). LCMS: 394 [M+H]$^+$; $^1$H NMR (400 MHz, DMSO-d6) δ 8.96 (s, 1H), 8.82 (s, 1H), 7.82 (d, J=4.82 Hz, 2H), 6.82 (s, 1H), 4.14 (d, J=8.33 Hz, 2H), 3.94 (s, 2H), 3.78 (d, J=9.21 Hz, 2H), 3.50 (d, J=10.96 Hz, 2H), 2.93 (d, J=11.84 Hz, 1H), 2.68 (br. s., 2H), 1.87 (br. s., 3H).

Example-14: Synthesis of 5-(6-methyl-5-(morpholin-2-ylmethylamino)pyridazin-3-ylamino)pyrazine-2-carbonitrile (Compound No. 1.14)

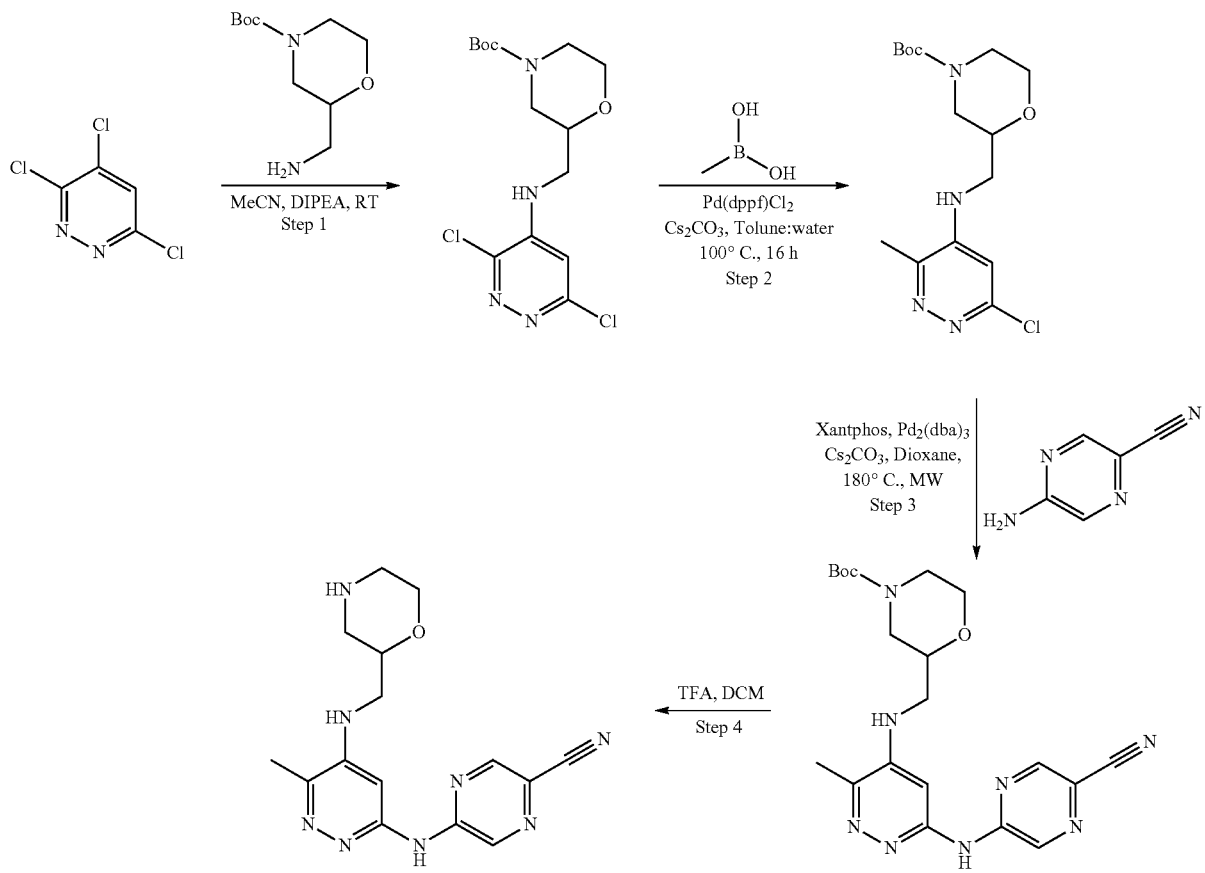

Step-1: Synthesis of tert-butyl 2-((3,6-dichloropyridazin-4-ylamino)methyl)morpholine-4-carboxylate: To a solution of 3,4,6-trichloropyridazine (0.500 g, 2.7 mmol, 1.0 eq) and tert-butyl 2-(aminomethyl)morpholine-4-carboxylate (0.590 g, 2.7 mmol, 1.0 eq) in ACN (5 mL) was added DIPEA (0.95 mL, 5.4 mmol, 2.0 eq). The reaction mixture was allowed to stir at RT for overnight and concentrated under vacuum to get the crude which was purified by normal phase silica gel column chromatography to get the title compound (0.500 g, 51%). LCMS: 363 [M+H]$^+$.

Step-2: Synthesis of tert-butyl 2-((6-chloro-3-methylpyridazin-4-ylamino)methyl)morpholine-4-carboxylate: To a stirred solution of tert-butyl 2-((3,6-dichloropyridazin-4-ylamino)methyl)morpholine-4-carboxylate (0.4 g, 1.1 mmol, 1.0 eq) in toluene:water (5 mL; 0.5 mL) was added methyl boronic acid (0.19 g, 3.3 mmol, 3.0 eq). The reaction mixture was purged with nitrogen for 5 min then charged with Cs$_2$CO$_3$ (0.72 g, 2.2 mmol, 2.0 eq.) and Pd(dppf)Cl$_2$ (45 mg, 5 mol %). The reaction mixture was again purged with nitrogen. The reaction mixture was allowed to heat at 100° C. for overnight. After completion, reaction was diluted with water and extracted with ethyl acetate. Combined organic layer was washed (brine) dried over anhydrous Na$_2$SO$_4$ and concentrated under reduced pressure. The crude product was purified by flash chromatography to obtain the title compound (0.2 g, 53%). LCMS: 343 [M+H]$^+$ Step-3: Synthesis of tert-butyl 2-((6-(5-cyanopyrazin-2-ylamino)-3-methylpyridazin-4-ylamino)methyl)morpholine-4-carboxylate: To a solution of tert-butyl 2-((6-chloro-3-methylpyridazin-4-ylamino)methyl)morpholine-4-carboxylate (0.22 g, 0.6 mmol, 1.0 eq) in DMF (5 mL) was added 5-aminopyrazine-2-carbonitrile (0.09 g, 0.77 mmol, 1.2 eq), Cs$_2$CO$_3$ (0.627 g, 1.9 mmol, 3.0 eq), Xantphos (0.038 g, 10 mol %) followed by the addition of Pd$_2$(dba)$_3$ (0.030 g, 5 mol %) under nitrogen atmosphere. The resulting reaction mixture was heated at 180° C. in microwave reactor for 90 min. Product formation was confirmed by LCMS. The reaction mixture was diluted with water and extracted with ethyl acetate (75 mL×3). Combined organic layer was dried over anhydrous Na$_2$SO$_4$ and concentrated under reduced pressure. The crude product was purified by normal phase silica gel column chromatography to obtain the title compound (0.03 g, 22%). LCMS: 427 [M+H]$^+$ Step-4: Synthesis of 5-(6-methyl-5-(morpholin-2-ylmethylamino)pyridazin-3-ylamino)pyrazine-2-carbonitrile: To a solution of tert-butyl 2-((6-(5-cyanopyrazin-2-ylamino)-3- methylpyridazin-4-ylamino)methyl)morpholine-4-carboxylate (0.03 g, 0.07 mmol, 1.0 eq) in DCM (5 mL) was added TFA (0.5 mL) and the resulting reaction mixture was allowed to stir at RT for 30 min. Progress of the reaction is monitored by LCMS. Diethyl ether (10 mL) was added and the resulting precipitates were filtered and washed with ether to get the title compound as TFA salt (10 mg, 43%). LCMS: 327[M+H]+; $^1$H NMR (400 MHz, DMSO-d6) δ 9.02 (br. s., 1H), 8.94 (br. s., 1H), 8.84 (s, 1H), 8.70 (br. s., 1H), 7.11 (s, 1H), 3.90-4.04 (m, 2H), 3.62-3.74 (m, 3H), 3.41 (br. s., 2H), 3.34 (d, J=12.28 Hz, 2H), 3.21 (d, J=12.28 Hz, 1H), 3.02 (br. s., 1H), 2.90 (d, J=11.40 Hz, 1H), 2.43 (s, 3H).

Example-15: Synthesis of 5-(6-methyl-5-(piperidin-4-ylmethylamino)pyridazin-3-ylamino)pyrazine-2-carbonitrile (Compound No. 1.15)

Step-2: Synthesis of tert-butyl 4-((6-chloro-3-methylpyridazin-4-ylamino)methyl)piperidine-1-carboxylate: To a stirred solution of tert-butyl 4-((3,6-dichloropyridazin-4-ylamino)methyl)piperidine-1-carboxylate (0.33 g, 0.9 mmol, 1.0 eq) in toluene:water (4 mL; 0.5 mL) was added methyl boronic acid (0.11 g, 1.8 mmol, 2.0 eq) and Cs$_2$CO$_3$ (0.59 g, 1.8 mmol, 2.0 eq) The reaction mixture was purged with nitrogen for 15 min and Pd(dppf)Cl$_2$ (36 mg, 5 mol %) was added. The reaction mixture was again purged with nitrogen. The reaction mixture was allowed to heat at 100° C. for 1 h using microwave irradiation. After completion, reaction was diluted with water and extracted with ethyl acetate. Combined organic layer was washed (brine) dried over anhydrous Na$_2$SO$_4$ and concentrated under reduced pressure. The crude product was purified by flash chromatography to obtain the title compound (0.15 g, 49%). LCMS: 341 [M+H]+

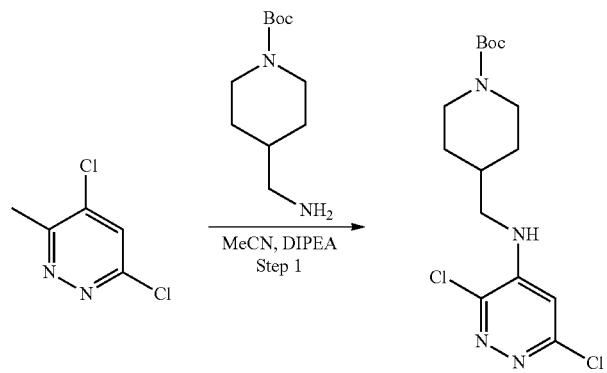
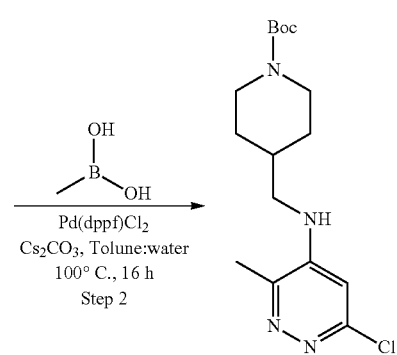
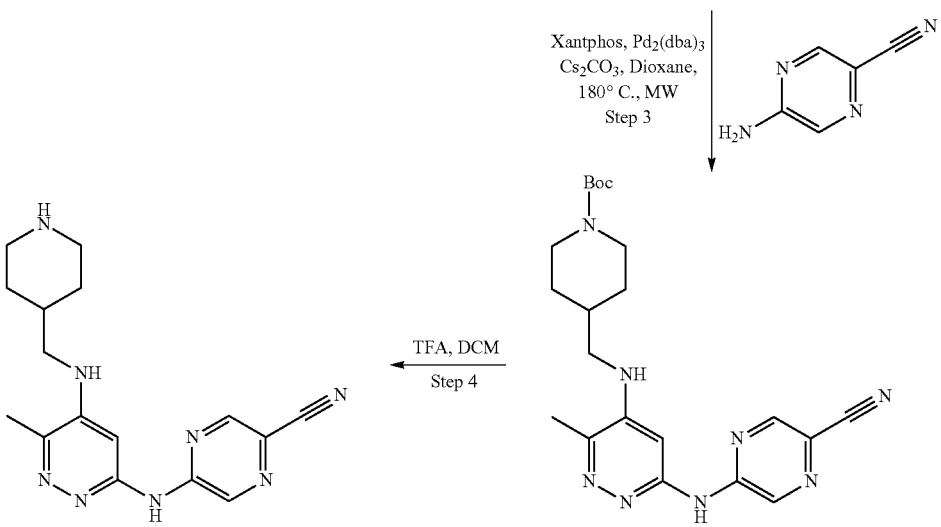

Step-1: Synthesis of tert-butyl 4-((3,6-dichloropyridazin-4-ylamino)methyl)piperidine-1-carboxylate: To a solution of 3,4,6-trichloropyridazine (1.0 g, 5.4 mmol, 1.0 eq) and tert-butyl 4-(aminomethyl)piperidine-1-carboxylate (1.16 g, 5.4 mmol, 1.0 eq) in ACN (10 mL) was added DIPEA (1.9 mL, 10.0 mmol, 2.0 eq). The reaction mixture was allowed to stir at RT for overnight and concentrated under vacuum to get the crude which was purified by normal phase silica gel column chromatography to get the title compound (1.5 g, 79%). LCMS: 361 [M+H]+.

Step-3: Synthesis of tert-butyl 4-((6-(5-cyanopyrazin-2-ylamino)-3-methylpyridazin-4-ylamino)methyl)piperidine-1-carboxylate: To a solution of tert-butyl 4-((6-chloro-3-methylpyridazin-4-ylamino)methyl)piperidine-1-carboxylate (0.15 g, 0.44 mmol, 1.0 eq) in DMF (5 mL) was added 5-aminopyrazine-2-carbonitrile (0.058 g, 0.48 mmol, 1.1 eq), Cs$_2$CO$_3$ (0.430 g, 1.3 mmol, 3.0 eq), Xantphos (0.025 g, 10 mol %) followed by the addition of Pd$_2$(dba)$_3$ (0.020 g, 5 mol %) under nitrogen atmosphere. The resulting reaction mixture was heated at 180° C. in microwave reactor for 90 min. Product formation was confirmed by LCMS. The reaction mixture was diluted with water and extracted with ethyl acetate (75 mL×3). Combined organic layer was dried over anhydrous Na$_2$SO$_4$ and concentrated under reduced pressure. The crude product was purified by normal phase silica gel column chromatography to obtain the title compound (0.100 g, 53%). LCMS: 425 [M+H]$^+$ Step-4: Synthesis of 5-(6-methyl-5-(piperidin-4-ylmethylamino)pyridazin-3-ylamino)pyrazine-2-carbonitrile: To a solution of tert-butyl 2-((6-(5-cyanopyrazin-2-ylamino)-3-methylpyridazin-4-ylamino)methyl) morpholine-4-carboxylate (0.1 g, 0.23 mmol, 1.0 eq) in DCM (5 mL) was added TFA (0.5 mL) and the resulting reaction mixture was allowed to stir at RT for 30 min. Progress of the reaction was monitored by LCMS. Diethyl ether (10 mL) was added and the resulting precipitates were filtered and washed with ether to get the title compound as TFA salt (20 mg, 56%). LCMS: 325[M+H]$^+$; $^1$H NMR (400 MHz, DMSO-d6) δ 8.81 (br. s., 2H), 8.49 (br. s., 1H), 8.21 (br. s., 1H), 7.07 (br. s., 1H), 3.15 (br. s., 2H), 2.84 (d, J=9.65 Hz, 3H), 2.40 (br. s., 3H), 1.88 (d, J=12.28 Hz, 3H), 1.34 (br. s., 3H).

Example-16: Synthesis of 5-(6-(4-fluoro-3-methylphenyl)-5-(piperidin-4-ylmethylamino)pyridazin-3-ylamino)pyrazine-2-carbonitrile (Compound No. 1.16)

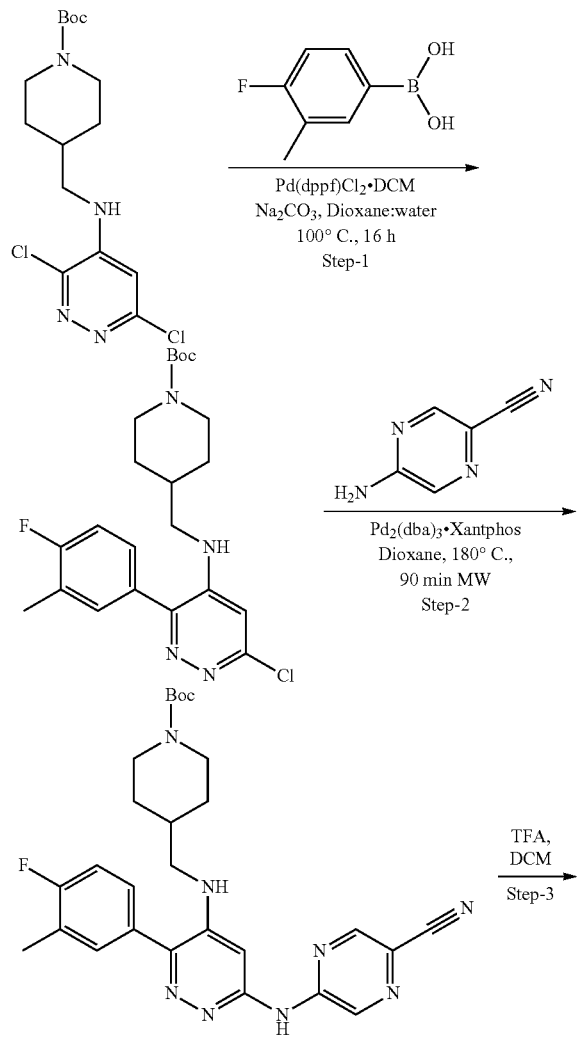

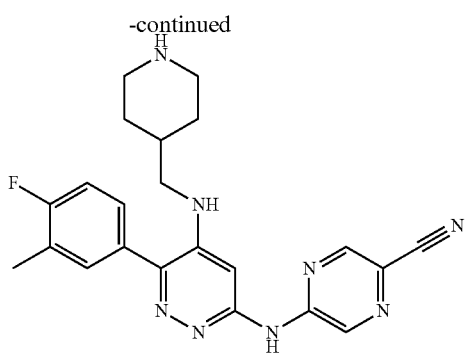

Step-1: Synthesis of tert-butyl 4-((6-chloro-3-(4-fluoro-3-methylphenyl)pyridazin-4-ylamino)methyl)piperidine-1-carboxylate: To a solution of tert-butyl 4-((3,6-dichloropyridazin-4-ylamino)methyl)piperidine-1-carboxylate (0.3 g, 0.830 mmol, 1.0 eq) in dioxane:water (5:05, 5.50 mL) under nitrogen purging was added sodium carbonate (0.218 g, 2.075 mmol, 2.5 eq), 4-fluoro-3-methylphenylboronic acid (0.152 g, 0.99 mmol, 1.2 eq) and Pd(dppf)Cl$_2$.DCM complex (0.027 g, 0.033 g, 0.04 eq). The reaction mixture was then further purged for 5 min and allowed to stir for 16 h at 100° C. The reaction mixture was diluted with water (50 ml) and extracted with ethyl acetate (50 mL×2). Combined organic layer was dried over anhydrous Na$_2$SO$_4$ and concentrated under reduced pressure to get crude product. The crude product was purified by flash chromatography to obtain the title compound (240 mg, 66%) LCMS: 434.19 [M+H]$^+$;

Step-2: Synthesis of tert-butyl 4-((6-(5-cyanopyrazin-2-ylamino)-3-(4-fluoro-3-methylphenyl)pyridazin-4-ylamino)methyl)piperidine-1-carboxylate: To a solution of tert-butyl 4-((6-chloro-3-(4-fluoro-3-methylphenyl)pyridazin-4-ylamino)methyl)piperidine-1-carboxylate (0.236 g, 0.54 mmol, 1.0 eq) in dioxane (4 mL) was added 5-aminopyrazine-2-carbonitrile (0.085 g, 0.70 mmol, 1.3 eq), Cs$_2$CO$_3$ (0.438 g, 1.35 mmol, 2.5 eq), X-phos (0.062 g, 0.108 mmol, 0.2 eq) followed by the addition of Pd$_2$(dba)$_3$ (0.049 g, 0.54 mmol, 0.1 eq) under nitrogen atmosphere. The resulting reaction mixture was heated at 180° C. in microwave reactor for 90 min. The TLC showed the formation of new spots along with starting material. Product formation was confirmed by LCMS. The reaction mixture was diluted with water (20 ml) and extracted with ethyl acetate (70 mL×2). Combined organic layer was dried over anhydrous Na$_2$SO$_4$ and concentrated under reduced pressure to get crude product. The crude product was purified by flash chromatography followed by RP-HPLC to obtain the title compound (45 mg, 16%). LCMS: 518.2 [M+H]$^+$ Step-3: Synthesis of 5-(6-(4-fluoro-3-methylphenyl)-5-(piperidin-4-ylmethylamino)pyridazin-3-ylamino)pyrazine-2-carbonitrile: To a solution of tert-butyl 4-((6-(5-cyanopyrazin-2-ylamino)-3-(4-fluoro-3-methylphenyl)pyridazin-4-ylamino)methyl)piperidine-1-carboxylate (0.045 g, 0.086 mmol) in DCM (3.0 ml) was added trifluoroacetic acid (0.4 mL) drop wise at 0° C. The resultant reaction mixture was then allowed to stir for 40 min. The LCMS showed the formation of desired product. To this reaction mixture, was added n-pentane (10 mL) under stirring, to get the suspension which was filtered to get title compound (21 mg, 59%). LCMS: 418.2 [M+H]$^+$; $^1$H NMR (400 MHz, DMSO-d$_6$) δ 8.85 (br. s., 2H), 8.52 (br. s., 2H), 8.25 (br. s., 2H), 7.50 (d, J=6.58 Hz, 1H), 7.43 (br. s., 1H), 7.27-7.35 (m, 2H), 3.30 (d, J=11.84 Hz, 2H), 3.09 (br. s., 2H), 2.84 (d, J=10.96 Hz, 3H), 2.32 (br. s., 3H), 1.94 (br. s., 1H), 1.84 (d, J=13.59 Hz, 2H), 1.34 (d, J=12.28 Hz, 2H)

Example-17: Synthesis of 5-(6-cyclopropyl-5-(morpholin-2-ylmethylamino)pyridazin-3-ylamino)pyrazine-2-carbonitrile (Compound No. 1.17)

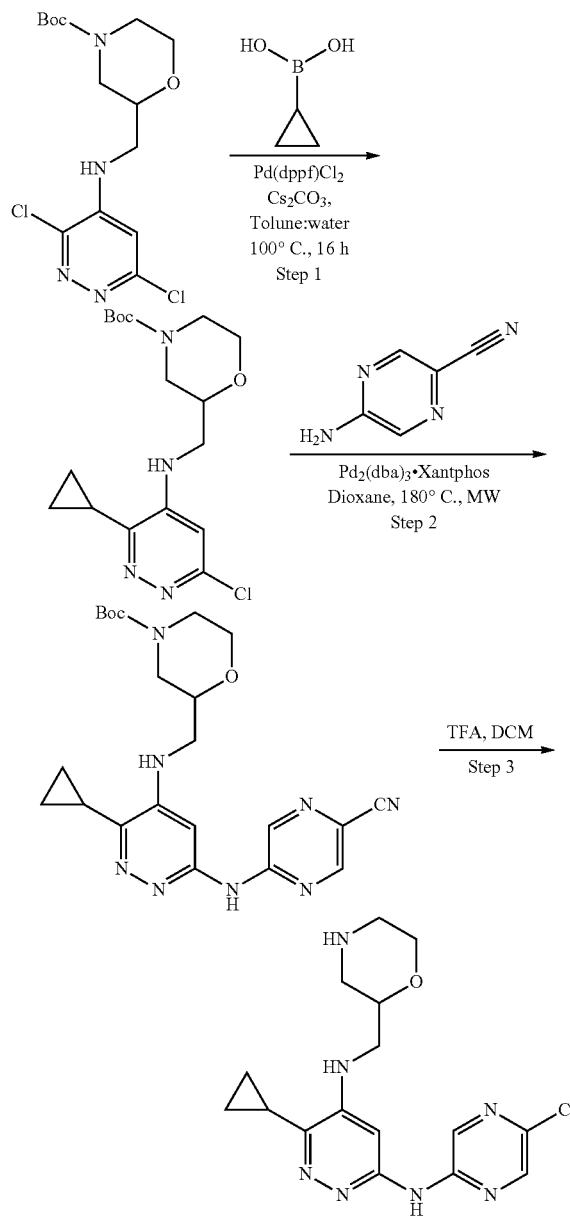

Step-1: Synthesis of tert-butyl 2-((6-chloro-3-cyclopropylpyridazin-4-ylamino)methyl)morpholine-4-carboxylate: To a stirred solution of tert-butyl 2-((3,6-dichloropyridazin-4-ylamino)methyl)morpholine-4-carboxylate (0.4 g, 1.1 mmol, 1.0 eq) in toluene:water (5 mL; 0.5 mL) was added cyclopropyl boronic acid (0.28 g, 3.3 mmol, 3.0 eq) and Cs$_2$CO$_3$ (0.72 g, 2.2 mmol, 2.0 eq). The reaction mixture was purged with nitrogen for 5 min then charged with and Pd(dppf)Cl$_2$ (44 mg, 5 mol %). The reaction mixture was again purged with nitrogen. The reaction mixture was allowed to heat at 100° C. for overnight. After completion, reaction was diluted with water and extracted with ethyl acetate. Combined organic layer was washed (brine) dried over anhydrous Na$_2$SO$_4$ and concentrated under reduced pressure. The crude product was purified by flash column chromatography to obtain the title compound (0.23 g, 57%). LCMS: 369 [M+H]$^+$ Step-2: Synthesis of tert-butyl 2-((6-(5-cyanopyrazin-2-ylamino)-3-cyclopropylpyridazin-4-ylamino)methyl)morpholine-4-carboxylate: To a solution of tert-butyl 2-((6-chloro-3-cyclopropylpyridazin-4-ylamino)methyl)morpholine-4-carboxylate (0.23 g, 0.62 mmol, 1.0 eq) in dioxane (4 mL) was added 5-aminopyrazine-2-carbonitrile (0.082 g, 0.68 mmol, 1.1 eq), Cs$_2$CO$_3$ (0.609 g, 1.9 mmol, 3.0 eq), Xantphos (0.036 g, 10 mol %) followed by the addition of Pd$_2$(dba)$_3$ (0.028 g, 5 mol %) under nitrogen atmosphere. The resulting reaction mixture was heated at 180° C. in microwave reactor for 90 min. Product formation was confirmed by LCMS. The reaction mixture was diluted with water and extracted with ethyl acetate (75 mL×3). Combined organic layer was dried over anhydrous Na$_2$SO$_4$ and concentrated under reduced pressure. The crude product was purified by normal phase silica gel column chromatography to obtain the title compound (0.1 g, 36%). LCMS: 453 [M+H]$^+$ Step-3: Synthesis of 5-(6-cyclopropyl-5-(morpholin-2-ylmethylamino)pyridazin-3-ylamino)pyrazine-2-carbonitrile: To a solution of tert-butyl 2-((6-(5-cyanopyrazin-2-ylamino)-3-cyclopropylpyridazin-4-ylamino)methyl) morpholine-4-carboxylate (0.1 g, 0.2 mmol, 1.0 eq) in DCM (5 mL) was added TFA (0.5 mL) and the resulting reaction mixture was allowed to stir at RT for 30 min. Progress of the reaction was monitored by LCMS. Diethyl ether (10 mL) was added and the resulting precipitates were filtered and washed with ether to get the title compound as TFA salt (7 mg, 10%). LCMS: 353 [M+H]$^+$; $^1$H NMR (400 MHz, DMSO-d$_6$) δ 9.02 (br. s., 1H), 8.71 (br. s., 1H), 6.97 (br. s., 1H), 6.79 (br. s., 1H), 3.75 (d, J=10.52 Hz, 2H), 3.60 (br. s., 1H), 3.16 (br. s., 2H), 2.86 (d, J=12.28 Hz, 1H), 2.65 (br. s., 1H), 2.08 (d, J=5.70 Hz, 1H), 1.79 (br. s., 4H), 1.23 (br. s., 1H), 0.93 (d, J=6.58 Hz, 2H).

Example-18: Synthesis of 5-(6-cyclopropyl-5-(piperidin-4-ylmethylamino)pyridazin-3-ylamino)pyrazine-2-carbonitrile (Compound No. 1.18)

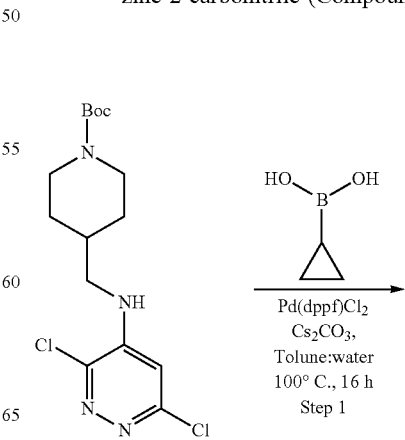

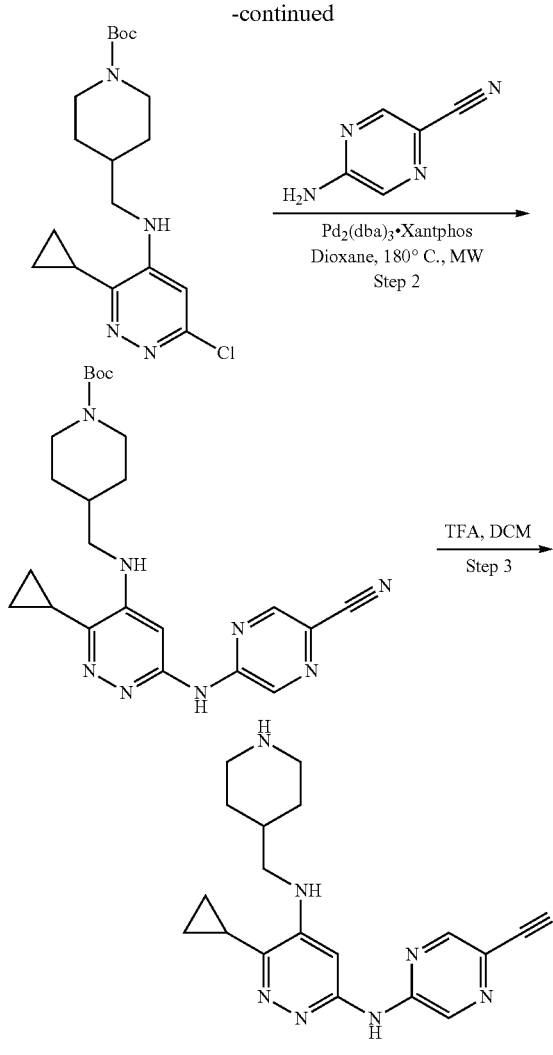

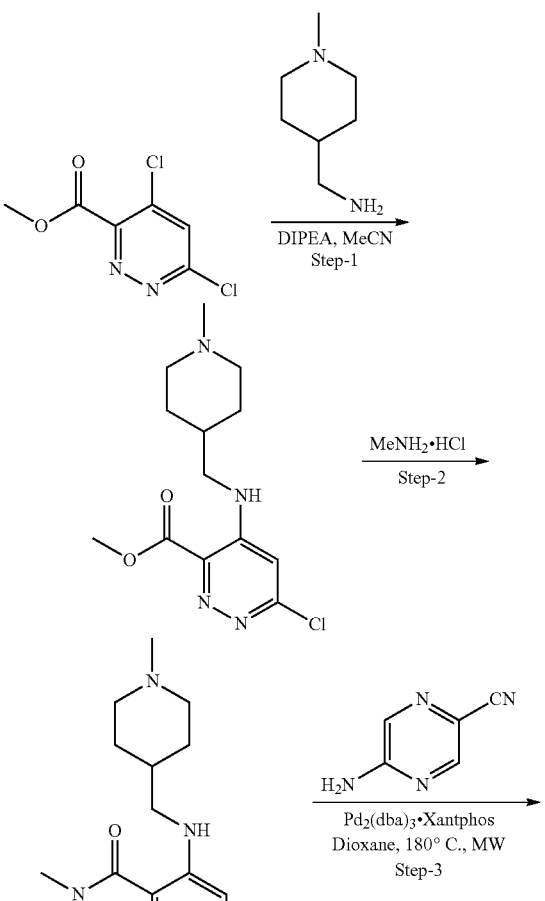

reaction mixture was heated at 180° C. in microwave reactor for 1 h. Product formation was confirmed by LCMS. The reaction mixture was diluted with water and extracted with ethyl acetate (75 mL×3). Combined organic layer was dried over anhydrous $Na_2SO_4$ and concentrated under reduced pressure. The crude product was purified by normal phase silica gel column chromatography to obtain the title compound (0.03 g, 12%). LCMS: 451 [M+H]$^+$ Step-3: Synthesis of 5-(6-cyclopropyl-5-(piperidin-4-yl-methylamino)pyridazin-3-ylamino)pyrazine-2-carbonitrile: To a solution of tert-butyl 4-((6-(5-cyanopyrazin-2-ylamino)-3-cyclopropylpyridazin-4-ylamino)methyl) piperidine-1-carboxylate (0.03 g, 0.06 mmol, 1.0 eq) in DCM (5 mL) was added TFA (0.5 mL) and the resulting reaction mixture was allowed to stir at RT for 30 min. Progress of the reaction was monitored by LCMS. Diethyl ether (10 mL) was added and the resulting precipitates were filtered and washed with ether to get the title compound as TFA salt (10 mg, 47%). LCMS: 351 [M+H]$^+$; $^1$H NMR (400 MHz, DMSO-$d_6$) δ 10.63 (s, 1H), 8.93 (br. s., 1H), 8.75 (br. s., 1H), 8.55 (br. s., 1H), 7.06 (br. s., 1H), 6.94 (br. s., 1H), 3.10 (br. s., 2H), 2.77-2.92 (m, 2H), 2.06 (br. s., 2H), 1.87 (d, J=13.59 Hz, 3H), 1.40 (d, J=11.84 Hz, 2H), 0.94 (s, 4H).

Example-19: Synthesis of 6-(5-cyanopyrazin-2-ylamino)-N-methyl-4-((1-methylpiperidin-4-yl)methylamino)pyridazine-3-carboxamide (Compound No. 1.19)

Step-1: Synthesis of tert-butyl 4-((6-chloro-3-cyclopropylpyridazin-4-ylamino)methyl)piperidine-1-carboxylate:
To a stirred solution of tert-butyl 4-((3,6-dichloropyridazin-4-ylamino)methyl)piperidine-1-carboxylate (0.5 g, 1.3 mmol, 1.0 eq) in toluene:water (5 mL; 0.5 mL) was added cyclopropyl boronic acid (0.35 g, 3.9 mmol, 3.0 eq) and $Cs_2CO_3$ (0.9 g, 2.7 mmol, 2.0 eq). The reaction mixture was purged with nitrogen for 5 min then charged with and Pd(dppf)Cl$_2$ (56 mg, 5 mol %). The reaction mixture was again purged with nitrogen. The reaction mixture was allowed to heat at 100° C. for overnight. After completion, reaction was diluted with water and extracted with ethyl acetate. Combined organic layer was washed (brine) dried over anhydrous $Na_2SO_4$ and concentrated under reduced pressure. The crude product was purified by normal phase column chromatography to obtain the title compound (0.200 g, 42%). LCMS: 367 [M+H]$^+$ Step-2: Synthesis of tert-butyl 4-((6-(5-cyanopyrazin-2-ylamino)-3-cyclopropylpyridazin-4-ylamino)methyl)piperidine-1-carboxylate: To a solution of tert-butyl 4-((6-chloro-3-cyclopropylpyridazin-4-ylamino)methyl)piperidine-1-carboxylate (0.2 g, 0.54 mmol, 1.0 eq) in DMF (4 mL) was added 5-aminopyrazine-2-carbonitrile (0.078 g, 0.6 mmol, 1.2 eq), $Cs_2CO_3$ (0.53 g, 1.6 mmol, 3.0 eq), Xantphos (0.031 g, 10 mol %) followed by the addition of Pd$_2$(dba)$_3$ (0.024 g, 5 mol %) under nitrogen atmosphere. The resulting -continued

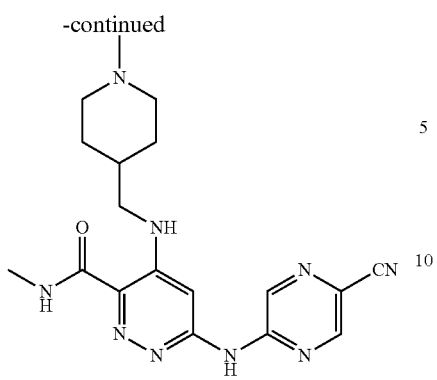

Step-1: Synthesis of 6-chloro-N-methyl-4-((1-methylpiperidin-4-yl)methylamino)pyridazine-3-carboxamide: To a solution of methyl 4,6-dichloropyridazine-3-carboxylate (0.500 g, 0.0024 mol, 1.0 eq) and (1-methylpiperidin-4-yl)methanamine (0.310 g, 0.0024 mol, 1.0 eq) in ACN (10 mL) was added DIPEA (0.83 mL, 0.0048 mmol, 2.0 eq). The reaction mixture was allowed to stir at RT for overnight. The reaction mixture concentrated under vacuum to get the crude which was purified by normal phase silica gel column chromatography to get the title compound (0.800 g, 63%). LCMS: 299[M+H]$^+$.

Step-2: Synthesis of 6-chloro-N-methyl-4-((1-methylpiperidin-4-yl)methylamino)pyridazine-3-carboxamide: To a solution of 6-chloro-N-methyl-4-((1-methylpiperidin-4-yl)methylamino)pyridazine-3-carboxamide (0.400 g, 0.0013 mol, 1.0 eq) in methanol (20 mL) was added $K_2CO_3$ (0.55 g, 0.004 mol, 3.0 eq) and methylamine hydrochloride (0.181 g, 0.0026 mol, 2.0 eq). The reaction mixture was allowed to stir at RT for 24 h and concentrated under vacuum to get the solid which was added with water (10 mL) and extracted using DCM (20×3 mL). The combined organic layers were concentrated to get the title compound (0.2 g, 63%). LCMS: 298 [M+H]$^+$.

Step-3: synthesis of 6-(5-cyanopyrazin-2-ylamino)-N-methyl-4-((1-methylpiperidin-4-yl)methylamino)pyridazine-3-carboxamide: To a solution of 6-chloro-N-methyl-4-((1-methylpiperidin-4-yl)methylamino)pyridazine-3-carboxamide (0.1 g, 0.3 mmol, 1.0 eq) in DMF (4 mL) was added 5-aminopyrazine-2-carbonitrile (0.048 g, 0.4 mmol, 1.2 eq), $Cs_2CO_3$ (0.32 g, 1.0 mmol, 3.0 eq), Xantphos (0.019 g, 0.03 mmol, 0.1 eq) followed by the addition of $Pd_2(dba)_3$ (0.015 g, 0.016 mmol, 0.05 eq.) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×2). Combined organic layer was dried over anhydrous $Na_2SO_4$ and concentrated under reduced pressure. The crude product was purified by RP-HPLC to obtain the title compound (0.096 g, 84%). LCMS: 382 [M+H]$^+$; $^1$H NMR (400 MHz, DMSO-$d_6$) δ 8.87 (d, J=4.39 Hz, 2H), 8.61 (br. s., 1H), 8.32 (br. s., 1H), 8.18 (br. s., 1H), 7.03 (s, 1H), 3.01 (t, J=6.14 Hz, 2H), 2.70-2.82 (m, 5H), 2.13 (s, 3H), 1.75-1.88 (m, 2H), 1.65 (d, J=12.28 Hz, 2H), 1.53 (br. s., 1H), 1.17-1.33 (m, 2H)

Example-20: Synthesis of 6-(5-cyanopyrazin-2-ylamino)-4-(1-methylpiperidin-4-ylamino)pyridazine-3-carboxamide (Compound No. 1.20)

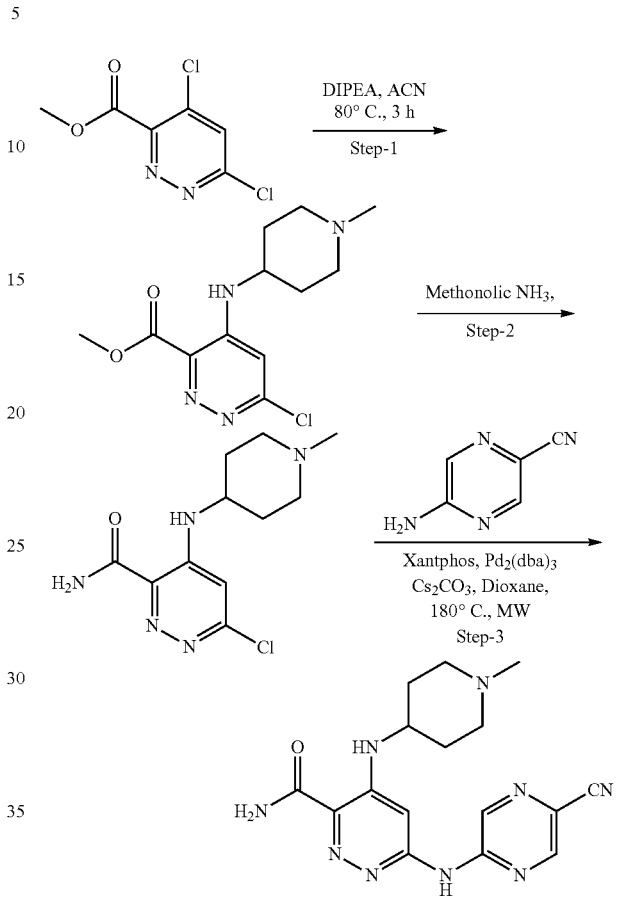

Step-1: Synthesis of methyl 6-chloro-4-(1-methylpiperidin-4-ylamino)pyridazine-3-carboxylate: to a solution of methyl 4,6-dichloropyridazine-3-carboxylate (0.5 g, 0.0024 mol, 1.0 eq) and (1-methylpiperidin-4-yl)methanamine (0.275 g, 0.0024 mol, 1.0 eq) in ACN (10 mL was added DIPEA (0.8 mL, 0.0048 mmol, 2.0 eq). The reaction mixture was stirred for 16 h. After completion of starting material, reaction mixture concentrated under vacuum to get the crude which was purified by normal phase silica gel column chromatography to get the title compound (0.500 g, 73%). LCMS: 285[M+H]$^+$.

Step-2: Synthesis of 6-chloro-4-(1-methylpiperidin-4-ylamino)pyridazine-3-carboxamide: to a solution of methyl 6-chloro-4-(1-methylpiperidin-4-ylamino)pyridazine-3-carboxylate (0.5 g, 0.0016 mol, 1.0 eq) was added methonolic ammonia (5 mL) at RT. The reaction mixture was stirred for 16 h. After completion of starting material, the obtained solid was filtered and dried to get title compound (0.3 g, 69%). LCMS: 270[M+H]$^+$.

Step-3: Synthesis of 6-(5-cyanopyrazin-2-ylamino)-4-(1-methylpiperidin-4-ylamino)pyridazine-3-carboxamide: To a solution of tert-butyl 6-chloro-4-(1-methylpiperidin-4-ylamino)pyridazine-3-carboxamide (0.3 g, 1.11 mmol, 1.0 eq) in dioxane (5 mL) was added 5-aminopyrazine-2-carbonitrile (0.147 g, 1.22 mmol, 1.1 eq), $Cs_2CO_3$ (1.09 g, 3.33 mmol, 3.0 eq), Xantphos (0.060 g, 10 mol %) followed by the addition of $Pd_2(dba)_3$ (0.050 g, 5 mol %) under nitrogen atmosphere. The resulting reaction mixture was heated at 180° C. in microwave reactor for 90 min. Product formation was confirmed by LCMS. The reaction mixture was diluted with water and extracted with ethyl acetate (75 mL×3). Combined organic layer was dried over anhydrous Na₂SO₄ and concentrated under reduced pressure. The crude product was purified by normal phase silica gel column chromatography to obtain the title compound (0.003 g, 1%). LCMS: 354 [M+H]⁺; ¹H NMR (400 MHz, DMSO-d6) δ 11.13 (br. s., 1H), 10.19 (br. s., 1H), 8.95 (s, 1H), 8.79-8.91 (m, 1H), 8.38-8.50 (m, 1H), 7.73 (br. s., 1H), 7.52 (s, 1H), 3.58 (m, 1H), 3.51 (d, J=12.28 Hz, 2H), 2.73-2.85 (m, 2H), 2.23 (d, J=12.72 Hz, 2H), 2.06 (d, J=10.52 Hz, 1H)

Example-21: Synthesis of 5-(6-(4-fluorophenyl)-5-(piperidin-4-ylmethylamino)pyridazin-3-ylamino)pyrazine-2-carbonitrile (Compound No. 1.21)

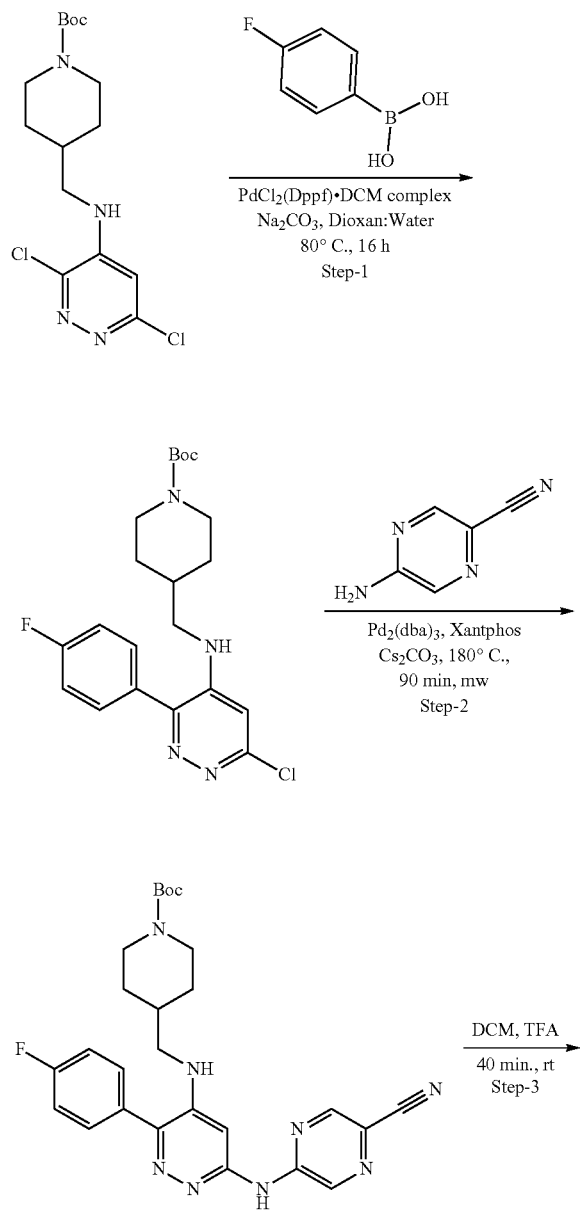

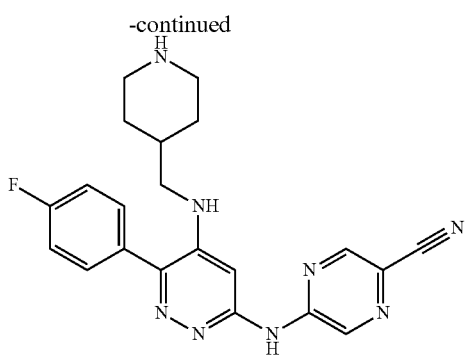

Step-1: Synthesis of tert-butyl 4-((6-chloro-3-(4-fluorophenyl)pyridazin-4-ylamino)methyl)piperidine-1-carboxylate: To a solution of tert-butyl 4-((3,6-dichloropyridazin-4-ylamino)methyl)piperidine-1-carboxylate (0.3 g, 0.830 mmol, 1.0 eq.) in Dioxane:water (4:1, 5.0 ml) under nitrogen purging was added sodium carbonate (0.219 g, 2.075 mmol, 2.5 eq.), 4-fluorophenylboronic acid (0.127 g, 0.913 mmol, 1.1 eq.) and Pd(dppf)Cl₂.DCM complex (0.033 g, 0.0415, 0.05 eq.). The reaction mixture was then further purged for 5 min and allowed to stir for 16 h at 80° C. The reaction mixture was diluted with water (10 mL) and extracted with ethyl acetate (20 mL×2). Combined organic layer was dried over anhydrous Na₂SO₄ and concentrated under reduced pressure to get crude product. The crude product was purified by flash chromatography to obtain 245 mg of title compound. LCMS: 421.1 [M+H]⁺;

Step-2: Synthesis of tert-butyl 4-((6-(5-cyanopyrazin-2-ylamino)-3-(4-fluorophenyl)pyridazin-4-ylamino)methyl)piperidine-1-carboxylate: To a solution of tert-butyl 4-((6-chloro-3-(4-fluorophenyl)pyridazin-4-ylamino)methyl)piperidine-1-carboxylate (0.22 g, 0.522 mmol, 1.0 eq.) in dioxane (3 mL) was added 5-aminopyrazine-2-carbonitrile (0.075 g, 0.627 mmol, 1.2 eq.), Cs₂CO₃ (0.340 g, 1.044 mmol, 2.0 eq.), X-phos (0.018 g, 0.0312 mmol, 0.06 eq.) followed by the addition of Pd₂(dba)₃ (0.014 g, 0.0156 mmol, 0.0.03 eq.) under nitrogen atmosphere. The resulting reaction mixture was heated at 180° C. in microwave reactor for 90 min. The TLC showed the formation of new spots along with starting material. Product formation was confirmed by LCMS. The reaction mixture was diluted with water (10 mL) and extracted with ethyl acetate (20 mL×2). Combined organic layer was dried over anhydrous Na₂SO₄ and concentrated under reduced pressure to get crude product. The crude product was purified by flash chromatography followed by flash chromatography to obtain the title compound (82 mg, 31%). LCMS: 505.2 [M+H]⁺

Step-3: Synthesis of 5-(6-(4-fluorophenyl)-5-(piperidin-4-ylmethylamino)pyridazin-3-ylamino)pyrazine-2-carbonitrile: To a solution of tert-butyl4-((6-(5-cyanopyrazin-2-ylamino)-3-(4-fluorophenyl)pyridazin-4-ylamino) methyl)piperidine-1-carboxylate (0.060 g, 0.118 mmol) in DCM (3.0 mL) was added trifluoroacetic acid (0.2 mL) drop wise at 0° C. The resultant reaction mixture was then allowed to stir for 40 min. The LCMS showed the formation of desired product. To this reaction mixture, was added pentane (10 mL) under stirring. After formation of suspension, the organic phase was decanted. The remained suspension/solid was again stirred after addition of pentane (10 mL) and filtered to get the title compound (13 mg, 27.0%). LCMS: 405 [M+H]⁺; ¹H NMR (400 MHz, DMSO-d₆) δ 8.77-8.88

(m, 2H), 8.51 (br. s., 1H), 8.23 (br. s., 1H), 7.64 (dd, J=5.70, 8.33 Hz, 2H), 7.40 (t, J=8.77 Hz, 2H), 7.31 (s, 1H), 3.30 (d, J=12.28 Hz, 2H), 3.10 (br. s., 2H), 2.84 (d, J=11.84 Hz, 2H), 1.95 (br. s., 1H), 1.85 (d, J=14.03 Hz, 2H), 1.27-1.39 (m, 2H).

Example-22: Synthesis of 5-(6-(4-phenoxyphenyl)-5-(piperidin-4-ylmethylamino)pyridazin-3-ylamino)pyrazine-2-carbonitrile (Compound No. 1.22)

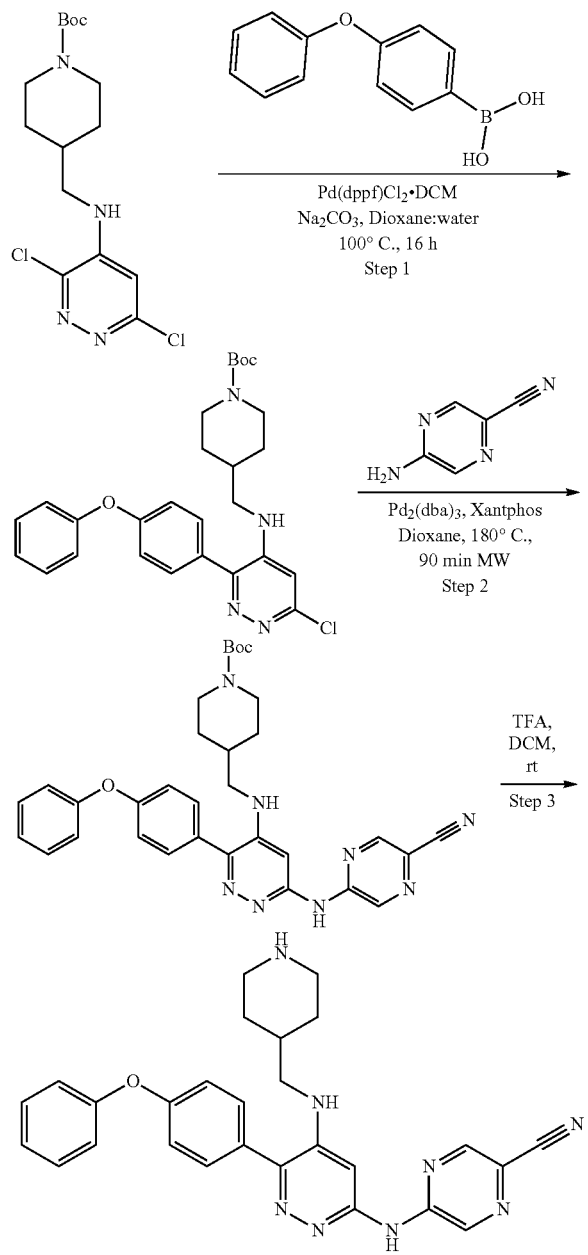

Step-1: Synthesis of tert-butyl 4-((6-chloro-3-(4-phenoxyphenyl)pyridazin-4-ylamino)methyl)piperidine-1-carboxylate: To a solution of tert-butyl 4-((3,6-dichloropyridazin-4-ylamino)methyl)piperidine-1-carboxylate (0.3 g, 0.828 mmol, 1.0 eq.) in Dioxane:water (5:05, 5.50 ml) under nitrogen purging was added sodium carbonate (0.217 g, 2.075 mmol, 2.5 eq), 4-phenoxyphenylboronic acid (0.212 g, 0.99 mmol, 1.2 eq) and Pd(dppf)Cl$_2$.DCM complex (0.027 g, 0.033 g, 0.04 eq). The reaction mixture was then further purged for 5 min and allowed to stir for 16 h at 100° C. The reaction mixture was diluted with water (50 mL) and extracted with ethyl acetate (50 mL×2). Combined organic layer was dried over anhydrous Na$_2$SO$_4$ and concentrated under reduced pressure to get crude product. The crude product was purified by flash chromatography to obtain the title compound (200 mg, 49%) LCMS: 495.21 [M+H]$^+$;

Step-2: Synthesis of tert-butyl 4-((6-chloro-3-(4-phenoxyphenyl)pyridazin-4-ylamino)methyl)piperidine-1-carboxylate: To a solution of tert-butyl 4-((6-chloro-3-(4-phenoxyphenyl)pyridazin-4-ylamino)methyl)piperidine-1-carboxylate (0.200 g, 0.40 mmol, 1.0 eq) in dioxane (4 mL) was added 5-aminopyrazine-2-carbonitrile (0.063 g, 0.52 mmol, 1.3 eq), Cs$_2$CO$_3$ (0.328 g, 1.0 mmol, 2.5 eq.), Xantphos (0.046 g, 0.08 mmol, 0.2 eq) followed by the addition of Pd$_2$(dba)$_3$ (0.036 g, 0.04 mmol, 0.1 eq) under nitrogen atmosphere. The resulting reaction mixture was heated at 180° C. in microwave reactor for 90 min. Product formation was confirmed by LCMS. The reaction mixture was diluted with water (10 mL) and suspensions obtained were filtered over Buchner funnel, washed with pentane. The solid obtained was re-dissolved in DCM and purified by flash chromatography to obtain the title compound (70 mg, 30%). LCMS: 579.2 [M+H]$^+$ Step-3: Synthesis of 5-(6-(4-phenoxyphenyl)-5-(piperidin-4-ylmethylamino)pyridazin-3-ylamino)pyrazine-2-carbonitrile: To a solution of tert-butyl 4-((6-(5-cyanopyrazin-2-ylamino)-3-(4-phenoxyphenyl)pyridazin-4-ylamino)methyl)piperidine-1-carboxylate (0.070 g, 0.012 mmol) in DCM (3.0 mL) was added trifluoroacetic acid (0.2 mL) drop wise at 0° C. The resultant reaction mixture was then allowed to stir for 2 h. The LCMS showed the formation of desired product. To this reaction mixture, was added pentane (10 mL) under stirring. After formation of suspension, the organic phase was decanted. The remained suspension/solid was again stirred after addition of pentane (10 mL) and filtered to get the title compound (49 mg, 84%). LCMS: 479.2 [M+H]$^+$; $^1$H NMR (400 MHz, DMSO-d$_6$) δ 8.85 (s, 1H), 8.75 (br. s., 1H), 7.60 (d, J=8.33 Hz, 2H), 7.47 (t, J=8.11 Hz, 2H), 7.23 (t, J=7.24 Hz, 2H), 7.07-7.19 (m, 4H), 3.29 (d, J=11.40 Hz, 2H), 3.14 (d, J=6.14 Hz, 2H), 2.78-2.88 (m, 2H), 1.94 (br. s., 1H), 1.84 (d, J=14.03 Hz, 2H), 1.33 (d, J=13.59 Hz, 2H)

Example-23: Synthesis of 5-(6-(4-methoxyphenyl)-5-(piperidin-4-ylmethylamino)pyridazin-3-ylamino)pyrazine-2-carbonitrile (Compound No. 1.23)

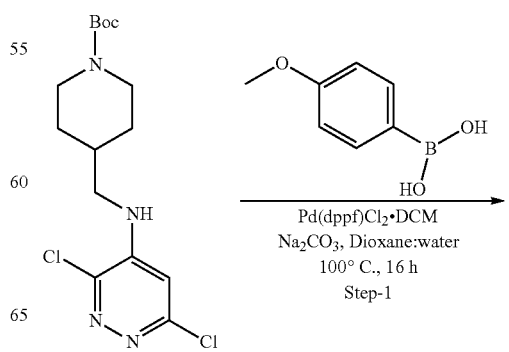

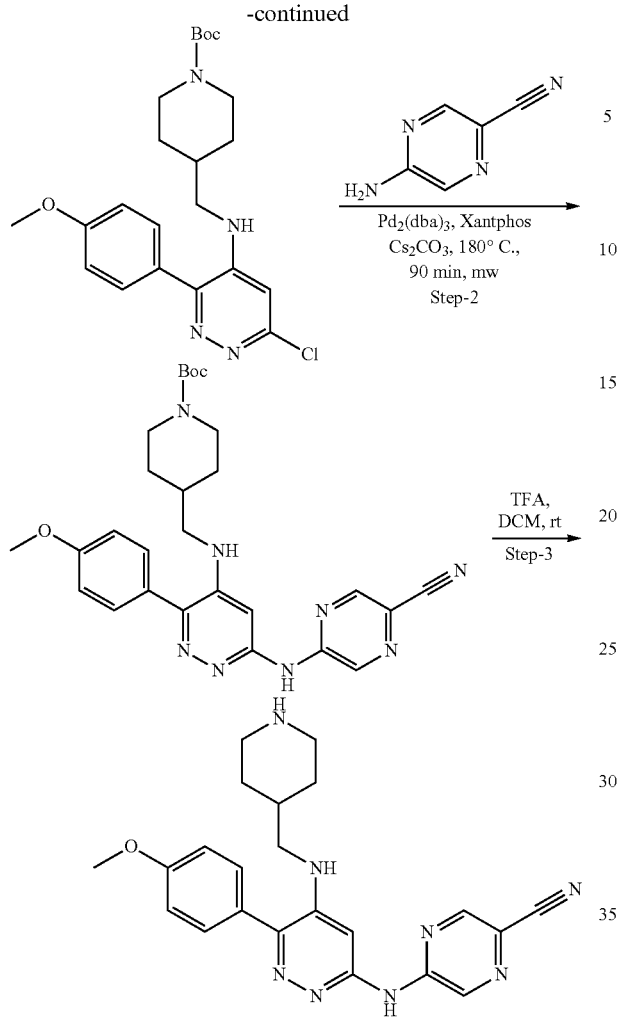

Step-1: Synthesis of tert-butyl 4-((6-chloro-3-(4-methoxyphenyl)pyridazin-4-ylamino)methyl)piperidine-1-carboxylate: To a solution of tert-butyl 4-((3,6-dichloropyridazin-4-ylamino)methyl)piperidine-1-carboxylate (0.300 g, 0.828 mmol, 1.0 eq) in Dioxane:water (5:05, 5.50 ml) under nitrogen purging was added sodium carbonate (0.217 g, 2.07 mmol, 2.5 eq), 4-methoxyphenylboronic acid (0.150 g, 099 mmol, 1.2 eq) and Pd(dppf)Cl$_2$.DCM complex (0.33 g, 0.041, 0.05 eq). The reaction mixture was then further purged for 5 min and allowed to stir for 16 h at 110° C. The TLC (50% ethyl acetate in hexane) showed that starting material was consumed completely. The reaction mixture was diluted with water (10 ml) and extracted with ethyl acetate (50 mL×2). Combined organic layer was dried over anhydrous Na$_2$SO$_4$ and concentrated under reduced pressure to get crude product. The crude product was purified by flash chromatography to obtain the title compound (200 mg, 56%). LCMS: 433 [M+H]$^+$;

Step-2: Synthesis of tert-butyl 4-((6-(5-cyanopyrazin-2-ylamino)-3-(4-methoxyphenyl)pyridazin-4-ylamino)methyl)piperidine-1-carboxylate: To a solution of tert-butyl 4-((6-chloro-3-(4-methoxyphenyl)pyridazin-4-ylamino)methyl)piperidine-1-carboxylate (0.200 g, 0.46 mmol, 1.0 eq.) in DMF (3 mL) was added 5-aminopyrazine-2-carbonitrile (0.067 g, 0.55 mmol, 1.2 eq.), Cs$_2$CO$_3$ (0.373 g, 1.15 mmol, 2.5 eq.), Xantphos (0.021 g, 0.037 mmol, 0.08 eq.) followed by the addition of Pd$_2$(dba)$_3$ (0.016 g, 0.0181 mmol, 0.04 eq.) under nitrogen atmosphere. The resulting reaction mixture was heated at 180° C. in microwave reactor for 90 min. Product formation was confirmed by LCMS. The reaction mixture was diluted with water (10 ml) and precipitates obtained were filtered over Buchner funnel, washed with pentane. Obtained material was re-dissolved in DCM and was purified by flash chromatography to the title compound (54 mg, 22%). LCMS: 517.25 [M+H]$^+$;

Step-3: Synthesis of 5-(6-(4-methoxyphenyl)-5-(piperidin-4-ylmethylamino)pyridazin-3-ylamino)pyrazine-2-carbonitrile: To a solution of tert-butyl 4-((6-(5-cyanopyrazin-2-ylamino)-3-(4-methoxyphenyl)pyridazin-4-ylamino)methyl)piperidine-1-carboxylate (0.055 g, 0.10 mmol) in DCM (3.0 ml) was added trifluoroacetic acid (0.2 ml) drop wise at 0° C. The resultant reaction mixture was then allowed to stir for 2 h. The LCMS showed the formation of desired product. The reaction mixture was then concentrated under reduced pressure to get crude product. The crude product was then purified using RP-HPLC to get the title compound (11 mg, 26%) LCMS: 417 [M+H]$^+$; $^1$H NMR (400 MHz, DMSO-d$_6$) δ 8.95 (br. s., 1H), 8.80 (s, 1H), 8.62 (br. s., 1H), 8.37 (br. s., 1H), 7.46-7.56 (m, J=8.33 Hz, 2H), 7.32 (s, 1H), 7.04-7.13 (m, J=8.77 Hz, 2H), 6.36 (br. s., 1H), 3.84 (s, 3H), 3.05 (t, J=5.70 Hz, 2H), 2.84 (d, J=11.40 Hz, 2H), 1.91 (s, 3H), 1.83 (d, J=13.59 Hz, 2H), 1.33-1.41 (m, 2H)

Example-24: Synthesis of 5-(6-(1H-indol-4-yl)-5-(piperidin-4-ylmethylamino)pyridazin-3-ylamino)pyrazine-2-carbonitrile (Compound No. 1.24)

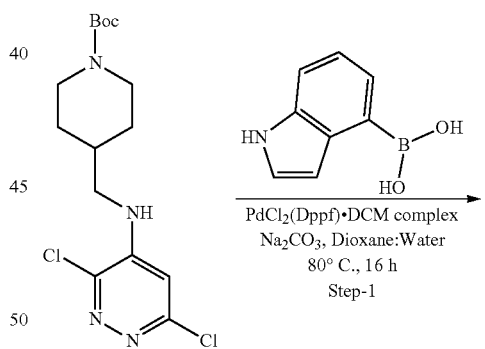

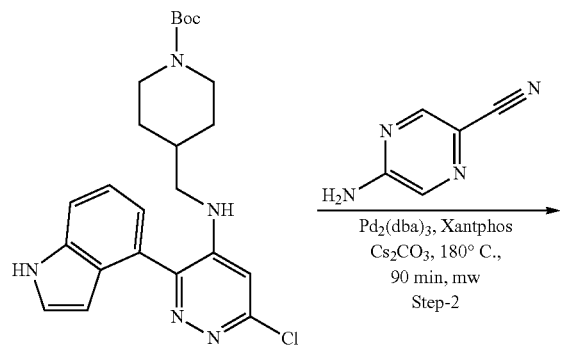

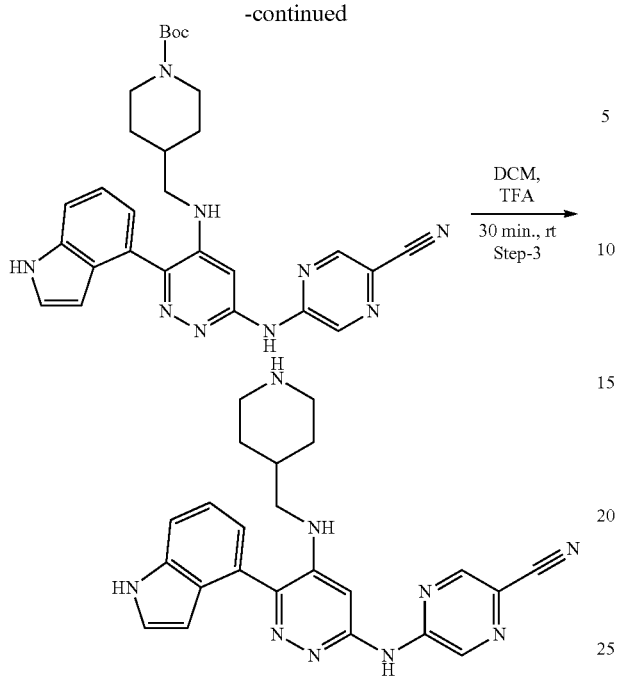

Step-1: Synthesis of tert-butyl 4-((6-chloro-3-(1H-indol-4-yl)pyridazin-4-ylamino)methyl)piperidine-1-carboxylate: To a solution of tert-butyl 4-((3,6-dichloropyridazin-4-ylamino)methyl)piperidine-1-carboxylate (0.5 g, 1.38 mmol, 1.0 eq.) in Dioxane:water (4:1, 10.0 ml) under nitrogen purging was added sodium carbonate (0.365 g, 3.45 mmol, 2.5 eq.), 1H-indol-4-ylboronic acid (0.397 g, 1.52 mmol, 1.1 eq.) and Pd(dppf)Cl$_2$.DCM complex (0.056 g, 0.069, 0.05 eq.). The reaction mixture was then further purged for 5 min and allowed to stir for 16 h at 80° C. The TLC (50% ethyl acetate in hexane) showed that starting material was consumed completely. The reaction mixture was diluted with water (10 ml) and extracted with ethyl acetate (20 mL×3). Combined organic layer was dried over anhydrous Na$_2$SO$_4$ and concentrated under reduced pressure to get crude product. The crude product was purified by flash chromatography followed by flash chromatography to obtain the title compound (240 mg, 39%). LCMS: 442 [M+H]$^+$ Step-2: Synthesis of tert-butyl 4-((6-chloro-3-(1H-indol-4-yl)pyridazin-4-ylamino)methyl)piperidine-1-carboxylate: To a solution of tert-butyl 4-((6-chloro-3-(1H-indol-4-yl)pyridazin-4-ylamino)methyl)piperidine-1-carboxylate (0.24 g, 0.543 mmol, 1.0 eq) in DMF (3 mL) was added 5-aminopyrazine-2-carbonitrile (0.078 g, 0.65 mmol, 1.2 eq), Cs$_2$CO$_3$ (0.442 g, 1.35 mmol, 2.5 eq.), Xantphos (0.025 g, 0.0434 mmol, 0.08 eq) followed by the addition of Pd$_2$(dba)$_3$ (0.020 g, 0.0217 mmol, 0.04 eq) under nitrogen atmosphere. The resulting reaction mixture was heated at 180° C. in microwave reactor for 90 min. The TLC (50% ethyl acetate in hexane) showed that starting material was consumed completely. Product formation was confirmed by LCMS. The reaction mixture was diluted with water (10 mL) and extracted with ethyl acetate (20 mL×3). Combined organic layer was dried over anhydrous Na$_2$SO$_4$ and concentrated under reduced pressure to get crude product. The crude product was purified by flash chromatography followed by flash chromatography to obtain the title compound (32 mg, 11%). LCMS: 526 [M+H]$^+$;

Step-3: Synthesis of 5-(6-(1H-indol-4-yl)-5-(piperidin-4-ylmethylamino)pyridazin-3-ylamino)pyrazine-2-carbonitrile: To a solution of tert-butyl 4-((6-(5-cyanopyrazin-2-ylamino)-3-(1H-indol-4-yl)pyridazin-4-ylamino)methyl)piperidine-1-carboxylate (0.030 g, 0.0578 mmol) in DCM (2.0 ml) was added trifluoroacetic acid (0.2 ml) drop wise at 0° C. The resultant reaction mixture was then allowed to stir for 30 min. The LCMS showed the formation of desired product. To this reaction mixture, was added pentane (15 mL) under stirring. After formation of suspension, the reaction mixture was filtered to get the title compound (15 mg, 62%) LCMS: 426.3 [M+H]$^+$; $^1$H NMR (400 MHz, DMSO-d6) δ 11.44 (br. s., 1H), 8.91 (br. s., 1H), 8.78 (br. s., 1H), 8.58 (br. s., 1H), 8.35 (br. s., 1H), 7.62 (d, J=8.33 Hz, 1H), 7.46 (br. s., 1H), 7.24-7.34 (m, 1H), 7.19 (d, J=7.02 Hz, 1H), 6.30 (br. s., 1H), 3.28 (d, J=11.84 Hz, 2H), 3.12 (br. s., 2H), 2.83 (d, J=9.21 Hz, 2H), 1.94 (br. s., 1H), 1.81 (d, J=13.15 Hz, 2H), 1.32 (d, J=12.72 Hz, 2H)

Example-25: Synthesis of 5-(6-(3-(piperidin-1-yl)phenyl)-5-(piperidin-4-ylmethylamino)pyridazin-3-ylamino)pyrazine-2-carbonitrile (Compound No. 1.25)

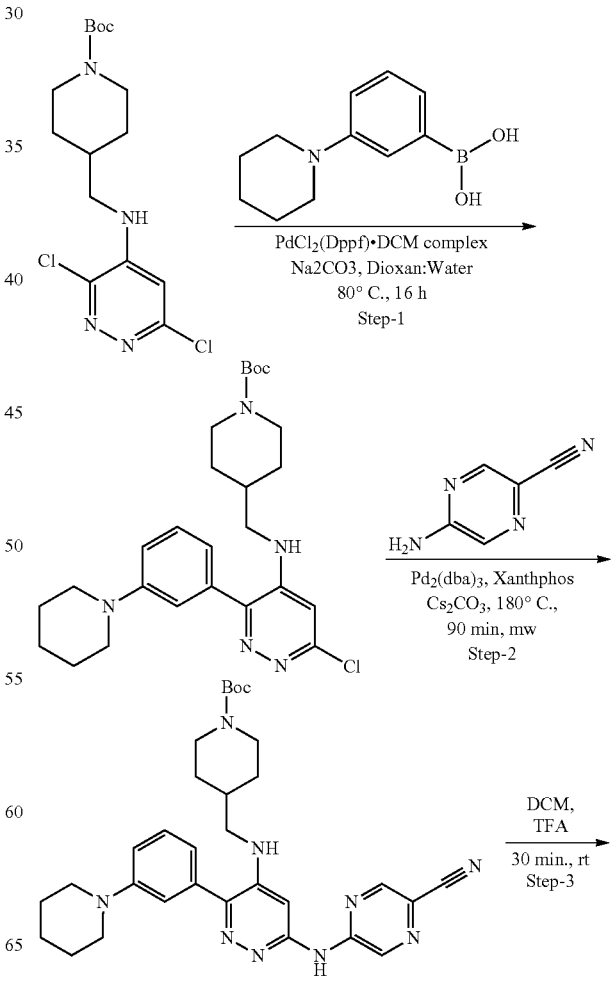

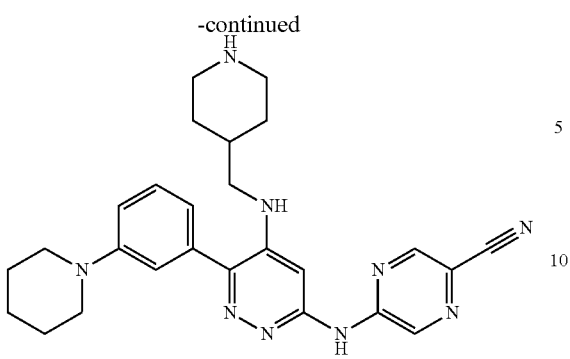

Step-1: synthesis of tert-butyl 4-((6-chloro-3-(3-(piperidin-1-yl)phenyl)pyridazin-4-ylamino)methyl)piperidine-1-carboxylate: to a solution of tert-butyl 4-((3,6-dichloropyridazin-4-ylamino)methyl)piperidine-1-carboxylate (0.5 g, 1.38 mmol, 1.0 eq.) in Dioxane:water (4:1, 5.0 ml) under nitrogen purging was added sodium carbonate (0.365 g, 3.45 mmol, 2.5 eq.), 3-(piperidin-1-yl)phenylboronic acid (0.312 g, 1.52 mmol, 1.1 eq.) and Pd(dppf)Cl$_2$.DCM complex (0.056 g, 0.069, 0.05 eq.). The reaction mixture was then allowed to stir for 16 h at 80° C. The TLC (40% ethyl acetate in hexane) showed that starting material was consumed completely. The reaction mixture was diluted with water (10 mL) and extracted with ethyl acetate (20 mL×3). Combined organic layer was dried over anhydrous Na$_2$SO$_4$ and concentrated under reduced pressure to get crude product. The crude product was purified by flash chromatography followed by flash chromatography to obtain the title compound (90 mg, 13%). LCMS: 486.2 [M+H]$^+$;

Step-2: Synthesis of tert-butyl 4-((6-(5-cyanopyrazin-2-ylamino)-3-(3-(piperidin-1-yl)phenyl)pyridazin-4-ylamino)methyl)piperidine-1-carboxylate: To a solution of tert-butyl 4-((6-chloro-3-(3-(piperidin-1-yl)phenyl)pyridazin-4-ylamino)methyl)piperidine-1-carboxylate (0.090 g, 0.185 mmol, 1.0 eq.) in DMF (3 mL) was added 5-aminopyrazine-2-carbonitrile (0.026 g, 0.22 mmol, 1.2 eq.), Cs$_2$CO$_3$ (0.150 g, 0.462 mmol, 2.5 eq.), Xantphos (0.008 g, 0.0148 mmol, 0.08 eq.) followed by the addition of Pd$_2$(dba)$_3$ (0.07 g, 0.0074 mmol, 0.04 eq.) under nitrogen atmosphere. The resulting reaction mixture was heated at 180° C. in microwave reactor for 90 min. The TLC (60% ethyl acetate in hexane) showed that starting material was consumed completely. Product formation was confirmed by LCMS. The reaction mixture was diluted with water (10 mL) and extracted with ethyl acetate (10 mL×3). Combined organic layer was dried over anhydrous Na$_2$SO$_4$ and concentrated under reduced pressure to get crude product. The crude product was purified by flash chromatography to obtain the title compound (20 mg, 19%). LCMS: 570 [M+H]$^+$;

Step-3: Synthesis of 5-(6-(3-(piperidin-1-yl)phenyl)-5-(piperidin-4-ylmethylamino)pyridazin-3-ylamino) pyrazine-2-carbonitrile: To a solution of tert-butyl 4-((6-(5-cyanopyrazin-2-ylamino)-3-(3-(piperidin-1-yl)phenyl)pyridazin-4-ylamino)methyl)piperidine-1-carboxylate (0.018 g, 0.0315 mmol) in DCM (2.0 mL) was added trifluoroacetic acid (0.15 mL) drop wise at 0° C. The resultant reaction mixture was then allowed to stir for 30 min. The TLC (80% ethyl acetate in hexane) showed that starting material consumed completely. The LCMS showed the formation of desired product. To this reaction mixture, was added pentane (15 mL) under stirring. After formation of suspension, the reaction mixture was stirred for 15 minutes and filtered to get the title compound (15 mg, 54%). LCMS: 470 [M+H]$^+$; $^1$H NMR (400 MHz, DMSO-d$_6$) δ 8.90 (d, J=0.88 Hz, 1H), 8.75 (s, 1H), 8.67 (br. s., 1H), 8.49 (br. s., 1H), 7.39-7.48 (m, 1H), 7.28 (s, 4H), 7.03 (d, J=7.89 Hz, 1H), 3.08-3.21 (m, 6H), 2.76-2.91 (m, 2H), 1.98 (br. s., 1H), 1.85 (d, J=13.15 Hz, 2H), 1.68 (br. s., 4H), 1.59 (br. s., 3H), 1.30-1.47 (m, 3H)

Example-26: Synthesis of 5-(6-(3-methoxyphenyl)-5-(piperidin-4-ylmethylamino)pyridazin-3-ylamino) pyrazine-2-carbonitrile (Compound No. 1.26)

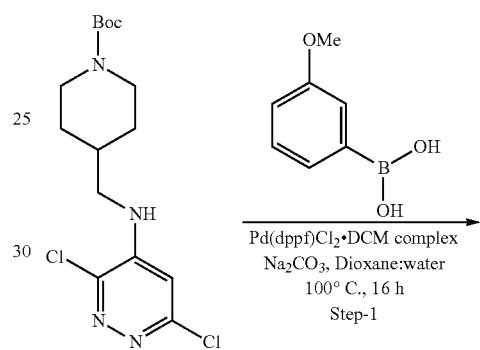

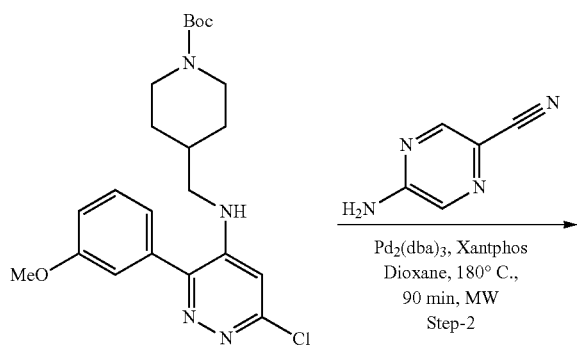

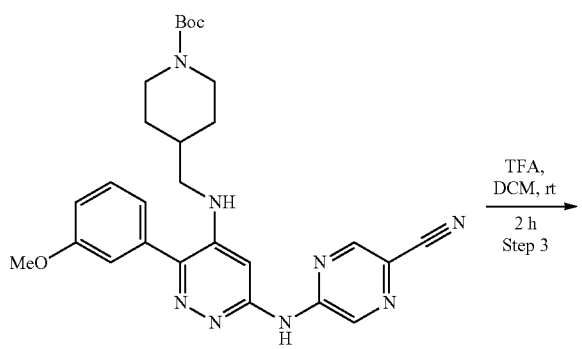

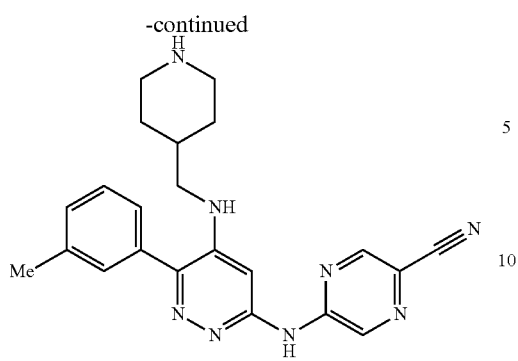

Step-1: Synthesis of tert-butyl 4-((6-chloro-3-(3-methoxyphenyl)pyridazin-4-ylamino)methyl)piperidine-1-carboxylate: To a solution of tert-butyl 4-((3,6-dichloropyridazin-4-ylamino)methyl)piperidine-1-carboxylate (0.400 g, 1.10 mmol, 1.0 eq.) in Dioxane:water (6:1, 7 ml) under nitrogen purging was added sodium carbonate (0.288 g, 2.7 mmol, 2.5 eq.), 3-methoxyphenylboronic acid (0.200 g, 1.32 mmol, 1.2 eq.) and Pd(dppf)Cl$_2$.DCM complex (0.035 g, 0.044 mmol, 0.04 eq.). The reaction mixture was then further purged for 5 min and allowed to stir for 16 h at 110° C. The TLC (50% ethyl acetate in hexane) showed that starting material was consumed completely. The reaction mixture was diluted with water (120 ml) and extracted with ethyl acetate (50 mL×2). Combined organic layer was dried over anhydrous Na$_2$SO$_4$ and concentrated under reduced pressure to get crude product. The crude product was purified by flash chromatography to obtain the title compound (365 mg, 77%). LCMS: 433.2 [M+H]$^+$;

Step-2: Synthesis of tert-butyl 4-((6-(5-cyanopyrazin-2-ylamino)-3-(3-methoxyphenyl)pyridazin-4-ylamino)methyl)piperidine-1-carboxylate: To a solution of tert-butyl 4-((6-chloro-3-(3-methoxyphenyl)pyridazin-4-ylamino)methyl)piperidine-1-carboxylate (0.365 g, 0.84 mmol, 1.0 eq.) in DMF (3 mL) was added 5-aminopyrazine-2-carbonitrile (0.132 g, 1.09 mmol, 1.3 eq.), Cs$_2$CO$_3$ (0.686 g, 2.11 mmol, 2.5 eq.), Xantphos (0.039 g, 0.067 mmol, 0.08 eq.) followed by the addition of Pd$_2$(dba)$_3$ (0.031 g, 0.033 mmol, 0.04 eq.) under nitrogen atmosphere. The resulting reaction mixture was heated at 180° C. in microwave reactor for 90 min. The TLC (50% ethyl acetate in hexane) showed that starting material was consumed completely. Product formation was confirmed by LCMS. The reaction mixture was diluted with water (10 mL) and precipitates obtained were filtered over Buchner funnel, washed with pentane and re-dissolved in DCM. The solution was concentrated under vacuum and was purified by flash column chromatography to obtain the title compound (50 mg, 11%). LCMS: 517.25 [M+H]$^+$;

Step-3: Synthesis of 5-(6-(3-methoxyphenyl)-5-(piperidin-4-ylmethylamino)pyridazin-3-ylamino)pyrazine-2-carbonitrile: To a solution of tert-butyl 4-((6-(5-cyanopyrazin-2-ylamino)-3-(3-methoxyphenyl)pyridazin-4-ylamino)methyl)piperidine-1-carboxylate (0.050 g, 0.096 mmol) in DCM (3.0 ml) was added trifluoroacetic acid (0.4 ml) drop wise at 0° C. The resultant reaction mixture was then allowed to stir for 2 h. The LCMS showed the formation of desired product. The reaction mixture was then concentrated under reduced pressure to get crude product. The crude product was then purified using RP-HPLC to obtain the title compound (6 mg, 15.0%). LCMS: 417.3[M+H]$^+$; $^1$H NMR (400 MHz, DMSO-d$_6$) δ 9.01 (br. s., 1H), 8.78 (d, J=1.32 Hz, 1H), 7.45 (t, J=8.11 Hz, 1H), 7.29 (s, 1H), 7.00-7.16 (m, 4H), 6.35 (br. s., 1H), 3.82 (s, 3H), 3.11 (d, J=11.84 Hz, 2H), 3.03 (d, J=5.70 Hz, 2H), 2.64 (d, J=19.73 Hz, 2H), 1.84 (br. s., 1H), 1.72 (d, J=12.72 Hz, 2H), 1.13-1.26 (m, 2H)

Example-27: Synthesis of 5-(6-(4-(hydroxymethyl)phenyl)-5-(piperidin-4-ylmethylamino)pyridazin-3-ylamino)pyrazine-2-carbonitrile (Compound No. 1.27)

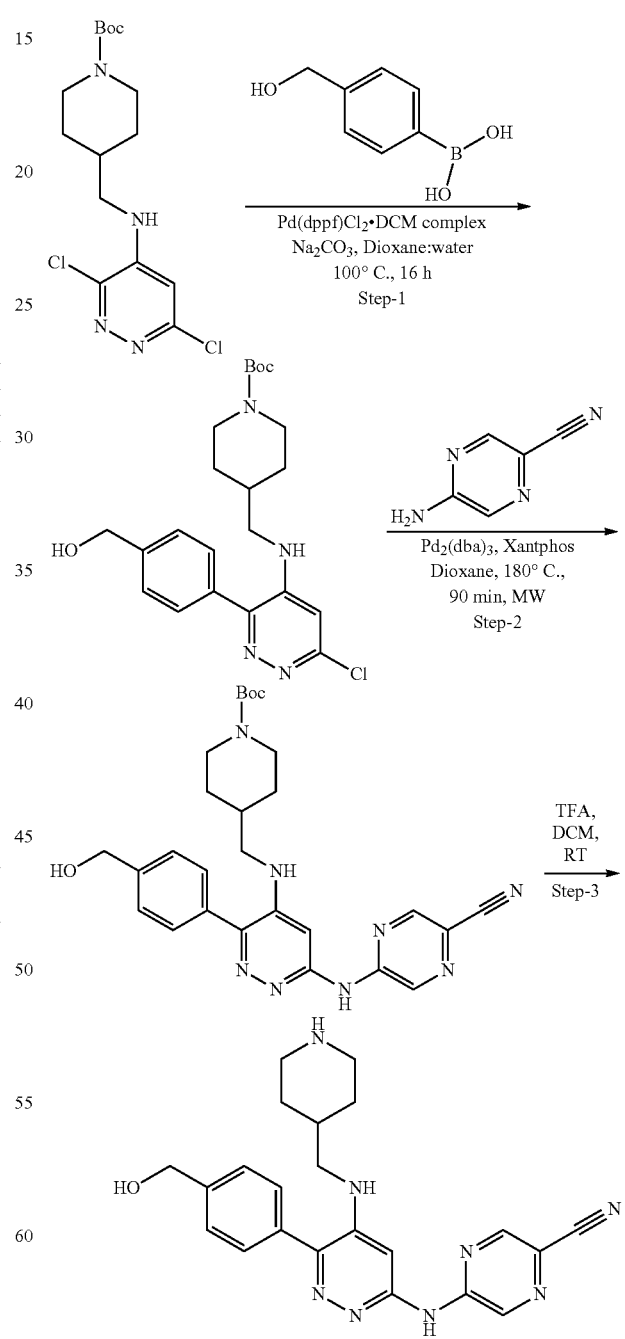

Step-1: Synthesis of tert-butyl 4-((3,6-dichloropyridazin-4-ylamino)methyl)piperidine-1-carboxylate: To a solution of 3,4,6-trichloropyridazine (1.0 g, 5.45 mmol) in acetonitrile (20.0 ml) was added DIPEA (2.37 ml, 13.62 mmol) at RT, followed by addition of tert-butyl 4-(aminomethyl) piperidine-1-carboxylate (1.22 g, 5.72 mmol). The resultant reaction mixture was allowed to stir for 2 h at room temperature. The TLC (50% ethyl acetate in hexane) showed that starting material was consumed completely. The reaction mixture was then concentrated, diluted with DM water (20 ml) and extracted using ethyl acetate (30 ml×2). Combined organic layer was dried over anhydrous $Na_2SO_4$ and concentrated under reduced pressure to get crude product. The crude product was purified by flash chromatography to obtain the title compound (850 mg, 43%). LCMS: 380.4 $[M+H]^+$ Step-2: Synthesis of tert-butyl 4-((6-chloro-3-(4-(hydroxymethyl)phenyl)pyridazin-4-ylamino)methyl)piperidine-1-carboxylate: To a solution of tert-butyl 4-((3,6-dichloropyridazin-4-ylamino)methyl)piperidine-1-carboxylate (0.400 g, 1.10 mmol, 1.0 eq.) in Dioxane:water (5:05, 5.5 ml) under nitrogen purging was added sodium carbonate (0.290 g, 2.76 mmol, 2.5 eq.), 4-(hydroxymethyl) phenylboronic acid (0.200 g, 1.32 mmol, 1.2 eq.) and $Pd(dppf)Cl_2 \cdot DCM$ complex (0.036 g, 0.044 mmol, 0.04 eq.). The reaction mixture was then further purged for 5 min and allowed to stir for 16 h at 110° C. The TLC (50% ethyl acetate in hexane) showed that starting material was consumed completely. The reaction mixture was diluted with water (50 ml) and extracted with ethyl acetate (50 mL×2). Combined organic layer was dried over anhydrous $Na_2SO_4$ and concentrated under reduced pressure to get crude product. The crude product was purified by flash chromatography to obtain the title compound (195 mg, 40.08%). LCMS: 433.2 $[M+H]^+$;

Step-3: Synthesis of tert-butyl 4-((6-(5-cyanopyrazin-2-ylamino)-3-(4-(hydroxymethyl)phenyl)pyridazin-4-ylamino)methyl)piperidine-1-carboxylate: To a solution of tert-butyl 4-((6-chloro-3-(4-(hydroxymethyl) phenyl)pyridazin-4-ylamino)methyl)piperidine-1-carboxylate (0.193 g, 0.446 mmol, 1.0 eq.) in DMF (3 mL) was added 5-aminopyrazine-2-carbonitrile (0.070 g, 0.58 mmol, 1.3 eq.), $Cs_2CO_3$ (0.362 g, 1.11 mmol, 2.5 eq.), Xantphos (0.020 g, 0.037 mmol, 0.08 eq.) followed by the addition of $Pd_2(dba)_3$ (0.016 g, 0.017 mmol, 0.04 eq.) under nitrogen atmosphere. The resulting reaction mixture was heated at 180° C. in microwave reactor for 90 min. The TLC (50% ethyl acetate in hexane) showed that starting material was consumed completely. Product formation was confirmed by LCMS. The reaction mixture was diluted with water (10 mL) and precipitates obtained were filtered over Buchner funnel, washed with pentane. Obtained material was re-dissolved in DCM and was purified by flash chromatography to obtain the title compound (57 mg, 13%). LCMS: 517 $[M+H]^+$ Step-4: Synthesis of 5-(6-(4-(hydroxymethyl)phenyl)-5-(piperidin-4-ylmethylamino)pyridazin-3-ylamino)pyrazine-2-carbonitrile: To a solution of tert-butyl 4-((6-(5-cyanopyrazin-2-ylamino)-3-(4-(hydroxymethyl)phenyl)pyridazin-4-ylamino)methyl)piperidine-1-carboxylate (0.048 g, 0.083 mmol) in DCM (3.0 ml) was added trifluoroacetic acid (0.4 ml) drop wise at 0° C. The resultant reaction mixture was then allowed to stir for 2 h. The LCMS showed the formation of desired product. The reaction mixture was then concentrated under reduced pressure to get crude product. The crude product was then purified using RF-HPLC to get the title compound (13.6 mg, 34%). LCMS: 417.3 $[M+H]^+$; $^1H$ NMR (400 MHz, DMSO-$d_6$) δ 8.87 (br. s., 1H), 8.80 (br.

s., 1H), 8.58 (br. s., 1H), 8.33 (br. s., 1H), 7.51 (s, 1H), 7.55 (s, 2H), 7.30 (br. s., 1H), 4.61 (br. s., 2H), 3.29 (br. s., 2H), 3.13 (br. s., 2H), 2.84 (d, J=11.84 Hz, 2H), 1.96 (br. s., 1H), 1.84 (d, J=12.28 Hz, 2H), 1.35 (d, J=10.96 Hz, 2H).

Example-28: Synthesis of 5-(6-(1-methyl-1H-pyrazol-3-yl)-5-(piperidin-4-ylmethylamino)pyridazin-3-ylamino)pyrazine-2-carbonitrile: (Compound No. 1.28)

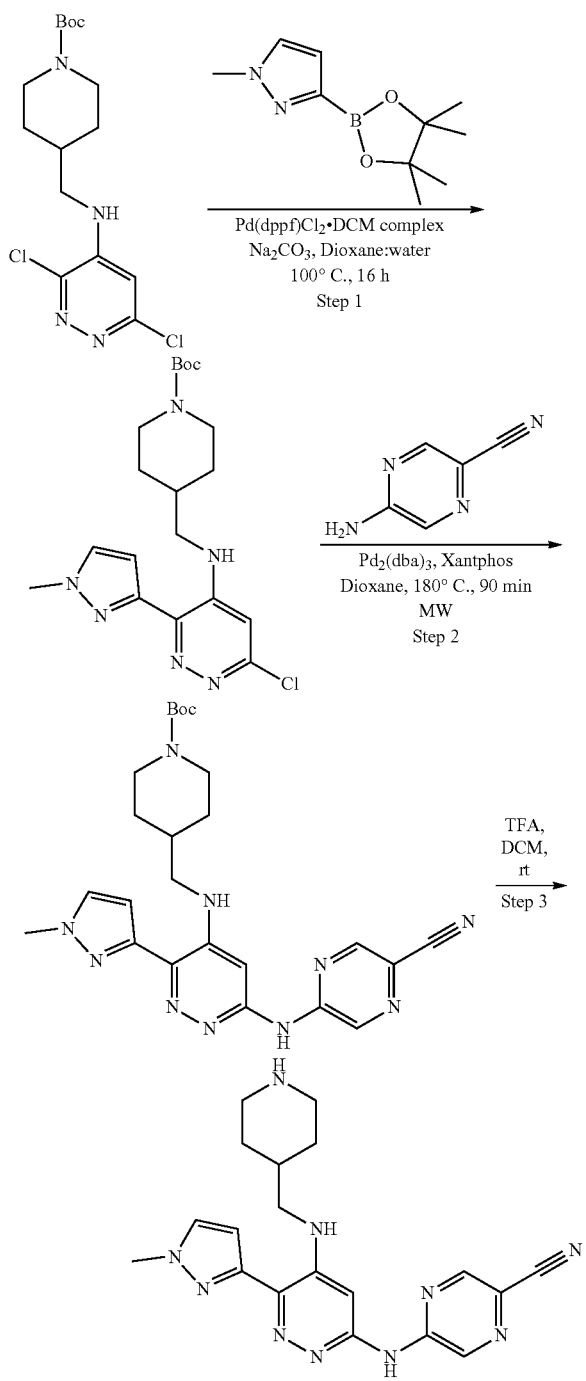

Step-1: Synthesis of tert-butyl 4-((6-chloro-3-(1-methyl-1H-pyrazol-3-yl)pyridazin-4-ylamino)methyl)piperidine-1-carboxylate: to a solution of tert-butyl 4-((3,6-dichloro-pyridazin-4-ylamino)methyl)piperidine-1-carboxylate (0.600 g, 1.65 mmol, 1.0 eq.) in dioxane:water (5:05, 5.5 ml) under nitrogen purging was added sodium carbonate (0.382.87 g, 3.64 mmol, 2.2 eq.), 1-methyl-3-(4,4,5,5-tetramethyl-1,3,2-dioxaborolan-2-yl)-1H-pyrazole (0.441.7 g, 2.15 mmol, 1.3 eq.) and Dikis (0.0446 g, 0.066, 0.04 eq.). The reaction mixture was then further purged for 5 min and allowed to stir for 16 h at 110° C. The TLC (50% ethyl acetate in hexane) showed that starting material was consumed completely. The reaction mixture was diluted with water (50 ml) and extracted with ethyl acetate (50 mL×2). Combined organic layer was dried over anhydrous $Na_2SO_4$ and concentrated under reduced pressure to get crude product. The crude product was purified by flash chromatography to obtain the title compound (280 mg, 52%). LCMS: 407.2 $[M+H]^+$;

Step-2: Synthesis of tert-butyl 4-((6-(5-cyanopyrazin-2-ylamino)-3-(1-methyl-1H-pyrazol-3-yl)pyridazin-4-ylamino)methyl)piperidine-1-carboxylate: To a solution of tert-butyl 4-((6-chloro-3-(1-methyl-1H-pyrazol-3-yl)pyridazin-4-ylamino)methyl)piperidine-1-carboxylate (0.280 g, 0.68 mmol, 1.0 eq.) in DMF (3 mL) was added 5-aminopyrazine-2-carbonitrile (0.108 g, 0.89 mmol, 1.3 eq.), $Cs_2CO_3$ (0.562 g, 1.72 mmol, 2.5 eq.), Xantphos (0.0318 g, 0.055 mmol, 0.08 eq.) followed by the addition of $Pd_2(dba)_3$ (0.025 g, 0.027 mmol, 0.04 eq.) under nitrogen atmosphere. The resulting reaction mixture was heated at 180° C. in microwave reactor for 90 min. The TLC (50% ethyl acetate in hexane) showed that starting material was consumed completely. Product formation was confirmed by LCMS. The reaction mixture was diluted with water (10 ml) and precipitates obtained were filtered over Buchner funnel, washed with pentane. Obtained material was re-dissolved in DCM and was purified by flash chromatography to obtain the title compound (40 mg, 11%). LCMS: 491.2 $[M+H]^+$;

Step-3: Synthesis of 5-(6-(1-methyl-1H-pyrazol-3-yl)-5-(piperidin-4-ylmethylamino)pyridazin-3-ylamino)pyrazine-2-carbonitrile: To a solution of tert-butyl 4-((6-(5-cyanopyrazin-2-ylamino)-3-(1-methyl-1H-pyrazol-3-yl)pyridazin-4-ylamino)methyl)piperidine-1-carboxylate (0.030 g, 0.061 mmol) in DCM (3.0 ml) was added trifluoroacetic acid (0.4 ml) drop wise at 0° C. The resultant reaction mixture was then allowed to stir for 2 h. The LCMS showed the formation of desired product. To this reaction mixture, was added pentane (15 mL) under stirring. After formation of suspension, the reaction mixture was filtered to get the title compound (11 mg, 46%). LCMS: 391.21$[M+H]^+$; $^1H$ NMR (400 MHz, DMSO-d6) δ 8.88 (br. s., 1H), 8.82 (s, 1H), 8.77 (br. s., 1H), 8.52 (br. s., 1H), 8.21 (br. s., 1H), 7.92 (br. s., 1H), 7.38 (s, 1H), 6.98 (br. s., 1H), 3.99 (s, 3H), 3.24-3.38 (m, 2H), 2.90 (d, J=9.65 Hz, 4H), 1.99 (br. s., 1H), 1.91 (d, J=12.72 Hz, 2H), 1.44 (d, J=14.91 Hz, 2H)

Example-29: Synthesis of 6-(5-cyanopyrazin-2-ylamino)-4-((tetrahydro-2H-pyran-4-yl)methyl-amino)pyridazine-3-carboxamide (Compound No. 1.29)

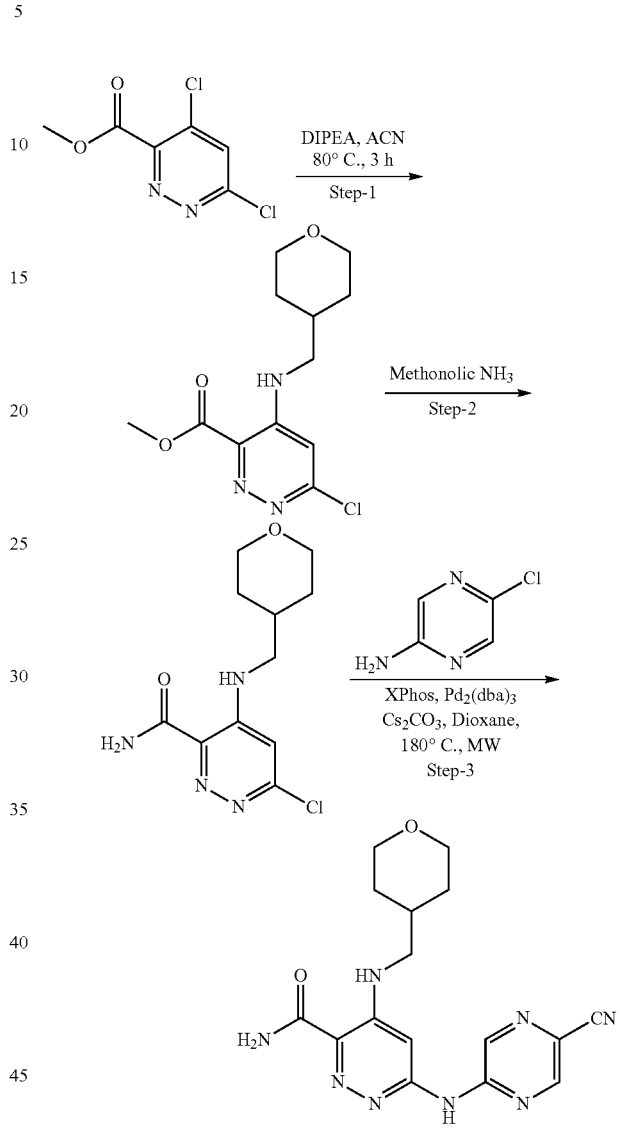

Step-1: Synthesis of methyl 6-chloro-4-((tetrahydro-2H-pyran-4-yl)methylamino)pyridazine-3-carboxylate: To a solution of methyl 4,6-dichloropyridazine-3-carboxylate (0.5 g, 0.0024 mol, 1.0 eq) and (1-methylpiperidin-4-yl)methanamine (0.275 g, 0.0024 mol, 1.0 eq) in ACN (10 mL was added DIPEA (0.8 mL, 0.0048 mmol, 2.0 eq). The reaction mixture was stirred for 16 h. After completion, reaction mixture was concentrated under vacuum to get the crude which was purified by normal phase silica gel column chromatography to get the title compound (1.0 g, 73%). LCMS: 286 $[M+H]^+$.

Step-2: Synthesis of 6-chloro-4-((tetrahydro-2H-pyran-4-yl)methylamino)pyridazine-3-carboxamide: To a solution of methyl 6-chloro-4-((tetrahydro-2H-pyran-4-yl)methyl-amino)pyridazine-3-carboxylate (0.5 g, 0.0017 mol, 1.0 eq) was added methonolic ammonia (10 mL) at RT. The reaction mixture was stirred for 30 min. After completion, the reaction was concentrated under vacuum to get title compound (0.4 g, 84%). LCMS: 271$[M+H]^+$.

Step-3: Synthesis of 6-(5-cyanopyrazin-2-ylamino)-4-((tetrahydro-2H-pyran-4-yl)methylamino)pyridazine-3-carboxamide: To a solution of 6-chloro-4-((tetrahydro-2H-pyran-4-yl)methylamino)pyridazine-3-carboxamide (0.2 g, 0.7 mmol, 1.0 eq) in DMF (4 mL) was added 5-aminopyrazine-2-carbonitrile (0.106 g, 0.8 mmol, 1.2 eq), Cs$_2$CO$_3$ (0.72 g, 2.2 mmol, 3.0 eq), xantphos (0.042 g, 10 mol %) followed by the addition of Pd$_2$(dba)$_3$ (0.033 g, 5 mol %) under nitrogen atmosphere. The resulting reaction mixture was heated at 180° C. using microwave reactor for 90 min. Product formation was confirmed by LCMS. The reaction mixture was diluted with water and extracted with ethyl acetate (75 mL×3). Combined organic layer was dried over anhydrous Na$_2$SO$_4$ and concentrated under reduced pressure. The crude product was purified by RP-HPLC to obtain the title compound (0.026 g, 10%). LCMS: 355 [M+H]$^+$; $^1$H NMR (400 MHz, DMSO-d$_6$) δ 11.00 (br. s., 1H), 8.89-9.04 (m, 2H), 8.75-8.84 (m, 1H), 8.37 (br. s., 1H), 7.64 (br. s., 1H), 7.40 (s, 1H), 3.87 (dd, J=3.07, 10.96 Hz, 2H), 3.23-3.30 (m, 2H), 3.11 (t, J=6.14 Hz, 2H), 1.87 (br. s., 1H), 1.62 (d, J=11.84 Hz, 2H), 1.21-1.37 (m, 2H)

Example-30: Synthesis of 6-(5-cyanopyrazin-2-ylamino)-N-methyl-4-((tetrahydro-2H-pyran-4-yl)methylamino)pyridazine-3-carboxamide (Compound No. 1.30)

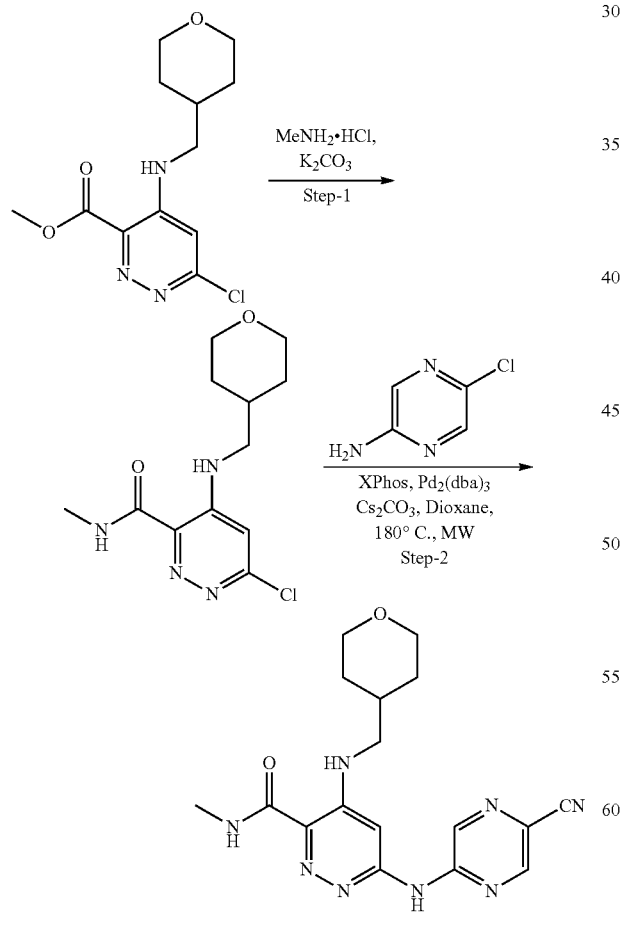

Step-1: Synthesis of 6-chloro-N-methyl-4-((tetrahydro-2H-pyran-4-yl)methylamino)pyridazine-3-carboxamide: To a solution of methyl 6-chloro-4-((tetrahydro-2H-pyran-4-yl)methylamino)pyridazine-3-carboxylate (0.500 g, 1.7 mmol, 1.0 eq) in methanol was added K$_2$CO$_3$ (0.726 g, 5.2 mmol, 3.0 eq) and methylamine hydrochloride (0.236 g, 3.5 mmol, 2.0 eq). The reaction mixture was allowed to stir at RT for 24 h. The reaction mixture was concentrated under vacuum and diluted with water and extracted with DCM (75 mL×3). Combined organic layers were dried over anhydrous Na$_2$SO$_4$ and concentrated under reduced pressure to get the title compound (0.230 g, 47%). LCMS: 285 [M+H]$^+$.

Step-2: Synthesis of 6-(5-cyanopyrazin-2-ylamino)-N-methyl-4-((tetrahydro-2H-pyran-4-yl)methylamino)pyridazine-3-carboxamide: To a solution of 6-chloro-N-methyl-4-((tetrahydro-2H-pyran-4-yl)methylamino)pyridazine-3-carboxamide (0.230 g, 0.8 mmol, 1.0 eq) in DMF (4 mL) was added 5-aminopyrazine-2-carbonitrile (0.116 g, 0.9 mmol, 1.2 eq), Cs$_2$CO$_3$ (0.79 g, 2.4 mmol, 3.0 eq), Xantphos (0.046 g, 10 mol %) followed by the addition of Pd$_2$(dba)$_3$ (0.037 g, 5 mol %) under nitrogen atmosphere. The resulting reaction mixture was heated at 180° C. using microwave reactor for 90 min. Product formation was confirmed by LCMS. The reaction mixture was diluted with water and extracted with ethyl acetate (75 mL×3). Combined organic layer was dried over anhydrous Na$_2$SO$_4$ and concentrated under reduced pressure. The crude product was purified by RP-HPLC to obtain the title compound (0.056 g, 19%). LCMS: 369 [M+H]$^+$; 1H NMR (400 MHz, DMSO-d6) δ 8.87-9.07 (m, 3H), 8.79 (s, 1H), 7.39 (s, 1H), 3.87 (d, J=7.89 Hz, 2H), 3.29 (t, J=10.96 Hz, 2H), 3.10 (t, J=5.92 Hz, 2H), 2.79 (d, J=4.82 Hz, 3H), 1.88 (br. s., 1H), 1.75 (s, 1H), 1.62 (d, J=11.84 Hz, 2H), 1.29 (dt, J=8.33, 12.06 Hz, 2H)

Example-31: Synthesis of 5-(6-isopropoxy-5-(piperidin-4-ylmethylamino)pyridazin-3-ylamino)pyrazine-2-carbonitrile (Compound No. 1.31)

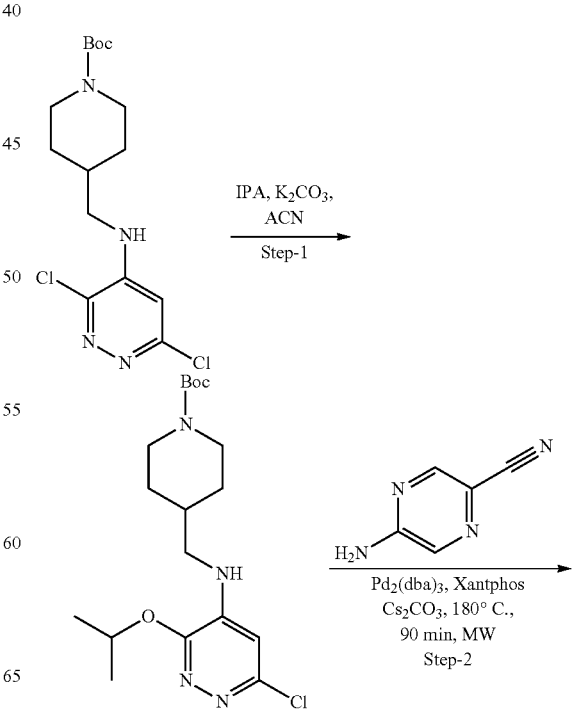

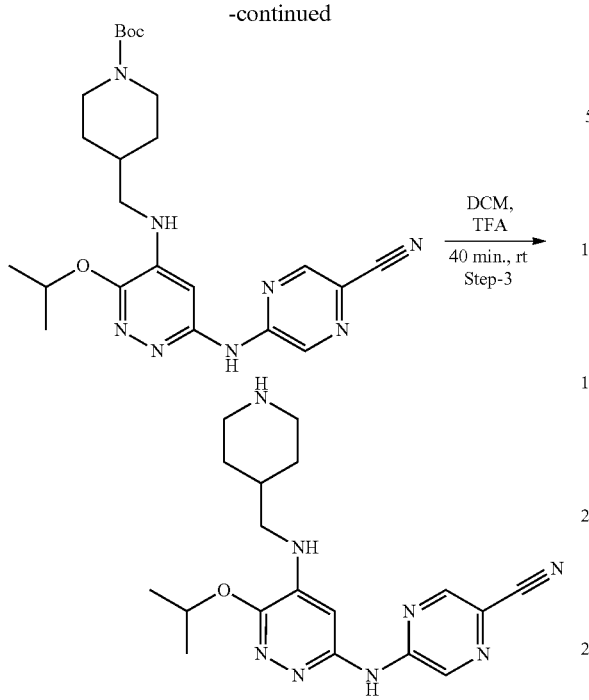

Step-1: Synthesis of tert-butyl 4-((6-chloro-3-isopropoxypyridazin-4-ylamino)methyl)piperidine-1-carboxylate: to a solution of tert-butyl 4-((3,6-dichloropyridazin-4-ylamino)methyl)piperidine-1-carboxylate (0.4 g, 1.1 mmol, 1.0 eq) in ACN (10 mL) was added isopropyl alcohol (0.2 mL) and $K_2CO_3$ (0.3 g, 2.2 mmol, 2.0 eq) at RT. The reaction mixture was allowed to heat at 80° C. stirred for 18 h. After completion, The reaction mixture was diluted with water and extracted with ethyl acetate (75 mL×3). Combined organic layer was dried over anhydrous $Na_2SO_4$ and concentrated under reduced pressure. The crude product was purified by normal phase silica-gel column chromatography to obtain the title compound (0.18 g, 42%). LCMS: 385[M+H]$^+$.

Step-2: Synthesis of tert-butyl 4-((6-(5-cyanopyrazin-2-ylamino)-3-isopropoxypyridazin-4-ylamino)methyl)piperidine-1-carboxylate: To a solution of tert-butyl 4-((6-chloro-3-isopropoxypyridazin-4-ylamino)methyl)piperidine-1-carboxylate (0.18 g, 0.4 mmol, 1.0 eq) in DMF (4 mL) was added 5-aminopyrazine-2-carbonitrile (0.068 g, 0.5 mmol, 1.2 eq.), $Cs_2CO_3$ (0.45 g, 1.3 mmol, 3.0 eq.), Xantphos (0.027 g, 10 mol %) followed by the addition of $Pd_2(dba)_3$ (0.020 g, 5 mol %) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×2). Combined organic layer was dried over anhydrous $Na_2SO_4$ and concentrated under reduced pressure. The crude product was purified by RP-HPLC to obtain the title compound (0.050 g, 57%). LCMS: 469 [M+H]$^+$ Step-3: Synthesis of 5-(6-isopropoxy-5-(piperidin-4-ylmethylamino)pyridazin-3-ylamino)pyrazine-2-carbonitrile: To a solution of tert-butyl 4-((6-(5-cyanopyrazin-2-ylamino)-3-isopropoxypyridazin-4-ylamino)methyl)piperidine-1-carboxylate (0.05 g, 0.1 mmol, 1.0 eq) in DCM (5 mL) was added TFA (0.5 mL) and the resulting reaction mixture was allowed to stir at RT for 30 min. Progress of the reaction was monitored by LCMS. Diethyl ether (10 mL) was added and the resulting precipitates were filtered and washed with ether to get the title compound as TFA salt (5 mg, 14%). LCMS: 369 [M+H]$^+$; $^1$H NMR (400 MHz, DMSO-d$_6$) δ 9.08 (br. s., 1H), 8.70 (s, 1H), 6.83 (s, 1H), 6.49 (br. s., 1H), 5.26-5.37 (m, 1H), 2.85-3.04 (m, 4H), 1.73 (br. s., 5H), 1.59 (d, J=13.59 Hz, 2H), 1.35 (d, J=6.14 Hz, 6H)

Example-32: Synthesis of 6-(5-cyanopyrazin-2-ylamino)-N,N-dimethyl-4-(piperidin-4-ylmethylamino)pyridazine-3-carboxamide (Compound No. 1.32)

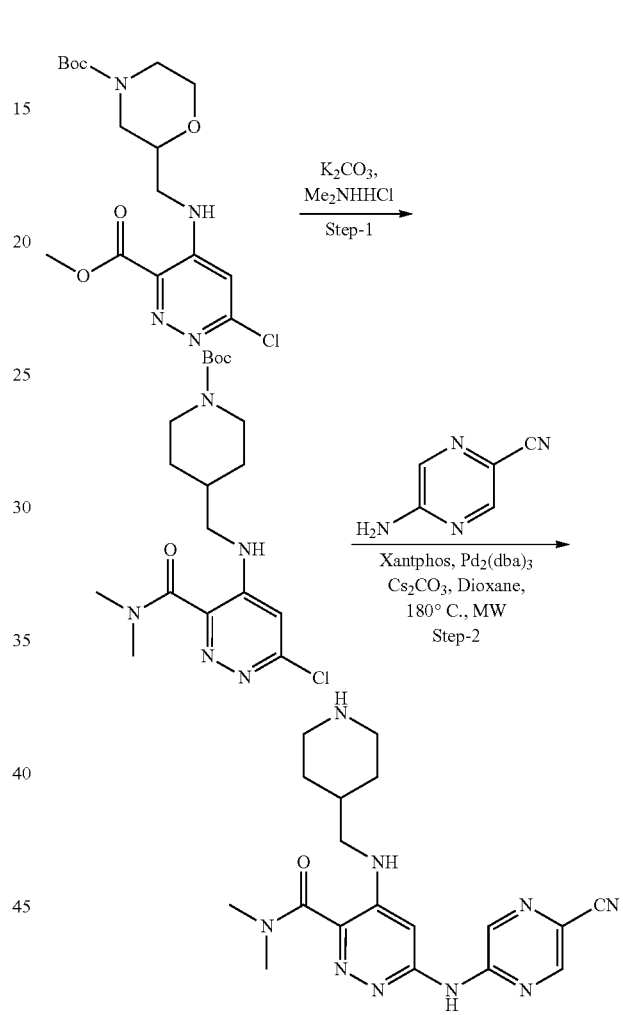

Step-1: Synthesis of tert-butyl 4-((6-chloro-3-(dimethylcarbamoyl)pyridazin-4-ylamino)methyl)piperidine-1-carboxylate: To a solution of methyl 4-((1-(tert-butoxycarbonyl)piperidin-4-yl)methylamino)-6-chloropyridazine-3-carboxylate (0.6 g, 1.56 mmol, 1.0 eq.) in methanol (50 mL), was added potassium carbonate (0.645 g, 4.68 mmol, 3.0 eq.) followed by dimethylamine hydrochloride (0.636 g, 7.80 mmol, 5.0 eq.). The resultant reaction mixture was allowed to stir for 6 h at room temperature. The TLC (60% ethyl acetate in hexane) showed that starting material consumed completely. The reaction mixture was concentrated. The reaction mixture was diluted with water (20 ml) and extracted using ethyl acetate (40 ml×2). Combined organic layer was dried over anhydrous $Na_2SO_4$ and concentrated under reduced pressure to get crude product. The crude product was purified by flash chromatography to obtain (320 mg, 51.6%). LCMS: 398.1 [M+H]$^+$;

Step-2: Synthesis of 6-(5-cyanopyrazin-2-ylamino)-N,N-dimethyl-4-(piperidin-4-ylmethylamino)pyridazine-3-carboxamide: To a solution of tert-butyl 4-((6-chloro-3-(dimethylcarbamoyl)pyridazin-4-ylamino)methyl)piperidine-1-carboxylate (0.300 g, 0.755 mmol, 1.0 eq.) in DMF (4.0 mL) was added 5-aminopyrazine-2-carbonitrile (0.108 g, 0.906 mmol, 1.2 eq.), $Cs_2CO_3$ (0.614 g, 1.88 mmol, 2.5 eq.), Xantphos (0.034 g, 0.060 mmol, 0.08 eq.) followed by the addition of $Pd_2(dba)_3$ (0.027 g, 0.0302 mmol, 0.04 eq.) under nitrogen atmosphere. The resulting reaction mixture was heated at 180° C. in microwave reactor for 90 min. The TLC (ethyl acetate) showed that starting material was consumed completely. The reaction mixture was diluted with water (15 ml) and precipitates obtained were filtered over Buchner funnel. The filterate was then concentrated to remove DMF. The resultant reaction mixture was diluted with DM water (10 mL) and washed with ethyl acetate (10 mL). The aqueous layer was then concentrated to get 300 mg of crude product then purified using RF-HPLC to get 10 mg of title compound. LCMS: 382 [M+H]⁺; 1H NMR (400 MHz, METHANOL-d4) δ 8.73 (br. s., 2H), 7.27 (br. s., 1H), 3.73 (td, J=6.58, 13.15 Hz, 2H), 3.45 (d, J=11.84 Hz, 2H), 3.23 (d, J=7.02 Hz, 2H), 3.15 (d, J=15.79 Hz, 6H), 3.01 (t, J=12.50 Hz, 2H), 2.05 (d, J=12.28 Hz, 3H)

Example-33: Synthesis of 5-(5-(piperidin-4-ylmethylamino)-6-(2,2,2-trifluoroethoxy)pyridazin-3-ylamino)pyrazine-2-carbonitrile (Compound No. 1.33)

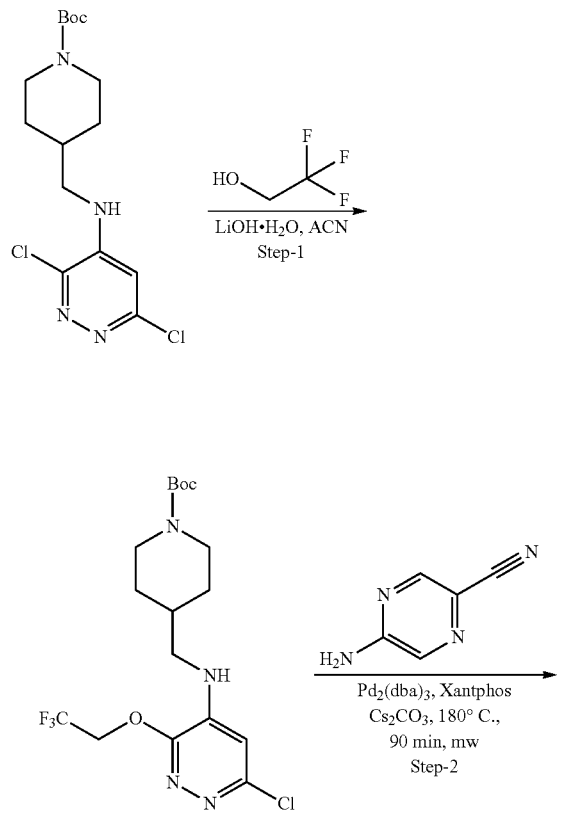

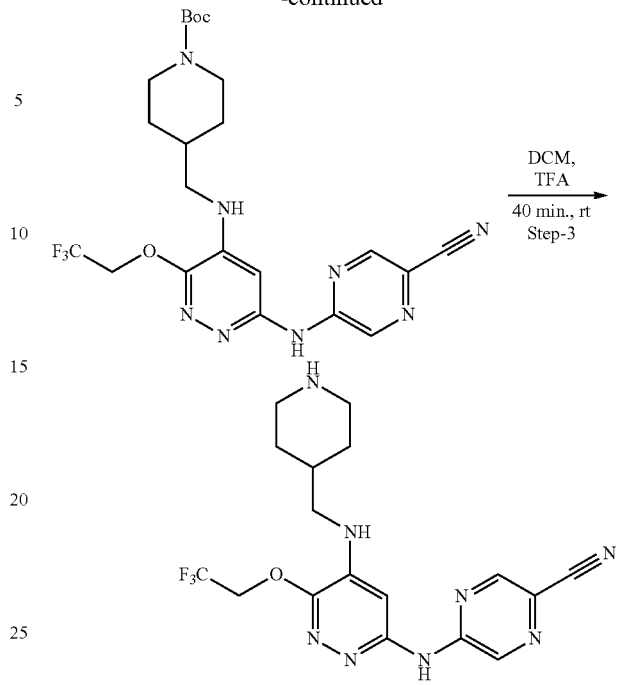

Step-1: Synthesis of tert-butyl 4-((6-chloro-3-(2,2,2-trifluoroethoxy)pyridazin-4-ylamino)methyl)piperidine-1-carboxylate: to a solution of tert-butyl 4-((3,6-dichloropyridazin-4-ylamino)methyl)piperidine-1-carboxylate (0.4 g, 1.1 mmol, 1.0 eq) in ACN (5 mL) was added 2,2,2-trifluoroethanol (0.13 g, 1.3 mmol, 1.2 eq) and LiOH·H₂O (0.09 g, 2.2 mmol, 2.0 eq) at RT. The reaction mixture was allowed to heat at 80° C. stirred for 18 h. After completion, The reaction mixture was diluted with water and extracted with ethyl acetate (75 mL×3). Combined organic layer was dried over anhydrous $Na_2SO_4$ and concentrated under reduced pressure. The crude product was purified by normal phase silica-gel column chromatography to obtain the title compound (0.35 g, 75%). LCMS: 425[M+H]⁺.

Step-2: Synthesis of tert-butyl 4-((6-(5-cyanopyrazin-2-ylamino)-3-(2,2,2-trifluoroethoxy)pyridazin-4-ylamino)methyl)piperidine-1-carboxylate: To a solution of tert-butyl 4-((6-chloro-3-(2,2,2-trifluoroethoxy)pyridazin-4-ylamino)methyl)piperidine-1-carboxylate (0.35 g, 0.8 mmol, 1.0 eq) in DMF (5 mL) was added 5-aminopyrazine-2-carbonitrile (0.12 g, 0.99 mmol, 1.2 eq.), $Cs_2CO_3$ (0.80 g, 2.4 mmol, 3.0 eq.), Xantphos (0.047 g, 10 mol %) followed by the addition of $Pd_2(dba)_3$ (0.037 g, 5 mol %) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×2). Combined organic layer was dried over anhydrous $Na_2SO_4$ and concentrated under reduced pressure. The crude product was purified by RP-HPLC to obtain the title compound (0.030 g, 7%). LCMS: 509 [M+H]⁺

Step-3: Synthesis of 5-(5-(piperidin-4-ylmethylamino)-6-(2,2,2-trifluoroethoxy)pyridazin-3-ylamino)pyrazine-2-carbonitrile: To a solution of tert-butyl 4-((6-(5-cyanopyrazin-2-ylamino)-3-(2,2,2-trifluoroethoxy)pyridazin-4-ylamino)methyl)piperidine-1-carboxylate (0.03 g, 0.06 mmol, 1.0 eq) in DCM (5 mL) was added TFA (0.5 mL) and the resulting reaction mixture was allowed to stir at RT for 60 min. Progress of the reaction was monitored by LCMS. Diethyl ether (10 mL) was added and the resulting precipitates were filtered and washed with ether to give the crude compound which was purified by RP-HPLC to get the title compound (2 mg, 8%). LCMS: 409[M+H]$^+$; $^1$H NMR (400 MHz, DMSO-d$_6$) δ 10.64 (br. s., 1H), 9.00 (br. s., 1H), 8.77 (br. s., 1H), 8.52 (br. s., 1H), 7.12 (br. s., 1H), 6.89 (br. s., 1H), 5.01-5.20 (m, 2H), 3.09 (br. s., 2H), 2.82 (t, J=11.40 Hz, 2H), 1.91 (br. s., 1H), 1.81 (d, J=11.40 Hz, 2H), 1.37 (d, J=11.84 Hz, 2H), 1.23 (br. s., 2H).

Example-34: Separation of racemic mixture of 6-(5-cyanopyrazin-2-ylamino)-N-methyl-4-(morpholin-2-ylmethylamino)pyridazine-3-carboxamide (Compound No. 1.34) and (Compound No. 1.35)

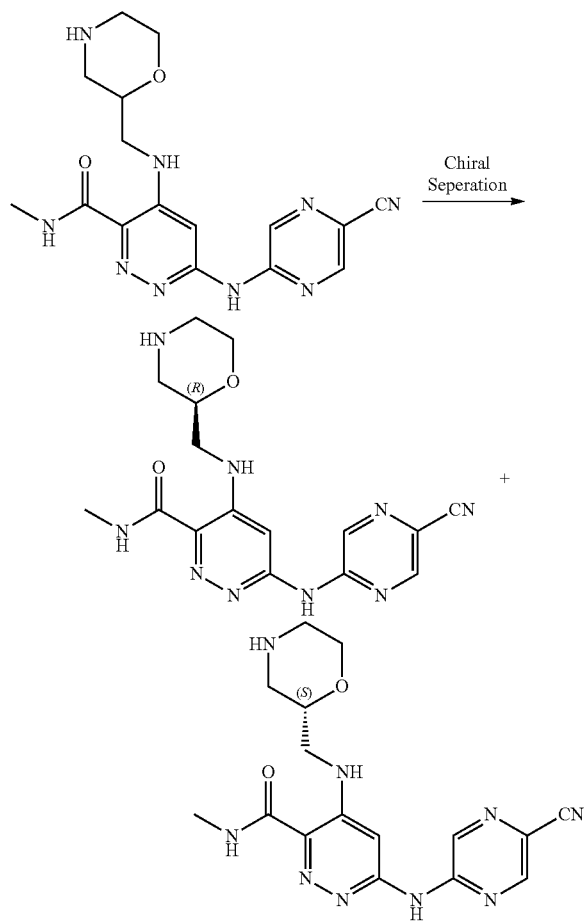

Racemic compound 6-(5-cyanopyrazin-2-ylamino)-N-methyl-4-(morpholin-2-ylmethylamino)pyridazine-3-carboxamide (25 mg) was chirally purified using SFC to get two isomers at Rt=9.10 and 10.12 respectively using following method.

Method: Eluent A: Liquid Carbon dioxide (food grade), Eluent B: 0.2% DEA in Methanol; Isocratic elution composition: Liquid Carbon dioxide (60%): Co-solvent percentage: 40%, (Run time: 20 min); Flow rate 56 g/min, Column Oven Temperature: 40° C.; PDA Scan: 210-400 nm. Instrument: Waters Method Station Column Chiralcel-OXH (250× 21) mm: 5 μm; LCMS: 370 [M+H]$^+$; $^1$H NMR (400 MHz, DMSO-d6) δ 11.11 (br. s., 1H), 8.97-9.08 (m, 2H), 8.86-8.95 (m, 2H), 8.81 (s, 1H), 7.50 (s, 1H), 4.05 (d, J=9.65 Hz, 1H), 3.91 (br. s., 1H), 3.68-3.76 (m, 2H), 3.43 (d, J=13.59 Hz, 2H), 3.33 (d, J=11.84 Hz, 2H), 3.22 (d, J=11.84 Hz, 1H), 3.03 (br. s., 1H), 2.89 (d, J=11.40 Hz, 1H), 2.80 (d, J=4.82 Hz, 2H).

Example-35: Synthesis of 6-(6-cyanopyridin-3-ylamino)-N-methyl-4-(morpholin-2-ylmethylamino)pyridazine-3-carboxamide (Compound No. 1.36)

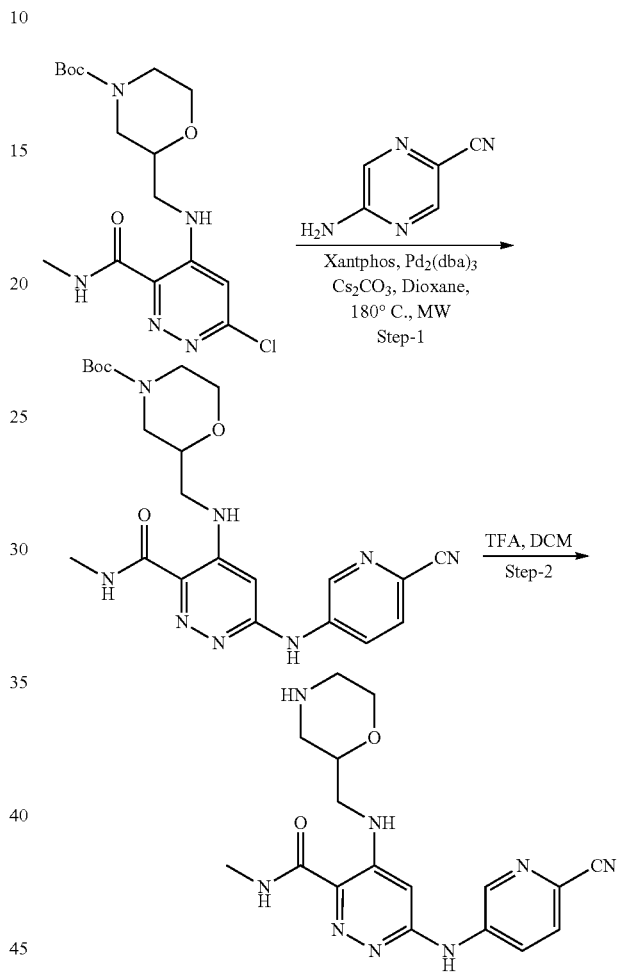

Step-1: Synthesis of tert-butyl 2-((6-(6-cyanopyridin-3-ylamino)-3-(methylcarbamoyl)pyridazin-4-ylamino)methyl)morpholine-4-carboxylate: To a solution of tert-butyl 2-((6-chloro-3-(methylcarbamoyl)pyridazin-4-ylamino)methyl)morpholine-4-carboxylate (0.100 g, 0.25 mmol, 1.0 eq) in dioxane (4 mL) was added 5-aminopyridine-2-carbonitrile (0.037 g, 0.31 mmol, 1.2 eq), Cs$_2$CO$_3$ (0.25 g, 0.77 mmol, 3.0 eq.), Xantphos (0.015 g, 0.025 mmol, 0.1 eq) followed by the addition of Pd$_2$(dba)$_3$ (0.011 g, 0.012 mmol, 0.05 eq) under nitrogen atmosphere. The resulting reaction mixture was heated at 180° C. in microwave reactor for 1 h. Product formation was confirmed by LCMS. The reaction mixture was diluted with water and extracted with ethyl acetate (50 mL×3). Combined organic layer was dried over anhydrous Na$_2$SO$_4$ and concentrated under reduced pressure. The crude product was purified by RP-HPLC to obtain the title compound (0.020 g, 17%). LCMS: 469 [M+H]$^+$ Step-2: Synthesis of 6-(6-cyanopyridin-3-ylamino)-N-methyl-4-(morpholin-2-ylmethylamino)pyridazine-3-carboxamide: To a solution of tert-butyl 2-((6-(6-cyanopyridin-3-ylamino)-3-(methylcarbamoyl)pyridazin-4-ylamino)methyl)morpholine-4-carboxylate (0.020 g, 0.04 mmol) in DCM (2 mL) was added TFA (0.20 mL) at RT and the resulting reaction mixture was allowed to stir at RT for 1 h. Product formation was confirmed by LCMS and TLC. Diethyl ether was added to the reaction mixture to get the precipitates which were filtered under vacuum to get the title compound (0.005 g, 36%). LCMS: 369 [M+H]$^+$; $^1$H NMR (400 MHz, DMSO-d6) δ 10.06 (br. s., 1H), 9.07 (br. s., 1H), 8.94 (br. s., 2H), 8.88 (br. s., 1H), 8.42 (d, J=7.89 Hz, 1H), 7.94 (d, J=8.33 Hz, 1H), 6.38 (br. s., 1H), 4.04 (d, J=12.72 Hz, 1H), 3.89 (br. s., 1H), 3.69-3.76 (m, 3H), 3.30 (d, J=8.33 Hz, 1H), 3.22 (d, J=12.72 Hz, 1H), 3.02 (br. s., 1H), 2.87 (d, J=10.09 Hz, 1H), 2.79 (d, J=3.51 Hz, 2H), 2.07 (s, 1H).

BIOLOGICAL EXAMPLES

Example-B1: CHK-1 Kinase Assay

IC$_{50}$ values of compounds for inhibition of CHK-1 kinase or percent inhibition at defined concentrations were determined by Z-LYTE™ based TR-FRET assay. Kinase reactions were performed in a 10 µL volume in low-volume 384-well plates. The concentration of substrate (Ser Thr 19) was maintained at 2 µM in the assay, and the kinase reaction buffer consisted of 50 mM HEPES pH 7.5, 0.01% BRIJ-35, 10 mM MgCl2, 1 mM EGTA, 2 mM DTT. Serially diluted compounds (3-fold) in DMSO (0.5% in final reaction) were incubated with cocktail of CHK-1 kinase (5 ng/ml; Cat #P3040, ThermoFisher), substrate Ser Thr 19, (2 µM; Cat #PV4529, ThermoFisher), ATP (53 µM; Cat #PV3227, ThermoFisher) and buffer. Kinase reactions were allowed to proceed for 1 hour at room temperature after which 5 µL of a 1:256 dilution of Development Reagent A was added. The plate was allowed to incubate at room temperature for 60 minutes before being read on a BMG Pherastar plate reader using the Z-LYTE™ filter block for Z-LYTE™ TR-FRET.

The resulting TR-FRET emission ratio was used to calculate percent inhibition by normalizing with the control using the following formula:

[% Inhibition=1−{(% Phosphorylation$_{sample}$/% Phosphorylation$_{control\ (0\%\ Inhibition)}$}·100]

For calculation of IC$_{50}$, the percent inhibition obtained was plotted against the concentration of inhibitor, and the data was fit to a sigmoidal dose-response curve with a variable slope. The IC$_{50}$ was calculated from the curve.

The results of % Inhibition of CHK-1 at 1 µM and at 5 µM are shown in the table-B1.

TABLE-B1

% Inhibition of CHK-1 at 1 µM and at 5 µM

| Cpd No. | % Inhibition of CHK-1 enzyme activity @ 0.1 µM | % Inhibition of CHK-1 enzyme activity @ 1 µM | % Inhibition of CHK-1 enzyme activity @ 5 µM |
|---|---|---|---|
| 1.1 | ND | 15 | 32 |
| 1.2 | ND | 96 | 100 |
| 1.3 | ND | 93 | 98 |
| 1.4 | ND | 3 | 5 |
| 1.10 | 8 | 3 | 15 |
| 1.11 | 91 | 100 | 100 |
| 1.12 | 63 | 96 | 98 |
| 1.13 | 9 | 9 | 11 |
| 1.14 | 2 | 15 | 45 |
| 1.15 | 7 | 8 | 23 |

TABLE-B1-continued

% Inhibition of CHK-1 at 1 µM and at 5 µM

| Cpd No. | % Inhibition of CHK-1 enzyme activity @ 0.1 µM | % Inhibition of CHK-1 enzyme activity @ 1 µM | % Inhibition of CHK-1 enzyme activity @ 5 µM |
|---|---|---|---|
| 1.17 | 3 | 12 | 41 |
| 1.18 | 6 | 24 | 59 |
| 1.19 | 49 | 90 | 99 |
| 1.20 | 61 | 93 | 100 |
| 1.21 | 3 | 5 | 33 |
| 1.22 | 8 | 27 | 65 |
| 1.23 | 7 | 18 | 41 |
| 1.24 | 2 | 2 | 34 |
| 1.25 | 8 | 10 | 42 |
| 1.26 | 0 | 9 | 26 |
| 1.27 | 0 | 8 | 34 |
| 1.28 | 13 | 48 | 86 |
| 1.29 | 19 | 60 | 93 |
| 1.30 | 28 | 78 | 97 |
| 1.31 | 0 | 11 | 25 |
| 1.32 | 3 | 3 | 15 |
| 1.33 | 10 | 35 | 75 |
| 1.34 | 77 | 96 | 99 |
| 1.35 | 86 | 100 | 100 |

Cpd = Compound;
*ND = Not Determined

The results of IC$_{50}$ against CHK-1 are shown in table-B2.

TABLE-B2

IC$_{50}$ against CHK-1

| Cpd No. | CHK-1 IC$_{50}$ (µM) |
|---|---|
| 1.2 | 0.070 |
| 1.3 | 0.092 |
| 1.5 | >10 |
| 1.7 | 2.01 |
| 1.8 | 5.81 |
| 1.9 | >10 |

Cpd = Compound;
*ND = Not Determined

Example-B2: CHK-2 Kinase Assay

IC$_{50}$ values of compounds for inhibition of CHK-2 kinase or percent inhibition at defined concentrations were determined by Z-LYTE™ based TR-FRET assay. Kinase reactions were performed in a 10 µL volume in low-volume 384-well plates. The concentration of substrate (Ser Thr 07) was maintained at 1 µM in the assay, and the kinase reaction buffer consisted of 50 mM HEPES pH 7.5, 0.01% BRIJ-35, 10 mM MgCl2, 1 mM EGTA. Serially diluted compounds (3-fold) in DMSO (0.5% in final reaction) were incubated with cocktail of CHK2 kinase (5 ng/ml; Cat #PV3367, ThermoFisher), substrate Ser Thr 07, (1 µM; Cat #PV3208, ThermoFisher), ATP (84 µM; Cat #PV3227, ThermoFisher) and buffer. Kinase reactions were allowed to proceed for 1 hour at room temperature after which 5 µL of a 1:45000 dilution of Development Reagent A was added. The plate was allowed to incubate at room temperature for 60 minutes before being read on a BMG Pherastar plate reader using the Z-LYTE™ filter block for Z-LYTE™ TR-FRET.

The resulting TR-FRET emission ratio was used to calculate percent inhibition by normalizing with the control using the following formula:

[% Inhibition=1−{(% Phosphorylation$_{sample}$/% Phosphorylation$_{control\ (0\%\ inhibition)}$}·100]

For calculation of IC$_{50}$, the percent inhibition obtained was plotted against the concentration of inhibitor, and the data was fit to a sigmoidal dose-response curve with a variable slope. The IC$_{50}$ was calculated from the curve.

The results of % Inhibition of CHK-2 at 0.1 μM & 1 μM are shown in the table-B3.

TABLE-B3

% Inhibition of CHK-2 at 0.1 μM & 1 μM

| Cpd No. | % Inhibition of CHK-2 enzyme activity @ 0.1 μM | % Inhibition of CHK-2 enzyme activity @ 1 μM |
|---|---|---|
| 1.2 | 8.28 | 30 |
| 1.3 | 12.1 | 36.7 |

Cpd = Compound

Example-B3: Cell Viability Assay

Protocol for Cell Viability Assay in Different Cell Lines for CHK-1 Inhibitors:

Cell lines such as HT29 ((ATCC® HTB-38™), colon cancer cell, A549 (ATCC® CCL-185™), lung epithelial carcinoma, MIA PaCa-2 (ATCC®CRL-1420™), Panc-1 (CRL-1469™) and AsPC-1 ((ATCC® CRL-1682™), pancreatic cancer cell lines, HCT-116 (ATCC® CCL-247™), colorectal carcinoma, MDAMB-231 (ATCC® HTB-26™), TNBC, THP-1 (ATCC® TIB-202™) and MV-4-11 (ATCC® CRL-9591™), peripheral blood cells were seeded in their respective medium [as suggested by ATCC] with 10% FBS, (Cat #16000044; Gibco) at a cell count of 2000-2500 cells per 100 μl per well (in case of adherent cells) and 15000-20000 cells (in case of suspension cells) in a 96 well edge plate (167425; ThermoFisher). Cells were allowed to grow at 37° C. for 24 hr (adherent cells) in 5% CO2 (culture conditions) in a Nuaire incubator (humidified). Following 24 hr (adherent cells), serially diluted compounds (100 μl) were added to the culture plate (immediately after plating in case of suspension cells) and the cultures were further incubated in culture conditions for 72-144 hr depending on the cell type. Experiment was terminated at the completion of respective incubation with drug by replacing the medium with 100 μl of 1 mM of resazurin (R7017; Sigma) prepared in culture medium and the plates were further incubated in culture conditions for 4 hr. In case of 144 hr incubation with the drug, the drug was replenished once with fresh medium after 72 hr. Fluorescence was then measured using a multimodal plate reader (Biotek Synergy Neo) at an excitation wavelength of 535 nm and emission wavelength of 590 nm to obtain relative fluorescence units. Data analysis was done by subtracting the background fluorescence (only medium blank) value from each reading and then normalizing with the vehicle control (DMSO treated cells) to obtain percent survival/proliferation. Percent survival at different doses was used to calculate IC$_{50}$ by fitting the curve to the "four-parameter variable slope logistic model" using Prism Graph Pad. The results of cell viability assay are provided in the table-B4.

TABLE-B4

Cell viability assay

| Cpd No. | A549 IC50 (μM) | AsPC-1 IC50 (μM) | HCT116 IC50 (μM) | MDA_MB-231 IC50 (μM) | MiaPaCa-2 IC50 (μM) | Panc-10.05 IC50 (μM) | THP1 IC50 (μM) | HT-29 IC50 (μM) | MV-4-11 IC50 (μM) |
|---|---|---|---|---|---|---|---|---|---|
| 1.1 | ND | ND | >30 | ND | ND | ND | ND | ND | ND |
| 1.2 | >30 | >30 | >30 | >30 | >30 | >30 | >30 | >30 | ND |
| 1.3 | >30 | >30 | >30 | >30 | >30 | >30 | >30 | >30 | ND |
| 1.7 | ND | ND | ND | ND | >30 | ND | >30 | >30 | ND |
| 1.11 | 11.4 | 6.41 | 17.2 | 13.0 | 13.42 | ND | 4.24 | 14.9 | 5.40 |
| 1.12 | ND | 12.93 | ND | ND | 23.25 | ND | 11.71 | >30 | ND |
| 1.19 | ND | 8.45 | ND | ND | 26.23 | ND | 13.08 | ND | ND |
| 1.20 | ND | 11.91 | ND | ND | 23.51 | ND | 21.75 | ND | ND |
| 1.34 | >30 | 13.2 | 27.9 | 12.44 | 10.82 | ND | 9.79 | 16.9 | 7.0 |
| 1.35 | >30 | 11.62 | 17.24 | 15.5 | 10.2 | ND | 6.23 | 14.52 | 5.38 |

Cpd = Compound;

*ND = Not Determined

It is understood that the foregoing examples and embodiments described above are for illustrative purposes only and that various modifications or changes in light thereof will be suggested to persons skilled in the art and are to be included within the spirit and purview of this application and the scope of the appended claims.

What is claimed is:

1. A compound of formula (IA):

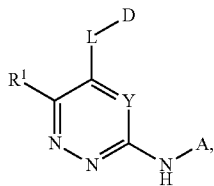

formula (IA)

wherein,
Y is $CR^y$;
A is

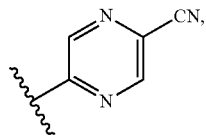

wherein, the wavy line denotes attachment points to rest of the molecule;

$R^y$ is hydrogen, $C_1$-$C_6$ alkyl, or halogen;

D is —($C_1$-$C_6$ alkylene)$NR^{11}R^{12}$, 3- to 6-membered heterocyclyl, —($C_1$-$C_6$ alkylene)$C_3$-$C_6$ cycloalkyl or —($C_1$-$C_6$ alkylene)3- to 6-membered heterocyclyl, each of which is optionally substituted by $R^2$;

L is —$CH_2$—, —O—, —NH—, or —N($CH_3$)—;

$R^1$ is hydrogen, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$ aryl, 5- to 10-membered heteroaryl, —CN, halogen, $C_1$-$C_6$ alkoxy, $C_1$-$C_6$ haloalkoxy, $C_1$-$C_6$ haloalkyl, —$OR^{13}$, —$SR^{13}$, —$S(O)_2R^{13}$, —$S(O)_2NR^{14}R^{15}$, —$NR^{14}R^{15}$, —$C(O)R^{13}$, —$C(O)OR^{13}$, or —$C(O)NR^{14}R^{15}$; wherein each of $R^1$ is optionally substituted by $R^3$;

$R^2$ is —$OR^{16}$, —$NR^{17}R^{18}$, —$C(O)R^{16}$, —$NR^{16}C(O)R^{17}$, —$C(O)OR^{16}$, or $C_1$-$C_6$ alkyl optionally substituted by oxo, —OH, halogen or —$NH_2$;

$R^3$ is $C_2$-$C_6$ alkenyl, —CN, halogen, $C_1$-$C_6$ alkoxy, $C_1$-$C_6$ haloalkoxy, —$OR^{16}$, —$NR^{17}R^{18}$, —$C(O)R^{16}$, —$NR^{16}C(O)R^{17}$, —$C(O)OR^{16}$, $C_3$-$C_6$ cycloalkyl, 3- to 6-membered heterocyclyl, or $C_1$-$C_6$ alkyl optionally substituted by oxo, —OH, halogen or —$NH_2$;

each $R^{11}$ and $R^{12}$ is independently hydrogen, or $C_1$-$C_6$ alkyl;

each $R^{13}$, $R^{14}$ and $R^{15}$ is independently hydrogen, $C_1$-$C_6$ alkyl, $C_1$-$C_6$ haloalkyl, $C_3$-$C_6$ cycloalkyl, or —($C_1$-$C_3$ alkylene)5- to 6-membered heteroaryl, wherein each of $R^{13}$, $R^{14}$ and $R^{15}$ is independently optionally substituted by halogen;

each $R^{16}$, $R^{17}$ and $R^{18}$ is independently hydrogen, $C_2$-$C_6$ alkenyl, or $C_1$-$C_6$ alkyl optionally substituted by oxo, —OH, halogen or —$NH_2$;

or a salt thereof.

2. The compound of claim 1, wherein $R^y$ is selected from hydrogen, F, Cl and $CH_3$.

3. The compound of claim 1, wherein D is selected from —($C_1$-$C_6$ alkylene)$NR^{11}R^{12}$, 3-to 6-membered heterocyclyl, —($C_1$-$C_6$ alkylene)$C_3$-$C_6$ cycloalkyl, or —($C_1$-$C_6$ alkylene) 3- to 6-membered heterocyclyl, wherein each of which is optionally substituted by $R^2$; wherein, $R^2$ is —$NR^{17}R^{18}$, $NR^{16}C(O)R^{17}$, or $C_1$-$C_6$ alkyl optionally substituted by oxo, —OH, halogen and —$NH_2$.

4. The compound of claim 1, wherein D is selected from

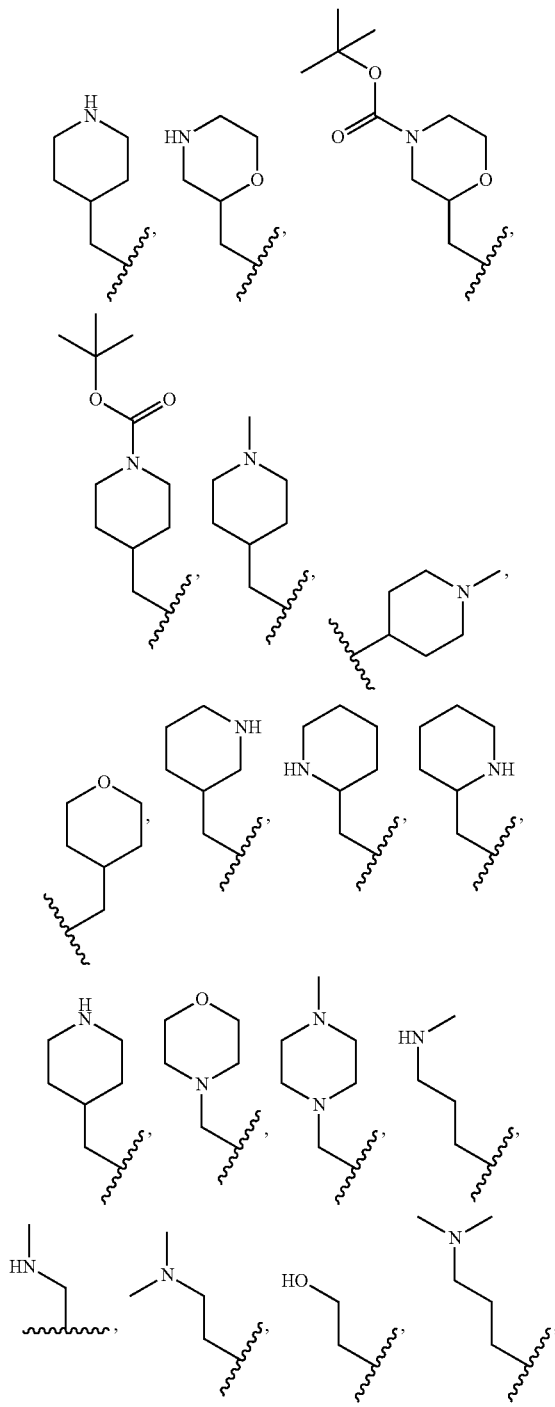

217
-continued
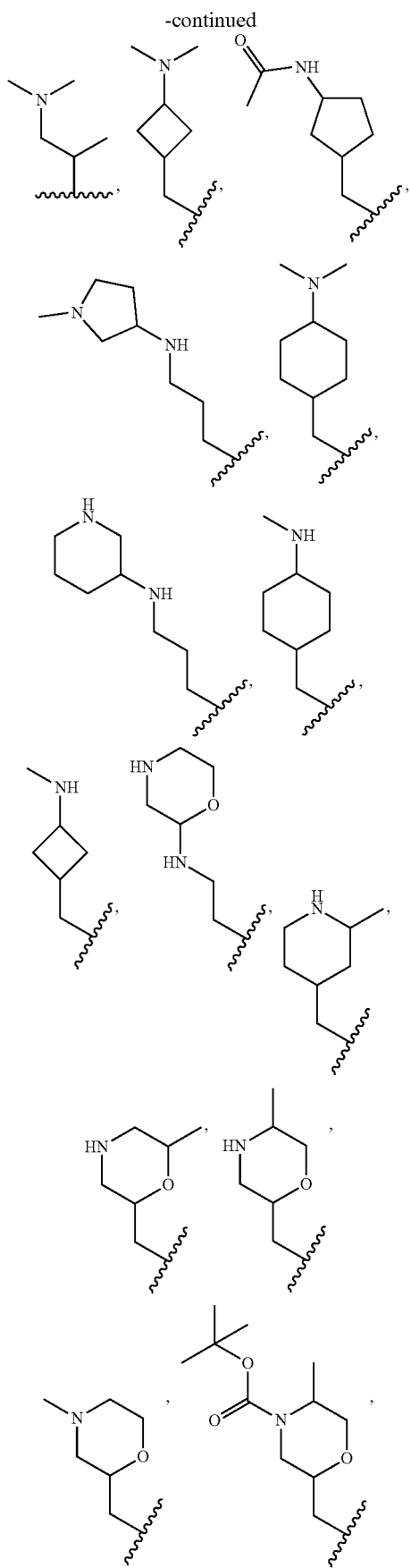
218
-continued
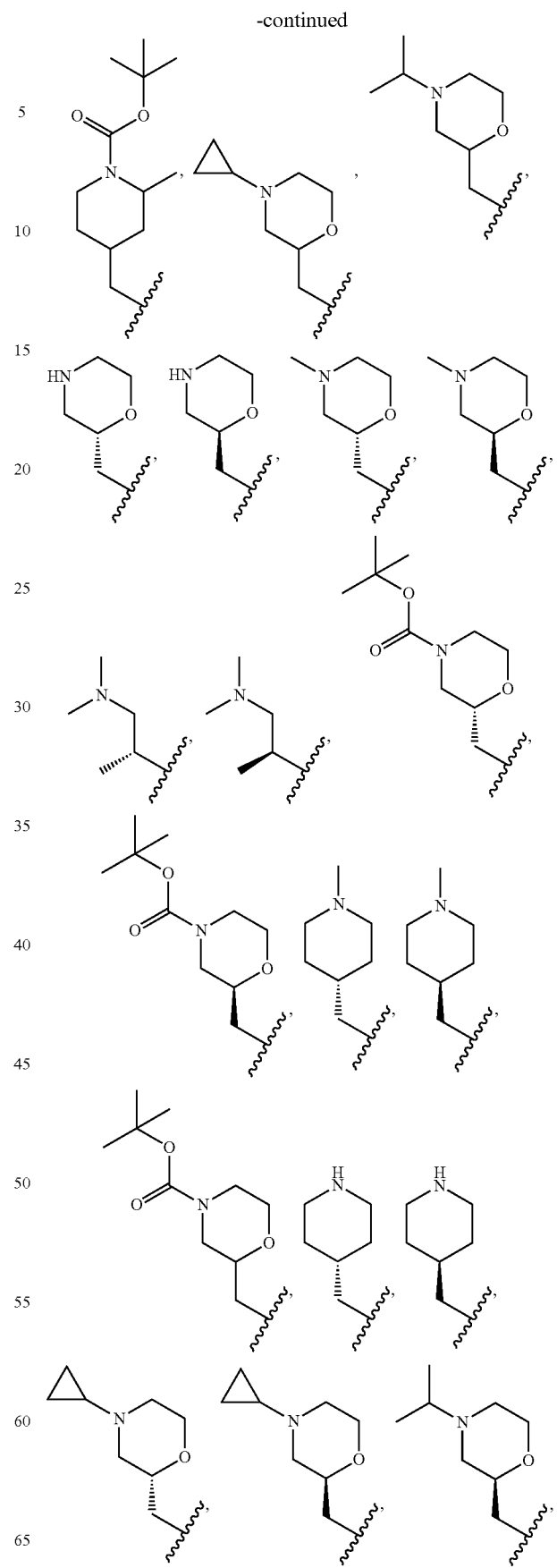

219

-continued

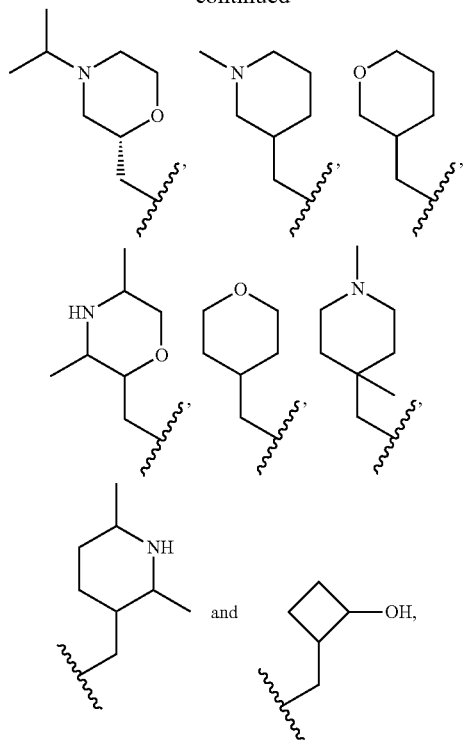

wherein the wavy lines denote attachment points to rest of the molecule.

5. The compound of claim 1, wherein D is

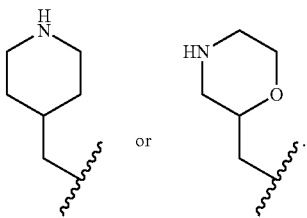

6. The compound of claim 1, wherein L is —NH— or —O—.

7. The compound of claim 1, wherein $R^1$ is —C(O)NR$^{14}$R$^{15}$, wherein $R^{14}$ and $R^{15}$ are independently selected from hydrogen, $C_1$-$C_6$ alkyl and $C_3$-$C_6$ cycloalkyl.

8. The compound of claim 1, wherein $R^1$ is selected from hydrogen, —CH$_3$,

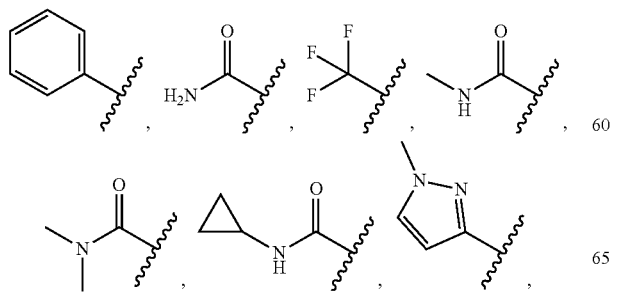

220

-continued

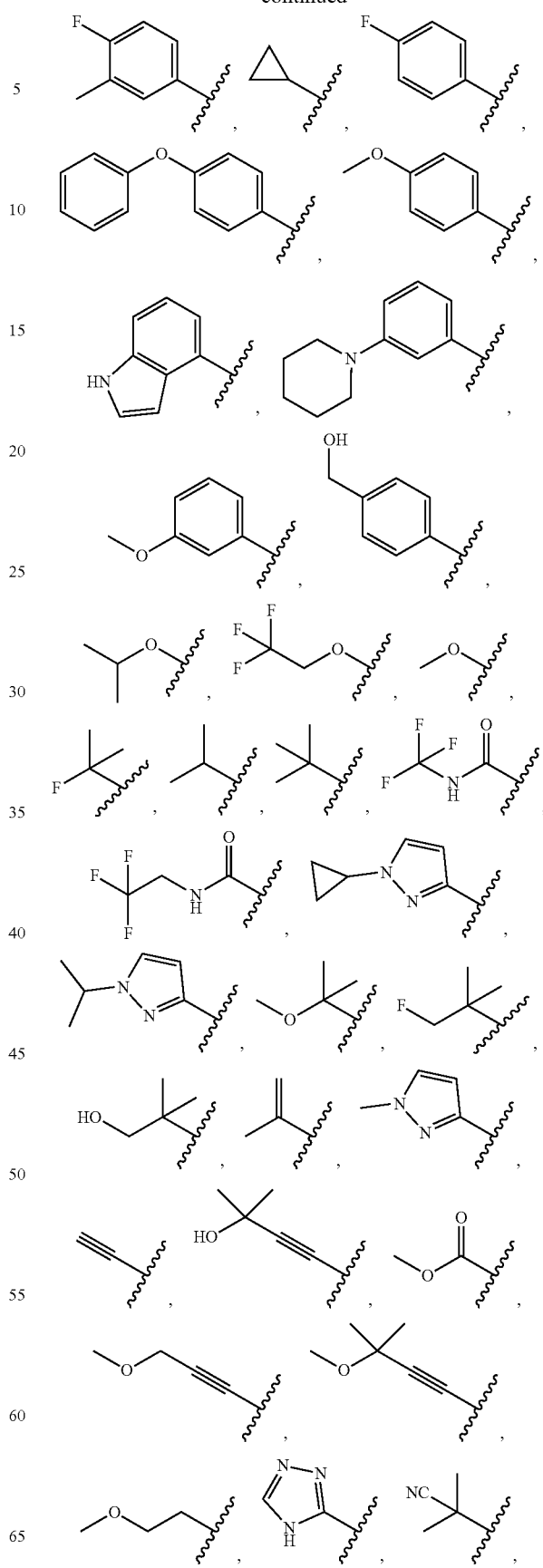

-continued
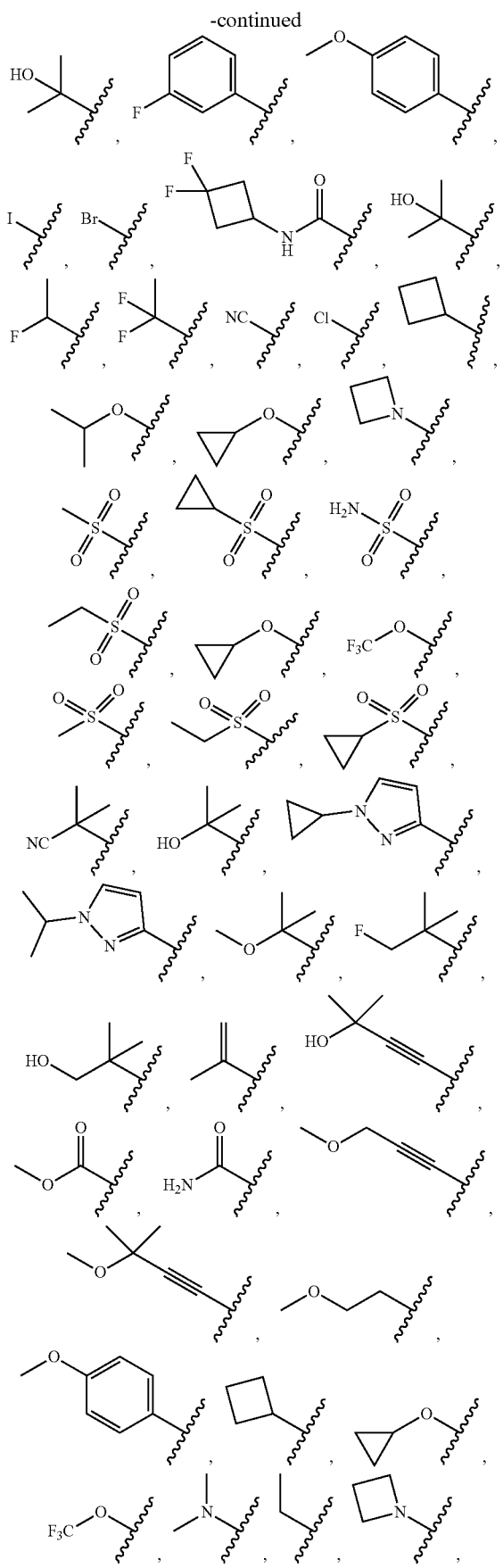
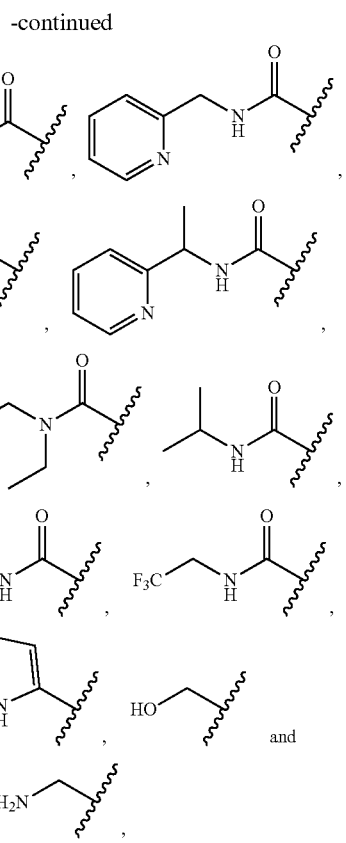
wherein the wavy lines denote attachment point to rest of the molecule.
9. The compound of claim 8, wherein $R^1$ is selected from hydrogen, —$CH_3$,
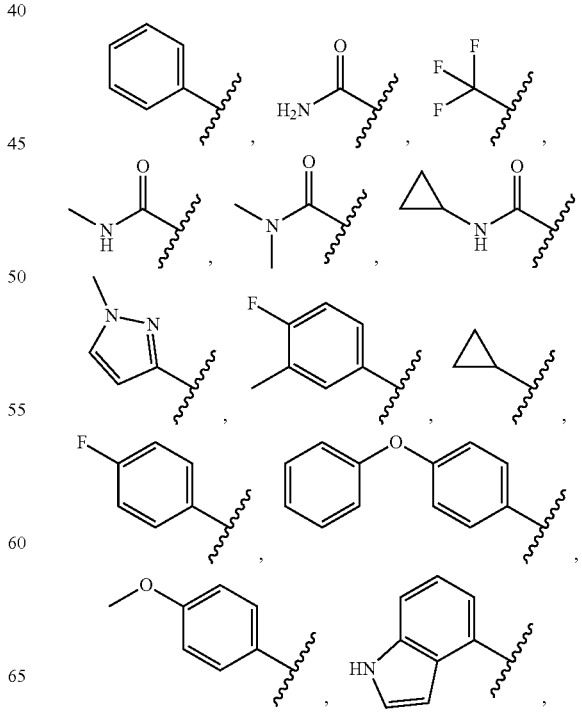

-continued

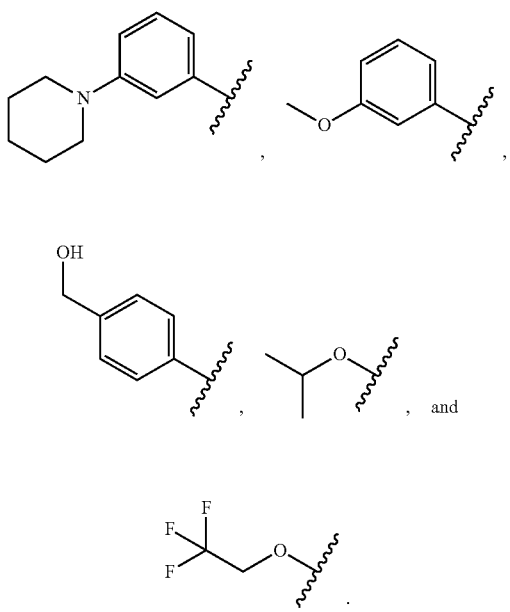
, and
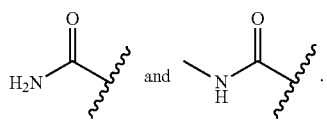
.

10. The compound of claim 9, wherein $R^1$ is selected

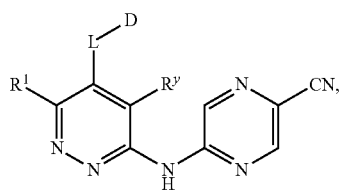

11. The compound of claim 1, wherein the compound is a compound of formula (IIa-8):

formula (IIa-8)

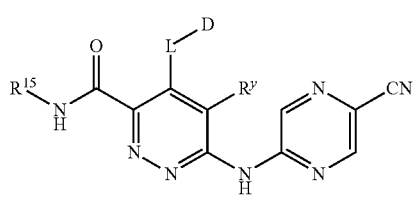

or a salt thereof, wherein D, L, $R^1$ and $R^y$ are as defined in claim 1, or salt thereof.

12. The compound of claim 1, wherein the compound is a compound of formula (IVa-8):

Formula (IVa-8)

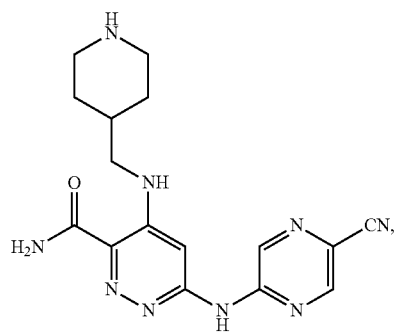

or a salt thereof, wherein D, L, $R^y$ and $R^{15}$ are as defined in claim 1.

13. The compound of claim 1, wherein the compound is a compound of formula (IVa-13):

Formula (IVa-13)

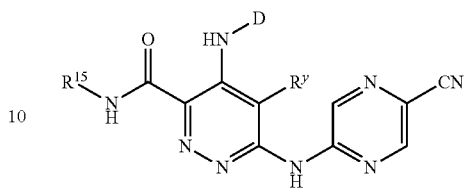

or a salt thereof, wherein D, $R^{15}$, $R^x$ and $R^y$ are as defined in claim 1.

14. The compound of claim 1, wherein the compound is selected from

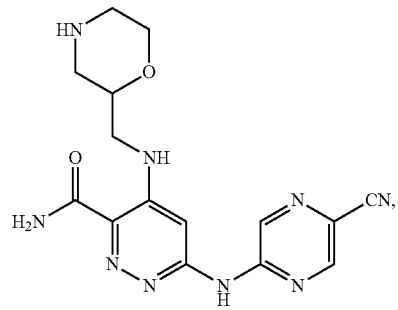

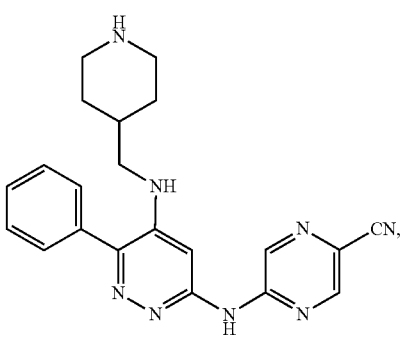

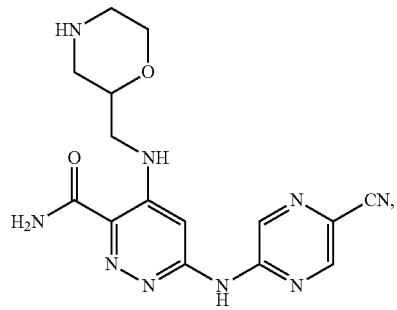

225
-continued
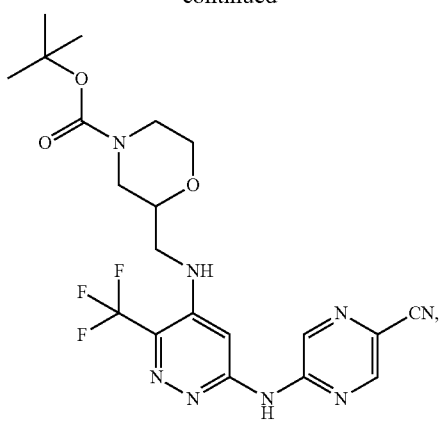
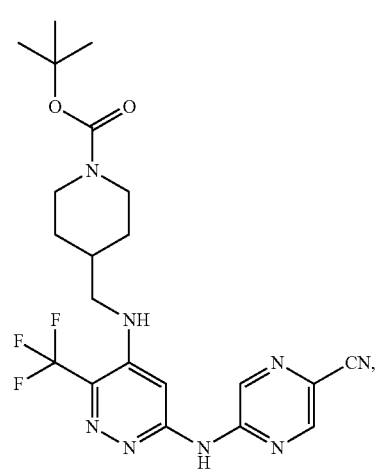
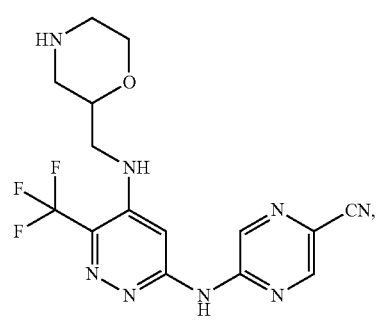
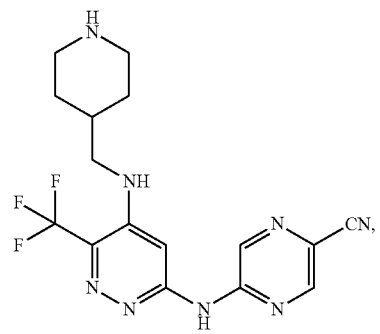
226
-continued
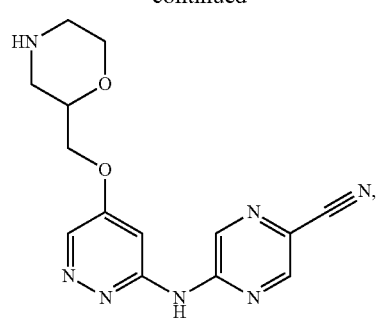
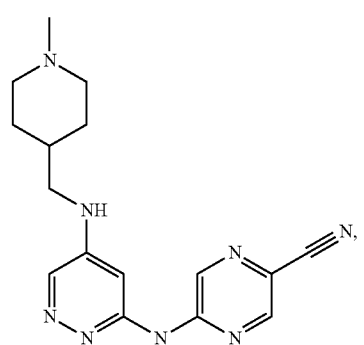
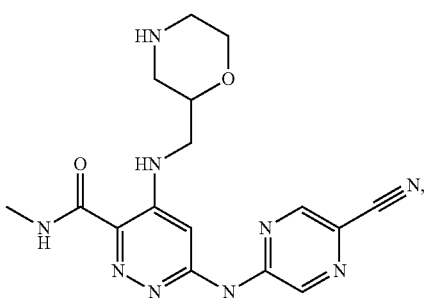
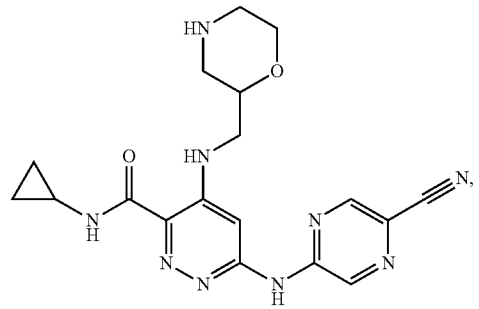
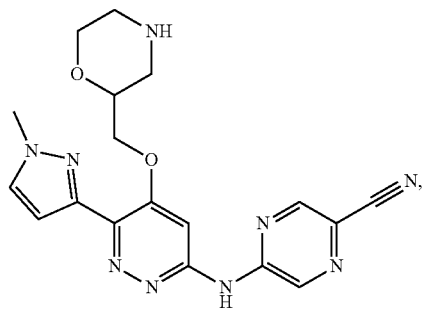

227
-continued
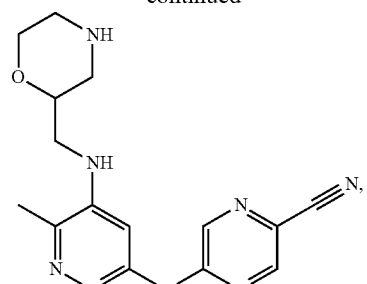
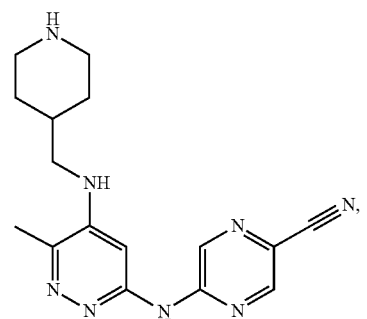
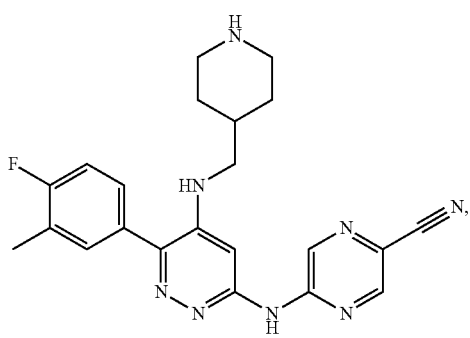
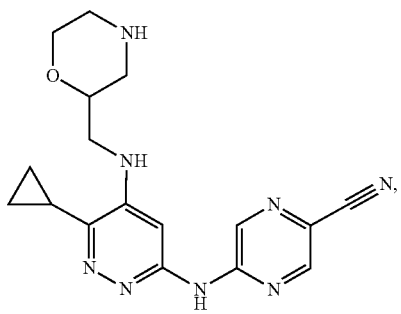
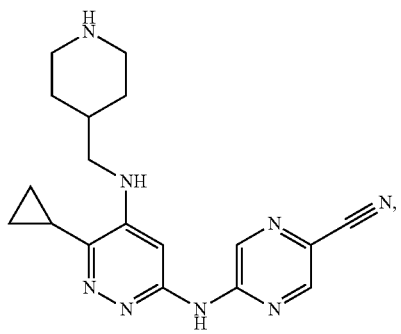
228
-continued
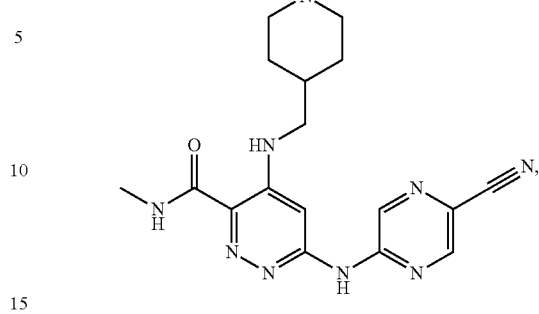
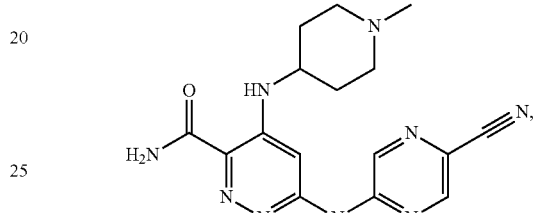
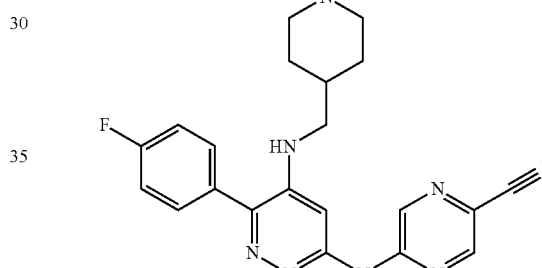
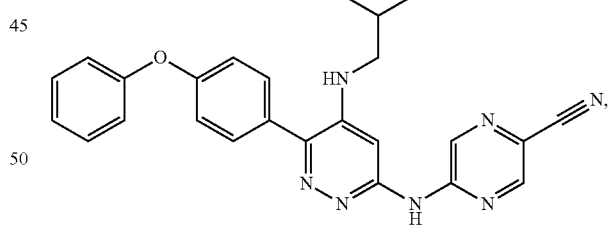
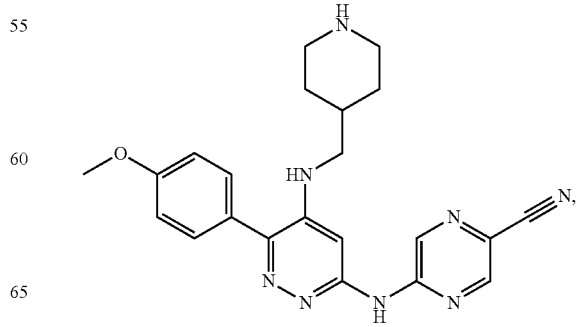

229
-continued
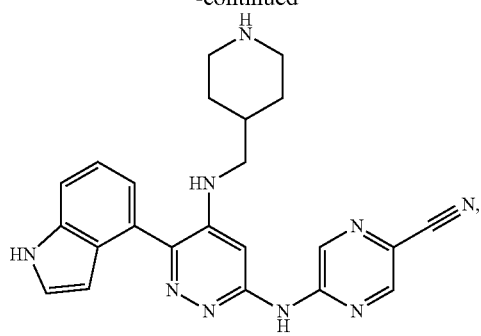
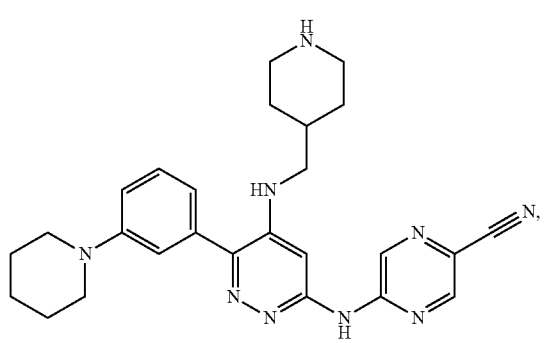
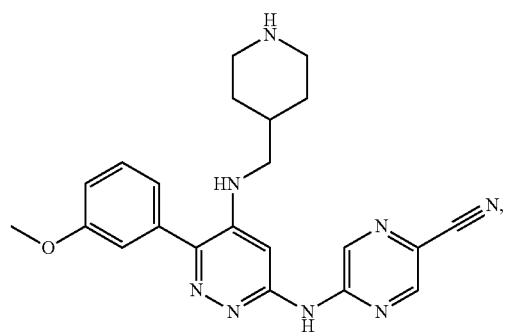
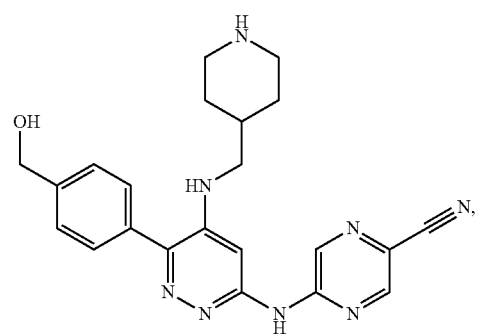
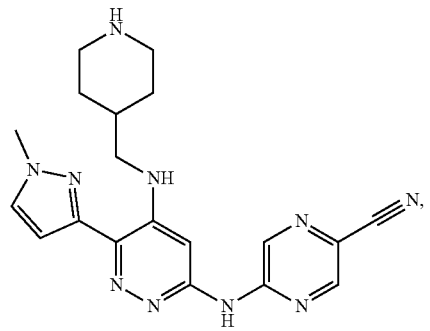
230
-continued
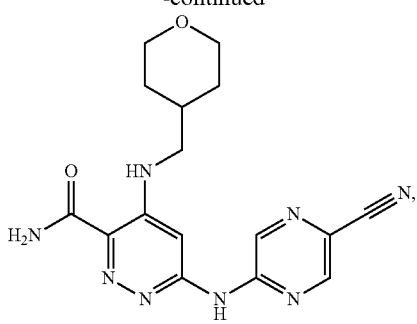
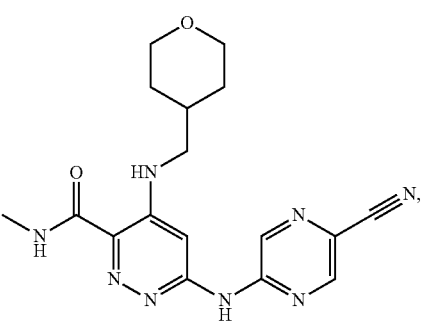
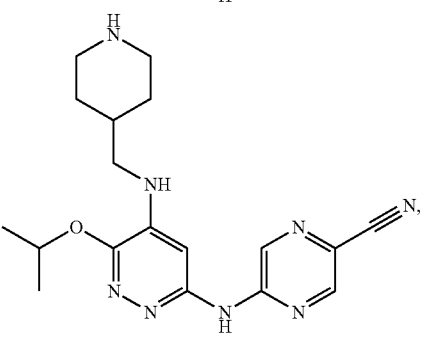
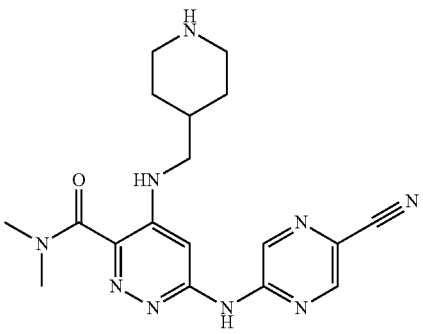
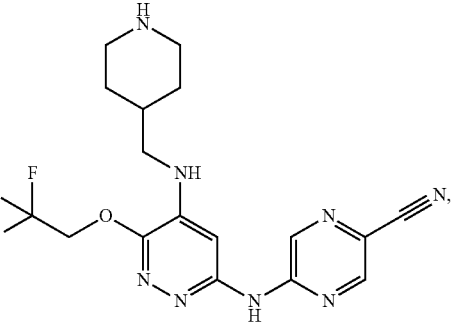

-continued
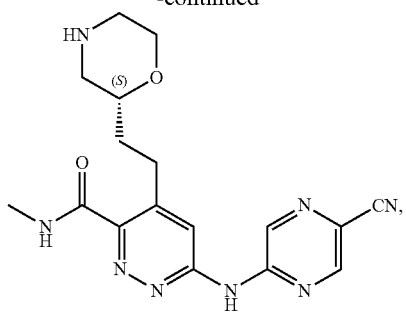
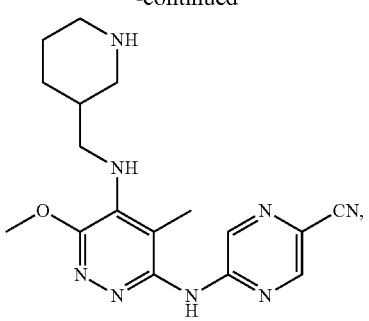
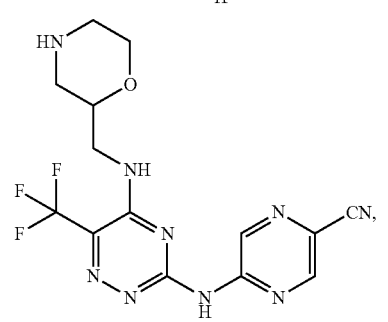
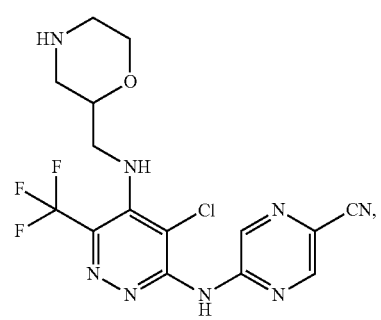

233
-continued
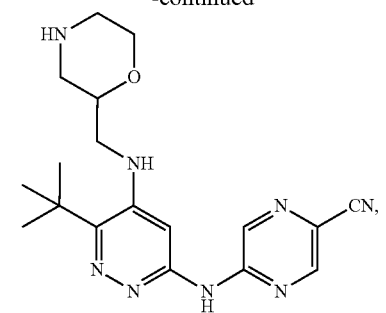
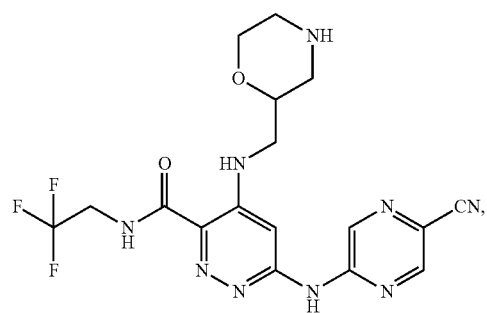
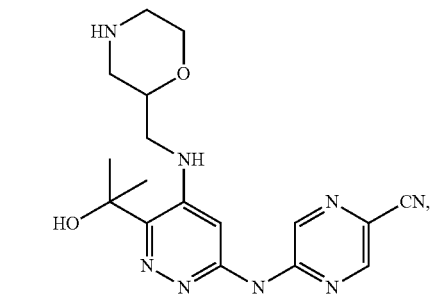
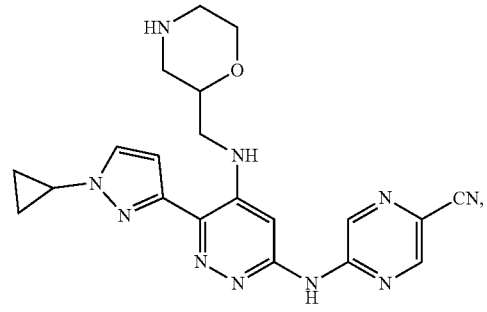
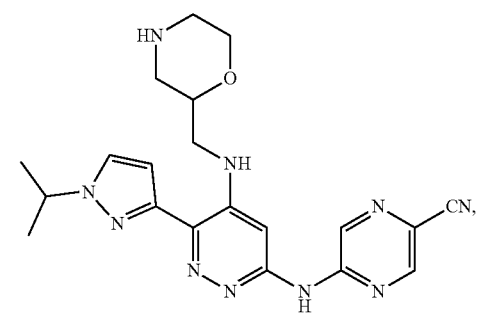
234
-continued
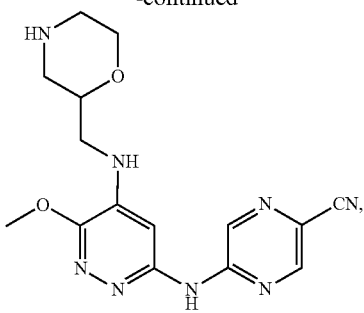
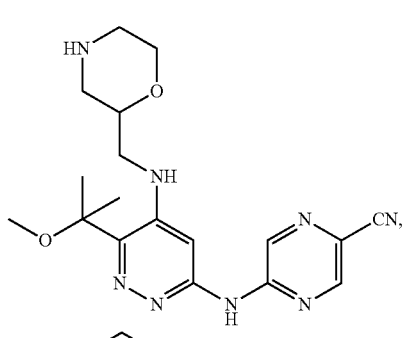
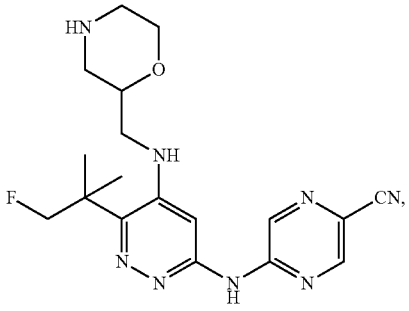
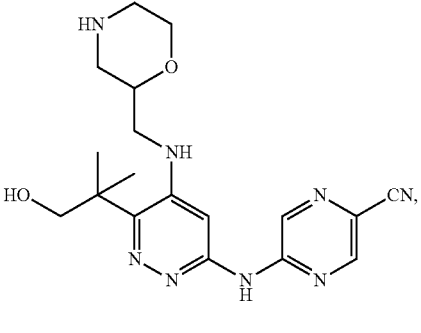
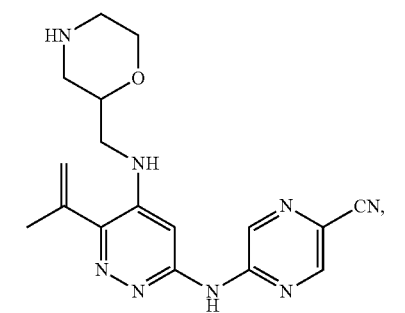

235
-continued
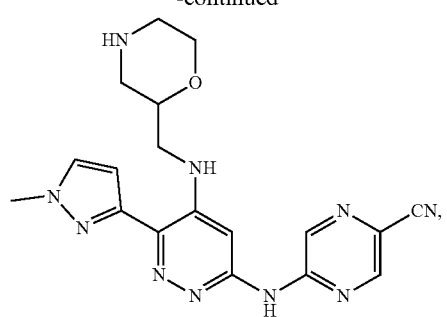
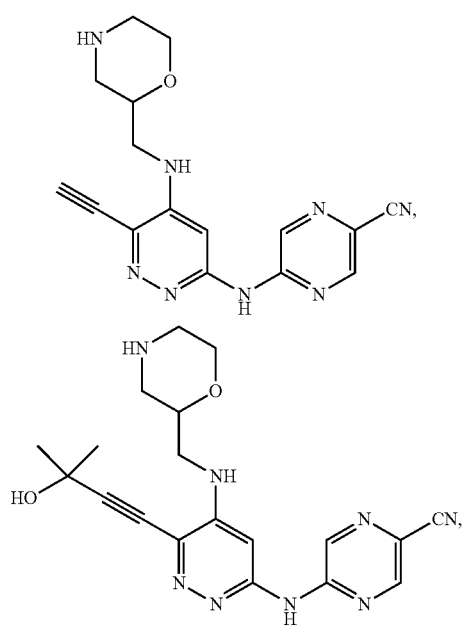
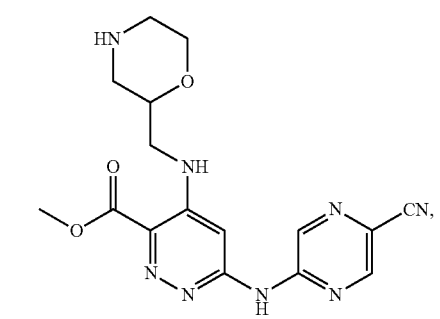
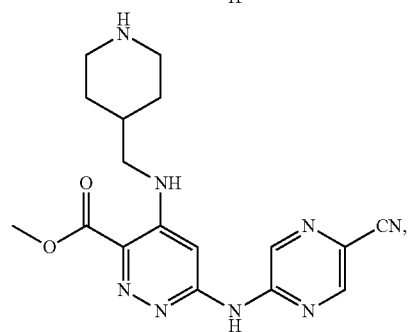
236
-continued
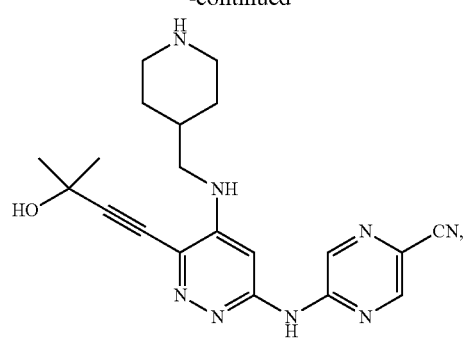
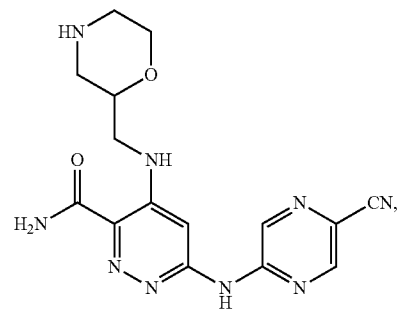
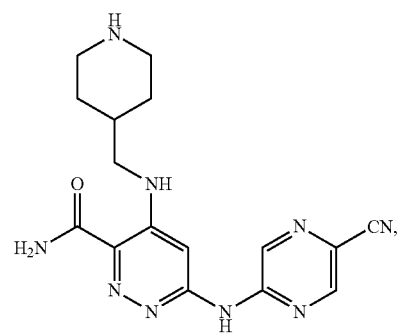
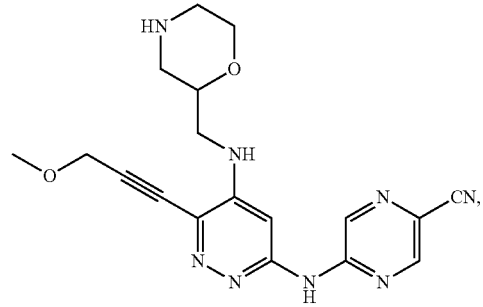
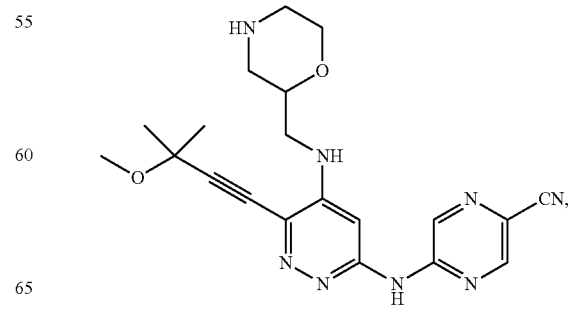

237
-continued
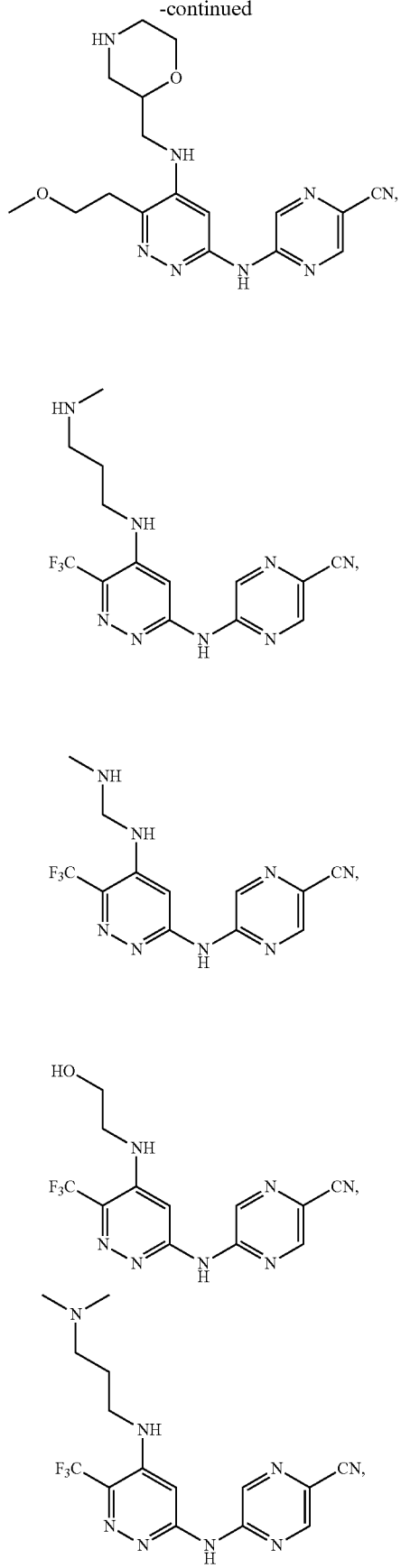
238
-continued
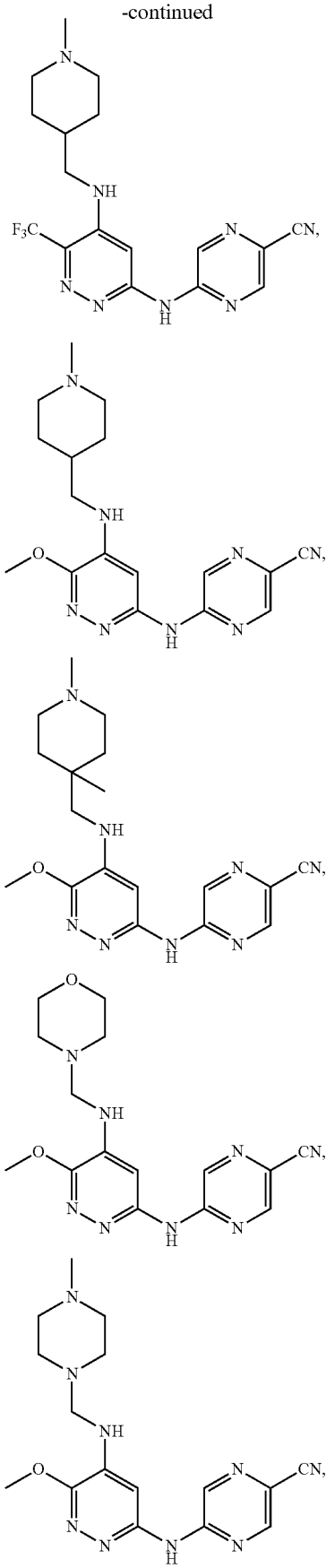

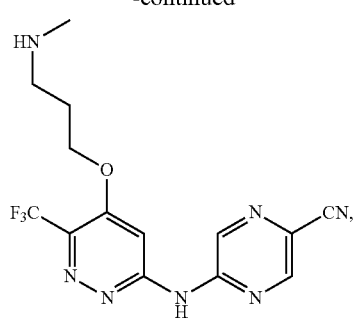
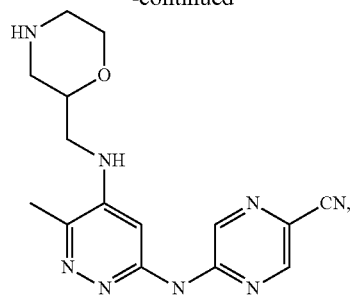
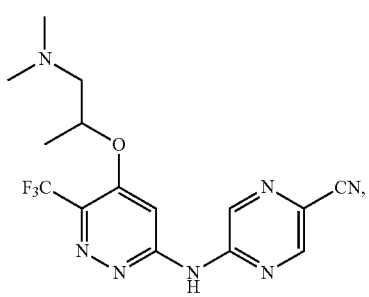
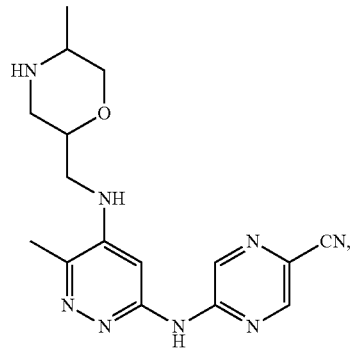
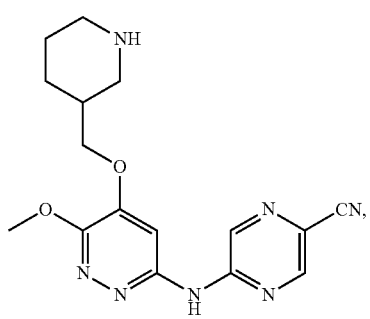
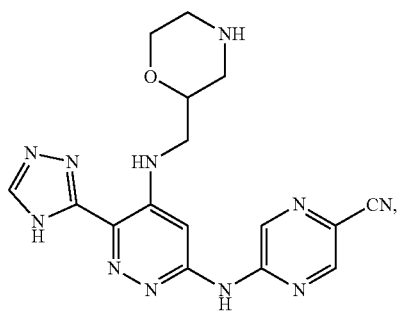
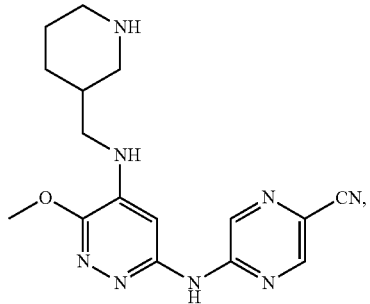
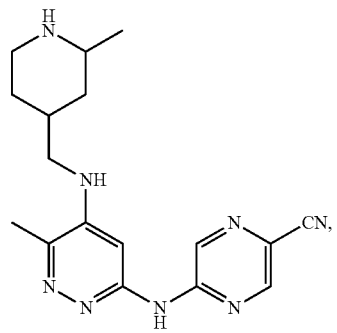
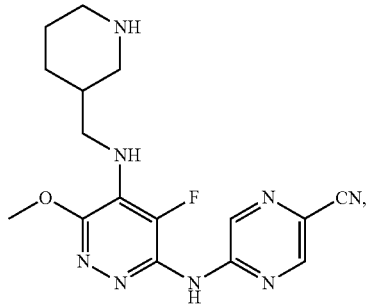
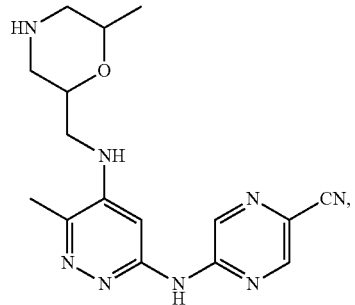

-continued
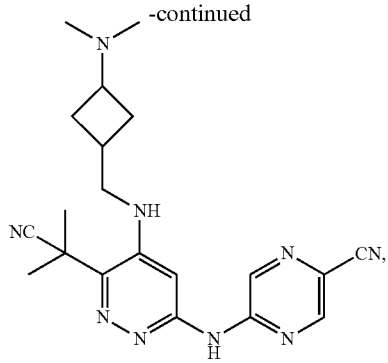
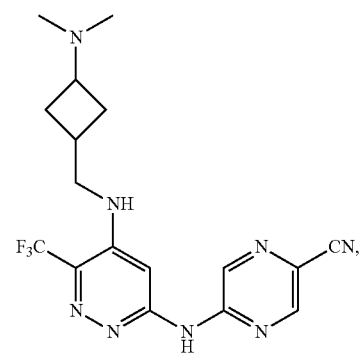
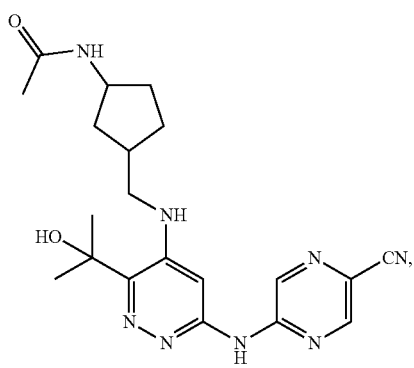
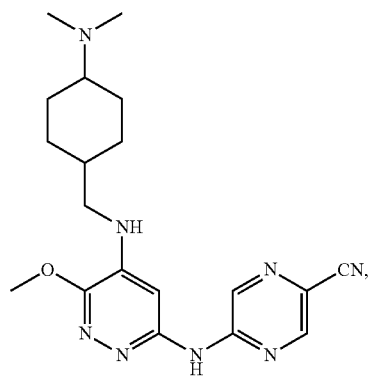
-continued
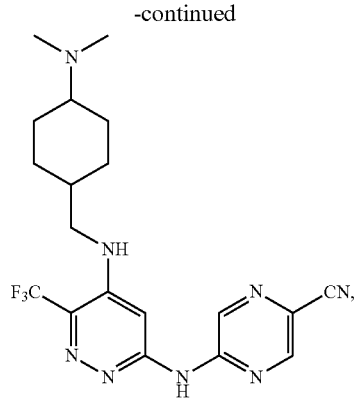
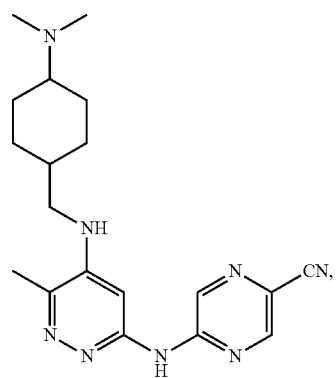
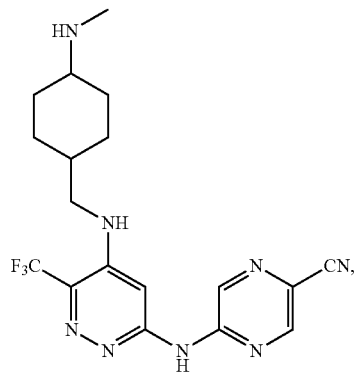
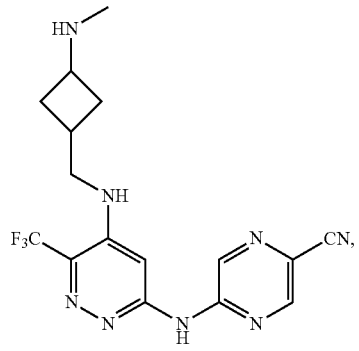

-continued
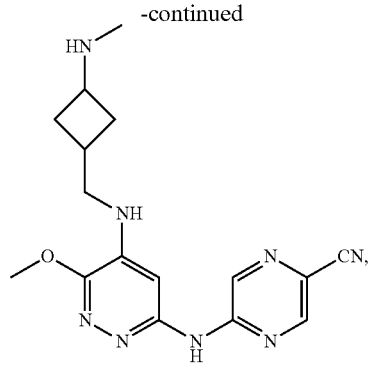
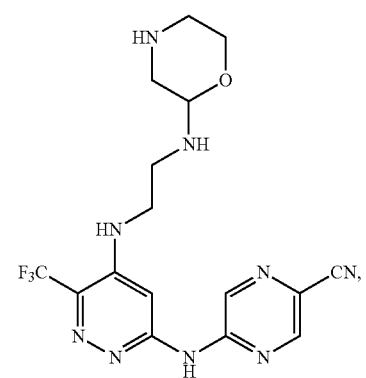
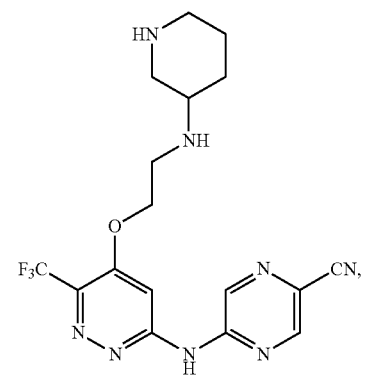
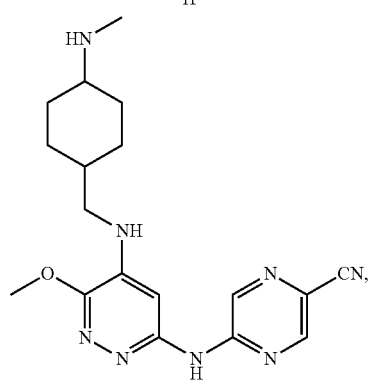
-continued
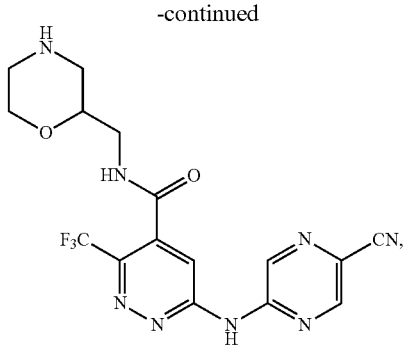
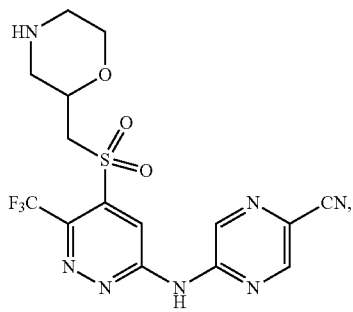
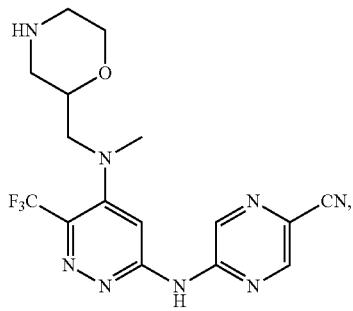
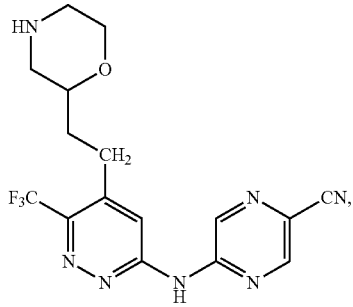
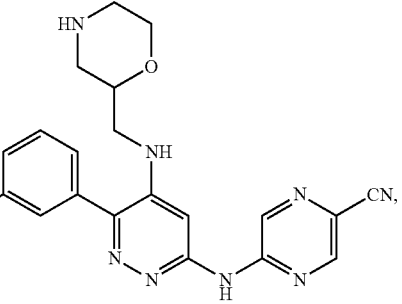

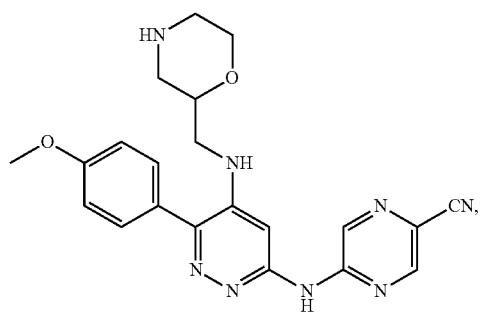
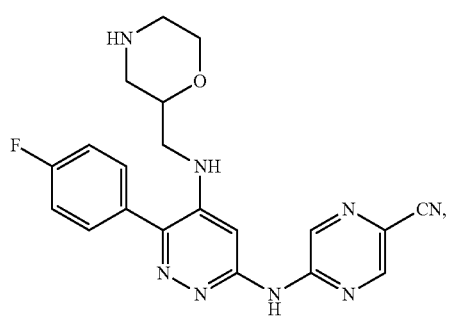
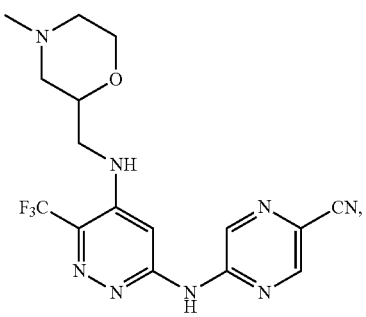
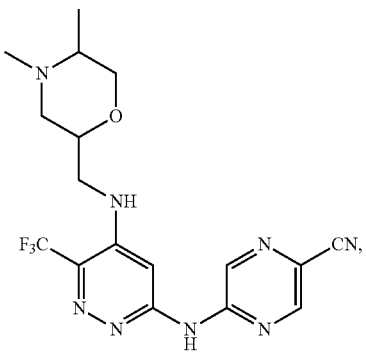
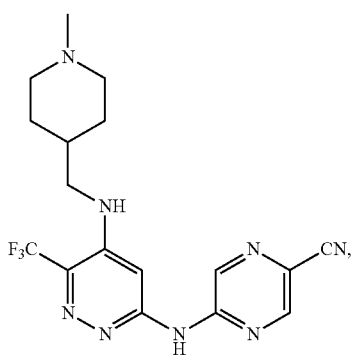
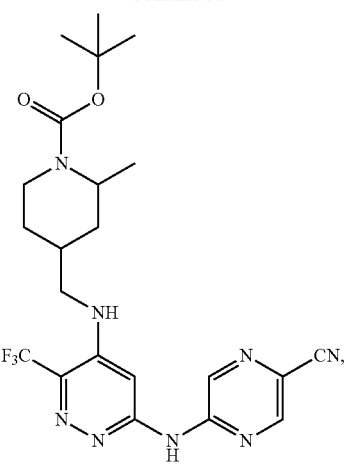
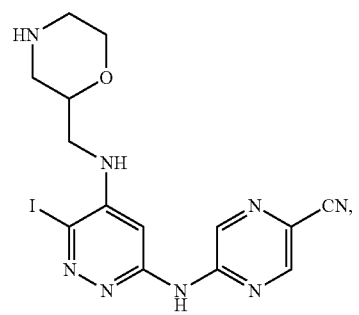
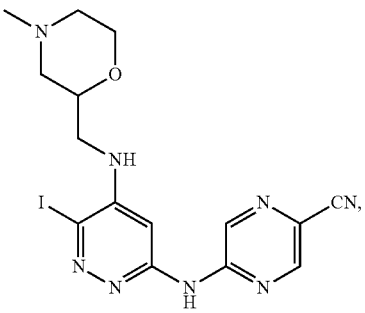
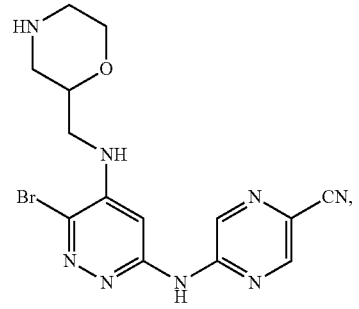
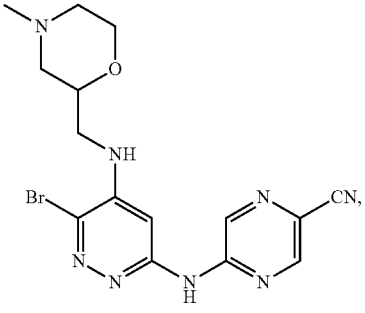

-continued
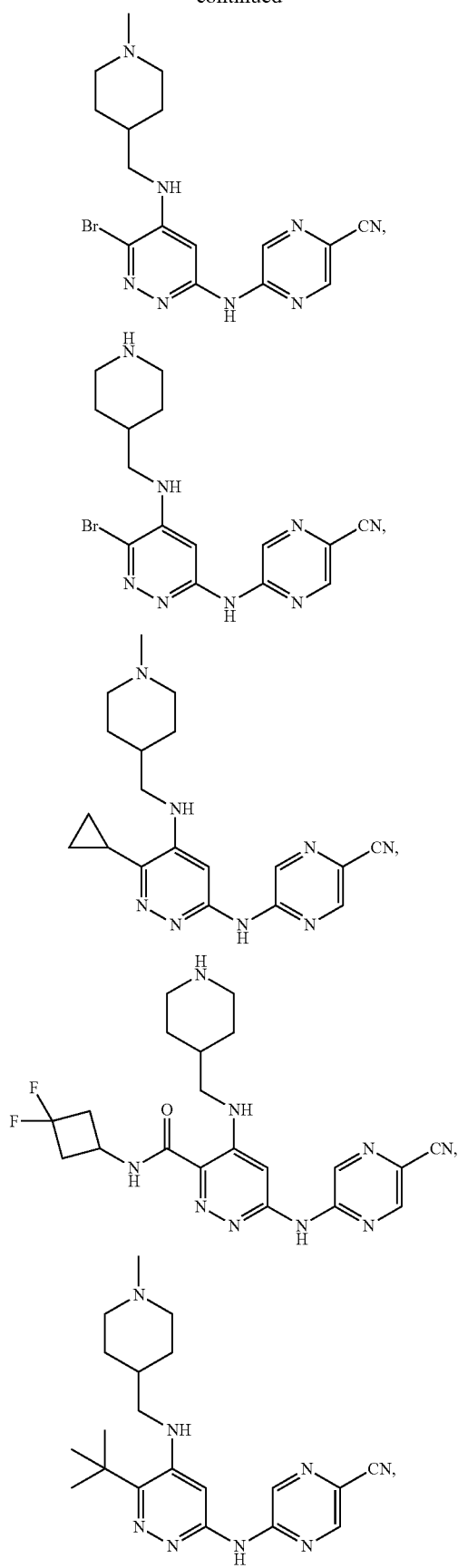
-continued
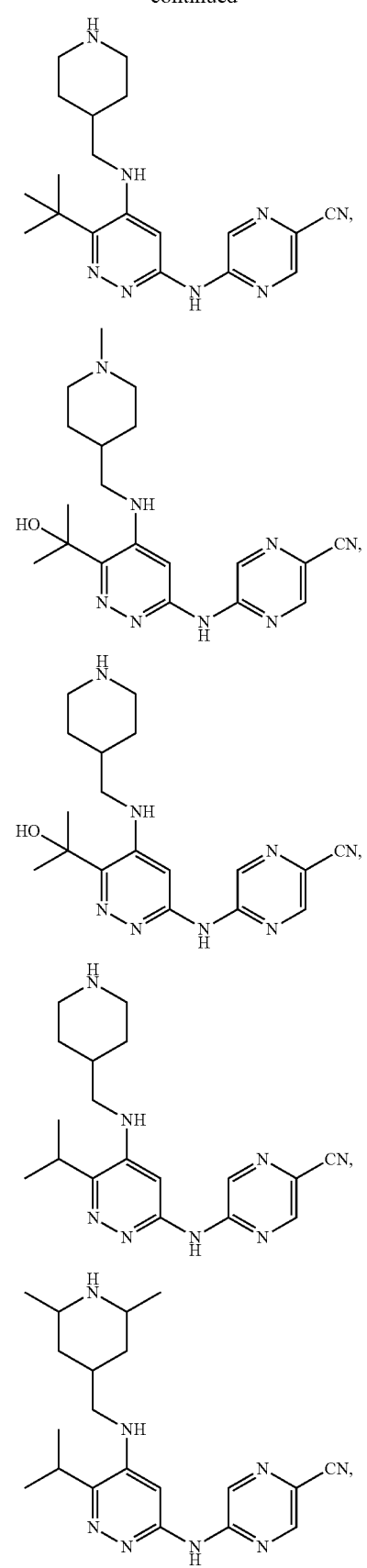

249
-continued
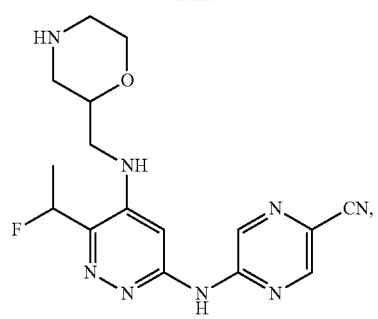
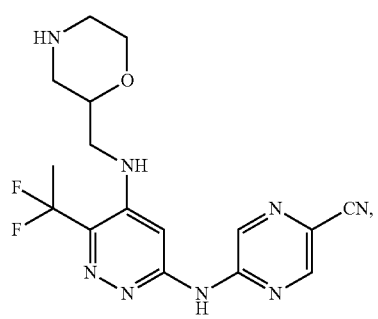
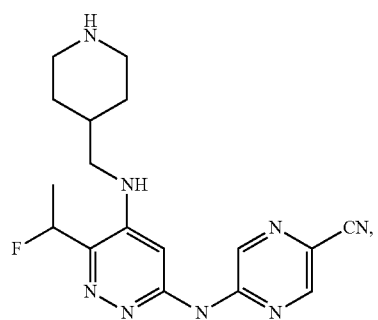
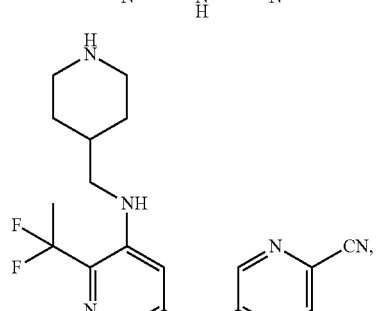
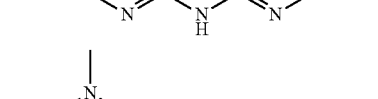
250
-continued
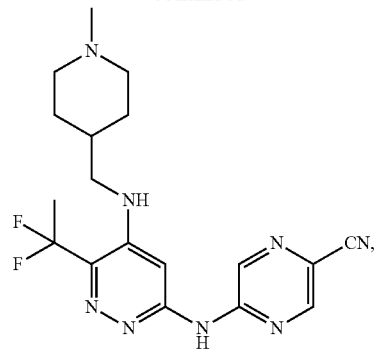
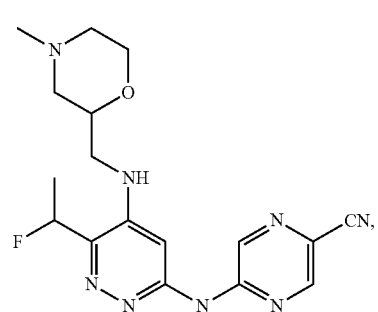
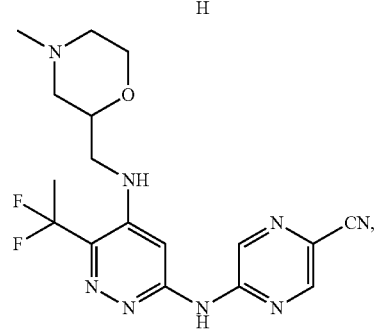
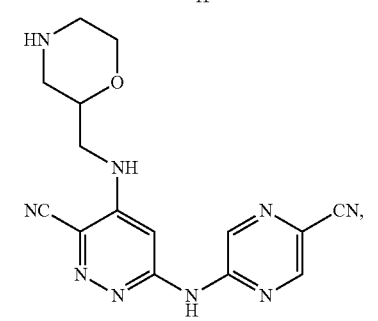

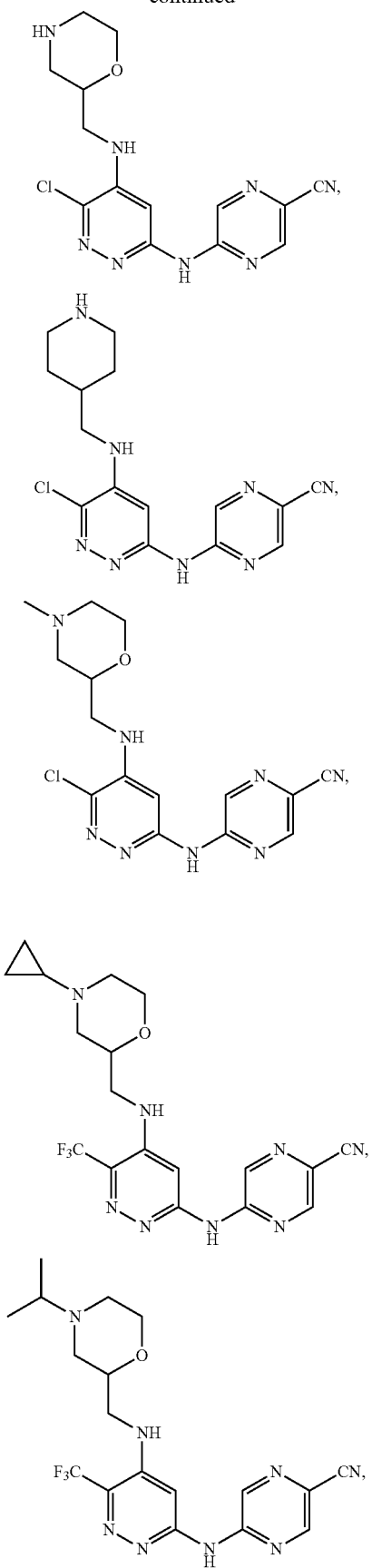
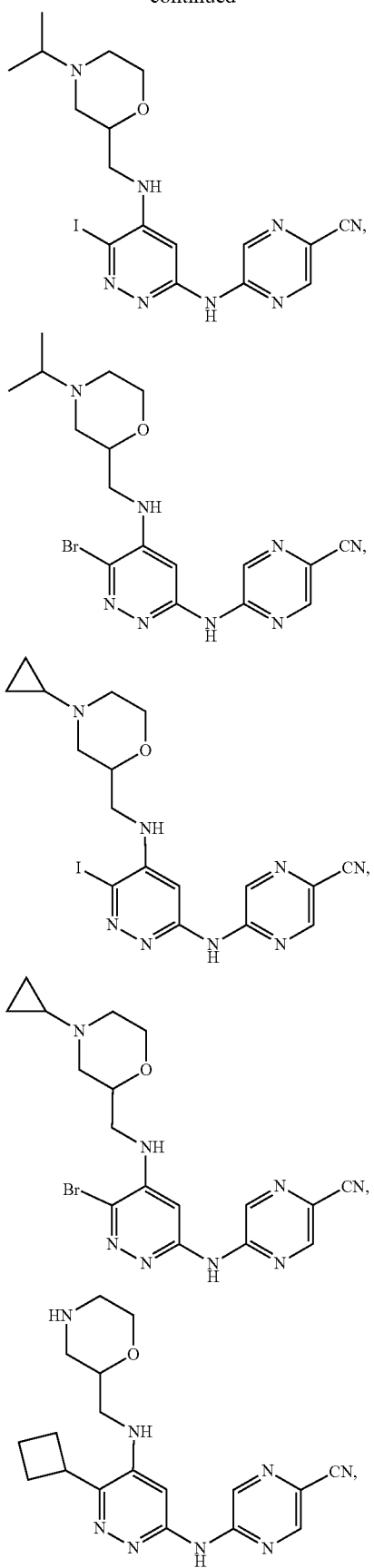

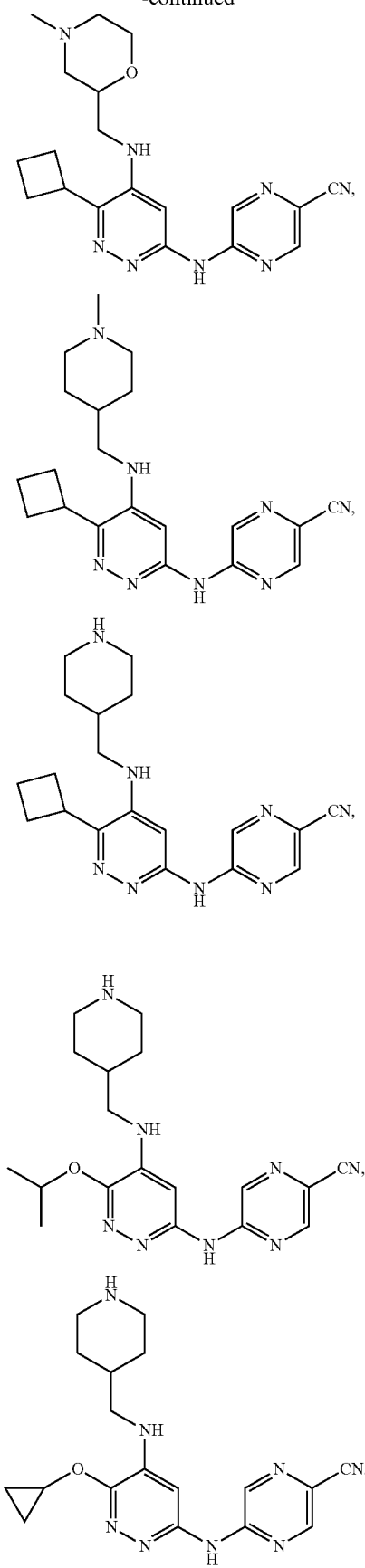
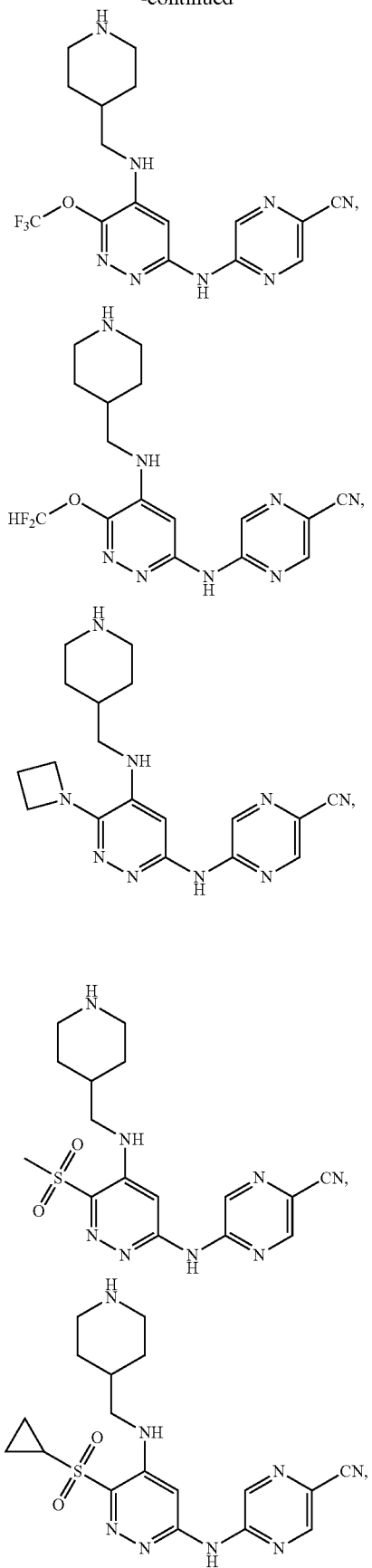

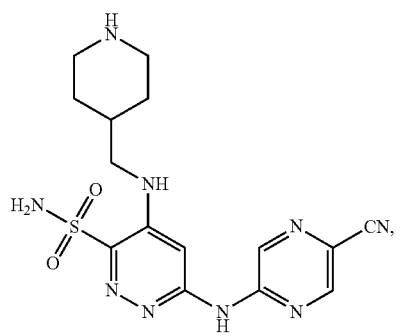
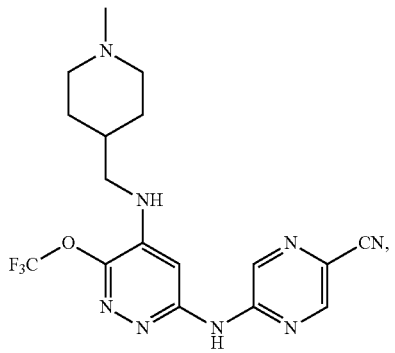
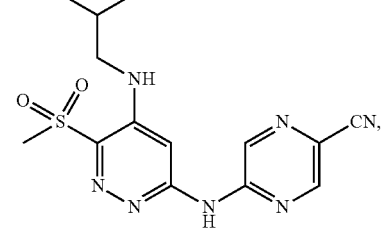
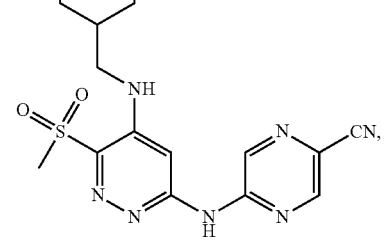
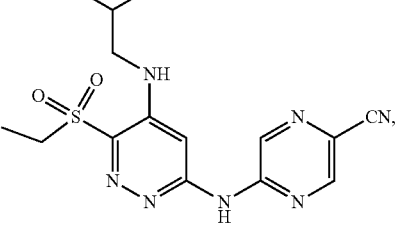
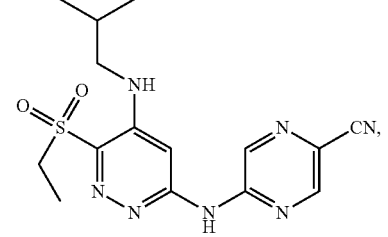

257
-continued
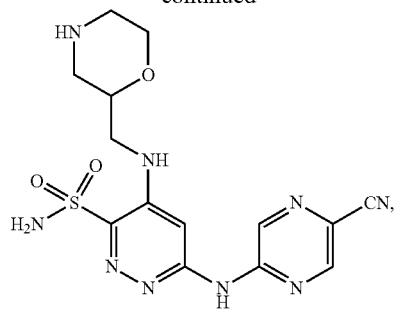
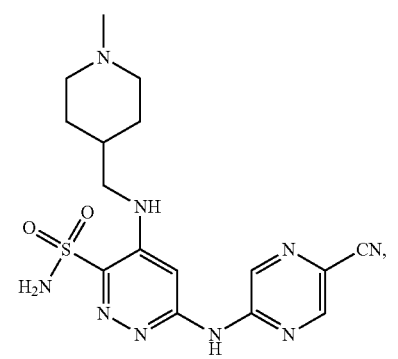
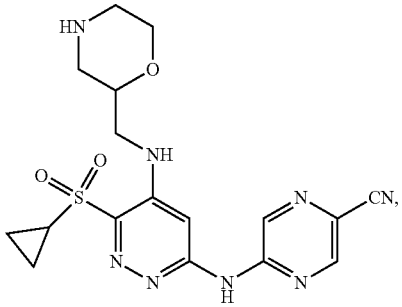
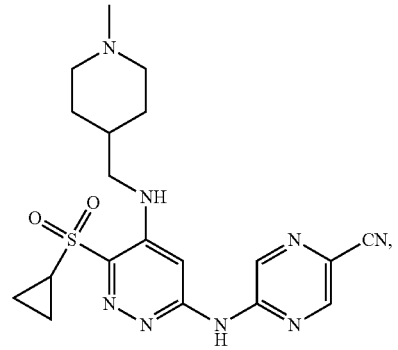
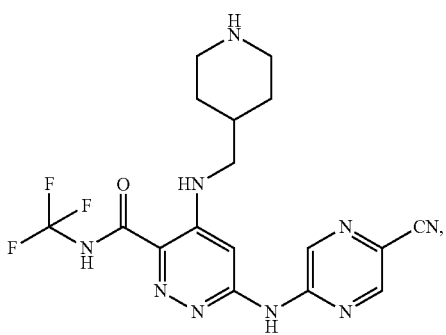
258
-continued
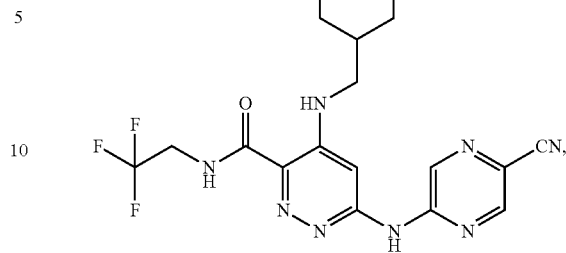
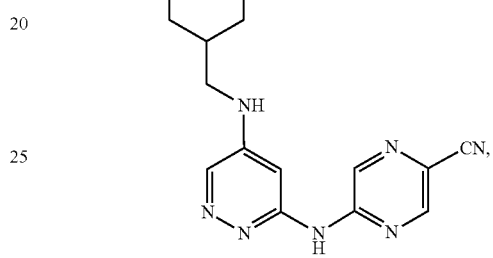
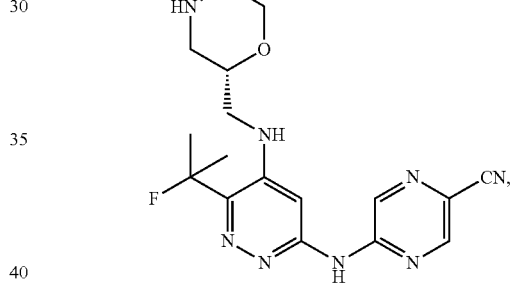
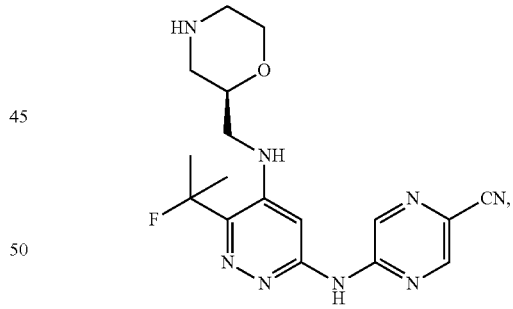
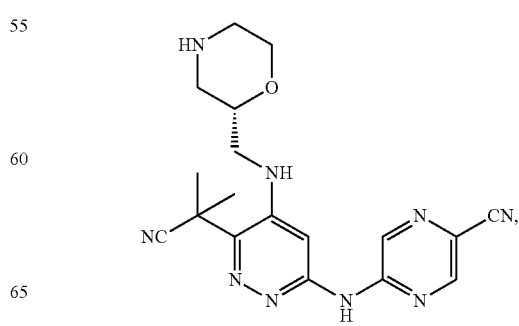

259
-continued
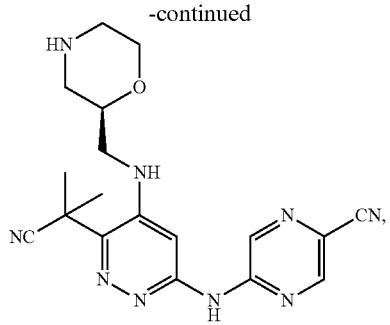
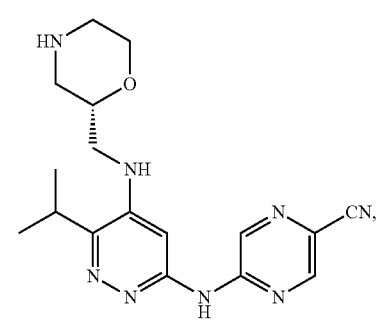
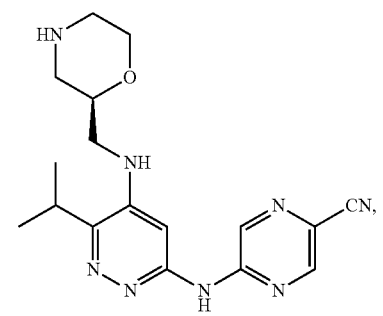
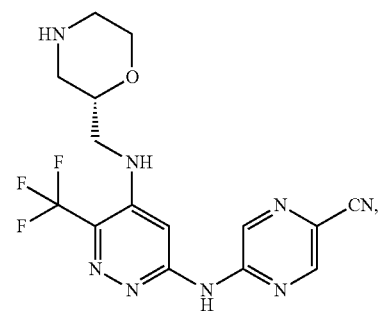
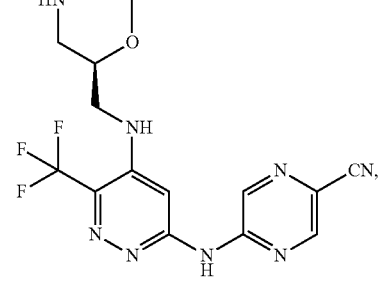
260
-continued
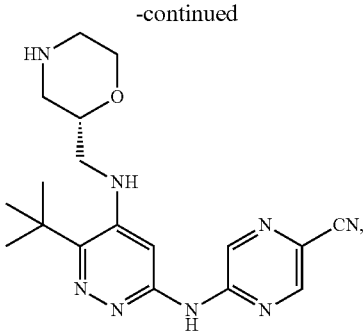
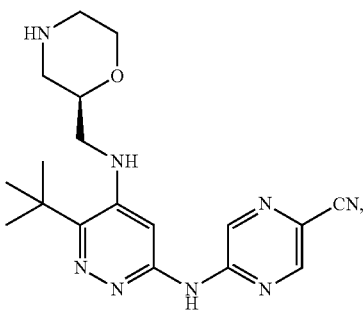
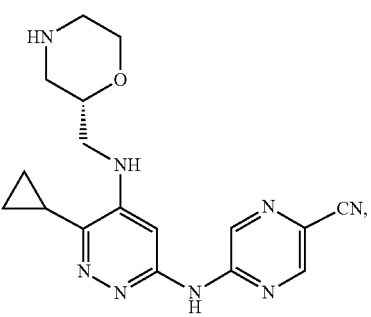
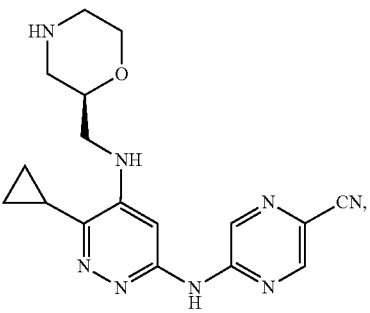
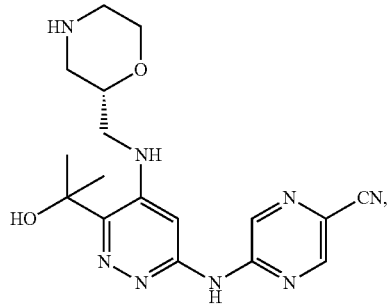

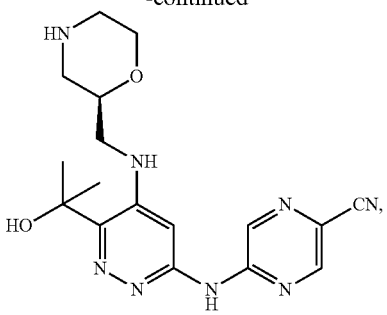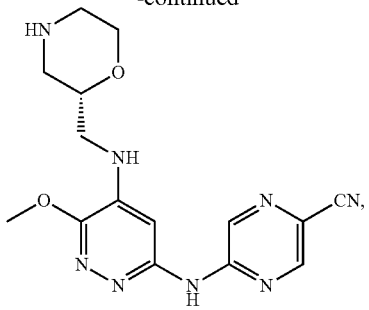

263
-continued
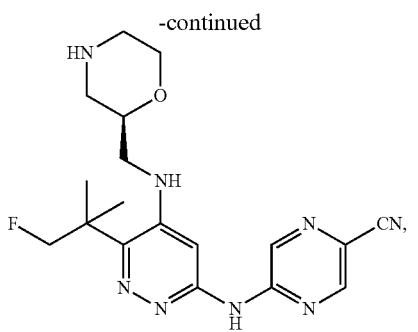
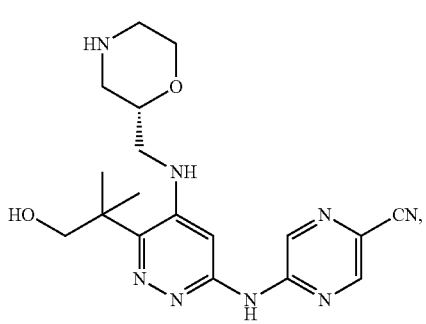
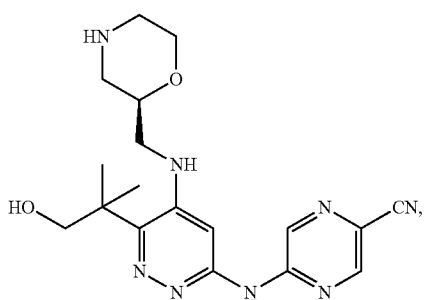
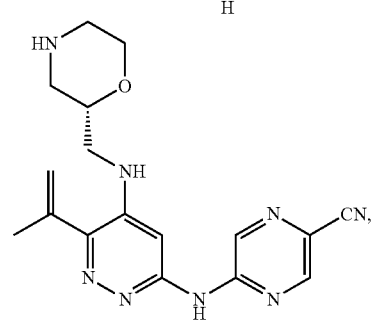
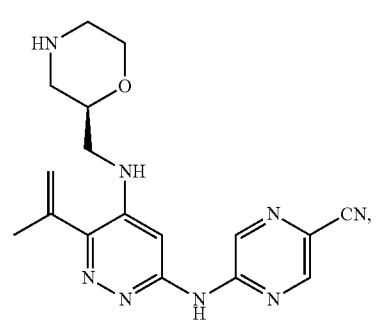
264
-continued
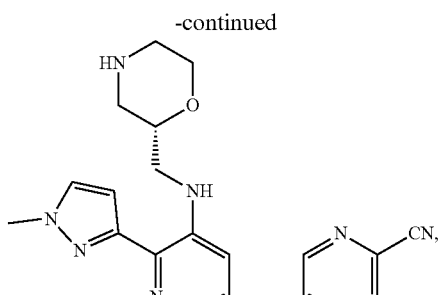
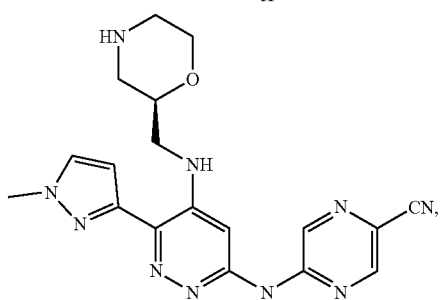
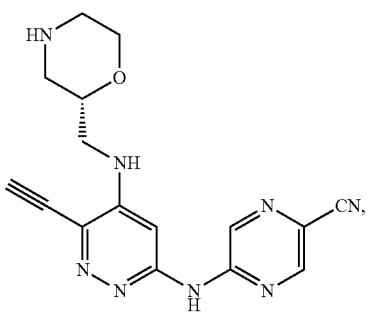
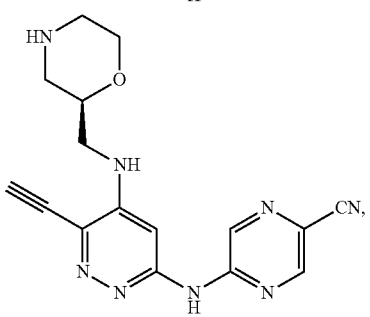
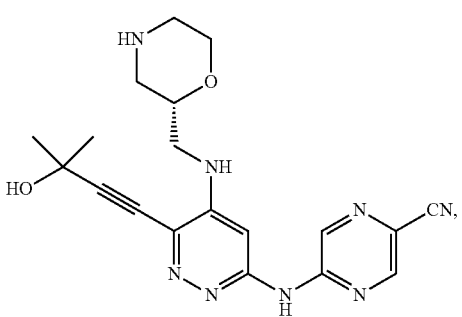

-continued
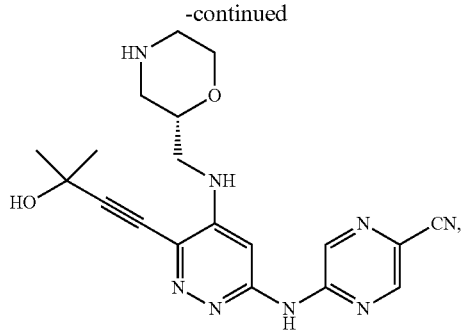
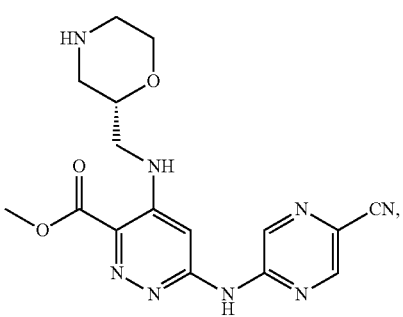
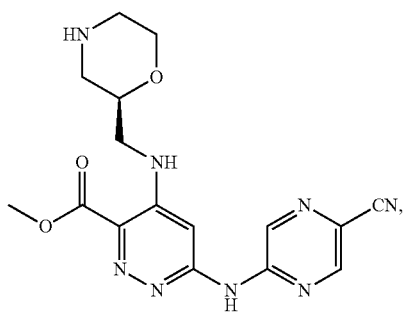
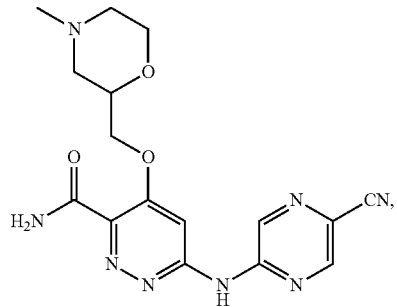
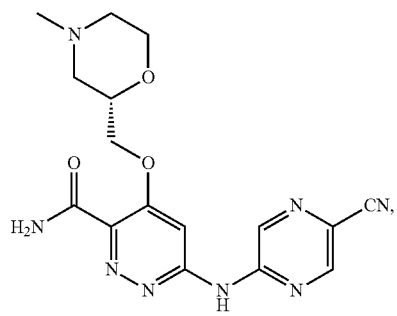
-continued
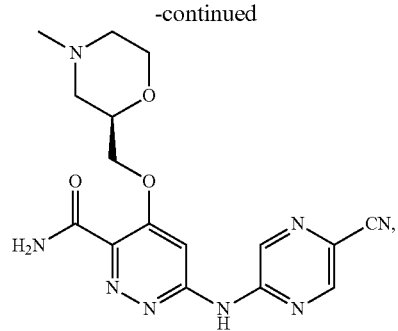
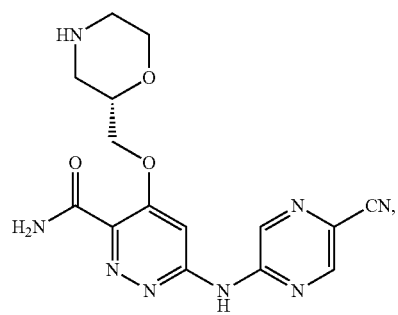
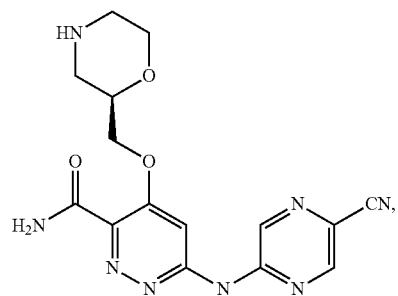
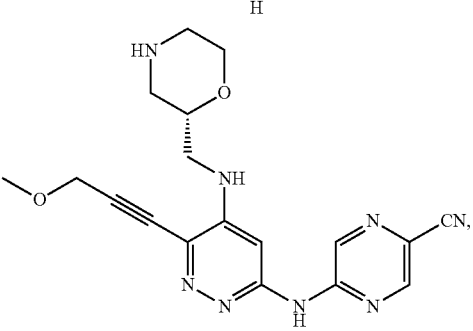
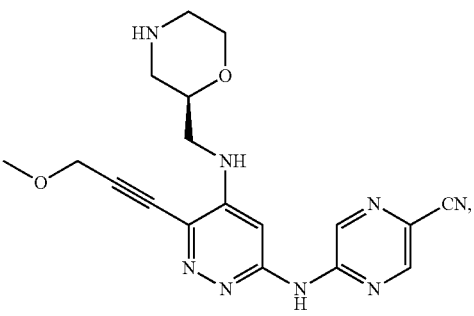

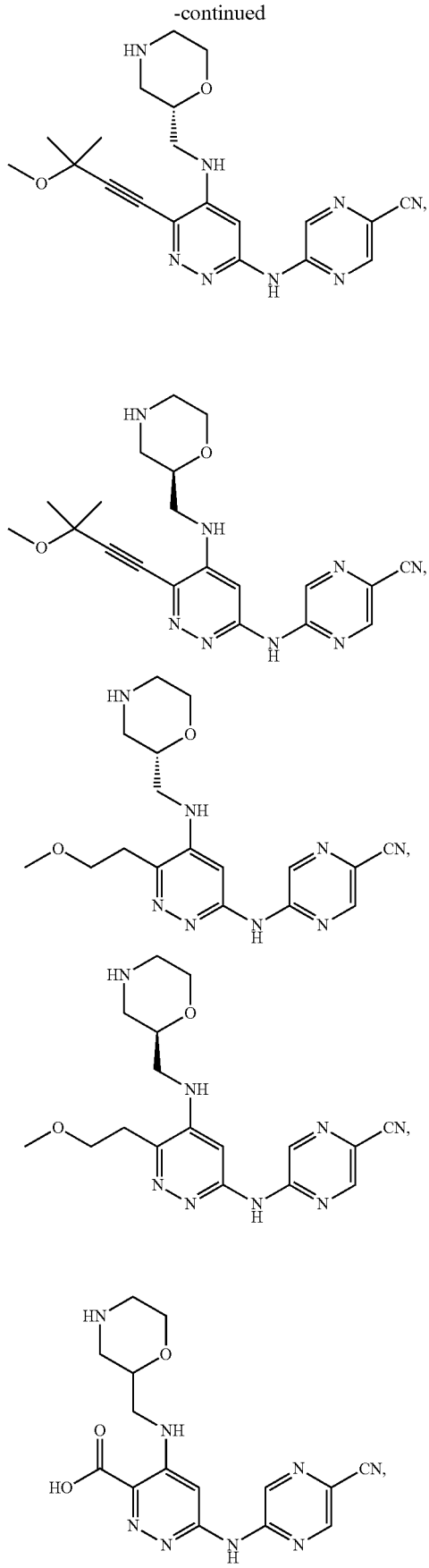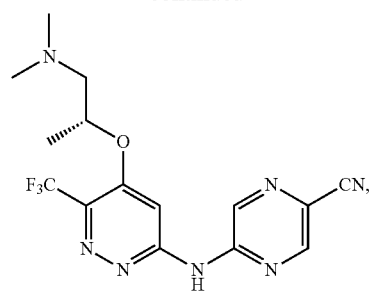

269
-continued
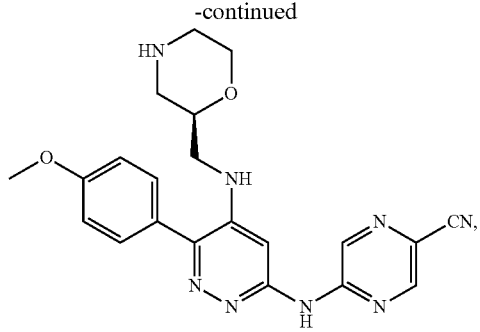
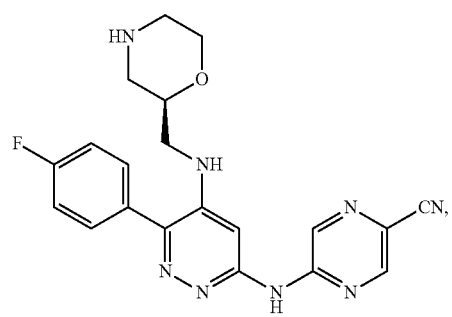
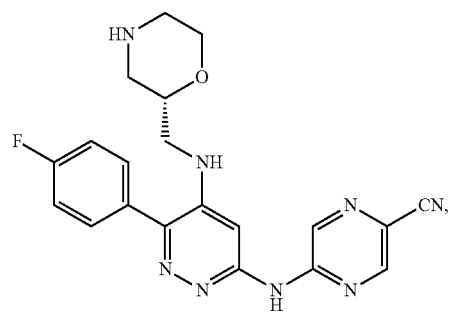
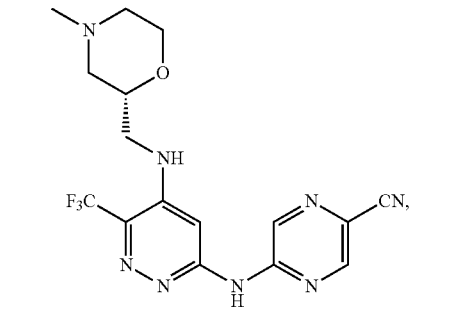
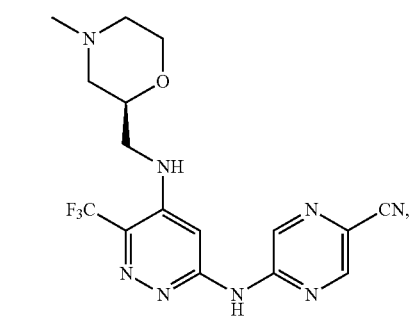
270
-continued
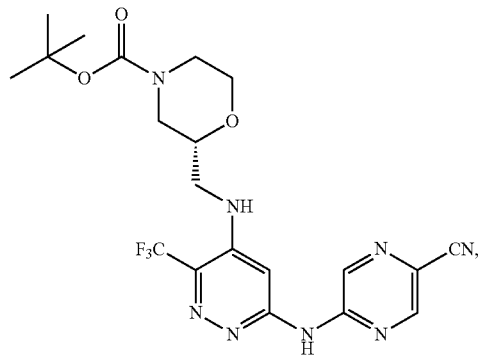 [SMILES: CC(C)(C)OC(=O)N1CCO[C@H](CNc2cc(Nc3cnc(C#N)cn3)nnc2C(F)(F)F)C1]
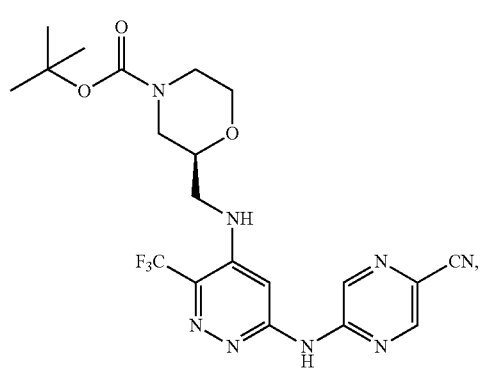 [SMILES: CC(C)(C)OC(=O)N1CCO[C@@H](CNc2cc(Nc3cnc(C#N)cn3)nnc2C(F)(F)F)C1]
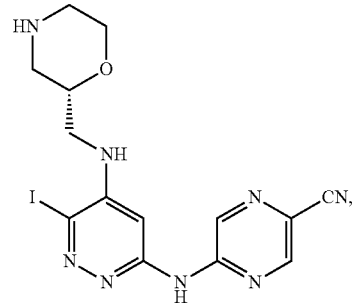
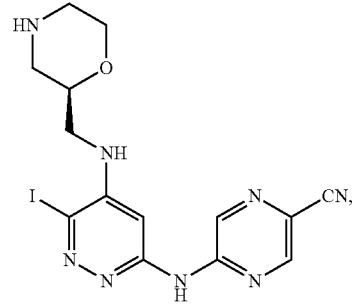
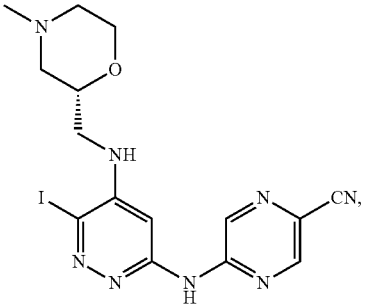

-continued
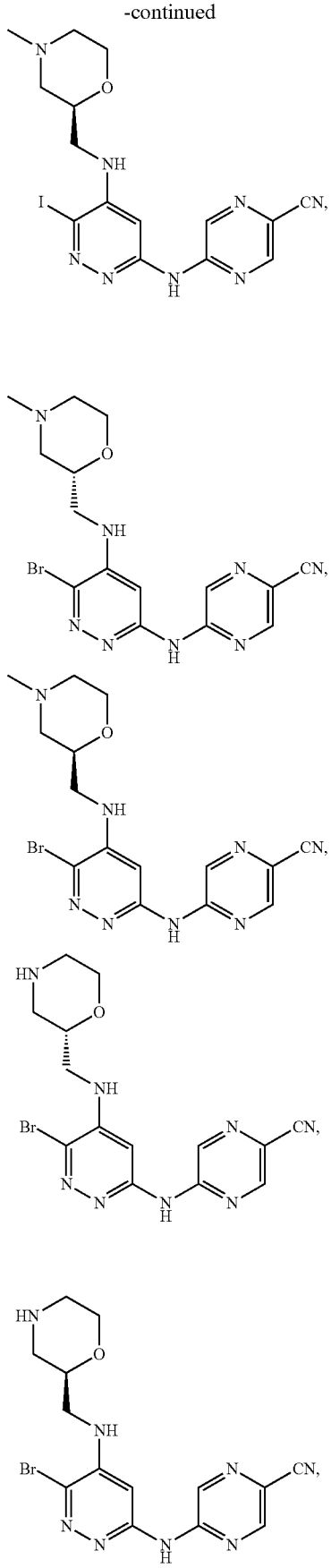
-continued
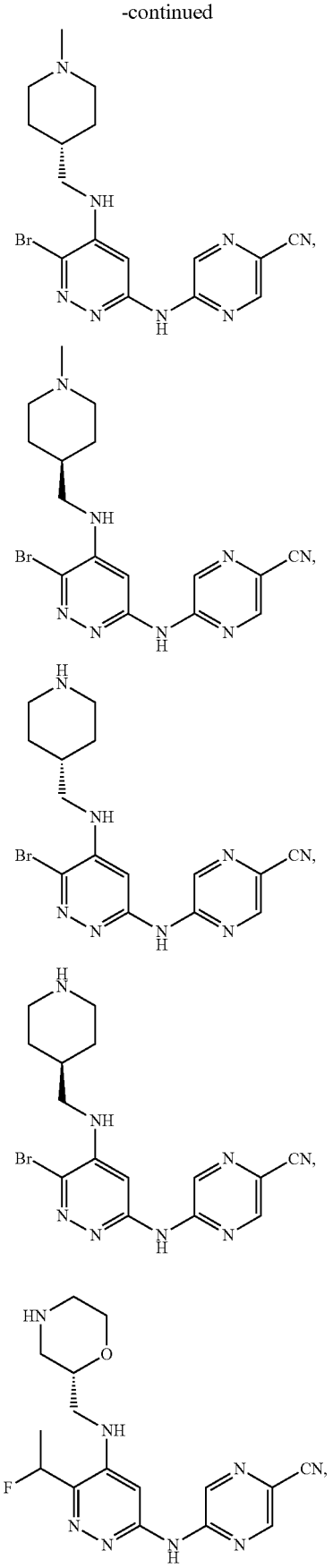

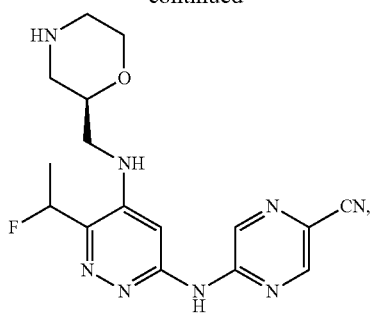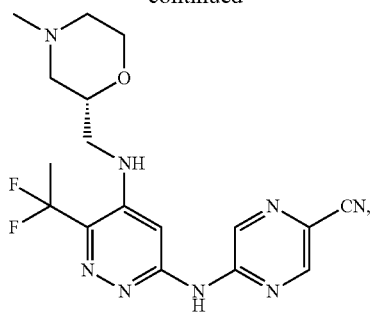

275
-continued
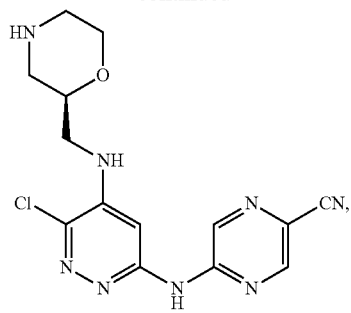
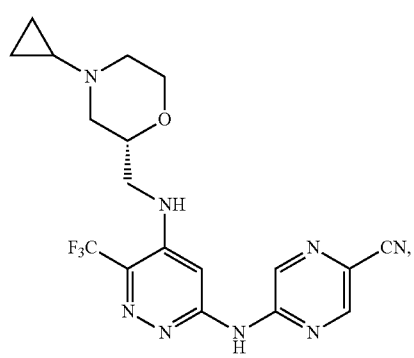
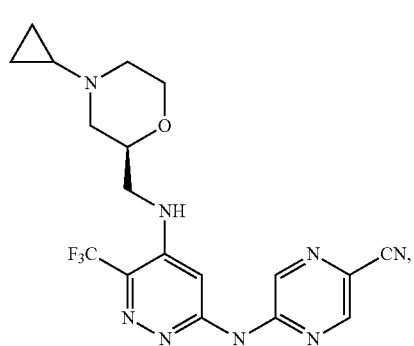
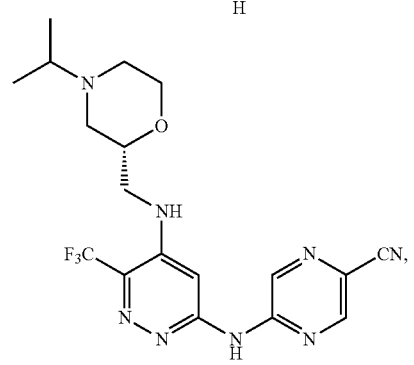
276
-continued
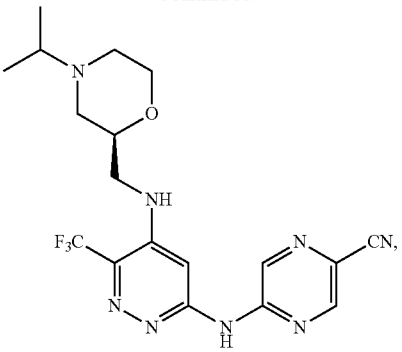 [SMILES: CC(C)N1CCO[C@@H](CNc2cc(Nc3cnc(C#N)cn3)nnc2C(F)(F)F)C1]
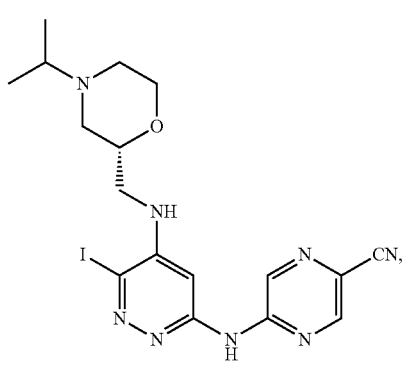 [SMILES: CC(C)N1CCO[C@H](CNc2cc(Nc3cnc(C#N)cn3)nnc2I)C1]
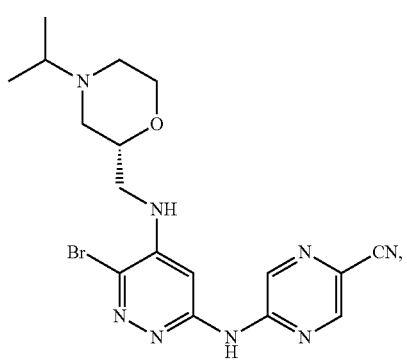 [SMILES: CC(C)N1CCO[C@H](CNc2cc(Nc3cnc(C#N)cn3)nnc2Br)C1]
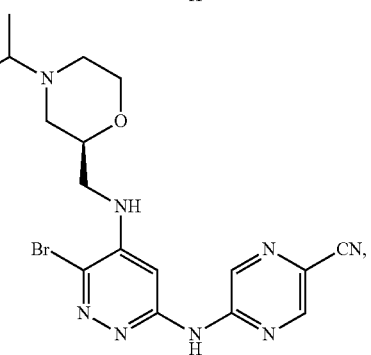

277 278
-continued -continued
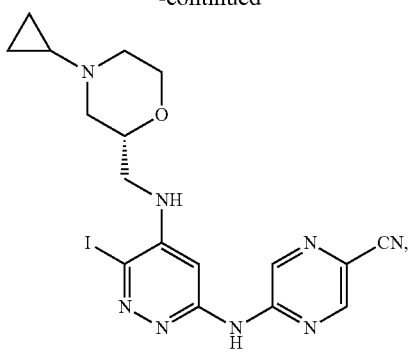
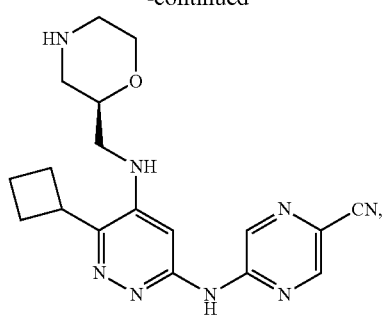
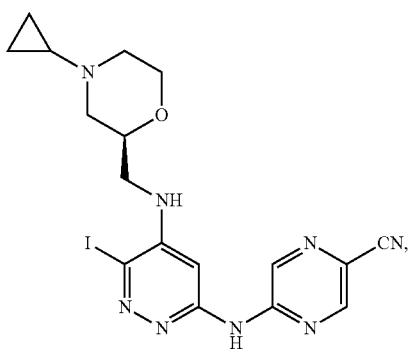 [SMILES: N#Cc1cnc(Nc2cc(NC[C@H]3CN(C4CC4)CCO3)c(I)nn2)cn1]
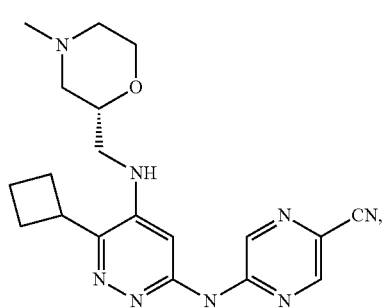
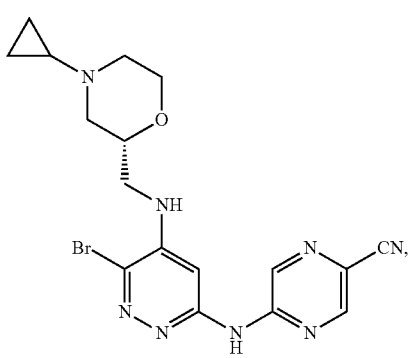
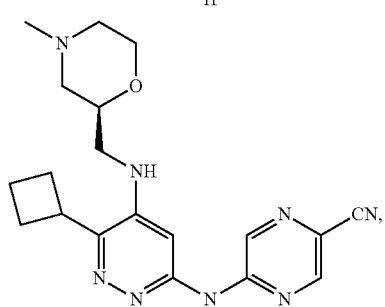
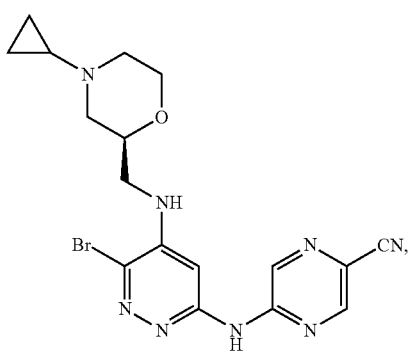 [SMILES: N#Cc1cnc(Nc2cc(NC[C@H]3CN(C4CC4)CCO3)c(Br)nn2)cn1]
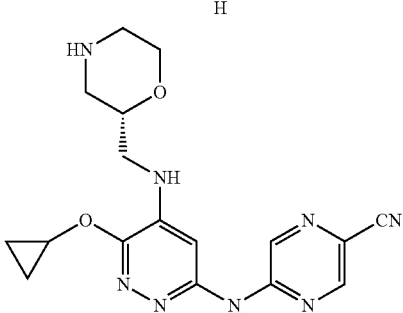
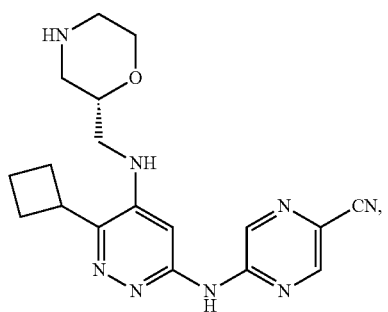
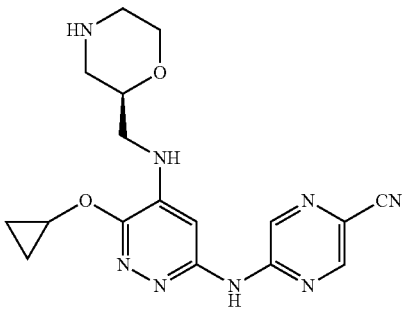 [SMILES: N#Cc1cnc(Nc2cc(NC[C@H]3CNCCO3)c(OC3CC3)nn2)cn1]

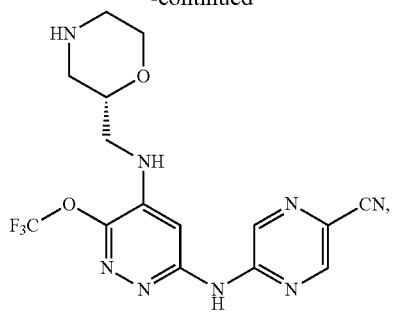
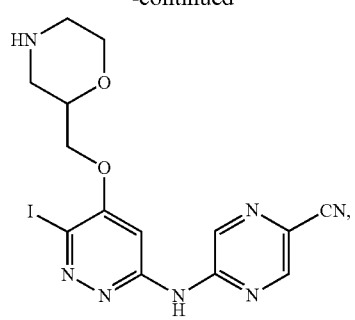
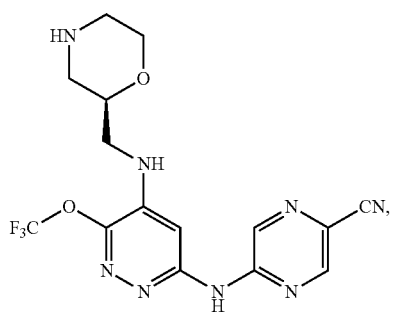
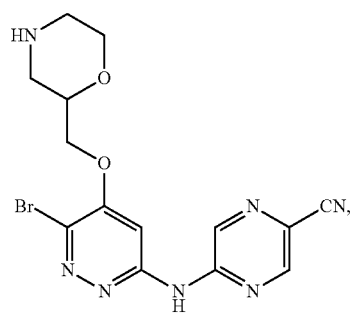
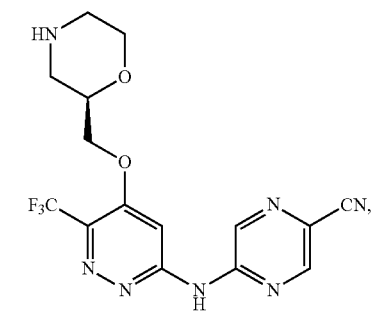
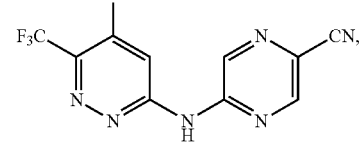
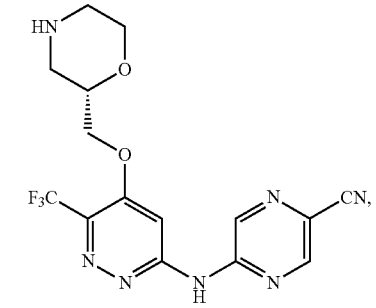 [SMILES: N#Cc1cnc(Nc2cc(OCC3CNCCO3)c(Br)nn2)cn1]
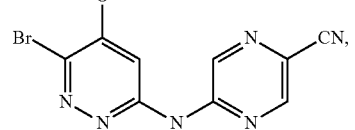
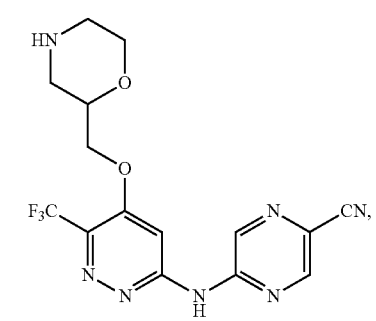
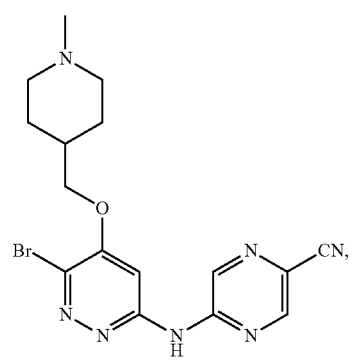

281
-continued
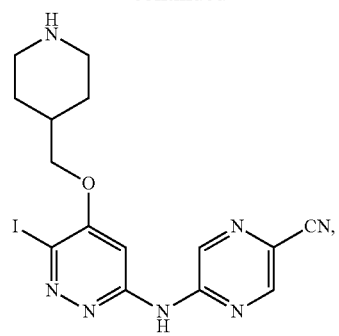
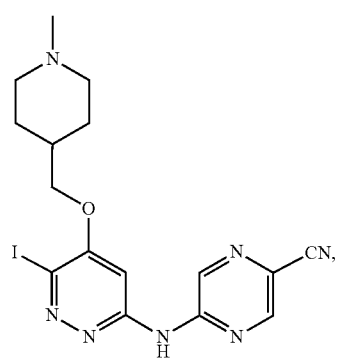
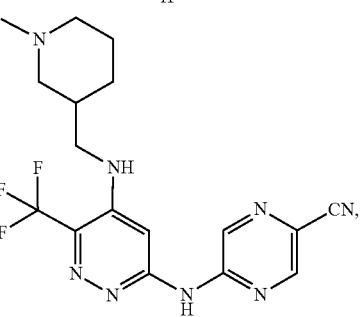
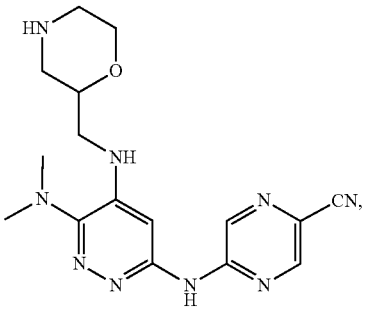
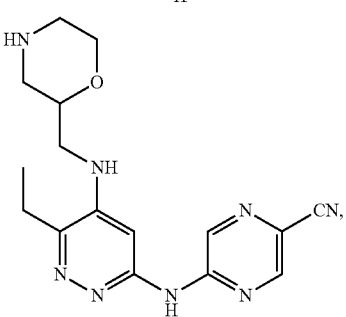
282
-continued
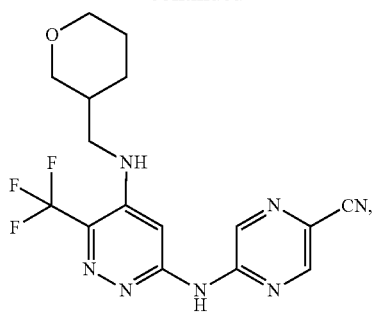
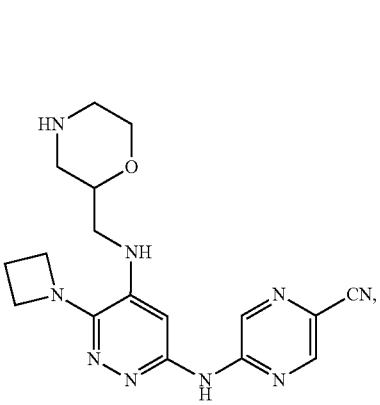
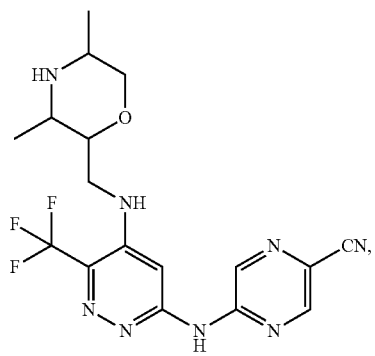
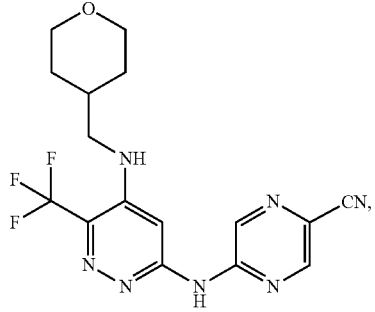
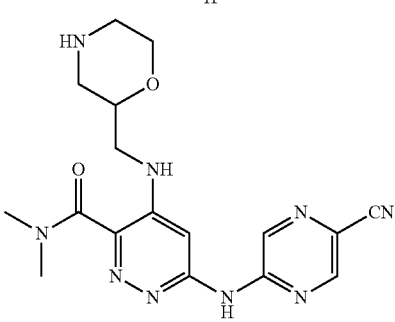

-continued
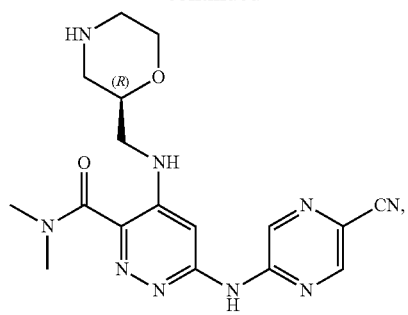
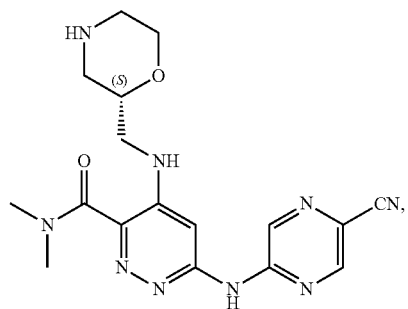
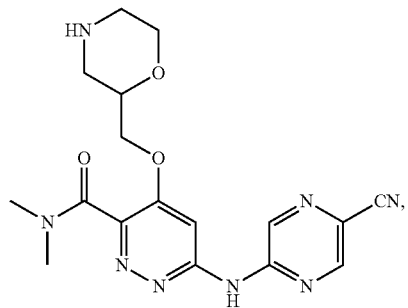
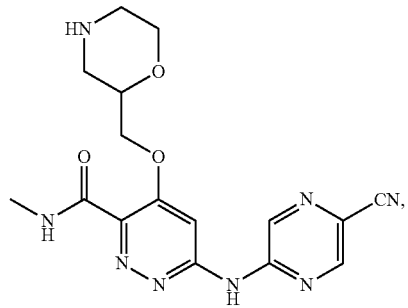
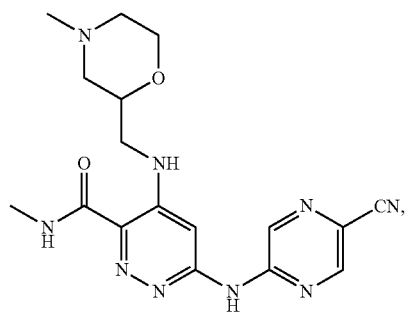
-continued
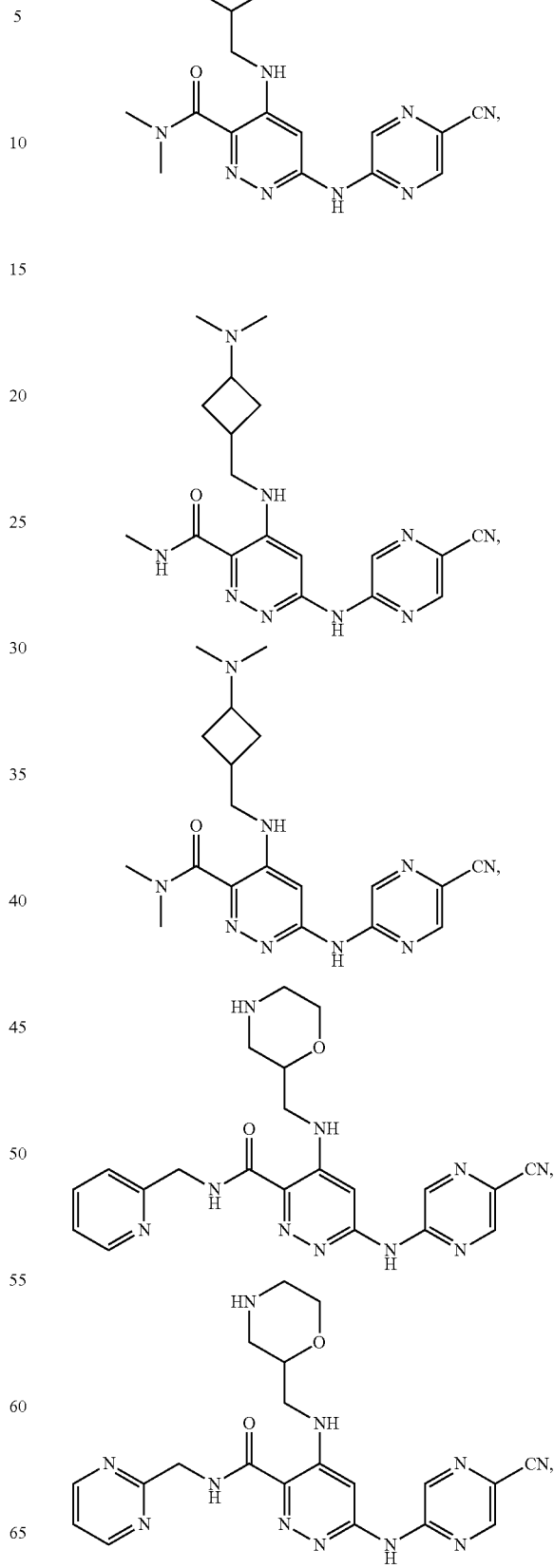

285
-continued
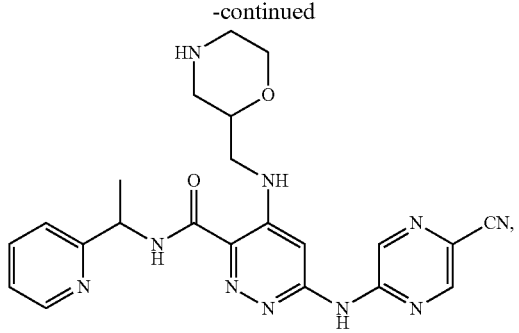
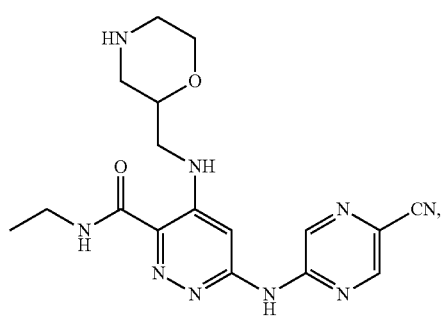 [SMILES: CCNC(=O)c1nnc(Nc2cnc(C#N)cn2)cc1NCC1CNCCO1]
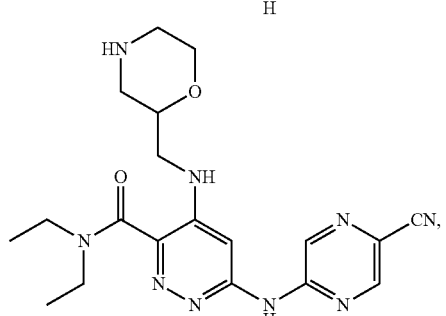
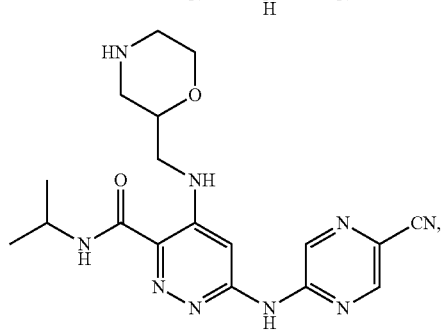
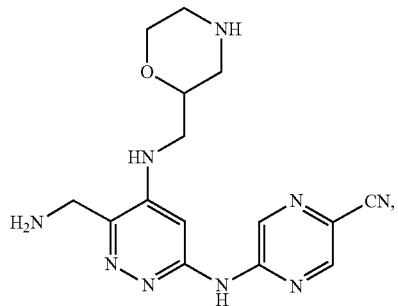
286
-continued
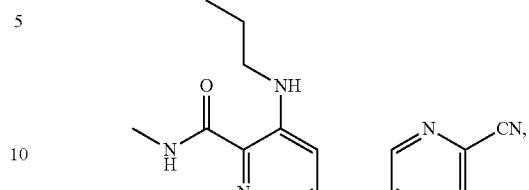
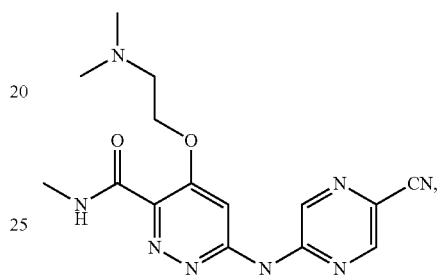
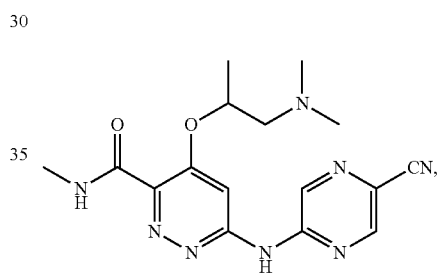
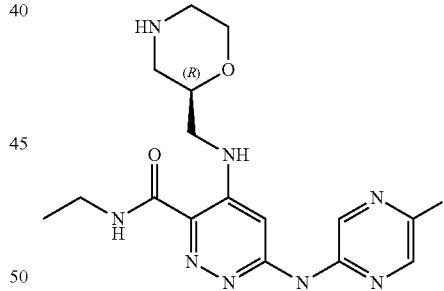
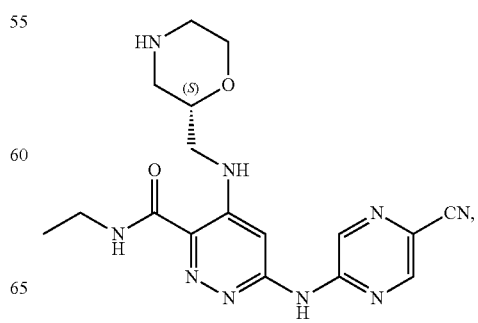

287
-continued
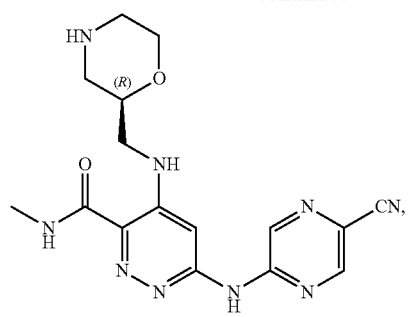
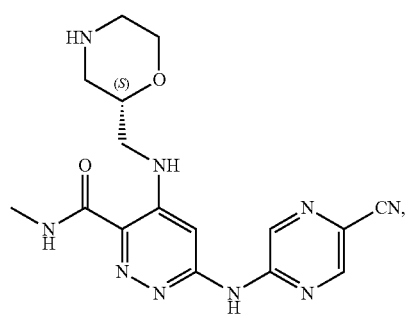
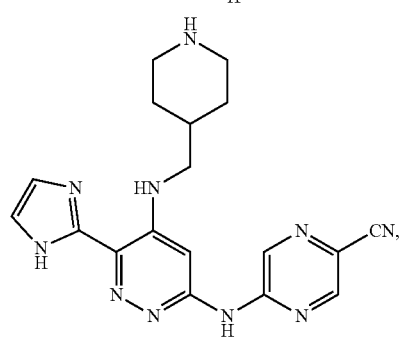
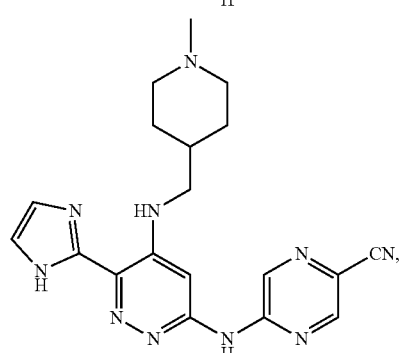
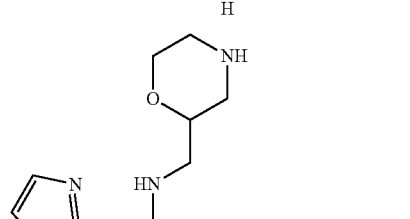
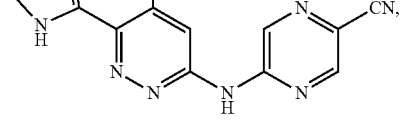
288
-continued
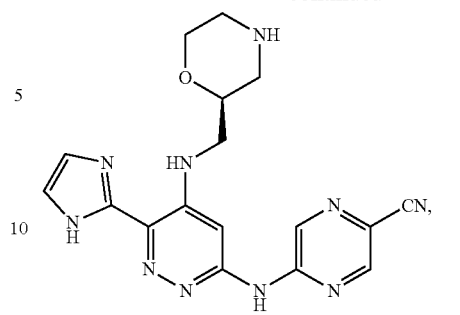
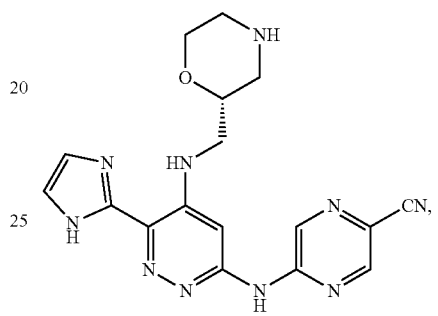
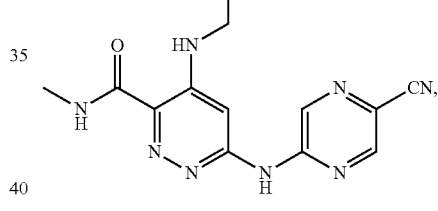
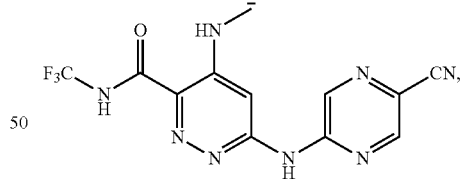
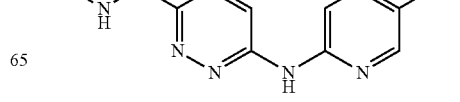

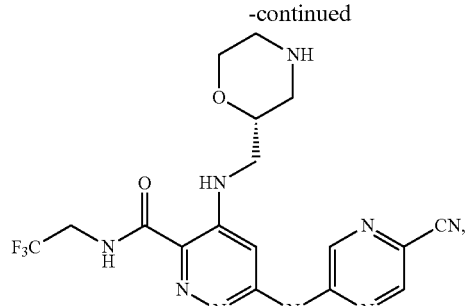
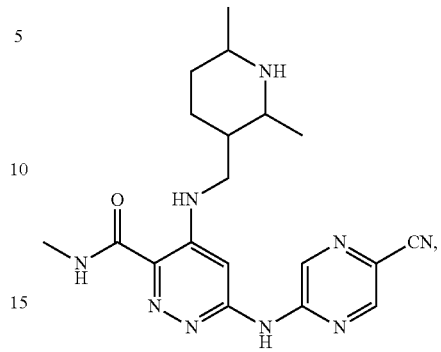
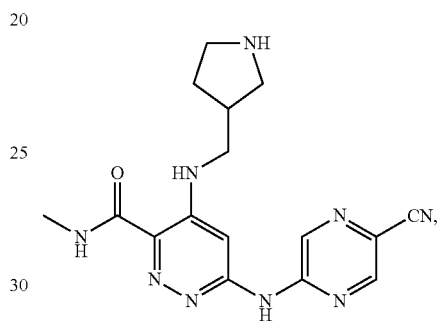
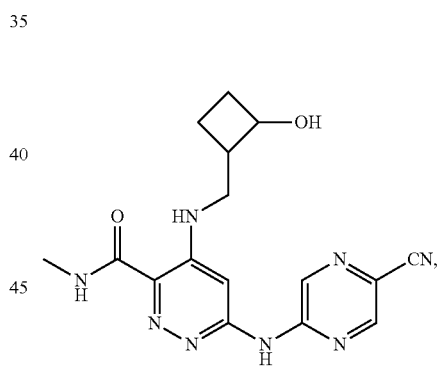
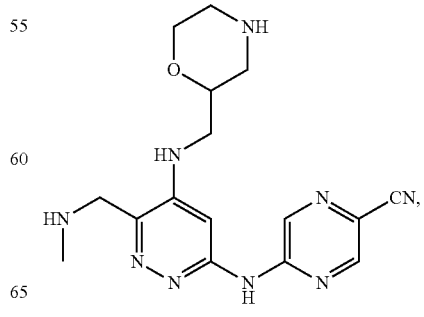

-continued

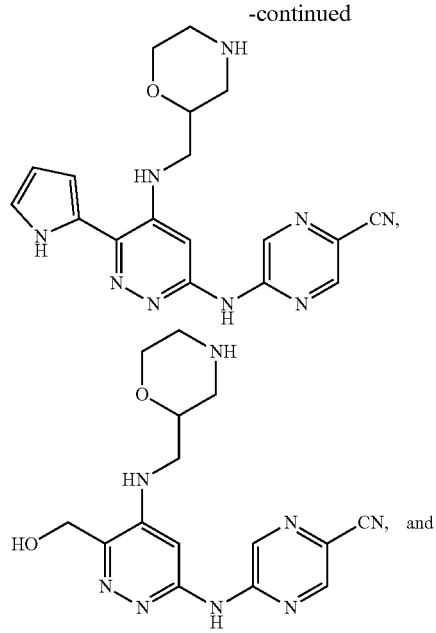

-continued

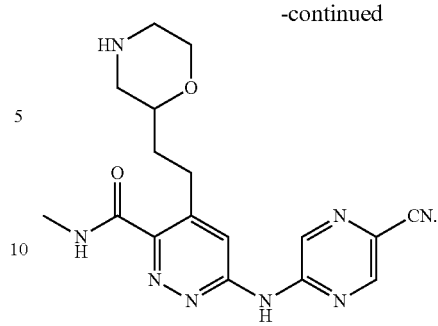

15. A pharmaceutical composition comprising a compound of claim 1, or a salt thereof, and a pharmaceutically acceptable carrier.

16. A method of treating disease or disorder associated with Checkpoint kinase (CHK) in an individual in need thereof comprising administering to the said individual a therapeutically effective amount of a compound of claim 1, or a salt thereof.

17. The method of claim 16, wherein the CHK is CHK-1.

18. The method of claim 16, wherein the disease is cancer.

* * * * *